(12) United States Patent
Williams et al.

(10) Patent No.: US 11,066,691 B1
(45) Date of Patent: Jul. 20, 2021

(54) THERAPEUTIC PHAGES AND METHODS THEREOF

(71) Applicant: National Technology & Engineering Solutions of Sandia, LLC, Albuquerque, NM (US)

(72) Inventors: Kelly Porter Williams, Livermore, CA (US); Steven Branda, Livermore, CA (US); Raga Krishnakumar, San Ramon, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/570,197

(22) Filed: Sep. 13, 2019

Related U.S. Application Data

(60) Provisional application No. 62/731,453, filed on Sep. 14, 2018.

(51) Int. Cl.
| | | |
|---|---|---|
| *A61K 35/76* | (2015.01) | |
| *C12Q 1/18* | (2006.01) | |
| *C12Q 1/6888* | (2018.01) | |
| *C12Q 1/04* | (2006.01) | |
| *C12N 15/10* | (2006.01) | |

(52) U.S. Cl.
CPC .......... *C12Q 1/18* (2013.01); *C12N 15/1034* (2013.01); *C12Q 1/04* (2013.01); *C12Q 1/6888* (2013.01)

(58) Field of Classification Search
None
See application file for complete search history.

(56) References Cited

U.S. PATENT DOCUMENTS

| | | | |
|---|---|---|---|
| 5,422,252 A | 6/1995 | Walker et al. | |
| 5,470,723 A | 11/1995 | Walker et al. | |
| 9,322,014 B1 | 4/2016 | VanderNoot et al. | |
| 2018/0028686 A1 | 2/2018 | Brinker et al. | |
| 2018/0049984 A1 | 2/2018 | Brinker et al. | |
| 2018/0178217 A1 | 6/2018 | Jebrail et al. | |
| 2020/0095558 A1* | 3/2020 | Loessner | C07K 14/195 |

OTHER PUBLICATIONS

Qiu et al. Interstrain transfer of the large pathogenicity island (PAPI-1) of Pseudomonas aeruginosa. PNAS Dec. 26, 2006 103 (52) 19830-19835. (Year: 2006).*
GenBank: CP011857.1. Pseudomonas aeruginosa strain ATCC 27853, complete genome. (Year: 2016).*
Freschi et al, Genomic characterisation of an international Pseudomonas aeruginosa reference panel indicates that the two major groups draw upon distinct mobile gene pools, FEMS Microbiology Letters, vol. 365, Issue 14, Jul. 2018. (Year: 2018).*
Abedon ST et al., "Phage treatment of human infections," *Bacteriophage* 2011;1:66-85.
Allen JE et al., "DNA signatures for detecting genetic engineering in bacteria," *Genome Biol.* 2008;9:R56 (10 pp.).

(Continued)

*Primary Examiner* — Michelle S Horning
(74) *Attorney, Agent, or Firm* — Helen S. Baca; Medley, Behrens & Lewis, LLC

(57) ABSTRACT

The present invention relates, in part, to engineered viruses (e.g., engineered phages), phage cocktails, and methods of producing and/or identifying viruses for targeting pathogenic bacteria.

20 Claims, 10 Drawing Sheets

Specification includes a Sequence Listing.

(56) References Cited

OTHER PUBLICATIONS

Ando H et al., "Engineering modular viral scaffolds for targeted bacterial population editing," *Cell Syst* 2015;1:187-96.
Arndt D et al., "PHASTER: a better, faster version of the PHAST phage search tool," *Nucleic Acids Res.* 216;44:W16-W21.
Barnes WM, "PCR amplification of up to 35-kb DNA with high fidelity and high yield from lambda bacteriophage templates," *Proc. Nat'l Acad. Sci. USA* 1994:91:2216-20.
Battle SE et al., "Genomic islands of *Pseudomonas aeruginosa*," *FEMS Microbiol. Lett.* 2009;290:70-8.
Brüssow H et al., "Phages and the evolution of bacterial pathogens: from genomic rearrangements to lysogenic conversion," *Microbiol. Mol. Biol. Rev.* 2004;68:560-602.
Bundy BC et al., "*Escherichia coli*-based cell-free synthesis of virus-like particles," *Biotechnol. Bioeng.* 2008;100:28-37.
Cao H et al., "Comparative genome and transciptome analysis reveals distinctive surface characteristics and unique physiological potentials of *Pseudomonas aeruginosa* ATCC 27853," *BMC Genomics* 2017;18:459 (17 pp.).
Ceyssens P-J. "Isolation and characterization of lytic bootericohages infecting *Pseudomonas aeruginosa*," Doctoral thesis No. 879, Faculty of Bioscience Engineering, Department of Biosystems, Katholieke Universiteit Leuven, Dec. 2009 (166 pp.).
Diffenbach CW et al., "General concepts for PCR primer design," *Genome Res.* 1993;3:S30-S37.
Dubos RJ et al., "The multiplication of bacteriophage in vivo and its protective effect against an experimental infection with *Shigella dysenteriae*," *J. Exp. Med.* 1943;78:161-8.
Eaton MD et al., "Bacteriophage therapy: review of the principles and results of the use of bacteriophage in the treatment of infections," *J. Am. Med. Assoc* 1934;103:1769-76.
Gibson DG et al., "Chemical synthesis of the mouse mitochondrial genome," *Nat. Methods* 2010,7:901-3.
Gibson DG et al., "Enzymatic assembly of DNA molecules up to several hundred kilobases," *Nat. Methods* 2006;6:343-5.
Gottesman ME & Weisberg RA, "Prophage insertion 25 and excision." in The Bacteriophage Lambda (ed. Hershey AD). 1971, Cold Spring Harbor Laboratory Press, Cold Spring Harbor, NY (pp. 113-138).
Green SI et al., "Bacteriophages from ExPEC reservoirs kill pandemic multidrug-resistant strains of clonal group ST131 in animal models of bacteremia," *Sci. Rep.* 2017;7:46151 (13 pp.).
Gu J et al., "A method for generation phage cocktail with great therapeutic potential," *PLoS One* 2012;7:e31698 (8 pp.).
Hagens S et al., "Bacteriophage for biocontrol of foodborne pathogens: calculations and considerations," *Curr. Pharm. Biotechol.* 2010;11:58-68.
Hatzopoulos T et al., "PhagePhisher: a pipeline for the discovery of covert viral sequences in complex genomic datasets," *Microb. Genom.* 2016;2:e000053 (5 pp.).
Hudson CM et al., "Islander: a databse of precisely mapped genomic islands in tRNA and tmRNA genes," *Nucleic Acids Res* 2015;43:D48-D53.
Hudson CM et al., "Resistance determinants and mobile genetic elements of an NDM-1 encoding *Klebsiella pneumoniae* strain," *PLoS One* 2014;9:e99209 (14 pp.).
Hudson CM et al., Supplementary Materials for "Resistance determinants and mobile genetic elements of an NDM-1-encoding Klebsiella pneumoniae strain," *PLoS One* 2014;9:e99209 (12 pp.).
Jani M et al., "Identification of novel genomic islands in Liverpool epidemic strain of *Pseudomonas aeruginosa* using segmentation and clustering," *Front. Microbiol* 2016;7:1210 (18 pp.).
Jaschke PR et al., "A fully decompressed synthetic bacteriophage øX174 genome assembled and archived in yeast," *Virology* 2012;434:278-84.
Kilcher S et al., "Cross-genus rebooting of custom-made, synthetic bacteriophage genomes in L-form bacteria," *Proc. Nat'l Acad. Sci. USA* 2018;115:567-72.
Kutter E et al., "Phage therapy in clinical practice: treatment of human infections," *Curr. Pharm. Biotechnol.* 2010;11:69-86.
Kutter E, "Phage therapy: bacteriophages as naturally occurring antimicrobials," in *Practical Handbook of Microbiology* (2d ed., Goldman E & Green LH (eds.)). 2008, CRC Press, Boca Raton, FL (Chapter 44, pp. 713-730).
Kutter EM et al., "Re-establishing a place for phage therapy in western medicine," *Future Microbiol.* 2015;10:685-8.
Lau B et al., "Discovering and converting temperate phages for therapy," *Sandia Report No. SAND2017-12724C* (22 pp.).
Lau BY et al., "Reconsidering temperate phages for therpay," *Sandia Report No. SAND2017-5803C* (1 p.).
Lau BY et al., "Reconsidering temperate phages for therpay," *Sandia Report No. SAND2017-5804A* (1 p.).
Ling LL et al., "A new antibiotic kills pathogens without detectable resistance," *Nature* 2015;517:455-9.
MacNeal WJ et al., "Staphylococcemia 1931-1940: five hundred patients," *Am. J. Clin. Pathol.* 1942;12:281-94.
Malki K et al., "Bacteriophages isolated from Lake Michigan demonstrate broad host-range across several bacterial phyla," *Virol. J.* 2015;12:164 (5 pp.).
Mantri Y et al., "Islander: a database of integrative islands in prokaryotic genomes, the associated integrases and their DNA site specificities," *Nucleic Acids Res.* 2004;32:D55-D58.
Marinelli LJ et al., "BRED: a simple and powerful tool for constructing mutant and recombinant bacteriophage genomes," *PLoS One* 2008;3:e3957 (8 pp.).
Mayhall CG, "The epidemiology of burn wound infections: then and now," *Clin. Infect. Dis.* 2003:37:543-50.
Morales-Espinoza R et al., "Genotypic and phenotypic characterization of *Pseudomonas aeruginosa* population with high frequency of genomic islands," *PLoS One* 2012;7:e37459 (11 pp.).
Morton HE et al., "The increase of bacteriophage in vivo during experimental infections with Shigella paradysenteria, Flexner, in mice," *J. Bacteriol.* 1945;49:237-44.
Ofir G et al., "Contemporary phage biology," *Cell* 2018;172:1260-70.
Ondov BD et al., "Mash: fast genome and metagenome distance estimation using MinHash," *Genome Biol.* 2016;17:132 (14 pp.).
Oppenheim AB et al., "Switches in bacteriophage lambda development," *Annu. Rev. Genet* 2005;39:409-29.
Pietilä MK et al., "Archaeal viruses and bacteriophages: comparisons and contrasts," *Trends Microbiol.* 2014;22:334-44.
Pires DP et al., "Genetically engineered phages: a review of advances over the last decade," *Microbiol. Mol Biol Rev.* 2016;80:523-43.
Sagona AP et al., "Genetically modified bacteriophages," *Integr Biol.* 2016;8:465-74.
Salmond GPC et al., "A century of the phage: past, present and future," *Nat. Rev. Microbiol.* 2015;13:777-86.
Sinha S et al., "Comparative analysis between genomic islands and host species," *Sandia Report No. SAND2017-7637D* (1 p.).
Schoeniger JS et al., "Experimental single-strain mobilomics reveals events that shape pathogen emergence," *Nucleic Acids Res.* 2016;44:6830-9.
Schoeniger JS et al., Supplementary Information for "Experimental single-strain mobilomics reveals events that shape pathogen emergence," *Nucleic Acids Res.* 2016;44:6830-9 (18 pp.).
Shen K et al., "Extensive genomic plasticity in *Pseudomonas aeruginosa* revealed by identification and distribution studies of novel genes among clinical isolates," *Infect. Immun.* 2006;74:5272-83.
Shin J et al., "Genome replication, synthesis, and assembly of the bacteriophage T7 in a single cell-free reaction," *ACS Synth Biol* 2012;1:408-13.
Sulakvelidze A & Kutter E, "Bacteriophage therapy in humans," in *Bacteriophages: Biology and Application* (eds. Kutter E & Sulakvelidze A), 2004, CRC Press, Boca Raton, FL (Chapter 14, pp. 381-436).
Van Kessel JC et al., "Recombineering in *Mycobacterium tuberculosis*," *Nat Methods* 2007;4:147-52.
Villaneuva VM et al., "An unusual phage repressor encoded by mycobacteriophage BPs," *PLoS One* 2015;10:e0137187 (21 pp.).

(56) References Cited

OTHER PUBLICATIONS

Wagner J et al., "Comparator: scaling up genomic island finding with a comparative genomic approach," *Sandia Report No. SAND2017-7636D* (1 p.).

Watkins SC et al., "Characterisation of host growth after infection with a broad host-range freshwater cyanopodophage," *PLoS One* 2014;9:e87339 (8 pp.).

Watkins SC et al., "The use of informativity in the development of robust viromics-based examinations," *PeerJ* 2017;5:3281 (18 pp.).

Weber-Dabrowska B et al., "Bacteriophage therapy of bacterial infections: an update of our institute's experience," *Arch. Immunol. Ther. Exp. (Warsz)* 2000;48:647-51.

Williams K et al., "Discovering and converting temperate phages for therapy," Chemical and Biological Defense Science & Technology Conference, held on Nov. 28-30, 2017 in Long Beach, CA, Abstract 172 (1 p.).

Williams K et al., "Discovering and converting temperate phages for therapy," Chemical and Biological Defense Science & Technology Conference, held on Nov. 28-30, 2017 in Long Beach, CA, Presentation 172 (24 pp.).

Williams KP, "Integration sites for genetic elements in prokaryotic tRNA and tmRNA genes: sublocation preference of integrase subfamilies," *Nucleic Acids Res.* 2002;30:866-75.

Williams KP, "Traffic at the tmRNA gene," *J. Bacteriol.* 2003;185:1059-70.

Xia G et al., "Phages of *Staphylococcus aureus* and their impact on host evolution," *Infect. Genet. Evol.* 2014;21:593-601.

Ye J et al., "Primer-BLAST: a tool to design target-specific primers for polymerase chain reaction," *BMC Bioinformatics* 2012;13:134 (11 pp.).

Bessen, et al., "Molecular Epidemiology and Genomics of Group A *Streptococcus*", Infect. Genet. Evol. (2015) 33:393-418.

Mageeney, et al., "New Candidates for Regulated Gene Integrity Revealed Through Precise Mapping of Integrative Genetic Elements", In Nucleic Acids Research, vol. 48, No. 8, Mar. 17, 2020, pp. 4052-4065.

Mantri, et al., "Islander: A Database of Integrative Islands in Prokaryotic Genomes, the Associated Integrases and Their DNA Site Specificities", In Nucleic Acids Research, vol. 32, 2004, pp. D55-D58.

Rahmer, et al., "Contruction of a Super-Competent Bacillus Subtilis 168 Using the PmtIA-comKS Inducible Cassette", In Microbiology, Frontiers, vol. 6, Article 1431, Dec. 21, 2015, pp. 1-11.

* cited by examiner

SEQUENCE LISTING

<160> NUMBER OF SEQ ID NOS: 19

<210> SEQ ID NO 1
<211> LENGTH: 41169
<212> TYPE: DNA
<213> ORGANISM: Artificial Sequence
<220> FEATURE:
<223> OTHER INFORMATION: Synthetic construct

<400> SEQUENCE: 1

```
tccgcaagcc aacagaatca aatgcttacg gtagcgtttt ggaggaaaaa aagaccaaat     60
cagcgctctg cctcgtagac cgccacgccc ttccccaccg gaatccactt ctcctccgga    120
tcacctggcc gacagatggc cacctctacc tcggtgctct tcccttctgc cggctcagcc    180
ggacggatgg ccgcgtgccg cagcaagtta ccatgcccg gcacgaacgt gctctcggag    240
caatggaacg accaaacccc cgcccgattc gcatcgttca ctttccgatc aagcttcagc    300
gtccacccct tcttgagtct caccaccagc acggtcatgc tcccattcaa aatgggtagt    360
ctacacgccg cccgcgtccg gcagcttata cctggccttg atctcctcga ccttggcgat    420
ccaggcgctg tagtccggct cggtgcctgc cttgatcgca tcgaattcag cctcggtctt    480
gagcgggtca ctttccaggc ggtaggcatt tgcccgcgcc gcggctgcgg catcgtactc    540
agcctgcctg cgatcttgcg cctgctgttc agtggtcttt accttgctcc agtcgatcat    600
cgcggtaact ccaccgggcc atcggcctcg atcagcaacg gttcagggaa gcgagcggcg    660
ccactggcat cggcagcaag cgggaaccgc aggatcaact ccagccggtc gccacgtcgc    720
actgcggaac cagcgaacca ctccgacccg atagcctcgg ccgcaactc gccgccgtcc    780
gggagcggag tgaagtcgaa cgactggccg ttcacggtga gcacatcgcc ggccctgctc    840
agcgacaggt gctcgtcgct gcctggcagt ggtgcgtacg gtgacaactt gatgatcatc    900
agaaccatct ccctaccaaa gtgaaaatca acgattggt ggccagtgcg tcctgaagga    960
tgaagaacaa tgtcgagccg tttgcatagg caactttcag cccgtttgcc acagaagggt   1020
tgctcacatg cgacgcccaa ctcacgctga caccggtggt ccaattaccc agaaatgcag   1080
ccggcagggg cagtgatata gacgtacctg gctgctgact accgtcgccc aacaacgtga   1140
ctatgcatat ttgcgttcca tcagcgaacc gcacgaactc accgttcgca ttactacccc   1200
gctggatcac tgcgccagtt ggcaccccgc tcgactgcga aaccgagcca aggatgctgt   1260
ctcgcgagta caaagccca gttgaaccca gggcagctct aactgcagca ctcccaagtc   1320
caagggatgt gcgagcgcca gcagcggttg cagcgccagt accacccagg caatcggca   1380
ccgtgtcgcc atcggagaac tcgcggaggc tgccatagcg gtttccgtcg gcctggagtt   1440
tcgtcgggcg tacatcagcc attgaaaagc acctgcaggt tgagagttgc gccgccggcg   1500
gtgtacgccg gcagttggcc gtcagggttc atcgtgagcc gaagcatgga gccgtcggcg   1560
agatagcccg gcacagccgc agggatgcgg acgttcatcg gataggccac caccacaccc   1620
gcgccattgg tgacgaactg gtcgtagccg gtgctgcgcc ggacgaagta gatcgcgttc   1680
ggctccaggg acgcggggag ttgcgccacg accttgtggg tctggaggac ggccattacc   1740
aggccgtccc attccactcg gccgggatcg gctggccgtt gaagcgcacc aggccgccgt   1800
cttcgctgaa cttgtcgagc gtcgacttgt tcgcgtgcgt gtgcgcctga gaaacggcgg   1860
tgtcgatctg cgctggcgtc gacgtcgggc gccgttgat cgcgtcccag ttgagctcga   1920
cgtccatcga ctcatactcg gccaccttca gccaggcgct ggtcgcaggg ttccatgcgt   1980
acaacgcagc gccggattcg actgtcgagt cggcggaagc gtcttgaacc agaacgaata   2040
tcgccgactc cggctccaga gcgtcgcgcg cggcgatatc cgcaacgaac aggatcggcg   2100
cgccggttcc gggtaggctg gacagcgcct cgttgatcag cgcgttgatc atcgcgctgt   2160
taccgatcga gcgcgccact ccggcgctgt tcgtcaggta ggactccgag tagctgccgt   2220
tctcgacgaa gtagaacgaa tcgggttcca gcgtacccgg cagggtcgcc actttgaaaa   2280
```

-continued

```
atcgaatctg ggccatgtca tcaccaatca gtcgcgcccc attgggcacc gtctacgcca    2340
tccctcccgg gaggcccttg gtcacccgca acaaccacaa gcacatcggc cggcggcgtc    2400
acggtgaccg cgtattcctg catctcgctg agcacaagcg gctcgcaatc aacctcgatc    2460
gccagcgccc agggctcggc ggtgtcatcc atcgcaccct cccccacggc tcacagtgat    2520
cggaccgctg tagtagcgat ggaccgttcc atccgggtat gtcacgtcca cgtcgtagac    2580
cgccgccgac cattccagcg ccgcggtagc cgatgccgat atctcgcgcg agatcgttcc    2640
ggcgccagcg atctcaaggc cggagccgag cgccagcgtc atcagcacag tcccgcctgg    2700
cgcgtcgcgg atctgcatcc gtacctcggc gccagccagg tcaacgggtg gctggtagat    2760
caattgcccg cccacaggcg ccagcccaac ggctgaaagc aggttgatct cgacggtgtt    2820
gtcgtcgatg gacgcgaccc ggtggggcaa ttgccgaagt cgagcgcggt tcagttcggg    2880
catgccctgg acaccatcga tccaggccag ccacgtgcca ggcaatccgt gcccagggat    2940
ggtcagccgg acgggagcag ccggcgcgat ctgggtgatc ggccggtaga caaggctcgg    3000
ttgcatgatc cgcatcgtgt cgcggaacgt cgccccttt tcaatgcgca ggggtacaca    3060
ggccggcgtc atgcggcttc tcctttggaa ggaatcaaac gtaggaatag aaggcgttcg    3120
ggtcgttgcg tatagcgtcg ccggtgattg ggttatatgc gcccttactc caagcctcga    3180
actggatgcc tgaatacgca ccaacatcta cgtcaacctg acgggttccg tgtacgccat    3240
gcggggtgaa tgcaactccg gcaagccgat agcgctcatc tggagttccg atagcgctat    3300
ttcgaaccgc tatgatgccc aacatcttgt tggagtatcg ctggactggc catgcgtatt    3360
gggcagcaaa cgacgaaaga tatccgtcgg ccgcgattgg aaacacatgg tagcgagagc    3420
cccaattcaa ccctctcgcg taggtatctc ccacgtctgg cgtatagata ttttgatctt    3480
gcagagttat cggccgggta ccagttgcga ctgtttgccc gctgatgcta tcggttatgt    3540
ttgcggtccc agggccaccg tcattgtata ttggccccga tatttcgact ttatttcgca    3600
gcgtctccaa cacctctcct gacgcagatc gcaatctgta gtcaaccacc caatcgtccg    3660
tttgattgaa tgcaacatga tcgcctgccg cacttgctgc gcgctggaga gaatgagaga    3720
cagataccct gatatgtacg aactcaagat ctcctgaaac tccgtaccaa gcggcagcaa    3780
tcgactctgc ccgcagagtc gccgtccatg cccctgaag cacccttgta tccacaggaa    3840
tgccaggggg atcgcttgtt cccgaaacgt aagagccgct cgcactgtcc caccagaacc    3900
gcgtatgagt atccgggtca acgtccggct tactgctgga caacgttgta aactggacct    3960
gactccacgt agccacgaca accaactcag cttgaaatcc ggacgctccg cttgggctaa    4020
tgcgcacctc caccatgccg ccggcaatca ccgttccgtc aacagtttct tgatagtcga    4080
cgcggaacac tcggcgcgtt ccgtcgtgat ttacatctag acttgaaaa gacatacctg    4140 ctggctggac ggggataccc agcgcagaag gcgcaatggt gttgcttgta atctgcccaa    4200
cgaatcctgt tacaccatcc cgaatagagc agattgcgga ggctgttccg agaaatgaat    4260
tgaacgtaac ctcaacgccg caacggacgg tgtacccacg gatgaatgcc ggctggagtg    4320 ataccctcc gtatgcctcg gctagtccgg ttccgcgcat gatcgctcgg ttgagccagc    4380
gctcgtcagg gtcatcggtt tcgacgttcg ggacaggcat acctacactc cagagcgcag    4440
tatcatttgc tgtcctgacc gccggcatct tcatcgttcg cccgcttggt aacgtcaatg    4500
tcgaatcaac ggcgttgatt ggctgtcgta ttaggccgtg ccatggccac cccatacct    4560 gcggagcttc atcgagcggg ctattgggaa acatcgttcg cgtactccat cacaacttct    4620
gcgcctgacg cgtcggtcat gacgatcttc ttcacgctgc gataccggag ccaggccagg    4680
```

```
ccatcgctgg tgggattgt ctgcagttcg tagtattcgc gctgggcggc atcttcttcg     4740
atcaggggc tcgcaatacc gccaccccca ccgagctgct ttccggcggg gttgtagtcc     4800
gcccgcccgc gctttgcatc cagggcgccg cgcggatcga tcttgcgcag tgcgcgcgcc     4860
tgacgctccg gctcgatcag ccggttgagc gccgccgtca agccctggtc accgcgtcgc     4920
tccgcttcga cccgctggcc gccggcgcgg cggatcgctt cgttccttgc gccgatgccg     4980
cggcgctcat ctgatagagc catgatccac ctccttatgc cggcgctggc acgtcagcga     5040
gcacaagcat ggtcatagtt ccggcgccgg cgtcgtaata cacccgcgcc caggcctcac     5100
cagctaggtc tatgcctcgg atctggaatc catactcgcg ggttgaagcc caattcctct     5160
gcatcccgac gatgaacgtc ccacccggca agtcgacgcc acccgcggtc ccgacaaaaa     5220
acactgaatc tgcgttcccc ttgacgtgca aatcaaattg ccgagaagag ctgtgtcga     5280
tatcgacagc cccgatctcg ttctcaggaa tgttattcag aggcgcctcg acaactgcgt     5340
gctgcggccc aagcgagaaa ctgcccgcgc cagttatgtg cagtacttcg gagggagcgc     5400
ttccaccgcc gccgccctgc ttcacccaat ccgccgcaga ggccgtgccc ttggcaaggt     5460
attggtcacc gtttgtcgtg tttacgtaat gagcgcccac gctgggcggg ccgagggtg     5520
gagcgccagc accggacagg acgtgcgtaa cagttgccat caaatgttct ccatgatcag     5580
gttgtttccg cgccatcga cgagggccga accgctcgca tcgaccaggg ctccgtcggg     5640
agtgccgccc tcaagggccg cgattcgcgc ttgcagtgcc atgagatcgc cggccgtgac     5700
ggctgcatag atcgccgttc ccgccggcca ggtgccatca gttgttcctt cctgtcggcg     5760
ctcaatcgtc agcacaccgc ccgcgcggac ggttgccttc acgatttcat gctgcgcgcc     5820
agcggcatcc gccagcgtca acagaaccca gctaccgccg gagagaggca gtaacgcggc     5880
ggcggcatcc ggaaccgtca ggctagtggc gccaggcgcc aagccggcgc tcagcgtcgt     5940
cttccagttg ttgatccagg ctctcgccat cgctacatct ccagtacgtc atcaggtaca     6000
gatacccggt aggtggccgc gatctccggc gcatgctcgt cccggtaggt ctccggaatg     6060
tcgtttgcgg tcaacgaaaa gcgccgcggg aacaactcgg cgccaggatc gcggttgctc     6120
cagttcccg agaatccgtc cgcatcatcg tcataagggg ggctgccgtt gcggcctcca     6180
agctgcgtcg agagctgtcc cccgcccgac ggtgggctga cgggaccgga cgagccagca     6240
ggaggaacaa gggggtctgc tgcgccaccg ccgcctcgca tcacagcgat agagatcgtg     6300
gtcagcgcgc ttccggatgc gaggtcgagc cggtcgacaa tgcgtcgaca cttgcccacc     6360
gcacgcgcgc cctgatcatc gaggcggagc gtatgtacaa gatcgatcgg caggaccatg     6420
gacgtcggca catcccaggt cacggtcgtg ccgcgatgcg cagcaatgag cgtcgtggcg     6480
ccctgggcca acaagcagtt cagcgcggac aaacgccggc ttccatcctt ctcgtcgtcg     6540
tggccggtgc tgccgccggt gatcgggtcg ctttcccagc gctcggcctt gtccgactcg     6600
atctcgaacg aggcgcgctg ccgaccgaca atcggaccgg tcgccgcaac gctcggctga     6660
acttccatga ccagccggta gcgctctgtg acggactgca cccagcgccg gccagctatc     6720
caatttccgc cgagcagcag ctcggtgaag tcatttctcc atgccgccgg cggattgcag     6780
tagacgcccg tgggcggaag tggataccag gtcgcataga acaacgtctg gccgctgctt     6840
tcggtcgctg aggtgatcat ctcgacatcc ggtagctcgg tgtcgtcgcc gcgccaatta     6900
cagaaccccg cctcgccaac agcgttaccc gtcccggggt gctgccatcc atacgatgcg     6960
ttcaactgcc agagccggct gaatcggtag tcgcactcga tctcgatcct gttcgtctgc     7020
```

```
gaactcaggt cggccaactc gaccgcaagc gacccgtata ccgtagagcc ttggccgaac      7080
tcgaaggcag gagccaccga aagccatgac gtgacgcgga gagcgccgta tggcgaacag      7140
tccaagctcc cggtaacgct ggtcaaacgc tcctgggcgt agtcccaccg cgagcgtcca      7200
tcgaccggct cgaacacatc ggcggaccag gcgccgccga ccaaggcgtc aacggccgca      7260
atctccatgg cctctacacg ctgctgcaac tggtcagtgc aactgacgtc caggacgcgc      7320
cgaacaggat tccaggctgg ctgcgtaacc cttcccgtaa accgccggcc ctgactcagc      7380
tcgccggcgg tctccgttgc gtagtcgatg gttacggttc gaccaatcca gtccgtaggg      7440
acaacagggc cgtcgccgag atagatcgaa aaggaagcga cgccagccgc ccctcttca      7500 cgatcgacct cgatctcccc ggtcaggagc ggtgtaacgt cgtcatcgcc aacacgcacg      7560
attgctcgcc aggtgaaagc gtagcctgga atgatcggct caggaccagg cacaacggat      7620
tgagcggccg agttcagctc agcgctattg agcggtccac cgttgagcat cagatttcct      7680
cagcgacaat ttgccaggtc cggctgttgt tcgaagaatc aagcgcttca ggagggaccg      7740
acgcgaagac gtggaacagc ggccaccact cgacgcggta gagttgcgcg cctgggatct      7800
ccgacacggt taccacctgg ccggcggacg acacgtccgt tctgacccac tcacggccga      7860
ccagcgccag cccccacgga ctggcatcgg ggcgaacctc tccagggatt gtgaatactc      7920
ggtcggcggc agtacggccg gaaatgccaa gcgacgcatt gcatcgcagc tccaacgggt      7980
tgtcgaagtc gagtccaagc atccccgtgc cgatccatcc tgaaccgctg atggtgattg      8040
ccgtcttgcg ccagtgcgtc atctgtactg ccgcacctcc gctgagcctc aatcgctcga      8100
cgccgccatc tacagcctgg tactgacact gcggggcgcc gccgtgtatc acgatcggta      8160
cgcccccaag catcacgttc ggaatgatca ttcccaactc cataaaaaaa gcccgcgcga      8220
ggcgggcttg gtcattttgg gcgcgtccgc ccgaacttcg aagcggcctt gcgtatatct      8280
cggagcgtgt cgtgtgtccc gaaaacggtg aaaccggcat cgtctccacc caggttgagg      8340
gtcagcgatc ccaggttttg catggctgcc ggcggattcg cctgctgaag cgccgcagtc      8400
ggaatctcgg gtatctcggg gagagttcgt tgatacctct gcgacatctg cagcgactgc      8460
accgcgttga agatgcgctc tcctccgcgc atcatcatca actccggccc acgctcccca      8520
acccacgcca taccagggg agcgctctgc gtaccagtgg caaacccggg tatcttgggg      8580
gtgatgctgg gcacgccagg caagcccatc tccggaggcg gaaccagcgt gataggtatc      8640
acgagctgct cagccagtcc ggcggcgatg tcggcgacct gttgcttcaa ggtctccgcg      8700 cttttcgaagt ccattccgaa cgacacctcg acgttttgca cagccttgat gcgctcctcg      8760
aggtcggcca ggttcaggcg gttgacgtca tccgcagcct tggcattacc agcctcgacc      8820
tctgcggcct tgttggcgat gcgctccacc tctttggcca cgccttcgaa gccatagctg      8880
ttcgcgccag cgtccttcag ttgctgaagg atctgcagcg cgcggcgcgc ctcctcgatc      8940 gcctttggt tgttgccggc ggtcagcgcg ttgcgagccg aggcctgggc cgcagtggca      9000
tcaccgaagg tctgcgttcc ggaggtgggc gtcgcctgga tgcccttcac caggtcggca      9060
aactccttgc ggacatctgc ctggcgcgaa agcgcgtcgt tgaggttctt ggtggactgc      9120
tcaagtaggg cctggtccg aacaacctca gactggagat cagcgacgtt ctgatcccga      9180
gcccgcttca gggcatcgtt ctggcgcttc acgatctgct cttgacgcgc cttctcggcg      9240
gcgagggtgg ccgtgaggct gccctcgccc ttttcacca gcgtattcgc cgtgttgatc      9300
cccttggcaa catcgttcaa ctggttcgca acccagtcga cgatgcctgt ttccttcgct      9360
ctgcgccccc aatatttctg ggtttcggaa aagatccggt tcaaccccgc gccgatctcc      9420
```

```
ggcgcaaacg aagccatctc ctcgcggagc ttcggaagtt ccttcctcag cgcgataacg   9480
atctgctccg aggtcaactc accggcggca gccatctcac gaagccggcc aacagtcacc   9540
ccgaaggagt ccgccagagc gccagcaatt cgatccgagg actccagaac ggtattgaac   9600
tcttcgcccc gcaggacgcc actggcaata gcctgggaga actgggtaat gaccgacgcc   9660
gactcctcgg cagaggctcc accgattttc aggccaaggg ataccgcctc tacggtttcg   9720
agggcggcgc gctgatccat gcccgcatcc gaagcgggc gctgcaacct cgaataaagg    9780
ccgatgaggt cgccgacgtc gccctgaaca tcatccgcga tacggtcgag ttcgatctgc   9840
gcagtgttga actcttcctg cgagcgggtc gccaggcgaa gccgggaatc gagccggcca   9900
acagtatcgg cgccgttcgc tagcttcgcc gttgcagcac ctactgcggc tgcgagaccc   9960
gcaaccgcca gcgctggacc gctcccgcgt agagagccga tgctcgacag ccgcgagccg  10020
gcaccaagcg agttgagttc gctcttggtc tccgcgatct gcttttgag cgcccgctgc   10080 gcaacggcaa gttcccttgt ggacagcgtt ccgctcgacc gaagcaagcg atattgctgg  10140
ttcaactgcc cgatagcagc ctgcagttcg cgcaccctgg cgactcccag ggtgctacgc  10200
gcttgctcca gttgaagcg gcgctgctct atcgcgctct gcttgatcgc tgcggcctgt   10260
tgccggaggc tggtggtggc cgcgtcattc cggcccgcct ggaggtttcg atccagctcc  10320
cgctggagcc gctgccgttc ggatgtcagg ctcctcgtat ccagcccggc ctgcttcaac  10380
tcccggcgca tcgctccgag cttggctacc tggacggtct ctgcccgctc caggcttcgc  10440
aggtccgaaa tggagtcccg gtaagcctgc tgcaattcgc gactcggcct gatcgtcgat  10500
gccagctcgt tgccgagcgt acggatctgc tcgcgcgccg aacgcgcctg gcgttgcgtg  10560
tcctcgaggg tgctttcgag agcagtgaaa tcgtttaaac gcttgagagg ttgcgcgacc  10620
tgcctgacca gttcggcata ttccttgcgg aagcctgaca cctcgcgcag cgcatcatcg  10680
aggtcagcgg tcagccggat ctttacgtca gccatttcat tcagccttca gcgcggtcaa  10740
gaacagtgac cagggatatt caaggacgtg gtgatggcca agcctcacca gaacgcaaat  10800
ggcgcgctcc aaactcctta tggcttgtcg tggagtttcg agagacggcc cagcattccg  10860
aaaaaatgcg ggttcacctc tttacatgca tcccgcaact ggcgagttg gctaggccgg   10920 agatcgttaa tttggctctt cgtaaccgac gtcatcaggc acagatcgga aagcctgata  10980
tcttcgaaga ggacattgtt gacgaggtct tgatcgctga cctcttgcat tagctttcga  11040
acatccgcaa cgctaagttc ccgcacggtc aactcaacgc catcaatatc tacaactcta  11100
cttgcagtaa agctggacat ttcaaccctc cagaaagcac aaaccccgcc gaatggcggg  11160
gctgtttaaa aagcgttata tcggctagtt cttgtggccc gattggtatg aaccctggac  11220
gcatccgtta cgatcaaacg aaacggtcgt ctggtcaaca tacttgtcat tccagtaggt  11280
gacagcaccc gcgccggcgg tactgccgtt gcggttcacc ttcccgtaga tgctttccac  11340
gtcctccctg gacattccag gaacgacctt gccctgacc ttggccttgc gaaggtcacg   11400
ctcagagagt cctgtggaac acgtagggct tggcgacgaa ccaccgacga cgatcactcc  11460
gctgccgacc tggtgactac ctctataggt acgacctgat ggctgcttgg gcttggccat  11520
gacagccgag gcacctgacc cgcttgggcg ctggttggtg gcagaaacca catcgttcag  11580
cgattggttg tcagggcaat tctgctgggt aaaagtgact tttccgtcag ggccgacgca  11640
cttaaagacc gtcgcccac tggcagaact gaccgcaaga atcaaggcga gaacgggaaa   11700
aatccgtgtc ataagcgact ctccattgga accgcttcac actttagcat caacaggcca  11760
```

-continued

| | | | | | |
|---|---|---|---|---|---|
| ttaccaagaa | cacaagccgg | cgatcaggtt | ggtttcttgg | cgcacttagg | gtctttagga | 11820 |
| tctttctcag | tgcagttcca | gccagacggc | ttgaacgtca | cccgccaagc | agccttgtcc | 11880 |
| agctcttcac | caccgaagaa | accagagtcg | taatactccc | ccgccggggc | aggcaccgcg | 11940 |
| ggtgcgctcc | cattggatac | gaatcgcaca | cacccagact | ccatagagcc | tttccacgct | 12000 |
| ccaactggat | ggatgttttt | atacttattt | tccttaagca | aaacagtctt | accagaatca | 12060 |
| gtgcggacga | tatatccgtc | agtccaccct | ccactttctg | cacagacttc | gacagttgtc | 12120 |
| tttttttgaca | gcgcatagga | cctggcaaat | tccaggtgct | ggagaaaaac | ttctttgccg | 12180 |
| gctagatggt | tgttcccctc | ctgcatagcc | ttaaagctcg | gaacggccat | gaatgccaaa | 12240 |
| acggccaaga | gtacgaccac | aaccatcaac | tcgataaggg | aaaatccgcg | cgacctagag | 12300 |
| tacatttcaa | cccctcccta | aatgccgcca | ctgtagcacc | acgcgggcga | accaacatcc | 12360 |
| ggcgtccctg | ccgggcatga | acggcgtcac | accgtcgcca | gttccttctt | gatgttgaag | 12420 |
| tacttcgact | ttccagcgcc | gaccttggtc | gggtccatca | gaaccttggc | agtggcctcg | 12480 |
| gcagcgagga | agtcttcggt | attgagccag | tcctgttggc | tcgacgggtt | caggcggcac | 12540 |
| cggaaatagc | gcgcctggat | acggcgctgg | gtaccggctg | cgttctcacc | ctcgaagagg | 12600 |
| cattcgaacg | tcttgccgct | gttggtcagc | gcttcgatca | catcaacggt | ggcggacttg | 12660 |
| taagtcacct | tgatcggcgt | ggccgcagag | atcgcacccc | cttcaacgat | ttcgataccg | 12720 |
| gcgccggtca | tgttccagtc | gtcgaactct | tcgtaggtcg | tggtgccgtc | atcactcttc | 12780 |
| acgctggtga | tctccagcgg | catgaagtcg | agcgcgatcg | tgcctcctgg | aacggcggtg | 12840 |
| tgcgcttcgt | cggtgtgggt | ggcagaagga | acgttggtgg | cgtcaccccca | caccaaggca | 12900 |
| gccaggatgc | tggtcttgag | ctcgcggaag | ttgatcgaca | aaccgaccga | agtgatgcgc | 12960 |
| gaaacggcat | cgtactcacc | gccctgcggg | gtggtggtat | ccggcagagt | gatctcgttg | 13020 |
| gtctcgatgg | tctgttggat | agtggacacc | aggccagcga | actggaaggg | ggtggtagcg | 13080 |
| ccggactcgc | ggatcttgaa | gggtccgccg | atcacgtacg | tctctttctc | gatagccata | 13140 |
| tcaggcctcc | ttcttgatca | cgccttcgcg | gcgcaggaat | tcaacctggt | cagggctgac | 13200 |
| gttgatcttt | tcgccggccg | ccttctcctt | gccctggtgc | caatgcacct | tggccagggt | 13260 |
| gacctcgacg | gccttgttca | gcgcagccgg | cggcgcggcg | tcgaccgcgg | ccggcacctg | 13320 |
| gggatcgctc | ttcatgggtt | acgcctcgat | gatggttttc | agatacacag | ggattcgaat | 13380 |
| cacggcagcg | gccactccat | cgcccggcgg | gtacggctca | ggcgccccca | acgtcacccc | 13440 |
| ggtaatgccg | cgctctcggg | gcagccagcc | caggaactga | cccttggggg | caggcatcag | 13500 |
| acacgccaga | aggtctagct | gtaggtcctc | cagagcctcc | tcatagtggt | catacccacc | 13560 |
| ttgcaccgca | cctaccacgt | cgaagccacg | atggaagcga | acggcggcat | caagatgctc | 13620 |
| cggcggctgc | tccttgcccg | gctggacgac | aatcagcgga | aagccctcat | gccgctcctt | 13680 |
| gaccagctcg | ttaaaccacc | cagagagcac | gcgagtgccc | gcgtccgtcc | ggtatccctg | 13740 |
| gtttggcgtg | atggtttgca | ggcgcgccag | caaggccaag | cggccgatcg | tgagcacgtt | 13800 |
| cggcttcatg | cttcctcctc | gatcgttgct | gccgtcagca | accaaccgtc | gttcgcaatg | 13860 |
| agcttttcga | cgagatagcg | cgacgacccg | ataacgaaga | ggtcgccacg | cgatgccgtg | 13920 |
| ggaacatctt | tcgccagcca | actgatccca | accttgtccg | tgatgaaaac | cccatcaggc | 13980 |
| ccgtcgtaac | tgaggtttcg | atcgacctgc | agaggtatcc | ccttgatcgg | ggggcgaccg | 14040 |
| atgccgcgga | actcgcccac | ggcatcgat | aaccgctctt | gccacgctc | gtggagccgt | 14100 |
| tggatcagcc | ggccaaaacg | gcccggcgcg | ctcattgttg | gatcagcatc | gccgacgcga | 14160 |

```
agccgtcaac ggtgggctcg gtgatcttgc cgaacgccac cgagtcggca gtggcagcag    14220
caaccagctc cccatcgagc acgctgcact tggcaccctg ggtcaggcct gcggcagcag    14280
gcaggctcca gacgccgcca gttttccgg cgaacggctc gcccgcggcg gcatctacca    14340
gcggcaccac caccaggtct ccgatcaccg caggtacgcc ggactgaacg ccgccagcgg    14400
gcgcaatgag agtcaggacg ttgccgtcct ccacatagtt cttcgccatg gttgattctc    14460
ctaatggcag aaacagaaag ccccgctagg tgcggggctc gggagttggc gccgatcagg    14520
caccgttgga tttctgcagc ccgcggaagt ccagcggcgc cacgccagcg tcgatgcgca    14580
ccttgctggc cacgccgtcg acagtgaagc cttcctgttg ctccaggtac ggggtatcga    14640
cgccgtccag gtaggccact tcgatggtgt cagagccttt cttggcagcc atgtaccagg    14700
cggtcgccga ggcatcgtcc aggcgcggct cgccgatcac ctgcgcgaat gcgcgaatcg    14760
ggttaacgat gccgctattg acgtcggcgc ccggcacgga ctcggagttg atgatctggt    14820
tggccttgtc ctcgagtgcc accggagtca gaacgaagcc cggacggatg ttgagggtgc    14880
gccccttgcc cttctctacc tgggctttct gggtggccat ctgggtcttg gccttgctca    14940
ggctgtcgat ggaaagcgcc gaagccgcgc cagtgagcag gttgctgtgg tcggcatgga    15000
acagggcctt gccatcgctc atcgccgggt taccggtcag aaccgcatag accaggtcgc    15060
cgatggtggc cttggccgcc tggcccagct tgaacgggat atccgagagc atctgcaggt    15120
cgtcgttgat gatcgcctga cgggtgatgc tgaacagctc tccgtaggta gccaggatga    15180
tctgctcgcc gcgctcgcca agggtgacgt acttgtactc ggcgccctca cgcacctgac    15240
gcagcgagga aaactcgccc agaccgacgc ggcgcgccgg cttgaagtca gtgagaatgc    15300
cgggcttggt ccacagcggg aaggtttctt cggcctcttc ccagcccgcc agcaccgact    15360
tgttggcgac gtccagaagg atcaggccga agtcgctgga agtgtgggtg aaggccaagc    15420
cgaccatttg cggggcgttg agcgaggcca cgccgatccc gcgatcgacc agcgaggcac    15480
gggccagttc gcggagcgtc atgccgttgt aggcgttatc ggcctggcgc tcgccgcgac    15540
cgatgcgggc cagcacgctc gcgcgcaccg agtcgcccac caggttgccg ttgccggcat    15600
ggatgtgggc gccagcgcca ggggtggcgg ccggcttggt atcggcgcca atggcagcca    15660
gcagcttctc gcgtgcctgg tcgacggtga tggtcatgtc gttcaggcag gtggcgagca    15720
gttcggcgtg cccgctggca aacgcgccga aggcagcagt gattgcgctg cggcgaccag    15780
attcctcggc gaggatgcgg gcgcgaatat cggcctcggt tggggcggcg gccacgggag    15840
ccgccggcac ggccggtgcc ggagtcggcg cgggagtgtt ggtcggcgcg gcggggtct    15900 gggcgcgcgg ggccagtaga gttttcagag cttcgggcat gtgggcgaac tcctgcatgc    15960
gtttggagga aaggtgagcg gccgcttgca gcggctcagt gagctggtcg gcgaaaccgg    16020
cagcgacggc ctctcggcca ttcatccagg tctcctcctt gaggagcgcc ttgatgtcgt    16080
cggcggactt cccggtcttg ttggcgtagg ccatgaccag ggtgtcctcg accttgtcga    16140
gcagttcggc atagcggcgc atgtcgtccg catctccgcc ctggatgccc cagggcttat    16200
gcaccatcat catggcgttc tcgggcatgt agatggtgtc tccggccatg gcgatgaccg    16260
aggccatcga ggccgccaag ccatcgatgt acacgtcgac gctggccggg tggttgcgca    16320
gcaggttata gatcgccgtc ccctcgaaga cgtcgccgcc cggggagtgg atgtgcaggt    16380
tgatcttgtt caggtcgccc attgccttga ggtctcgagc gaactgcagc gcggtgatgc    16440
cccagacgcc gatctcgtcg tacaacagca cctcggcgac gccgcgaccg gcagccttga    16500
```

```
tgctgtacca ggactcatgc ggggcgttgg cctcagtcaa cgccgccgcc atcggcagca   16560
tcaggctttt atggatcagg gtttgatggc tgcccatcgg cgcctccatt gttgctctcg   16620
ttggggaaat ccggcccagg cacgggtagg ccggcgccgt atctgttgac gagctcgcga   16680
gcctcgtcgg cggtaagcat cttcccgacg cccagataca ctttctgcac cgcctcaacc   16740
gggtccatcc cggacttgac cagttggtgg taggcatccg aactgaagac caggccggct   16800
gcccggttcg ccttgatctc cgtctcacgc gacttcttca gctcgcgcgg atctcgacca   16860
cgagcgcggg caacttccgc ctcatcggcg aagccggcct tgaccagcaa ctcccatgcg   16920
ttggcctcat gcatcgggtt aatccatggc atgaccggcc cctggtagac cgccgcgtag   16980
agagtgcggt gatcaacgtc ggcgggcagg cgctccttcc gagccaacag gtacatctgc   17040
agccaggacc gatagacagg ccggcaccag tagtcgatga actcgtgctg caacaggtcg   17100
tagcccagcc agccctcgac cagttcctgg cgctgtgccg agtaggtgcc gtcgtaggcc   17160
ctggacaccg aggagtaggt gctgcgagtg ccagcgccga tcatccgcag ctggccgttg   17220
cggaaacctt caaggaaggg gttcggccgg ttgctctcga tcatcccgac gtcttcacct   17280
ggctcgaggt cgtcgaagac catgccgggg gcgatgggga tcgttcggtt cttccggtcc   17340
ttcccgggct ccaccgtgta gctgtcgggg ttgcccttct tgatatacat cgccagggca   17400
gcactgatgc gcgccgccac ccgctcgctc tcctcgtagt ccttcaagtc ggcaaggcgg   17460
atcagcactg cgtgcaacat cggcacgcct cggttctggc cgatccgctt gcggtaggcg   17520
atgtggatga tccgttccgc ttcgacgcgc ttcaccgcca ggctgccgcc cagcgtctgc   17580
aggttgccgg ggtgatcctt gagcaggtga taggccctt tccggcgcca ggtgtcacgc   17640
tcgatacgct ggacaatgcc tttcgacagg ttgttgtagc tgaagggcaa gtagtcgggc   17700
tccagcagct ccagggcaaa aggcaccgac gtggcaaacg tgtagttcgg gactcgtccc   17760
atcagcttct gcgccaatcc ctcgccatcg cgcagccagg ttcggcacat cagacgctct   17820
acctggggcc tcgtcagctc accagaggtc tccggcgaga gtgaccactc ggcccacgcg   17880
ctgcggatct ccatggccaa ctcagcatgc accgagccat ccaggcgcag cggcagcggt   17940
tccacgccga taccactgcc gcccaccacc ctctcctcga ggcgatcgag caggccggta   18000
accagatcgt gatcttcgtc cagtttccgg cactgctctc gcatagagac cgcagacttc   18060
tgtagcgagg tgtcggcgcc cagcggctga cgcttggcct tgtgggttcg ccctggcctg   18120
gcagcctcat acgcctggat tgcctcgcga gcggccaagc gccgagccac cagctcgggg   18180
gccaagggtt ccagtagtcg atcgatcagg ttcatcagca gaactccgcc agtgccgggc   18240
caggacggcg accggcggcg cggtcccgct ctgcggctgc gcggcgctcc cactcctggc   18300
gtccggcgcg gatcttctcg atatcctcca tggtgtgggt gcgtccgttg aagatcactg   18360
tccgcccttc cagcacggcg gcctcggcct ccaggtattt gtcgagcatc tgctgcgctg   18420
tcagagccat ggtccgcttc cagtgttgag ccagccctgg gaggtgctgg catggttatc   18480
gttcgaaggt tgctgttggg cgaccggctc cggcacggga tcaacgcgca cgcgctccag   18540
ctggtcgagg tcgaggccga agcgttgctg gctgatgcgc agcgcggcaa gggcgtaaac   18600
gaagcaatcc aacgcctcgt ttcgccgccc gccggaatcc cagcgcagga cgcgaacacc   18660
cttcgccatc accggcttct tcttctcggc ggtgatctgc ttcagttcgt cttcgtcgca   18720
gatgtcgctg tcgatcggga agtgcacaca gccggcgtc ggttgccacg ggatgggcac   18780
atcaatgcgc aggcggctgt agatcagctc cttcgcgtta tcggtgccca gttcggtctt   18840
gtagaccttg cgcttgcggc gcttcgggaa gttggcgatt ggcttgccgt atgtgctggc   18900
```

```
cccgaaagtc ggaaccaccc agtgcacgcc atgcttgatg ctctcggcct ctacctcatc    18960
ggaatagtgg ccgccagcat cccagcacca acgctcgaca cgcattggaa cgccatcagc    19020
ccgagtgaac tgccgatgaa tttccaagcc caccttgcgc cgcagttcct cgctggccgg    19080
atcgccggtc agaatgaaac ggtgaacaag ccatgcctcc tcgcccaggc cgaaagccca    19140
aacgcggccc tcgtagcggt cgtcctgggt gtcgattccg cccatcagga caagcgcttg    19200
cggcggcacc ttcgggtagt tctcgcgcg ggcatagagt gtctgccact ccacccgctc    19260
cccctcgtcc tcaacccata cctcgccgag gatggtgttg gtgaaggtct tcagcttctc    19320
gcgatcaccc ttgaccttca gccattcgtc gatcaggtca agccagctgg tccacgtgct    19380
gtacacggcc cagcagtaga atgcgacgga acgcggcgtc cttatcggct ggtcatccgg    19440
gccgaaccac tccatagcgt cccgcgtcca gaccccgac acttcgcact tccagcggcc    19500
tcgctcggag gcaaccacca tttcgtggtg ctcaaacgtc ccgctgcacc gctcgttctc    19560
gcaggcgtac caaactgaag aggcctcgcc tagatcgttc gcgatgtact tcaccccaaa    19620
ggcgcaatct ttaccgcccc acttcagcgt ctgctcatgc ccacaatgcg ggcacgggat    19680
gtagtaccgc aggcgacgcg gagactcatc ggccgccttc gtgatctggc attggccctc    19740
ggtaccaggc gtcgatccac ggatggactt cgggtaaaca gcaccgcgca gacgttggtc    19800
gccaaggaac gttggggaac cttcaccttc aatatcggcg tcgaacttcg acagctcgtc    19860
atagatcacc tcgtcggcag atctctcacg gtagttgcga gcagccttgc cgccgagcgt    19920
ccaaagggtc cgccggtttg caaacacctt ggtgtcgagc gtgttgtcgc tatgcttgcg    19980
gccataccat ggggccagcg ccagcagcac cggaacatcg cgaatcaggc cattaacgtg    20040
gctcttgctg atccctcgg cgtctgggtc agtcgggctc cacatcagca cattacggcg    20100
cttgtgctga atcttgtagc cgatgttggc catcagcatt ttcgtgtagc cgatgcgtgc    20160
cgacttcacg aagtttacga cccgaatcag gtcgttaccc atggcgttca ggatggcgac    20220
ctgaaatggc gccgtcttcc acttgccctc gttgtacgag gattccgccg acatgtagaa    20280
accgtcgtcg ggatcttccg cccactccac cgccgtcatc ggcggcgact tgtacagccc    20340
ctgcaaacct agatcgaccg cttccgtag gtcattcatc cagggtggca gagtactcat    20400
caaggatttc cggtaggtct tcagcaaact ccacggccag atttcgggcc agcgctatct    20460
cgcgctcaaa ggcctccagc accaacgcg gtgtatcggg tatttggctg cggaccgtct    20520
tgcagaccgt ctccagtttc gagccgatct tggacgcgat cctggcaaga gcgaaggtgg    20580
cgaacggagt tggaacaagg gtcttcgctt ggacctggtt cttctgctcc tgggcgtcag    20640
cctgagcagt cgtcagtcgc aggcgctcct gtagcaattt cttttcagcg agcgggtcga    20700
gaccttccgc atctaggccc tcaggttgtt gtttctgggt cacatgatcg aggcgattct    20760
gtagcaccgc ctgggcggta tagaacacct cgcggccgat cttggcggca ggctcaacgc    20820
cccatttatc aaaggcttgc ggagaaatcc cgaggctcgc ggccatctcg gacttgttca    20880
gccatccgcg cttttttttgg aggtcttctg tgctcatgac aaaacaacaa ccaacctccg    20940
aaaaaaggtc atacatattt ggcgcgcggg gctcgaatta ccctctgacg ggggcacccc    21000
ggggaggacc cgcgacgcac cactttggtg catcagtcag cgcctcgcag cgaaccgagc    21060
agcaacgccg cgcatcgcca cctcgaactc gcgtggcagg ttctcgtcgg cgtactgctg    21120
cgcgatctcg aagaagctca gccggcgcg gtacgaaggg cgagacacga aggccatgat    21180
gaccgagaca gcatcccggc ctcggcctgt gcgctcagca atgcctatgg gctggccctt    21240
```

```
acgggtcatg acgaagtagc ggcgagcatt acccttcgct cggctccgtc tgctatcggt    21300
agcgttcgcg ttgtacccgg cctggctgaa gccgcggatg ccgctcaatg ccctggtgac    21360
ctggccgcgc ctgatgttcc cgtagcgatc caggtccgcg ccggcgccgg gcaccacgta    21420
cttgccttcg ggcagtatcc ccttggccct aagctgaagc tcggccggct tattccgacg    21480
cgggccaccg tagacctcgg gggcaatcca caccgatgca ggctgcgcac cgtccgcttc    21540
gtccttgaac caaacacgcg cttccagccg gtctttcctg gccggcacca tgcggaggct    21600
gttcagggtg tacggggtcg ggcggtcgaa tacgacacgc atctcatcgc gcaagcgatc    21660
catcagccct tgcgcggtcc gcgtaagggc cgtggctgtc gcgtaaggaa tctgccgctg    21720
ctcaagctca gtcaggtcgg cgagctgctg ctggaaccct tccggcttga tgctgatcat    21780
cttctgcaat acctcggaag gcctgcgatg tgcttacgca gcgcctcaat catcagttcg    21840
cgtcgctcga ctccggctcg gagatcagaa acaacttgtc catcagcggc agcaaggacg    21900
gctcttcctg catcagcgct gccggaggct ccgggagcct ggtgcactcc atctgcgggg    21960
cagcgggctt tgacgtacac gacgcgagca ccagtgccga tagcatcgcg gcgcaattgg    22020
ttttcttcat gggaggcctg cagtgctgct tggtaggttc gagccagggc atcggtctgg    22080
acctgcgcct ggatgtcgcg ctgggcctgc tgggccatcg cggtgatcgt ctcggcggat    22140
tgctcgacag cggcctggag gtcgtcacgc tgagcggtca catggtccag acgccagagc    22200
accagcgcgg cgaccagggt gaccaccaac catggccgcc aggtcactgg tcgatcctcc    22260
gaccaacctt gaacatgaac gtcggctctt gattgagcat cgagttgacg atgccttcga    22320
tgaccgagag cagggagacg accatctcaa gcggcgccca cttggcgaac gccagcgggc    22380
aatcgctatc gacatccccc agccacatcg gaatgccgta atagctgcca tggtgcgaga    22440
cgccgagctg tcgagcttcg tctttcgtcg tgaacccgag catcattccc ccttgagcgc    22500
agcacgcgcc cattcgaggc gagccgcacg gtcgtctgcg ccgttgtagc cactgttgat    22560
cttgagggtg atccgctcga agcgaccctg atcggccagt tcgtttaaac ccctcgactt    22620
ccaccaccat gccgacgcga tggcagccca ggtccgttgc tcaagcaact ccggttgcgc    22680
caccagtggc agcgccaggg cgcggcggc ttcggcgtag ttgtcgtggc cggtgatcat    22740
gatcaggccg cgaccacggt atcgataccc atcgcccgta tctggcgacc cattgcccat    22800
cctgttggca tagacgcggt tcgcgatgcg ctctggctgg cgtgcgtact gcttcgcctc    22860
taccggcgtg aaccgcttcg gccaggtctt gagcagcccc tcggcggagt agttcaggtt    22920
ctcgaccagg cgcttgaggc tctggctttc gtgcccgacc tgagccagga acatcgccac    22980
gcgctcgggc gtgttgatct cgaaccgagc catggcgccg ttgatgtgtt cgacccaagt    23040
cgaggcagta gcagcaccgc agccggtagc gcggtcgagc tgatcggcag tgatcttcat    23100
tcgccagacc ctcgacgcgg cagcttgatc ccagcgtaac ggtcggccag gtcgcggatc    23160
ttctcgacgc ccaggaagcc gatccagcca ccaatgaagg tggccatgct ctgcggcacg    23220
ccaaagaact cgaagccgct gatgatcgtc agcgccagcc caccacacag cgcgccctcc    23280
aagagggcct gccggcgagt gccgccgccg tagatgatcc tggccatagc catggcccac    23340
gacagcaggg aggcgtagat gatcggcgca tgctggctca gccaggcgaa cagagccgcc    23400
caagtgtcgg gtttgtcagg catcttcatc gtctcagttc ccctcgccgg ggcggaaatg    23460
aaaaagccca gcgcgagggc tgggccggga atgggtgcag gtacggcctt tcaagggggc    23520
cgcgcgcccc gcagcgcaat gcgccaccctg cagaaacgga aaagcccagc tcgaaggctg    23580 ggctctttc tatggcgatc cgctctgcgg cagttcgcct aagcggcaaa accgcaatgt    23640
```

```
atgacgaaag gtacagggcg cgattatcac tgtcaatacg tccagcctgt acattttttc   23700
aggcagcctt tttatcctcc atcacgaagc acgccagcag agccgacagg cctgctcgaa   23760
ccagcatgcg tgcgtccgcg tagctgatcc ccatccggtc ctggatatct cggtacgaca   23820
tgccatggat gaagtagagg atcaggctgc ggatggcatc cgggtcttcg tcgtagaggc   23880
gtgcgagaaa ccggtctact tgcaacgccc gatcatcact gatgcagggg atcacagcag   23940
caaaccgttt ttcgttcgcc gggttccgtt tcatcagcgc cagcatgggc gaagagccgc   24000
gaggcgtccc attgtcggac caaacccaaa gcccgtattg ctccatcaga aattccaacg   24060
ccttgatgtt catttcagtc gcctctgaag tgggagccgc cggcgcccct ctggttgttc   24120
tcttctcgcg ccagcctgct cgcctggcgt cgctgttctt caagcaaccg cttaacccac   24180
atccgcagtt gcacaaccgc atcccgctgc tccagcgcca gcccgtcgcc ccgtcgacg   24240 aagccagcgg cgccgcacgc gtcgcaatca atgtcgtaga cactccccg gtgctgaccg   24300 tggccattgc atgcggggca cggaaccagg tgacgcgggt tgttcgtaag atccggacca   24360
tgcttcttca tgcggcagcc ctcttcgcgt ccctggcctt ggttcgatac agggccttga   24420
ttgccttgat ctcttccaca gtccacttcc ttgcatcgtg cggaccctcc aggcgcgcta   24480
cagccgcagc gccgatcttc gccaccaggt tgatccggta gttcacgacg tctcccgact   24540
tgtggttgtt gcatggggcg cattgcttgt ggacgttgtc ctcgtcgaac ctcaactcgg   24600
gatgggagcc gacggagcgg taatgcccgg cgtgatactg cccgtcatga aagcgcccac   24660
aactaatgca ggggcggtcc cagtcgcgcc agcggatgaa ctcgttgaat gcggcctgag   24720
cctctctcaa gtggtctgca cggctcttca acttctcttt ccgaaccttg acctcgcggc   24780
gctcgcgctg ctggatcgat ttgcgctcct tctcctgctt ctgccgagcg atgacaattc   24840
cgcactctgg gctgcaccac gtctgaaacg acttcaccgg gacgaagggc gcgcggcacg   24900
tcgacactgc gcacttcttc ggccggggct tccgtgcgga caacgtcatg ccacctcccg   24960
cggataggtg atctggtgat ggcgctcgca aacaccgcac gcctccttcg cagtcgcaac   25020
cggggtgcaa atgaactcac cctgtacgct ggcccggtag tgagcctcgc cggcgaccag   25080
gagcttgcag accttgtagg gcggctgggt gtcgctaacc atcagatagt cgttgagtac   25140
actccacttc atgagcgatc tcctcctttg agttgttttc gaagctgcgc aagggcagca   25200 attcaacgg attgggttcg cgcttttctgg tgggtgacct ctccctccgg agccttcccg   25260
agcgcctcgc cgcgcgccag cttcttgatg atctgtcggt acgagatctc cagcgccgcc   25320
agcccatcct ttcttgccag agcctgcagc cggctgaatc cagcgccagc ggctgcccaa   25380
tacaccgcag ggcaactcca tttcgcggct ccgaccatgg ctgggtgggt attggccagc   25440
gcctcgcgat atgcgtcatc gagggatggc aggccgaaga cctcaggagc ccagcaccag   25500
gcgcagaact ggccggcaga cggaacaagc ggcctggcct gcgcgctcaa cgctcttacc   25560
ccggcctgca gttgctcgcg gcgcgcaacc tgttgccgga cgatctctgc cagccactcc   25620
gccttcgcgg cgttctcgac ctcatcgctg ggccaggagc ttcgccatcc agggcagatc   25680
gccttgatcc gcaagaacaa ccggtcgacc tcgcctctcg tctggggatc gaccttcacc   25740
gccggctggg acaaggggcg cagccccgcg ccctgattca catgcgccag cacagcaccg   25800
accgattgcg gttcgaactg cctgcgggtc atagctgcac ctggtcagtc caatcggtcg   25860
acggcgcgga accggctgtc gcccacttcg tccggtaagc gccagccttg gccagtagca   25920
acccgaactc atggcaactg tcgaccagga acttgtcatc cagcccgacg aagaacgccg   25980
```

```
ccaccgcagg cgcctcggcg ccgagggcgg ccaccagttg cttcacctgg gaattgacct    26040
ttgcgttccg cactggctga acactccagc gcgcctcgta ggcagcccgg tacgctgccc    26100
acacactccg gcaagcctcc tgcagcgctt cgccagccgc cggcccggaa cgggtcggca    26160
aaggtgacgg ttcccctgat ggttcccttg taggttctat tacggttctg ggtgcagcat    26220
ctgcggggt gcatttcctg cgggggtgaa ccttctgcgg gggtgcaaat gctgcggggg    26280
ttacggtgaa catcgtcgag cgccctggc gcgcttcaat gctcagcgcc ttgcactcgt    26340
tcagcacctt gatggcctgc tgcacggcac gttcggacag gcaggtgcgc tcggcgatct    26400
tcgccaccga aggccagcac acgccctcgt cgttcgcgtt atccgccagg ctgatcagca    26460
cagccttctg cgccggcgtc aggccctgga gtggccagca ggccgacatg atgatcgtgc    26520
tcactgactc acctccggcg acacattttc ttgattcgtg atttcgtgtc gcgacacgct    26580
accgaggatc acagcttgcc ctcctcgatc ttccgcgcca gcaccgacag ccccttggca    26640
gtgatgcgta cctggctcgc cgcacgctcg tcgccctgat cgtcacgacc gagaaccgtc    26700
accttgtgca tgatccagcc gtcctggatt cgtggctgat agccgatcca gcgagcagag    26760
ccgctccggc ggtagatcca tcggttctgc tggagccagt cgaagagccg ggcggggttg    26820
atcttgaggt gcttcgctgc gtcggttatg cacatcgtgc cggccgcacc gctgagccgc    26880
tccagggcct ggaccttagg cgcctgctcg ctgatgacca actgcagcgc ctgattcttc    26940
tcgacctgat cagcagccag cctcagtgca tccgccagat tcgtagggac ggcgggcaca    27000
ccatgcgcta gctgagactc caactcctgc cagcggtcca ccaggcgcgc agtgaattcc    27060
gggctgagct gggcaacaac aacgaagctg tcgcgcttgt cgacgaggta aacgctcacg    27120
gccgcgccc cagcgccagc gtgggaggtt tcctccgatg gagtaaacct gatgaccccc    27180
ttctcgccga ggcgctcgat ggtcctcttc acgttgtcgt gtcgggactc gaccagcgcc    27240
gcaatctcgc ggctgctcat cgccaggacc gggccttgtt ggatgactgc aacttgtgac    27300
atattcgtct ccgttggatg ttcggcaccg cctactggtg cctcctcaga aagcccggtt    27360
gcccccgggc ttttgctgt ctgctctact ggatgcctga acaggggtca tcgggaactg    27420
accagcgcca gcacaagcca gtagcattcg aatctctgtt aagcggcctg gacgccagtc    27480
cgcgtcgaag ccctgagatc ggcgggagat agatcgaaac ccttccctct tgctaacccg    27540
cagatccgct ccgcgtagtc cgtttcgccg gtgtagtcag tccgcggaag acggccgctt    27600
gccagccact tgtaaacggc tcgaggactt acctcgcagc tcgcagccac ctgacttacg    27660
ccgccggctt tctcgacggc ttgcttgagt tcgcgcatgc ggcctccggc caatatgaac    27720
attaggtaca tattaggcag gaactgaaag tacatgcaag gacgtgagaa agtgaacgaa    27780
tggttcaaga catgcagaca atccgcgcag cgttcatcgc ccgcctgaag gaggccgcat    27840
ctgatgcagg ctttcaggag tggggcctcg gcgctcgact ggcaaaaatc acaaagcgca    27900
caccgaaagc tgtcagcaag tggatgaact tggagagcat gcccgagcgc gatgccatgc    27960
tgtcgatcgc cgatgcgttc ggcgtgcgcg ttgactggct tgagcatgga cagggcgaaa    28020
agaacagccg gtacatgacg tccaatcgga cagaagacgc ggtgcgcaac ctggttgcgg    28080
agcgggctgg cgattatggc aacgtgcaac ccaccgctca gccctcaagg aagaagaagg    28140
ggtatccatt gatcagttgg gtagctgctg gcgcatgggc ggaaagccat gacaacttcc    28200
aacccggcga tgctgaggag tggattgagt ccgaagcgaa ggccggcgag aacggctact    28260
ggcttgaagt ccatggcgac tcgatgctgc cctcattccc cgaagggact aggattctcg    28320
tccagccaga gggttttgat ttggtaagtg ggaagttcta tgtcgccctc ctgtatgagc    28380
```

```
cggggaaaca gcgcgagact accttcaagc aatacgtgcg ggacgcaggg cgcgagtacc    28440
tgatgcctct gaacaaggac tacaagcccc tgcaggttac cgagaacgtt cgagtaatcg    28500
ggcgagtcat tgacctgaag cctccaaaat ccctcctctg atcccctccc ccaagcccgc    28560
ctagcgcggg cttttcttg cctatcgaaa aaatatgtac ttttggttct tgacctaata    28620
tgaaccaatg gtacatattt aattcacggc agcgatgccg aggccgccga gccgaccgct    28680
ctttaacaac caggcatgag ccaacaggcg ccagtaacgc ttctgcaatc gggcatcgtt    28740
tgcggaggta ggcaagtgag acctgttgga cggtacgaaa tgcgcaatgc gctcaccacc    28800
gactaccggc gtgagggttt gcgagaaaca ccgatttccc agatgcccctt cgcaagaggg    28860 gcatcgagga agtcaacacg ccctggaggg catgcgatga atgaaaaggc ctcactagcg    28920
ttacgccagt ctcttcgaat cactcgcagg agaacgacg tacaccgagc gcgcatcgag    28980
tactacgaaa cggtcggaat gctgcgcgga ttgcactacg gcggagcgat cgactcctgg    29040
cagctattag ctctaaccga gctagcagga agcgcataca tcaacgccgg taaaccctgg    29100
taaggagact gaaatggctc aattcaatgt cgatgcgcac ctgagcaacg gcaagcgcct    29160
ggactggatt gccctgccgg aaggcaacga gacaccggat gacgtgctga tcaaggtacg    29220
ccaggccgcc atgaagaagt tcggcgacct catctggttc aaccgatggg accacgttgt    29280
tgccagcaac ggctacatca ccgtgcggat gcacgcgtga ggtaccagtt cttcaagccg    29340
atgcggggct gccgcatctt cgccagtgag cagcacatga ccaagccagc cggcgagctg    29400
atcggttggt gcgagaaagt cgacgggaat atctgcattt tcaaaccgcc atgttcgcat    29460
gagcttgacc gattcatctg gaggcacaag gacggtttaa accttggta tctctactca    29520 gcataaaccc atgaataaac gatttctcag atgcccttcg caagagggggc atcgaggaag    29580 tcaacgagca agccaaggaa accgtggcga cataacggaa ccagtcagag cgctacccaa    29640
ggttttgctc ctgtaaggct ggggcttttcc ggaccggcgt tgtgggtgcc ccaagtgggg    29700
ataagcctgt gtcgtacgac gaggaaagtg cgtgatctga ccgacttgcc gccgtaagcg    29760
gcatccgatt tctcagatgc gcttgggtac aggcgcatcg aggaagtcaa cgaatccggt    29820
caagagggca agacatgaac gcatacaagg caggtgacaa agcctgctac ctcggtcgag    29880
cacgcgccac tgtactgggc aagacatcgc gcggctaccg catcgaatac tgggggccagg   29940 gtgcccgcga tggcgaactg atccgcgcaa ctgttccggc gcgcgacctg atgccgattt    30000
gaccacttca ctgatgccgc ttcgatgagg cggcattggg aagtcaaccg aggattcaga    30060
gatgaaccag atttcaatcg tgggctacga aagcgactgc aattgcgagc actgtggtcg    30120
cgccctgaaa catggagttc gccttagcga tgggcgattg gttggggcca cctgcctcga    30180
caagaagctg acaaagccgc gccagtacaa aggcaagtcg ttccgctttg gcgccgagca    30240
catcatcaaa attgccaaag tcgttcagtt ctactcgccg tccaattggg cgcgctttgg    30300
tgtttccgca tcgagcacaa cttttgaagg tatcgcatga agataagacc aaaagctggg    30360
ccagcaagct tgaaaggaga cgggcgtgac tactcgcgcc tagtcctcgc ggcattcgcc    30420
cagatcaccg aagacgatga aattgatcgg attgttgagc taaatcgcag gaagcgcgaa    30480
gtgaatgaaa atgccaagaa gcggttctaa cccgccgccc tgccggcatc accgaggaaa    30540
ggacatgaga gttcacgaga aattcagcaa gaaggggcg aggccgctgg agtgcgtaca    30600
accaactgtt cgcactatcg ccggcgccgt acatccagtc gcggttgagt tcttccagac    30660
gagcgattcc tgcgatggcc gcaccctcac tgcattcatg acgccgcaag aggcgatgaa    30720
```

```
gttggccctg catctgctgc acgtcgtgca gggcgctatg cgctaacccg ccgccctgcc    30780
ggtaacaggg taccacccgc gcctgccggg ttccccaacg caggcccgat ccacctggct    30840
ccccatcgcc aggctgtatc ggagagtggt ctggccgcac agcgctaggg gtatagcgtg    30900
tgctgcgggt accacctgaa tcagttcaga gtcacgccgc cagatgaccc aatccagtcg    30960
gacagagact cagcaccggc cagaccactc ccccatacag ccaccacgca atcacaacag    31020
acggaggccc catggcggcc aaatcgttca agcagatgat caaggacggc gacctgaagc    31080
gcgcggatgc gatgaaggct cgcctcgaag accttcacga agagcccggc ttcaacctgc    31140
gcgccgaggg cgaagacctc gagcagagca tcgcggatct ggccgactac ctgcaccagg    31200
gcggcatcgt tcctgccctc gaagtgcgac cgcgcgaaga aggcggcatg tgggttgtcg    31260
acggacaccg ccgccggcgc gcttacctca agctcgacgc cgagggccgt ctgccgcgtg    31320
acccgaacgg cgagttctgg gtgcccatcg ttgcgttcgc cggtaacgac gctgagcgcg    31380
tgctccgcgt gatcacgtcc caggagggc gcaagctctc ccctctggag ctcgcacacg    31440
gctacaagcg gctcattgcg ttcgggtgga ccgtcgaaca gatcgcccaa aagatggggc    31500
gcacccgtca gcacgtcgac caggtgttgg tcgtaggcaa cgcgaatacc gatgttcagc    31560
agttgatcag ctccggcgcg gtagcggcca ccaccgccgc gcggatcgtc aggaagcacg    31620
gcgagaaggc cgggcaggtg ctcggccagc agctcgcgaa ggtgatcgca gcgggaggga    31680
caaaggtcac ccccagagcg gtagccgagc cgaccgtgcc gcgcgccatt tcgatgatcc    31740
tgctgaaggt cactaccgat atcgtcgatg ccttccctac ggcactccgc gcaggcctgg    31800
ccgaaggccc ggaatcgatc accctcacca ctcgctcggc atgggtagag cggttgatgg    31860
atctcgtcgc tcaggcgaaa gagtccctcc agggggtaagc catgttcatc cttccattcc    31920
tcatcggcct ggtgcttcac gaccagcggc ccgaaccgct cgcgcgcctc gaaagcgaca    31980
gcgccgatcc tgacctgggc gcctcggcgc cagcaggccg agaacgatgt accgcggggc    32040
gtccggagtt cgggctccag gcgtcccgcc caaaatgctt caaaccataa ggcggttgtg    32100
aagtagaggc ggggcggtgg gcgccccgct tcacctctct ctcgacttca tgcgcgagca    32160
ctccacgcaa tgccgagtgc tgacccatgc agccaaggag ctattcccat gcaagcaatc    32220
caatgcggcg gatggatcgg ccgccagggc ctcggcctgg ctccccgcga actcgaagct    32280
accgcctgga gcgccagcga actgaccgcg aaagaggtcg cgcggcgcat gggaatcgcc    32340
ccagggaccg tcgagaagcg cctagacgac gccaaattca agctcggcgt gcgcagcgtg    32400
cgcggactgg tgcttgaggc gttccgacgc ggaatcatct cgcctgccgt cgtcttgctc    32460
gcattcctcg tcgccggcca cccgctgatc gatgacgacc acatgaaccg gaaccgcagg    32520
ccgagcaacg agcggcgaat caccgaagcc cgcaccgttc gccggatcga cgaaatcacc    32580
atcaacgcgt aggagaacca caatgctcaa gcatcaggaa caaaccgaag ttctcgccgg    32640
cctgccctcc cagaccgccc tcgcccgcct ggcgttcgtt cagcggctca tggctcctgc    32700
ggtggaggaa ccctaccagg tcgtgcctca gggtcgcgga ttcttccaca tcgtcgagac    32760
cgctactggc gcggtgcgcg gattccgccg gaaccacaac gaagcttgcg cctacgcaga    32820
gcatttgaag cgccagcagg ccgctaagtg accaggcgca gagcaattcg aaccggcggc    32880
atcggtgcag ccctgggctt catcgtgctt gtgttcgtgc tccccgcggc tgttcggcaa    32940
cagccaccca ggacgccgcc gtccgccgcc gcgccagcag ttcaagaggc gaagcctcga    33000
acggtctcct accgctcaag cgccagccgc caacactcct acatcttctg accggagccg    33060
aatggtgatc agcaaacgcc aggccctgct caggaagcca tggcgagagc tgactacccg    33120
```

```
aacgactgaa ctcggcgtcg agaagctttg ccccggctgc ctgcagtggt ggccacaaga    33180
tgaagagttc ttctccttca tctccaccag atgccacttc cacaacgaat gccgcgcatg    33240
cagggcagca gcccaagcca ggcggcgaca atcgaggatc gcagcatgag cctgccaatc    33300
aatgcactga aggatgacga actgctgcac tactcgcagt tcgattcagg ggcggccgac    33360
gagctggcaa gacggctcgc aacgggcgac ctgcatatag tcgatgagct aagcgagctt    33420
gaggaatacg ccagggagct ggaagaaggg aaagaagagg cagacgacga ccttgaggtt    33480
gagcgggcaa agtgccgcga tgcgatcgcc gttctcgaag ccacagtgca gtttaagcca    33540
aagacggtag acgacgcgct gcatgcaatc aggtcggcga tagaaattct ggagggctga    33600
tggccaagac caacgcccag cgccagcggg agaaacgcca gcgacagcga gaggcaggca    33660
tccccgagcg caagctaccc tcaccgcccc aatcgacgc agcgtttgag cgcctgcagg    33720
cggtcggcga tttcgaggac tggcgagaag cgttctcgac gctgctactc aacgcctcag    33780
ccctgcccga tgccgatctc ctgcctctcc tcgtcgtgtc gcgacacgaa tacacgccca    33840
gcgaaaacgt gtcgcgacaa ctactcgccg ccgaactctc cgtcgccgac gacgaacagt    33900
aacccaccac cagatcaccg acgctagcac gcctggcgcg gctctactcg tcctgaggat    33960
taccacatga gcacttttgc cgtgttcggc atgacgcgag acgtagcgct cgccatggcc    34020
aataaagaag tgaagtcggt acgcaagaca ccgctcgggg atgagcatgt tccgatgagc    34080
gaatggctcg ccgcagtcga gcggaaggcc gacaacatca tgaccggaac caaggtcgtc    34140
cagttgagcc aactcctgga tacgccggac ttctgtcagc agttcatcga cctcgcacgg    34200
aagaccctgg aatgccgcga catgcagatc cgcgccaggg tccagctttg gaatgacgac    34260
ggaacgccag tcctgaccaa gaagcgcaag cacaaggtcg agtggcagca gttcggccac    34320
cagccaggga gagcagcagc atgatgcgcc gcgtctactt gtccggcccc atgaccggca    34380
tcccagactt caactacccc gcgttcaacg ccgaggagcg gcggatcaga gccctcggct    34440
atatcgtcga gaacccggcg gtcaacatgg tctaccgtgg cgcgccgtgg gagacgttca    34500
tgcgcgacgg gatcaagcgg ctcatggact gcgacattct cgcgttgctc cctgggtggg    34560
agcgttctcg cggcgcgaac atcgagcgca acctcgctat caccctcggc atgcacgtcg    34620
tcgacgccga ggcgctcccc gcgcccgact tcgtctgcaa gtgccgcgca attcagttca    34680
cctgctgctc cgtaccgagt gacaacgatc cgttcgtctg ccgtcgcctg ccgacatgc    34740 cggcataccT ctccccggag gatcaactgg caaacgcacg ccaggcgctc gaaaagatcg    34800
ccgcactcac cgacgtctct accggcggta tcggtatgga cgtgctcaag atcgccaagc    34860
aagcccTttc caactgatca gcgccagcag gcgagaggta ttccttatgt ccgcagaaaa    34920
gccgcgggag cggccaatcc tgttcaacga ccagatggtc cgagccatcc tggaaggccg    34980
gaagacggtg acgcgacgcg ccgtaaaggg cttgcagata ccaaccgagg acaaaaccac    35040
gcctcacgag ggcctccgct ggagtgcgct cggccagcgc cacctgcgct acgggttcaa    35100
cgtgttcgga tccacggagg aggaatgcgc gcatgagctt gctcggtgcg gggtctgccc    35160
tttcgggaag cccggcgacc ggctgtgggt gcgcgagacc ttcgccgaca ttggatgccg    35220
tctcaccttc cgcgccgatc tcgaagacgg ggctcactgt tccgtcacac gctggacccc    35280
atcgctgcac atgccacgct gggcctcccg catcctgctg gagatcaccg ctgttcgcgt    35340
cgagcgcctc caacaaatca ccataggcga gatatgtaag gaaggcctcg cgcgctcaat    35400
gtatgagttt atccccgtga ctactgcgtt cgatgccttc gccgaactgt ggaactccac    35460
```

-continued

```
cggtggcgac tgggacgcca acccctgggt ctgggtcatc gagttcaagc gggtgacgcc    35520
gtgaacgctc ccatctactg ccgcacaaca ggccagcgca tcgggcaatg caattgcatc    35580
cggtgccggc ctcctgagga acgccatgc cgggcgccta ctacaacgaa ttcgacccat     35640
atgccgctca gtggcttcga aacctgatcc ccgccggcca catagcacct ggcgacgtcg    35700
acgaacgatc gatcgaggat gttcacccag atgacctcaa gcactacaca caatgccact    35760
tcttcgcggg aatcggcgtc tggtcgctcg cccttcggcg ctccggctgg ccagatgatc    35820
gacctgtttg gaccggttcc tgtccttgcc aaccttactc caaggcaggc aagagacttg    35880
ggtttgctga tccacgacac ctctggccgt catggagcca tctcatcaga gagcggcgcc    35940
ctgcagagtt gtttggcgag cagtctcctg aagcgcttgt ccatggctgg tttgatctcg    36000
tcctgggcga ccttgaagaa gctggatacg ccgctgggc gatacatttt gcagctgcct     36060
catgcgggga gccgatcctc aggaagcggg tctactttgc tgccaagcat ctcggcgagg    36120
gagcacaagg acagcagtcg cgcagaagtc cttgccaggc tggaccgcgg agatggcgtg    36180
gcgaagcgga tctgcgcgct atcgcagact ctccgctcca gcccggagat cgttggcctc    36240
agcccatcgt tcgcagcatg gaccatggct attccggtcg aatgggtgct ctgcatgcca    36300
tcggaaacgc cctcaatgct gaagcggcga cgcagttcat agccgcagac ctcgacgcta    36360
cctcatagcg aggaaccccc atggaatccc tcaacctgac cgcgctgttc ctggacggcg    36420
aggatggcca gcgcctggcc gaggtcaacg gcctcccacg cctcggcgcc ccgctctcct    36480
cctctcaact gcgccagctc gcacgccagc tcaacgagat cgcaaacgac gcagaccagg    36540
acgcaactgg tttgcacaca tacgcagcgc caccgtatgg agcctgccca tcatgccatt    36600
cgacgaaagc cccgcagtcc gccgcataaa cgccctctac ccctctaacg cgccagcccg    36660
ctacctgcac attcccaccg gcattcactg ggtcgtcatc gacagcctgg gtgaggtcat    36720
tcaactcgaa aacatcgagc gccggcgccg actgataacc gtttctgacc tcgaaaccga    36780
ggcctggaga aagctcccat gaccaaagca aatgaatgca cctgcccttc cggagacggc    36840
tccctccgcc atccgtgccc ggcacacatc ggtccattcg acaaactcgt cggctccccg    36900
gtacacaacg aaagcgagcc agacttgcct cctctcgacg aacatcttgc acaagttttc    36960
gagacaggta tggcgctcag agaatcggta gagcaggcag gcggggatga gcgcgcggcg    37020
ttcgaggcct ggtggcaatc cgccgaagtg ctgaagtgca agcgggatgt cgccatggaa    37080
gcatggcaag cccgcgccgc cctggcgcaa ccctcccagg cgcaggccga gcaggccacc    37140
gccgacgact acgaggaagt cctggccgat caccgtcgtc tggtgcgcga gttggacgtg    37200
ctgctgaacg gagaggaagg cgccgccaag caggcaagcc tctgcgatct ggtcgggcag    37260
gtgtccgcca tcgtgcgcga gcgtcgcgtg cctctgctgt cccgttcgca ggcagaggac    37320
gctccggtaa tcggatgcct ctgcggcatg cccatgaccg aaggtcatca ctcgccggag    37380
ggttgcacca gccttgaaga gttcgcacca caggcgcagg ccgagcaggc agaggcggag    37440
cggccggaag tggtggcgtg gcgttacggc tccagcggcg gaatcgtcag cgacaaggca    37500
tgtctcgatg aatggaaatc cggcggcgaa tatcaatcgc tgatgaccgt cgcccagcat    37560
gagcgcatcg tcggtgagct acgagcgag aacgagcgac tggcgaacga ccgcgaccga    37620
gcgaatcaat tcgctaatgg cgctgccttg gaaattaatg ccgccctggc cagggtcgcg    37680
gagctggagc acgtcctgcg ggtagtggtc aacgctgccg accatggctc atggccgacc    37740
acggtgatgc atggcatcga gaaggtgcgt gaagttctcg caggctcagc cccgcccgcc    37800
aaggctcagc acagcgtgcc ggaggggtgg aaacttgtgc catcggacaa aggttgcgtc    37860
```

```
accagttcga tgaaagctga gtgcatcgga gagttctcgt tttacatccg tgcagcttgc    37920
gccgagtgcc ttgatgttgg caccgatagc gattgccatg tctgcggtgg tgatatcgag    37980
tacgaccaaa aaatcgacgt gccgtgggat acctgcaagg agatctacaa gaccatgctc    38040
gccgccgcgc ccggcaaggc tcagcacagc gttccggagg tgtcagggat cggacgagac    38100
ttcgcctatc cgcgctccgt agttctgtac ctgcgcacag agccgaccga cgacgacctg    38160
cgagccatcc atgatggcct gcgatctctc gccgccgcgc cgcagccagt agcgtaggga    38220
gagtgaccat gaagcaatcc gaattccgtg ccgagttggt caagatcatg cccggctaca    38280
actgacggt tcatgcgagc cgcagcagcg aaaagctgtt ggtcgccacc ggcatccagt      38340
ccagcggctc caaccggctc tcgacgctgc gcgtggagcg gcgtgacgac tacgccggtt    38400
ccggcaagcc tcgctacgaa gtgagcagcg cgggatacgg aacccgatcc ccctggctgc    38460
acaccgccca ggacaaaact ctggtacgag cccttcgctc gcttcaggag cactacgagg    38520
gcaatgcgcg taagtacagc atccacgcga gcgacctaca gcgtggacgg atagctaccc    38580
cgccaacgcc cggagcttct acagatgaat gactacaaat cagccttcaa cgccgcggcc    38640
gccgacatca gcgcgatcat cgcactgctg gggttcacca agtatcccgg cgttgatccg    38700
gtgctgcgcg caattgctga cctgatactc gaaaaagccg agaaccaggt actcagggag    38760
gagcgcgacg ccgccaacaa gcgcgccgac actctcgaac accgcatgat gggcatgatg    38820
acccgccact tcgccgaggc atggcgcaac cgagacacgc agaaggcgct cgacggctac    38880
ctgtctgctg gtatcgcgca gttggagcag gagcgcgacg ccgcccaggc cagggtcgcg    38940
gagctgactg caacccgcaa tcgctacggg ttagacgccc actacttcaa caagaacctc    39000
cagcgcatcc tgcgcgactt cgagagcttc acgcccgacg aactcgctcg ctccctgatc    39060
atcctggcga aggtcgccga cgaaaaggtc gtagcccagg ctcagcacag cgtgccggag    39120
gggtggatgc tcgtcgagtg cggaatctgg acgcaggaac aggtggacga gatgcagaag    39180
acggtggctc gattccgcaa ttcagaattc gtcgacgacc gcgcgctggc gatggctgtt    39240
gctgacgcag gccagtgcaa ggctccagag atatcgctgg ccgagctgct cgccgccgcg    39300
cccggcaagg aggggttgtg atggccgttt acgtcgacga catgaacgca acgtttggcc    39360
gcatgaagat gtgccacatg ctcgcggaca cgaccgagga actgctcgca atggcagaca    39420
agatcggtgt tcagcggaag tggattcagc atgccggac catcaaggag cacttcgata    39480
tctgcctgtc gaagaagtca gcagctctcg cagccggggc cgtggctatc acgtaccccg    39540
acggcgtagc agagatcatg aagaagcgcc gagcagccag caaggaggta ggtcatgagt    39600
gaggtgaagc ggttcgacca cgtgaaccat gctcacgttg atgactgtga gcacattgat    39660
aaccccgaag gagcgtgggt gaaggcctcc gactacgacg ccctcgccgc cgaggcccag    39720
gcgctcaggg aggaagtcgc acgcgctgag cagcaccgca acgatcaggc tgacttgatt    39780
gtgtcgctac gcaccgaagt cgcagcactg cgaatggcga gagatgatct caaactcgaa    39840
cgagaccttg ctcgacaaaa cttctgcgac gagcaggcag cgaattatca gttgcaagcg    39900
cacttgaaag cctgcctcgg cgaactatcg gaactgcgcg caagggtggt tgtgctcccc    39960
agcgttgata acgtcatgaa tatcgtcatg cgttaccagt ggaacgagaa gaccaacgtc    40020
accggaacta cgaactgggc ggccaacctc ggtatgaggg ttgtcgaagt ggtcaagcgc    40080
ctcaacggca agacggtcag cgaggggctg ttgcggcgca tcagcgatct gttcccggct    40140
gacatgggag atgacggatc aggccgcgcc ggttggtttc cgcatgtgcg cgagacggtt    40200
```

-continued

```
gcagagcttc gcgccctgct caaccaggac aaggagaacg gcgaccatgc tgcatgagcc      40260
ggaggagtac cgattgttca gtctatggat gctggtcttc atggccatcg gctggttcgg      40320
tggctggata cacgcccatt acaccgtagc cgaagaatgc cggaagctcg gcaagttcta      40380
cgtcggcaag accgtattcg agtgcaaggc gatcaccgag gaagacaagg agaacggcaa      40440
tggctgaaga actgaaaccc tgcccgttct gcggagaaga agccgctttt gtcgagctgg      40500
aagacggcgg aatagttgcg gtgtgcgcat caaaaggatg cgtcgcgagc ggtgttgcac      40560
gctacgcatg tggagacgac ccgagaccgc ttattgccga gacctggaac accagagcag      40620
tccccgcagg ccatgtggtg gtcagcgagg cactgttgcg gcgtcttgcc aggccggcag      40680
accgttacga tgaggttttc actttggatc gacatgaggc cgccgaagaa ctccgcgccc      40740
tgctgagcga gcaggcatag ccacccatcg ccatccactg tacgcatata cagcaattcg      40800
gataatggtc tacccactac ccggattgaa tatgcgcacg aaaaccttcc gcccgccgcg      40860
tcggcatgaa ctggctggcc ttcgctacta ccgcaccgcg tcagcttaca actggctcgg      40920
gatcacgatg gcgcacccga cccgcgcaat ccagttgctg ctcgagcagt gcgagccaga      40980
cgtgctctcg ccgatgttcg agattgagat cgacgcgatc ctgcgccagg ccgacgagta      41040
tgcgaaaacc ggacaggtgc tagagcgcga gcaactgcgc gaaatgctca tgcacctgat      41100
ctcgaaggcc gcgggcgact gatccggagc ccttcacatg aagaaagccc tatccagact      41160
tgcggcagt                                                            41169
```

<210> SEQ ID NO 2
<211> LENGTH: 41169
<212> TYPE: DNA
<213> ORGANISM: Artificial Sequence
<220> FEATURE:
<223> OTHER INFORMATION: Synthetic construct

<400> SEQUENCE: 2

```
actgccgcaa gtctggatag ggctttcttc atgtgaaggg ctccggatca gtcgcccgcg        60
gccttcgaga tcaggtgcat gagcatttcg cgcagttgct cgcgctctag cacctgtccg       120
gttttcgcat actcgtcggc ctggcgcagg atcgcgtcga tctcaatctc gaacatcggc       180
gagagcacgt ctggctcgca ctgctcgagc agcaactgga ttgcgcgggt cgggtgcgcc       240
atcgtgatcc cgagccagtt gtaagctgac gcggtgcggt agtagcgaag gccagccagt       300
tcatgccgac gcggcgggcg gaaggttttc gtgcgcatat tcaatccggg tagtgggtag       360
accattatcc gaattgctgt atatgcgtac agtggatggc gatgggtggc tatgcctgct       420
cgctcagcag ggcgcggagt tcttcggcgg cctcatgtcg atccaaagtg aaaacctcat       480
cgtaacggtc tgccggcctg gcaagacgcc gcaacagtgc ctcgctgacc accacatggc       540
ctgcggggac tgctctggtg ttccaggtct cggcaataag cggtctcggg tcgtctccac       600
atgcgtagcg tgcaacaccg ctcgcgacgc atccttttga tgcgcacacc gcaactattc       660
cgccgtcttc cagctcgaca aaagcggctt cttctccgca gaacgggcag ggtttcagtt       720
cttcagccat tgccgttctc cttgtcttcc tcggtgatcg ccttgcactc gaatacggtc       780
ttgccgacgt agaacttgcc gagcttccgg cattcttcgg ctacggtgta atgggcgtgt       840
atccagccac cgaaccagcc gatggccatg aagaccagca tccatagact gaacaatcgg       900
tactcctccg gctcatgcag catggtcgcc gttctccttg tcctggttga gcagggcgcg       960
aagctctgca accgtctcgc gcacatgcgg aaaccaaccg gcgcggcctg atccgtcatc      1020
tcccatgtca gccgggaaca gatcgctgat gcgccgcaac agcccctcgc tgaccgtctt      1080
```

```
gccgttgagg cgcttgacca cttcgacaac cctcataccg aggttggccg cccagttcgt   1140
agttccggtg acgttggtct tctcgttcca ctggtaacgc atgacgatat tcatgacgtt   1200
atcaacgctg gggagcacaa ccaccccttgc gcgcagttcc gatagttcgc cgaggcaggc   1260
tttcaagtgc gcttgcaact gataattcgc tgcctgctcg tcgcagaagt tttgtcgagc   1320
aaggtctcgt tcgagtttga gatcatctct cgccattcgc agtgctgcga cttcggtgcg   1380
tagcgacaca atcaagtcag cctgatcgtt gcggtgctgc tcagcgcgtg cgacttcctc   1440
cctgagcgcc tgggcctcgg cggcgagggc gtcgtagtcg gaggccttca cccacgctcc   1500
ttcggggtta tcaatgtgct cacagtcatc aacgtgagca tggttcacgt ggtcgaaccg   1560
cttcacctca ctcatgacct acctccttgc tggctgctcg gcgcttcttc atgatctctg   1620
ctacgccgtc ggggtacgtg atagccacgg ccccggctgc gagagctgct gacttcttcg   1680
acaggcagat atcgaagtgc tccttgatgg tcccggcatg ctgaatccac ttccgctgaa   1740
caccgatctt gtctgccatt gcgagcagtt cctcggtcgt gtccgcgagc atgtggcaca   1800
tcttcatgcg gccaaacgtt gcgttcatgt cgtcgacgta aacggccatc acaaccccctc  1860 cttgccgggc gcggcggcga gcagctcggc cagcgatatc tctggagcct tgcactggcc   1920
tgcgtcagca acagccatcg ccagcgcgcg gtcgtcgacg aattctgaat tgcggaatcg   1980
agccaccgtc ttctgcatct cgtccacctg ttcctgcgtc cagattccgc actcgacgag   2040
catccacccc tccggcacgc tgtgctgagc ctgggctacg accttttcgt cggcgacctt   2100
cgccaggatg atcagggagc gagcgagttc gtcgggcgtg aagctctcga agtcgcgcag   2160
gatgcgctgg aggttcttgt tgaagtagtg ggcgtctaac ccgtagcgat tgcgggttgc   2220
agtcagctcc gcgaccctgg cctgggcggc gtcgcgctcc tgctccaact gcgcgatacc   2280
agcagacagg tagccgtcga gcgccttctg cgtgtctcgg ttgcgccatg cctcggcgaa   2340
gtggcgggtc atcatgccca tcatgcggtg ttcgagagtg tcggcgcgct tgttggcggc   2400
gtcgcgctcc tccctgagta cctggttctc ggcttttcg agtatcaggt cagcaattgc   2460
gcgcagcacc ggatcaacgc cgggatactt ggtgaacccc agcagtgcga tgatcgcgct   2520
gatgtcggcg gccgcggcgt tgaaggctga tttgtagtca ttcatctgta gaagctccgg   2580
gcgttggcgg ggtagctatc cgtccacgct gtaggtcgct cgcgtggatg ctgtacttac   2640
gcgcattgcc ctcgtagtgc tcctgaagcg agcgaagggc tcgtaccaga gttttgtcct   2700
gggcggtgtg cagccagggg gatcgggttc cgtatcccgc gctgctcact tcgtagcgag   2760
gcttgccgga accggcgtag tcgtcacgcc gctccacgcg cagcgtcgag agccggttgg   2820
agccgctgga ctggatgccg gtggcgacca acagcttttc gctgctgcgg ctcgcatgaa   2880
ccgtccagtt gtagccgggc atgatcttga ccaactcggc acggaattcg gattgcttca   2940
tggtcactct ccctacgcta ctggctgcgg cgcggcggcg agagatcgca ggccatcatg   3000
gatggctcgc aggtcgtcgt cggtcggctc tgtgcgcagg tacagaacta cggagcgcgg   3060
ataggcgaag tctcgtccga tccctgacac ctccggaacg ctgtgctgag ccttgccggg   3120
cgcggcggcg agcatggtct tgtagatctc cttgcaggta tcccacggca cgtcgatttt   3180
ttggtcgtac tcgatatcac caccgcgac atggcaatcg ctatcggtgc caacatcaag   3240
gcactcggcg caagctgcac ggatgtaaaa cgagaactct ccgatgcact cagctttcat   3300
cgaactggtg acgcaacctt tgtccgatgg cacaagtttc cacccctccg gcacgctgtg   3360
ctgagccttg gcgggcgggg ctgagcctgc gagaacttca cgcaccttct cgatgccatg   3420
```

```
catcaccgtg gtcggccatg agccatggtc ggcagcgttg accactaccc gcaggacgtg    3480
ctccagctcc gcgaccctgg ccagggcggc attaatttcc aaggcagcgc cattagcgaa    3540
ttgattcgct cggtcgcggt cgttcgccag tcgctcgttc tccgctcgta gctcaccgac    3600
gatgcgctca tgctgggcga cggtcatcag cgattgatat tcgccgccgg atttccattc    3660
atcgagacat gccttgtcgc tgacgattcc gccgctggag ccgtaacgcc acgccaccac    3720
ttccggccgc tccgcctctg cctgctcggc ctgcgcctgt ggtgcgaact cttcaaggct    3780
ggtgcaaccc tccggcgagt gatgaccttc ggtcatgggc atgccgcaga ggcatccgat    3840
taccggagcg tcctctgcct gcgaacggga cagcagaggc acgcgacgct cgcgcacgat    3900
ggcggacacc tgcccgacca gatcgcagag gcttgcctgc ttggcggcgc cttcctctcc    3960
gttcagcagc acgtccaact cgcgcaccag acgacggtga tcggccagga cttcctcgta    4020
gtcgtcggcg gtggcctgct cggcctgcgc ctgggagggt tgcgccaggg cggcgcgggc    4080
ttgccatgct ccatggcga catcccgctt gcacttcagc acttcggcgg attgccacca    4140
ggcctcgaac gccgcgcgct catccccgcc tgcctgctct accgattctc tgagcgccat    4200
acctgtctcg aaaacttgtg caagatgttc gtcgagagga ggcaagtctg gctcgctttc    4260
gttgtgtacc gggagccga cgagtttgtc gaatggaccg atgtgtgccg ggcacggatg    4320
gcggagggag ccgtctccgg aagggcaggt gcattcattt gctttggtca tgggagcttt    4380
ctccaggcct cggtttcgag gtcagaaacg gttatcagtc ggcgccggcg ctcgatgttt    4440
tcgagttgaa tgacctcacc caggctgtcg atgacgaccc agtgaatgcc ggtgggaatg    4500
tgcaggtagc gggctggcgc gttagagggg tagagggcgt ttatgcggcg gactgcgggg    4560
ctttcgtcga atggcatgat gggcaggctc catacggtgg cgctgcgtat gtgtgcaaac    4620
cagttgcgtc ctggtctgcg tcgtttgcga tctcgttgag ctggcgtgcg agctggcgca    4680
gttgagagga ggagagcggg gcgccgaggc gtgggaggcc gttgacctcg ccaggcgct    4740 ggccatcctc gccgtccagg aacagcgcgg tcaggttgag ggattccatg ggggttcctc    4800
gctatgaggt agcgtcgagg tctgcggcta tgaactgcgt cgccgcttca gcattgaggg    4860
cgtttccgat ggcatgcaga gcacccattc gaccggaata gccatggtcc atgctgcgaa    4920
cgatgggctg aggccaacga tctccgggct ggagcggaga gtctgcgata gcgcgcagat    4980
ccgcttcgcc acgccatctc cgcggtccag cctggcaagg acttctgcgc gactgctgtc    5040
cttgtgctcc ctcgccgaga tgcttggcag caaagtagac ccgcttcctg aggatcggct    5100
ccccgcatga ggcagctgca aaatgtatcg ccccagcggc gtatccagct tcttcaaggt    5160
cgcccaggac gagatcaaac cagccatgga caagcgcttc aggagactgc tcgccaaaca    5220
actctgcagg gcgccgctct ctgatgagat ggctccatga cggccagagg tgtcgtggat    5280
cagcaaaccc aagtctcttg cctgccttgg agtaaggttg gcaaggacag gaaccggtcc    5340
aaacaggtcg atcatctggc cagccggagc gccgaagggc gagcgaccag acgccgattc    5400
ccgcgaagaa gtggcattgt gtgtagtgct tgaggtcatc tgggtgaaca tcctcgatcg    5460
atcgttcgtc gacgtcgcca ggtgctatgt ggccggcggc gatcaggttt cgaagccact    5520
gagcggcata tgggtcgaat tcgttgtagt aggcgcccgg catggcgttt cctcaggagg    5580
ccggcaccgg atgcaattgc attgcccgat gcgctggcct gttgtgcggc agtagatggg    5640
agcgttcacg gcgtcacccg cttgaactcg atgaccagga cccagggggtt ggcgtcccag    5700 tcgccaccgg tggagttcca cagttcgcg aaggcatcga acgcagtagt cacgggata    5760 aactcataca ttgagcgcgc gaggccttcc ttacatatct cgcctatggt gatttgttgg    5820
```

```
aggcgctcga cgcgaacagc ggtgatctcc agcaggatgc gggaggccca gcgtggcatg    5880
tgcagcgatg gggtccagcg tgtgacggaa cagtgagccc cgtcttcgag atcggcgcgg    5940
aaggtgagac ggcatccaat gtcggcgaag gtctcgcgca cccacagccg gtcgccgggc    6000
ttcccgaaag ggcagacccc gcaccgagca agctcatgcg cgcattcctc ctccgtggat    6060
ccgaacacgt tgaacccgta gcgcaggtgg cgctggccga gcgcactcca gcggaggccc    6120
tcgtgaggcg tggttttgtc ctcggttggt atctgcaagc cctttacggc gcgtcgcgtc    6180
accgtcttcc ggccttccag gatggctcgg accatctggt cgttgaacag gattggccgc    6240
tcccgcggct tttctgcgga cataaggaat acctctcgcc tgctggcgct gatcagttgg    6300
aaagggcttg cttggcgatc ttgagcacgt ccataccgat accgccggta gagacgtcgg    6360
tgagtgcggc gatcttttcg agcgcctggc gtgcgtttgc cagttgatcc tccggggaga    6420
ggtatgccgg catgtcggcc aggcgacggc agacgaacgg atcgttgtca ctcggtacgg    6480
agcagcaggt gaactgaatt gcgcggcact tgcagacgaa gtcgggcgcg gggagcgcct    6540
cggcgtcgac gacgtgcatg ccgagggtga tagcgaggtt gcgctcgatg ttcgcgccgc    6600
gagaacgctc ccacccaggg agcaacgcga gaatgtcgca gtccatgagc cgcttgatcc    6660
cgtcgcgcat gaacgtctcc cacggcgcgc cacggtagac catgttgacc gccgggttct    6720
cgacgatata gccgagggct ctgatccgcc gctcctcggc gttgaacgcg gggtagttga    6780
agtctgggat gccggtcatg gggccggaca agtagacgcg gcgcatcatg ctgctgctct    6840
ccctggctgg tggccgaact gctgccactc gaccttgtgc ttgcgcttct tggtcaggac    6900
tggcgttccg tcgtcattcc aaagctggac cctggcgcgg atctgcatgt cgcggcattc    6960
cagggtcttc cgtgcgaggt cgatgaactg ctgacagaag tccggcgtat ccaggagttg    7020
gctcaactgg acgaccttgg ttccggtcat gatgttgtcg gccttccgct cgactgcggc    7080
gagccattcg ctcatcggaa catgctcatc cccgagcggt gtcttgcgta ccgacttcac    7140
ttctttattg gccatggcga gcgctacgtc tcgcgtcatg ccgaacacgg caaaagtgct    7200
catgtggtaa tcctcaggac gagtagagcc gcgccaggcg tgctagcgtc ggtgatctgg    7260
tggtgggtta ctgttcgtcg tcggcgacgg agagttcggc ggcgagtagt tgtcgcgaca    7320
cgttttcgct gggcgtgtat tcgtgtcgcg acacgacgag gagaggcagg agatcggcat    7380
cgggcagggc tgaggcgttg agtagcagcg tcgagaacgc ttctcgccag tcctcgaaat    7440
cgccgaccgc ctgcaggcgc tcaaacgctg cgtcgattgc gggcggtgag ggtagcttgc    7500
gctcggggat gcctgcctct cgctgtcgct ggcgtttctc ccgctggcgc tgggcgttgg    7560
tcttggccat cagccctcca gaatttctat cgccgacctg attgcatgca gcgcgtcgtc    7620
taccgtcttt ggcttaaaact gcactgtggc ttcgagaacg gcgatcgcat gcggcactt    7680
tgcccgctca acctcaaggt cgtcgtctgc ctcttctttc ccttcttcca gctccctggc    7740
gtattcctca agctcgctta gctcatcgac tatatgcagg tcgccgttg cgagccgtct    7800
tgccagctcg tcggccgccc ctgaatcgaa ctgcgagtag tgcagcagtt cgtcatcctt    7860
cagtgcattg attggcaggc tcatgctgcg atcctcgatt gtcgccgcct ggcttgggct    7920
gctgccctgc atgcgcggca ttcgttgtgg aagtggcatc tggtggagat gaaggagaag    7980
aactcttcat cttgtggcca ccactgcagg cagccggggc aaagcttctc gacgccgagt    8040
tcagtcgttc gggtagtcag ctctcgccat ggcttcctga gcaggcctg gcgtttgctg    8100
atcaccattc ggctccggtc agaagatgta ggagtgttgg cggctggcgc ttgagcggta    8160
```

| | |
|---|---|
| ggagaccgtt cgaggcttcg cctcttgaac tgctggcgcg gcggcggacg gcggcgtcct | 8220 |
| gggtggctgt tgccgaacag ccgcggggag cacgaacaca agcacgatga agcccagggc | 8280 |
| tgcaccgatg ccgccggttc gaattgctct gcgcctggtc acttagcggc ctgctggcgc | 8340 |
| ttcaaatgct ctgcgtaggc gcaagcttcg ttgtggttcc ggcggaatcc gcgcaccgcg | 8400 |
| ccagtagcgg tctcgacgat gtggaagaat ccgcgaccct gaggcacgac ctggtagggt | 8460 |
| tcctccaccg caggagccat gagccgctga acgaacgcca ggcgggcgag ggcggtctgg | 8520 |
| gagggcaggc cggcgagaac ttcggtttgt tcctgatgct tgagcattgt ggttctccta | 8580 |
| cgcgttgatg gtgatttcgt cgatccggcg aacggtgcgg gcttcggtga ttcgccgctc | 8640 |
| gttgctcggc ctgcggttcc ggttcatgtg gtcgtcatcg atcagcgggt ggccggcgac | 8700 |
| gaggaatgcg agcaagacga cggcaggcga gatgattccg cgtcggaacg cctcaagcac | 8760 |
| cagtccgcgc acgctgcgca cgccgagctt gaatttggcg tcgtctaggc gcttctcgac | 8820 |
| ggtccctggg gcgattccca tgcgccgcgc gacctctttc gcggtcagtt cgctggcgct | 8880 |
| ccaggcggta gcttcgagtt cgcggggagc caggccgagg ccctggcggc cgatccatcc | 8940 |
| gccgcattgg attgcttgca tgggaatagc tccttggctg catgggtcag cactcggcat | 9000 |
| tgcgtggagt gctcgcgcat gaagtcgaga gagaggtgaa gcggggcgcc caccgccccg | 9060 |
| cctctactta caaaccgcct tatggtttga agcattttgg gcgggacgcc tggagcccga | 9120 |
| actccggacg ccccgcggta catcgttctc ggcctgctgg cgccgaggcg cccaggtcag | 9180 |
| gatcggcgct gtcgctttcg agcgcgcgca gcggttcggg ccgctggtcg tgaagcacca | 9240 |
| ggccgatgag gaatggaagg atgaacatgg cttaccctg gagggactct ttcgcctgag | 9300 |
| cgacgagatc catcaaccgc tctacccatg ccgagcgagt ggtgagggtg atcgattccg | 9360 |
| ggccttcggc caggcctgcg cggagtgccg tagggaaggc atcgacgata tcggtagtga | 9420 |
| ccttcagcag atcatcgaga atggcgcgcg gcacggtcgg ctcggctacc gctctggggg | 9480 |
| tgacctttgt ccctcccgct gcgatcacct tcgcgagctg ctggccgagc acctgcccgg | 9540 |
| ccttctcgcc gtgcttcctg acgatccgcg cggcggtggt ggccgctacc gcgccggagc | 9600 |
| tgatcaactg ctgaacatcg gtattcgcgt tgcctacgac caaacacctgg tcgacgtgct | 9660 |
| gacgggtgcg ccccatcttt tgggcgatct gttcgacggt ccacccgaac gcaatgagcc | 9720 |
| gcttgtagcc gtgtgcgagc tccagagggg agagcttgcg cccctcctgg gacgtgatca | 9780 |
| cgcggagcac gcgctcagcg tcgttaccgg cgaacgcaac gatgggcacc cagaactcgc | 9840 |
| cgttcgggtc acgcggcaga cggccctcgg cgtcgagctt gaggtaagcg cgccggcggc | 9900 |
| ggtgtccgtc gacaacccac atgccgcctt cttcgcgcgg tcgcacttcg agggcaggaa | 9960 |
| cgatgccgcc ctggtgcagg tagtcggcca gatccgcgat gctctgctcg aggtcttcgc | 10020 |
| cctcggcgcg caggttgaag ccgggctctt cgtgaaggtc ttcgaggcga gccttcatcg | 10080 |
| catccgcgcg cttcaggtcg ccgtccttga tcatctgctt gaacgatttg ccgccatgg | 10140 |
| ggcctccgtc tgttgtgatt gcgtggtggc tgtatggggg agtggtctgg ccggtgctga | 10200 |
| gtctctgtcc gactggattg ggtcatctgg cggcgtgact ctgaactgat tcaggtggta | 10260 |
| cccgcagcac acgctatacc cctagcgctg tgcggccaga ccactctccg atacagcctg | 10320 |
| gcgatgggga gccaggtgga tcgggcctgc gttggggaac ccgcaggcg cgggtggtac | 10380 |
| cctgttaccg gcagggcggc gggttagcgc atagcgccct gcacgacgtg cagcagatgc | 10440 |
| agggccaact tcatcgcctc ttgcggcgtc atgaatgcag tgagggtgcg gccatcgcag | 10500 |
| gaatcgctcg tctggaagaa ctcaaccgcg actggatgta cggcgccggc gatagtgcga | 10560 |

```
acagttggtt gtacgcactc cagcggcctc gcccccttct tgctgaattt ctcgtgaact    10620
ctcatgtcct ttcctcggtg atgccggcag ggcggcgggt tagaaccgct tcttggcatt    10680
ttcattcact tcgcgcttcc tgcgatttag ctcaacaatc cgatcaattt catcgtcttc    10740
ggtgatctgg gcgaatgccg cgaggactag gcgcgagtag tcacgcccgt ctcctttcaa    10800
gcttgctggc ccagcttttg gtcttatctt catgcgatac cttcaaaagt tgtgctcgat    10860
gcggaaacac caaagcgcgc ccaattggac ggcgagtaga actgaacgac tttggcaatt    10920
ttgatgatgt gctcggcgcc aaagcggaac gacttgcctt tgtactggcg cggctttgtc    10980
agcttcttgt cgaggcaggt ggccccaacc aatcgcccat cgctaaggcg aactccatgt    11040
ttcagggcgc gaccacagtg ctcgcaattg cagtcgcttt cgtagcccac gattgaaatc    11100
tggttcatct ctgaatcctc ggttgacttc ccaatgccgc ctcatcgaag cggcatcagt    11160
gaagtggtca aatcggcatc aggtcgcgcg ccggaacagt tgcgcggatc agttcgccat    11220
cgcgggcacc ctggccccag tattcgatgc ggtagccgcg cgatgtcttg cccagtacag    11280
tggcgcgtgc tcgaccgagg tagcaggctt tgtcacctgc cttgtatgcg ttcatgtctt    11340
gccctcttga ccggattcgt tgacttcctc gatgcgcctg tacccaagcg catctgagaa    11400
atcggatgcc gcttacggcg gcaagtcggt cagatcacgc actttcctcg tcgtacgaca    11460
caggcttatc cccacttggg gcacccacaa cgccggtccg gaaagcccca gccttacagg    11520
agcaaaacct tgggtagcgc tctgactggt tccgttatgt cgccacggtt tccttggctt    11580
gctcgttgac ttcctcgatg cccctcttgc gaagggcatc tgagaaatcg tttattcatg    11640
ggtttatgct gagtagagat accaagggtt taaaccgtcc ttgtgcctcc agatgaatcg    11700
gtcaagctca tgcgaacatg gcggtttgaa aatgcagata ttcccgtcga ctttctcgca    11760
ccaaccgatc agctcgccgg ctggcttggt catgtgctgc tcactggcga agatgcggca    11820
gccccgcatc ggcttgaaga actggtacct cacgcgtgca tccgcacggt gatgtagccg    11880
ttgctggcaa caacgtggtc ccatcggttg aaccagatga ggtcgccgaa cttcttcatg    11940
gcggcctggc gtaccttgat cagcacgtca tccggtgtct cgttgccttc cggcagggca    12000
atccagtcca ggcgcttgcc gttgctcagg tgcgcatcga cattgaattg agccatttca    12060
gtctccttac cagggtttac cggcgttgat gtatgcgctt cctgctagct cggttagagc    12120
taatagctgc caggagtcga tcgctccgcc gtagtgcaat ccgcgcagca ttccgaccgt    12180
ttcgtagtac tcgatgcgcg ctcggtgtac gtcgttctcc ctgcgagtga ttcgaagaga    12240
ctggcgtaac gctagtgagg ccttttcatt catcgcatgc cctccagggc gtgttgactt    12300
cctcgatgcc cctcttgcga agggcatctg ggaaatcggt gtttctcgca aaccctcacg    12360
ccggtagtcg gtggtgagcg cattgcgcat ttcgtaccgt ccaacaggtc tcacttgcct    12420
acctccgcaa acgatgcccg attgcagaag cgttactggc gcctgttggc tcatgcctgg    12480
ttgttaaaga gcggtcggct cggcggcctc ggcatcgctg ccgtgaatta aatatgtacc    12540
attggttcat attaggtcaa gaaccaaaag tacatatttt ttcgataggc aagaaaaagc    12600
ccgcgctagg cgggcttggg ggaggggatc agaggaggga ttttggaggc ttcaggtcaa    12660
tgactcgccc gattactcga acgttctcgg taacctgcag gggcttgtag tccttgttca    12720
gaggcatcag gtactcgcgc cctgcgtccc gcacgtattg cttgaaggta gtctcgcgct    12780
gtttccccgg ctcatacagg agggcgacat agaacttccc acttaccaaa tcaaaaccct    12840
ctggctggac gagaatccta gtcccttcgg ggaatgaggg cagcatcgag tcgccatgga    12900
```

-continued

```
cttcaagcca gtagccgttc tcgccggcct tcgcttcgga ctcaatccac tcctcagcat   12960
cgccgggttg gaagttgtca tggctttccg cccatgcgcc agcagctacc caactgatca   13020
atggataccc cttcttcttc cttgagggct gagcggtggg ttgcacgttg ccataatcgc   13080
cagcccgctc cgcaaccagg ttgcgcaccg cgtcttctgt ccgattggac gtcatgtacc   13140
ggctgttctt ttcgccctgt ccatgctcaa gccagtcaac gcgcacgccg aacgcatcgg   13200
cgatcgacag catggcatcg cgctcgggca tgctctccaa gttcatccac ttgctgacag   13260 cttttcggtgt gcgctttgtg attttttgcca gtcgagcgcc gaggccccac tcctgaaagc   13320
ctgcatcaga tgcggcctcc ttcaggcggg cgatgaacgc tgcgcggatt gtctgcatgt   13380
cttgaaccat tcgttcactt tctcacgtcc ttgcatgtac tttcagttcc tgcctaatat   13440
gtacctaatg ttcatattgg ccggaggccg catgcgcgaa ctcaagcaag ccgtcgagaa   13500
agccggcggc gtaagtcagg tggctgcgag ctgcgaggta agtcctcgag ccgtttacaa   13560
gtggctggca agcggccgtc ttccgcggac tgactacacc ggcgaaacgg actacgcgga   13620
gcggatctgc gggttagcaa gagggaaggg tttcgatcta tctcccgccg atctcagggc   13680
ttcgacgcgg actggcgtcc aggccgctta acagagattc gaatgctact ggcttgtgct   13740
ggcgctggtc agttcccgat gaccctgtt caggcatcca gtagagcaga cagcaaaaag   13800
cccgggggca accgggcttt ctgaggaggc accagtaggc ggtgccgaac atccaacgga   13860
gacgaatatg tcacaagttg cagtcatcca acaaggcccg gtcctggcga tgagcagccg   13920
cgagattgcg gcgctggtcg agtcccgaca cgacaacgtg aagaggacca tcgagcgcct   13980
cggcgagaag ggggtcatca ggtttactcc atcggaggaa acctcccacg ctggcgctgg   14040
ggcgcggccc gtgagcgttt acctcgtcga caagcgcgac agcttcgttg ttgttgccca   14100
gctcagcccg gaattcactg cgcgcctggt ggaccgctgg caggagttgg agtctcagct   14160
agcgcatggt gtgcccgccg tccctacgaa tctggcggat gcactgaggc tggctgctga   14220
tcaggtcgag aagaatcagg cgctgcagtt ggtcatcagc gagcaggcgc ctaaggtcca   14280
ggccctggag cggctcagcg gtgcggccgg cacgatgtgc ataaccgacg cagcgaagca   14340
cctcaagatc aaccccgccc ggctcttcga ctggctccag cagaaccgat ggatctaccg   14400
ccggagcggc tctgctcgct ggatcggcta tcagccacga atccaggacg gctggatcat   14460
gcacaaggtg acggttctcg gtcgtgacga tcagggcgac gagcgtgcgg cgagccaggt   14520
acgcatcact gccaaggggc tgtcggtgct ggcgcggaag atcgaggagg caagctgtg   14580 atcctcggta gcgtgtcgcg acacgaaatc acgaatcaag aaaatgtgtc gccgaggtg   14640 agtcagtgag cacgatcatc atgtcggcct gctggccact ccagggcctg acgccggcgc   14700
agaaggctgt gctgatcagc ctggcggata acgcgaacga cgaggcgtg tgctggcctt   14760 cggtggcgaa gatcgccgag cgcacctgcc tgtccgaacg tgccgtgcag caggccatca   14820
aggtgctgaa cgagtgcaag gcgctgagca ttgaagcgcg ccaggggcgc tcgacgatgt   14880
tcaccgtaac ccccgcagca tttgcacccc cgcagaaggt tcacccccgc aggaaatgca   14940 ccccccgcaga tgctgcaccc agaaccgtaa tagaacctac aagggaacca tcagggggaac   15000 cgtcaccttt gccgacccgt tccggccgg cggctggcga agcgctgcag gaggcttgcc   15060
ggagtgtgtg ggcagcgtac cgggctgcct acgaggcgcg ctggagtgtt cagccagtgc   15120
ggaacgcaaa ggtcaattcc caggtgaagc aactggtggc cgccctcggc gccgaggcgc   15180
ctgcggtggc ggcgttcttc gtcgggctgg atgacaagtt cctggtcgac agttgccatg   15240 agttcggggtt gctactggcc aaggctggcg cttaccggac gaagtgggcg acagccggtt   15300
```

```
ccgcgccgtc gaccgattgg actgaccagg tgcagctatg acccgcaggc agttcgaacc   15360
gcaatcggtc ggtgctgtgc tggcgcatgt gaatcagggc gcggggctgc gccccttgtc   15420
ccagccggcg gtgaaggtcg atccccagac gagaggcgag gtcgaccggt tgttcttgcg   15480
gatcaaggcg atctgccctg gatggcgaag ctcctggccc agcgatgagg tcgagaacgc   15540
cgcgaaggcg gagtggctgg cagagatcgt ccggcaacag gttgcgcgcc gcgagcaact   15600
gcaggccggg gtaagagcgt tgagcgcgca ggccaggccg cttgttccgt ctgccggcca   15660
gttctgcgcc tggtgctggg ctcctgaggt cttcggcctg ccatccctcg atgacgcata   15720
tcgcgaggcg ctggccaata cccacccagc catggtcgga gccgcgaaat ggagttgccc   15780
tgcggtgtat tgggcagccg ctggcgctgg attcagccgg ctgcaggctc tggcaagaaa   15840
ggatgggctg gcgcgcgctgg agatctcgta ccgacagatc atcaagaagc tggcgcgcgg   15900
cgaggcgctc gggaaggctc cggagggaga ggtcacccac cagaaagcgc gaacccaatc   15960
cgttggaatt gctgcccttg cgcagcttcg aaaacaactc aaaggaggag atcgctcatg   16020
aagtggagtg tactcaacga ctatctgatg gttagcgaca cccagccgcc ctacaaggtc   16080
tgcaagctcc tggtcgccgg cgaggctcac taccggccca gcgtacaggg tgagttcatt   16140
tgcaccccgg ttgcgactgc gaaggaggcg tgcggtgttt gcgagcgcca tcaccagatc   16200
acctatccgc gggaggtggc atgacgttgt ccgcacggaa gccccggccg aagaagtgcg   16260
cagtgtcgac gtgccgcgcg cccttcgtcc cggtgaagtc gtttcagacg tggtgcagcc   16320
cagagtgcgg aattgtcatc gctcggcaga agcaggagaa ggagcgcaaa tcgatccagc   16380
agcgcgagcg ccgcgaggtc aaggttcgga agagaagtt gaagagccgt gcagaccact   16440
tgagagaggc tcaggccgca ttcaacgagt tcatccgctg gcgcgactgg gaccgcccct   16500
gcattagttg tgggcgctttt catgacgggc agtatcacgc cgggcattac cgctccgtcg   16560
gctcccatcc cgagttgagg ttcgacgagg acaacgtcca caagcaatgc gccccatgca   16620
acaaccacaa gtcgggagac gtcgtgaact accggatcaa cctggtggcg aagatcggcg   16680
ctgcggctgt agcgcgcctg gagggtccgc acgatgcaag gaagtggact gtggaagaga   16740
tcaaggcaat caaggccctg tatcgaacca aggccaggga cgcgaagagg gctgccgcat   16800
gaagaagcat ggtccggatc ttacgaacaa gccgcgtcac ctggttccgt gccccgcatg   16860
caatggccac ggtcagcacc ggggagtgtt ctacgacatt gattgcgacg cgtgcggcgc   16920
cgctggcttc gtcgacgggg cgacggggct ggcgctggag cagcgggatg cggttgtgca   16980
actgcgcgat tgggttaagc ggttgcttga agaacagcga cgccaggcga gcaggctggc   17040
gcgagaagag aacaaccaga ggggcgccgg cggctcccac ttcagaggcg actgaaatga   17100
acatcaaggc gttggaattt ctgatggagc aatacgggct ttgggttggg tccgacaatg   17160
ggacgcctcg cggctcttcg cccatgctgg cgctgatgaa acggaacccg gcgaacgaaa   17220
aacggtttgc tgctgtgatc ccctgcatca gtgatgatcg ggcgttgcaa gtagaccggt   17280
ttctcgcacg cctctacgac gaagacccgg atgccatccg cagcctgatc ctctacttca   17340
tccatggcat gtcgtaccga gatatccagg accggatggg gatcagctac gcggacgcac   17400
gcatgctggt tcgagcaggc ctgtcggctc tgctggcgtg cttcgtgatg gaggataaaa   17460
aggctgcctg aaaaaatgta caggctggac gtattgacag tgataatcgc gccctgtacc   17520
tttcgtcata cattgcggtt ttgccgctta ggcgaactgc cgcagagcgg atcgccatag   17580
aaaagagccc agccttcgag ctgggctttt ccgtttctgc aggtggcgca ttgcgctgcg   17640
```

```
gggcgcgcgg ccccttgaa aggccgtacc tgcacccatt cccggcccag ccctcgcgct    17700
gggcttttc atttccgccc cggcgagggg aactgagacg atgaagatgc ctgacaaacc    17760
cgacacttgg gcggctctgt tcgcctggct gagccagcat gcgccgatca tctacgcctc    17820
cctgctgtcg tgggccatgg ctatggccag gatcatctac ggcggcggca ctcgccggca    17880
ggccctcttg gagggcgcgc tgtgtggtgg gctggcgctg acgatcatca gcggcttcga    17940
gttctttggc gtgccgcaga gcatggccac cttcattggt ggctggatcg gcttcctggg    18000
cgtcgagaag atccgcgacc tggccgaccg ttacgctggg atcaagctgc cgcgtcgagg    18060
gtctggcgaa tgaagatcac ctgccgatcag ctcgaccgcg ctaccggctg cggtgctgct    18120
actgcctcga cttgggtcga acacatcaac ggcgccatgg ctcggttcga gatcaacacg    18180
cccgagcgcg tggcgatgtt cctggctcag gtcgggcacg aaagccagag cctcaagcgc    18240
ctggtcgaga acctgaacta ctccgccgag gggctgctca agacctggcc gaagcggttc    18300
acgccggtag aggcgaagca gtacgcacgc cagccagagc gcatcgcgaa ccgcgtctat    18360
gccaacagga tgggcaatgg gtcgccagat acgggcgatg ggtatcgata ccgtggtcgc    18420
ggcctgatca tgatcaccgg ccacgacaac tacgccgaag ccgccgcgc cctggcgctg    18480
ccactggtgg cgcaaccgga gttgcttgag caacggacct gggctgccat cgcgtcggca    18540
tggtggtgga agtcgagggg tttaaacgaa ctggccgatc agggtcgctt cgagcggatc    18600
accctcaaga tcaacagtgg ctacaacggc gcagacgacc gtgcggctcg cctcgaatgg    18660
gcgcgtgctg cgctcaaggg ggaatgatgc tcgggttcac gacgaaagac gaagctcgac    18720
agctcggcgt ctcgcaccat ggcagctatt acggcattcc gatgtggctg ggggatgtcg    18780
atagcgattg cccgctggcg ttcgccaagt gggcgccgct tgagatggtc gtctccctgc    18840
tctcggtcat cgaaggcatc gtcaactcga tgctcaatca agagccgacg ttcatgttca    18900
aggttggtcg gaggatcgac cagtgacctg gcggccatgg ttggtggtca ccctggtcgc    18960
cgcgctggtg ctctggcgtc tggaccatgt gaccgctcag cgtgacgacc tccaggccgc    19020
tgtcgagcaa tccgccgaga cgatcaccgc gatggcccag caggcccagc gcgacatcca    19080
ggcgcaggtc cagaccgatg ccctggctcg aacctaccaa gcagcactgc aggcctccca    19140
tgaagaaaac caattgcgcc gcgatgctat cggcactggt gctcgcgtcg tgtacgtcaa    19200
agcccgctgc cccgcagatg gagtgcacca ggctcccgga gcctccggca gcgctgatgc    19260
aggaagagcc gtccttgctg ccgctgatgg acaagttgtt tctgatctcc gagccggagt    19320
cgagcgacgc gaactgatga ttgaggcgct gcgtaagcac atcgcaggcc ttccgaggta    19380
ttgcagaaga tgatcagcat caagccggaa gggttccagc agcagctcgc cgacctgact    19440
gagcttgagc agcggcagat tccttacgcg acagccacgg cccttacgcg gaccgcgcaa    19500
gggctgatgg atcgcttgcg cgatgagatg cgtgtcgtat tcgaccgccc gaccccgtac    19560
accctgaaca gcctccgcat ggtgccggcc aggaaagacc ggctggaagc gcgtgtttgg    19620
ttcaaggacg aagcggacgg tgcgcagcct gcatcggtgt ggattgcccc cgaggtctac    19680
ggtggcccgc gtcggaataa gccggccgag cttcagctta gggccaaggg gatactgccc    19740
gaaggcaagt acgtggtgcc cggcgccggc gcggacctgg atcgctacgg gaacatcagg    19800
cgcggccagg tcaccagggc attgagcggc atccgcggct tcagccaggc cgggtacaac    19860
gcgaacgcta ccgatagcag acggagccga gcgaagggta atgctcgccg ctacttcgtc    19920
atgacccgta agggccagcc cataggcatt gctgagcgca caggccgagg ccgggatgct    19980
gtctcggtca tcatggcctt cgtgtctcgc ccttcgtacc gccgccggct gagcttcttc    20040
```

```
gagatcgcgc agcagtacgc cgacgagaac ctgccacgcg agttcgaggt ggcgatgcgc    20100
ggcgttgctg ctcggttcgc tgcgaggcgc tgactgatgc accaaagtgg tgcgtcgcgg    20160
gtcctccccg gggtgccccc gtcagagggt aattcgagcc ccgcgcgcca aatatgtatg    20220
acctttttc ggaggttggt tgttgttttg tcatgagcac agaagacctc caaaaaaagc    20280
gcggatggct gaacaagtcc gagatggccg cgagcctcgg gatttctccg caagcctttg    20340
ataaatgggg cgttgagcct gccgccaaga tcggccgcga ggtgttctat accgccagg    20400
cggtgctaca gaatcgcctc gatcatgtga cccagaaaca acaacctgag ggcctagatg    20460
cggaaggtct cgacccgctc gctgaaaaga aattgctaca ggagcgcctg cgactgacga    20520
ctgctcaggc tgacgcccag gagcagaaga accaggtcca agcgaagacc cttgttccaa    20580
ctccgttcgc caccttcgct cttgccagga tcgcgtccaa gatcggctcg aaactggaga    20640
cggtctgcaa gacggtccgc agccaaatac ccgatacacc gccgttggtg ctggaggcct    20700
ttgagcgcga gatagcgctg gcccgaaatc tggccgtgga gtttgctgaa gacctaccgg    20760
aaatccttga tgagtactct gccaccctgg atgaatgacc tacggaaagc ggtcgatcta    20820
ggtttgcagg ggctgtacaa gtcgccgccg atgacggcgg tggagtgggc ggaagatccc    20880
gacgacggtt tctacatgtc ggcggaatcc tcgtacaacg agggcaagtg gaagacggcg    20940
ccatttcagg tcgccatcct gaacgccatg ggtaacgacc tgattcgggt cgtaaacttc    21000
gtgaagtcgg cacgcatcgg ctacacgaaa atgctgatgg ccaacatcgg ctacaagatt    21060
cagcacaagc gccgtaatgt gctgatgtgg agcccgactg acccagacgc cgaggggatc    21120
agcaagagcc acgttaatgg cctgattcgc gatgttccgg tgctgctggc gctggcccca    21180
tggtatggcc gcaagcatag cgacaacacg ctcgacacca aggtgtttgc aaaccggcgg    21240
acccttgga cgctcggcgg caaggctgct cgcaactacc gtgagagatc tgccgacgag    21300
gtgatctatg acgagctgtc gaagttcgac gccgatattg aaggtgaagg ttccccaacg    21360
ttccttggcg accaacgtct cgcgcggtgct gttacccga agtccatccg tggatcgacg    21420
cctggtaccg agggccaatg ccagatcacg aaggcggccg atgagtctcc gcgtcgcctg    21480
cggtactaca tcccgtgccc gcattgtggg catgagcaga cgctgaagtg gggcggtaaa    21540
gattgcgcct ttggggtgaa gtacatcgcg aacgatctag gcgaggcctc ttcagtttgg    21600
tacgcctgcg agaacgagcg gtgcagcggg acgtttgagc accacgaaat ggtggttgcc    21660
tccgagcgag gccgctggaa gtgcgaagtg tcggggtctc ggacgcggga cgctatggag    21720
tggttcggcc cggatgacca gccgataagg acgccgcgtt ccgtcgcatt ctactgctgg    21780
gccgtgtaca gcacgtggac cagctggctt gacctgatcg acgaatggct gaaggtcaag    21840
ggtgatcgcg agaagctgaa gaccttcacc aacaccatcc tcggcgaggt atgggttgag    21900
gacgaggggg agcgggtgga gtggcagaca ctctatgccc gccgcgagaa ctacccgaag    21960
gtgccgccgc aagcgcttgt cctgatgggc ggaatcgaca cccaggacga ccgctacgag    22020
ggccgcgttt gggctttcgg cctgggcgag gaggcatggc ttgttcaccg tttcattctg    22080
accggcgatc cggccagcga ggaactgcgc gcaaggtgg gcttggaaat tcatcggcag    22140
ttcactcggg ctgatggcgt tccaatgcgt gtcgagcgtt ggtgctggga tgctggcggc    22200
cactattccg atgaggtaga ggccgagagc atcaagcatg gcgtgcactg ggtggttccg    22260
actttcgggg ccagcacata cggcaagcca atcgccaact tcccgaagcg ccgcaagcgc    22320
aaggtctaca agaccgaact gggcaccgat aacgcgaagg agctgatcta cagccgcctg    22380
```

```
cgcattgatg tgcccatccc gtggcaaccg acgccgggct gtgtgcactt cccgatcgac    22440
agcgacatct gcgacgaaga cgaactgaag cagatcaccg ccgagaagaa gaagccggtg    22500
atggcgaagg gtgttcgcgt cctgcgctgg gattccggcg ggcggcgaaa cgaggcgttg    22560
gattgcttcg tttacgccct tgccgcgctg cgcatcagcc agcaacgctt cggcctcgac    22620
ctcgaccagc tggagcgcgt gcgcgttgat cccgtgccgg agccggtcgc ccaacagcaa    22680
ccttcgaacg ataaccatgc cagcacctcc cagggctggc tcaacactgg aagcggacca    22740
tggctctgac agcgcagcag atgctcgaca aatacctgga ggccgaggcc gccgtgctgg    22800
aagggcggac agtgatcttc aacggacgca cccacaccat ggaggatatc gagaagatcc    22860
gcgccggacg ccaggagtgg gagcgccgcg cagccgcaga gcgggaccgc ccgccggtc    22920 gccgtcctgg cccggcactg gcggagttct gctgatgaac ctgatcgatc gactactgga    22980
acccttggcc cccgagctgg tggctcggcg cttggccgct cgcgaggcaa tccaggcgta    23040
tgaggctgcc aggccagggc gaacccacaa ggccaagcgt cagccgctgg gcgccgacac    23100
ctcgctacag aagtctgcgg tctctatgcg agagcagtgc cggaaactgg acgaagatca    23160
cgatctggtt accggcctgc tcgatcgcct cgaggagagg gtggtgggcg gcagtggtat    23220
cggcgtggaa ccgctgccgc tgcgcctgga tggctcggtg catgctgagt tggccatgga    23280
gatccgcagc gcgtgggccg agtggtcact ctcgccggag acctctggtg agctgacgag    23340
gccccaggta gagcgtctga tgtgccgaac ctggctgcgc gatggcgagg gattggcgca    23400
gaagctgatg ggacgagtcc cgaactacac gtttgccacg tcggtgcctt ttgccctgga    23460
gctgctggag cccgactact tgcccttcag ctacaacaac ctgtcgaaag cattgtcca    23520 gggtatcgag cgtgacacct ggcgccggaa aagggcctat cacctgctca aggatcaccc    23580
cggcaacctg cagacgctgg gcggcagcct ggcggtgaag cgcgtcgaag cggaacggat    23640
catccacatc gcctaccgca agcggatcgg ccagaaccga ggcgtgccga tgttgcacgc    23700
agtgctgatc cgccttgccg acttgaagga ctacgaggag agcgagcggg tggcggcgcg    23760
catcagtgct gccctggcga tgtatatcaa gaagggcaac cccgacagct acacggtgga    23820
gcccgggaag gaccggaaga accgaacgat ccccatcgcc cccggcatgg tcttcgacga    23880
cctcgagcca ggtgaagacg tcgggatgat cgagagcaac cggccgaacc ccttccttga    23940
aggtttccgc aacggccagc tgcggatgat cggcgctggc actcgcagca cctactcctc    24000
ggtgtccagg gcctacgacg gcacctactc ggcacagcgc caggaactgg tcgagggctg    24060
gctgggctac gacctgttgc agcacgagtt catcgactac tggtgccggc ctgtctatcg    24120
gtcctggctg cagatgtacc tgttggctcg gaaggagcgc ctgcccgccg acgttgatca    24180
ccgcactctc tacgcggcgg tctaccaggg gccggtcatg ccatggatta acccgatgca    24240
tgaggccaac gcatgggagt tgctggtcaa ggccggcttc gccgatgagg cggaagttgc    24300
ccgcgctcgt ggtcgagatc cgcgcgagct gaagaagtcg cgtgagacgg agatcaaggc    24360
gaaccgggca gccggcctgg tcttcagttc ggatgcctac caccaactgg tcaagtccgg    24420
gatggacccg gttgaggcgg tgcagaaagt gtatctgggc gtcgggaaga tgcttaccgc    24480
cgacgaggct cgcgagctcg tcaacagata cggcgccggc ctaccgtgc ctgggccgga    24540 tttccccaac gagagcaaca atggaggcgc cgatgggcag ccatcaaacc ctgatccata    24600
aaagcctgat gctgccgatg gcggcggcgt tgactgaggc caacgccccg catgagtcct    24660
ggtacagcat caaggctgcc ggtcgcgcg tcgccgaggt gctgttgtac gacgagatcg    24720
gcgtctgggg catcaccgcg ctgcagttcg ctcgagacct caaggcaatg ggcgacctga    24780
```

```
acaagatcaa cctgcacatc cactccccgg gcggcgacgt cttcgagggg acggcgatct   24840
ataacctgct gcgcaaccac ccggccagcg tcgacgtgta catcgatggc ttggcggcct   24900
cgatggcctc ggtcatcgcc atggccgag acaccatcta catgcccgag aacgccatga   24960
tgatggtgca taagccctgg ggcatccagg cggagatgc ggacgacatg cgccgctatg   25020
ccgaactgct cgacaaggtc gaggacaccc tggtcatggc ctacgccaac aagaccggga   25080
agtccgccga cgacatcaag gcgctcctca aggaggagac ctggatgaat ggccgagagg   25140
ccgtcgctgc cggtttcgcc gaccagctca ctgagccgct gcaagcggcc gctcaccttt   25200
cctccaaacg catgcaggag ttcgcccaca tgcccgaagc tctgaaaact ctactggccc   25260
cgcgcgccca accccgcc gcgccgacca acactcccgc gccgactccg gcaccggccg   25320
tgccggcggc tcccgtggcc gccgccccaa ccgaggccga tattcgcgcc cgcatcctcg   25380
ccgaggaatc tggtcgccgc agcgcaatca ctgctgcctt cggcgcgttt gccagcgggc   25440
acgccgaact gctcgccacc tgcctgaacg acatgaccat caccgtcgac caggcacgcg   25500
agaagctgct ggctgccatt ggcgccgata ccaagccggc cgccacccct ggcgctggcg   25560
cccacatcca tgccggcaac ggcaacctgg tgggcgactc ggtgcgcgcg agcgtgctgg   25620
cccgcatcgg tcgcggcgag cgccaggccg ataacgccta caacggcatg acgctccgcg   25680
aactggcccg tgcctcgctg gtcgatcgcg ggatcggcgt ggcctcgctc aacgcccgc   25740 aaatggtcgg cttggccttc acccacactt ccagcgactt cggcctgatc cttctggacg   25800
tcgccaacaa gtcggtgctg gcgggctggg aagaggccga agaaaccttc ccgctgtgga   25860
ccaagcccgg cattctcact gacttcaagc cggcgcgccg cgtcggtctg ggcgagtttt   25920
cctcgctgcg tcaggtgcgt gagggcgccg agtacaagta cgtcacccttt ggcgagcgcg   25980 gcgagcagat catcctggct acctacggag agctgttcag catcacccgt caggcgatca   26040
tcaacgacga cctgcagatg ctctcggata tcccgttcaa gctgggccag gcggccaagg   26100
ccaccatcgg cgacctggtc tatgcggttc tgaccggtaa cccggcgatg agcgatggca   26160
aggccctgtt ccatgccgac cacagcaacc tgctcactgg cgcggcttcg gcgcttttcca   26220 tcgacagcct gagcaaggcc aagacccaga tggccaccca gaaagccag gtagagaagg   26280 gcaaggggcg cacccctcaac atccgtccgg gcttcgttct gactccggtg gcactcgagg   26340
acaaggccaa ccagatcatc aactccgagt ccgtgccggg cgccgacgtc aatagcggca   26400
tcgttaaccc gattcgcgca ttcgcgcagg tgatcggcga ccgcgcctg gacgatgcct   26460 cggcgaccgc ctggtacatg gctgccaaga aaggctctga caccatcgaa gtggcctacc   26520
tggacggcgt cgataccccg tacctggagc aacaggaagg cttcactgtc gacggcgtgg   26580
ccagcaaggt gcgcatcgac gctggcgtgg cgccgctgga cttccgcggg ctgcagaaat   26640
ccaacggtgc ctgatcggcg ccaactcccg agcccgcac ctagcggggc tttctgtttc   26700
tgccattagg agaatcaacc atggcgaaga actatgtgga ggacggcaac gtcctgactc   26760
tcattgcgcc cgctggcggc gttcagtccg gcgtacctgc ggtgatcgga gacctggtgg   26820
tggtgccgct ggtagatgcc gccgcgggcg agccgttcgc cggaaaaact ggcggcgtct   26880
ggagcctgcc tgctgccgca ggcctgaccc agggtgccaa gtgcagcgtg ctcgatgggg   26940
agctggttgc tgctgccact gccgactcgg tggcgttcgg caagatcacc gagcccaccg   27000
ttgacggctt cgcgtcggcg atgctgatcc aacaatgagc gcgccgggcc gttttggccg   27060
gctgatccaa cggctccacg agcgtgggca agagcggtta tctgatgccg tgggcgagtt   27120
```

```
ccgcggcatc ggtcgccccc cgatcaaggg gataccctctg caggtcgatc gaaacctcag    27180
ttacgacggg cctgatgggg ttttcatcac ggacaaggtt gggatcagtt ggctggcgaa    27240
agatgttccc acggcatcgc gtggcgacct cttcgttatc gggtcgtcgc gctatctcgt    27300
cgaaaagctc attgcgaacg acggttggtt gctgacggca gcaacgatcg aggaggaagc    27360
atgaagccga acgtgctcac gatcggccgc ttggccttgc tggcgcgcct gcaaaccatc    27420
acgccaaacc agggataccg gacggacgcg ggcactcgcg tgctctctgg gtggtttaac    27480
gagctggtca aggagcggca tgagggcttt ccgctgattg tcgtccagcc gggcaaggag    27540
cagccgccgg agcatcttga tgccgccgtt cgcttccatc gtggcttcga cgtggtaggt    27600
gcggtgcaag gtgggtatga ccactatgag gaggctctgg aggacctaca gctagacctt    27660
ctggcgtgtc tgatgcctgc ccccaagggt cagttcctgc gctggctgcc ccgagagcgc    27720
ggcattaccg gggtgacgtt gggggcgcct gagccgtacc cgccgggcga tggagtggcc    27780
gctgccgtga ttcgaatccc tgtgtatctg aaaaccatca tcgaggcgta acccatgaag    27840
agcgatcccc aggtgccggc cgcggtcgac gccgcgccgc cggctgcgct gaacaaggcc    27900
gtcgaggtca ccctggccaa ggtgcattgg caccagggca aggagaaggc ggccggcgaa    27960
aagatcaacg tcagccctga ccaggttgaa ttcctgcgcc gcgaaggcgt gatcaagaag    28020
gaggcctgat atggctatcg agaaagagac gtacgtgatc ggcggacccct tcaagatccg    28080 cgagtccggc gctaccaccc ccttccagtt cgctggcctg gtgtccacta ccaacagac    28140 catcgagacc aacgagatca ctctgccgga taccaccacc ccgcagggcg gtgagtacga    28200
tgccgtttcg cgcatcactt cggtcggttt gtcgatcaac ttccgcgagc tcaagaccag    28260
catcctggct gccttggtgt ggggtgacgc caccaacgtt ccttctgcca cccacaccga    28320
cgaagcgcac accgccgttc caggaggcac gatcgcgctc gacttcatgc cgctggagat    28380
caccagcgtg aagagtgatg acggcaccac gacctacgaa gagttcgacg actggaacat    28440
gaccggcgcg ggtatcgaaa tcgttgaagg gggtgcgatc tctgcggcca cgccgatcaa    28500
ggtgacttac aagtccgcca ccgttgatgt gatcgaagcg ctgaccaaca gcggcaagac    28560
gttcgaatgc ctcttcgagg gtgagaacgc agccggtacc cagcgccgta tccaggcgcg    28620
ctatttccgg tgccgcctga acccgtcgag ccaacaggac tggctcaata ccgaagactt    28680
cctcgctgcc gaggccactg ccaaggttct gatggacccg accaaggtcg gcgctggaaa    28740
gtcgaagtac ttcaacatca gaaggaact ggcgacggtg tgacgccgtt catgcccggc    28800
agggacgccg gatgttggtt cgcccgcgtg gtgctacagt ggcggcattt agggaggggt    28860
tgaaatgtac tctaggtcgc gcggattttc ccttatcgag ttgatggttg tggtcgtact    28920
cttggccgtt ttggcattca tggccgttcc gagctttaag gctatgcagg aggggaacaa    28980
ccatctagcc ggcaaagaag ttttctcca gcacctggaa tttgccaggt cctatgcgct    29040
gtcaaaaaag acaactgtcg aagtctgtgc agaaagtgga gggtggactg acggatatat    29100
cgtccgcact gattctggta agactgtttt gcttaaggaa aataagtata aaacatcca    29160 tccagttgga gcgtggaaag gctctatgga gtctgggtgt gtgcgattcg tatccaatgg    29220
gagcgcaccc gcggtgcctg ccccggcggg ggagtattac gactctggtt tcttcggtgg    29280
tgaagagctg gacaaggctg cttggcgggt gacgttcaag ccgtctggct ggaactgcac    29340
tgagaaagat cctaaagacc ctaagtgcgc caagaaacca acctgatcgc cggcttgtgt    29400
tcttggtaat ggcctgttga tgctaaagtg tgaagcggtt ccaatggaga gtcgcttatg    29460
acacggattt ttcccgttct cgccttgatt cttgcggtca gttctgccag tggggcgacg    29520
```

```
gtctttaagt gcgtcggccc tgacggaaaa gtcactttta cccagcagaa ttgccctgac  29580
aaccaatcgc tgaacgatgt ggtttctgcc accaaccagc gcccaagcgg gtcaggtgcc  29640
tcggctgtca tggccaagcc caagcagcca tcaggtcgta cctatagagg tagtcaccag  29700
gtcggcagcg gagtgatcgt cgtcggtggt tcgtcgccaa gccctacgtg ttccacagga  29760
ctctctgagc gtgaccttcg caaggccaag gtccagggca aggtcgttcc tggaatgtcc  29820
agggaggacg tggaaagcat ctacgggaag gtgaaccgca acggcagtac cgccggcgcg  29880
ggtgctgtca cctactggaa tgacaagtat gttgaccaga cgaccgtttc gtttgatcgt  29940
aacgatgcgc tccagggttc ataccaatcg ggccacaaga actagccgat ataacgcttt  30000
ttaaacagcc ccgccattcg gcggggtttg tgctttctgg agggttgaaa tgtccagctt  30060
tactgcaagt agagttgtag atattgatgg cgttgagttg accgtgcggg aacttagcgt  30120
tgcggatgtt cgaaagctaa tgcaagaggt cagcgatcaa gacctcgtca caatgtcct   30180 cttcgaagat atcaggcttt ccgatctgtg cctgatgacg tcggttacga agagccaaat  30240
taacgatctc cggcctagcc aactcgccaa gttgcgggat gcatgtaaag aggtgaaccc  30300 gcatttttc ggaatgctgg gccgtctctc gaaactccac gacaagccat aaggagtttg   30360
gagcgcgcca tttgcgttct ggtgaggctt ggccatcacc acgtccttga atatccctgg  30420
tcactgttct tgaccgcgct gaaggctgaa tgaaatggct gacgtaaaga tccggctgac  30480
cgctgacctc gatgatgcgc tgcgcgaggt gtcaggcttc cgcaaggaat atgccgaact  30540
ggtcaggcag gtcgcgcaac ctctcaagcg tttaaacgat ttcactgctc tcgaaagcac  30600
cctcgaggac acgcaacgcc aggcgcgttc ggcgcgcgag cagatccgta cgctcggcaa  30660
cgagctggca tcgacgatca ggccgagtcg cgaattgcag caggcttacc gggactccat  30720
ttcggacctg cgaagcctgg agcgggcaga gaccgtccag gtagccaagc tcggagcgat  30780
gcgccgggag ttgaagcagg ccgggctgga tacgaggagc ctgacatccg aacggcagcg  30840
gctccagcgg gagctggatc gaaacctcca ggcgggccgg aatgacgcgg ccaccaccag  30900
cctccggcaa caggccgcag cgatcaagca gagcgcgata gagcagcgcc gcttcaactt  30960
ggagcaagcg cgtagcaccc tgggagtcgc cagggtgcgc gaactgcagg ctgctatcgg  31020
gcagttgaac cagcaatatc gcttgcttcg gtcgagcgga acgctgtcca caagggaact  31080
tgccgttgcg cagcgggcgc tcaaaaagca gatcgcggag accaagagcg aactcaactc  31140
gcttggtgcc ggctcgcggc tgtcgagcat cggctctcta cgcgggagcg gtccagcgct  31200
ggcggttgcg ggtctcgcag ccgcagtagg tgctgcaacg gcgaagctag cgaacggcgc  31260
cgatactgtt ggccggctcg attcccggct tcgcctggcg accccgctcgc aggaagagtt  31320 caacactgcg cagatcgaac tcgaccgtat cgcggatgat gttcagggcg acgtcggcga  31380
cctcatcggc ctttattcga ggttgcagcg cccgcttcgg gatgcgggca tggatcagcg  31440
cgccgccctc gaaaccgtag aggcggtatc ccttggcctg aaaatcggtg gagcctctgc  31500
cgaggagtcg gcgtcggtca ttacccagtt ctcccaggct attgccagtg gcgtcctgcg  31560
gggcgaagag ttcaataccg ttctggagtc ctcggatcga attgctggcg ctctggcgga  31620
ctccttcggg gtgactgttg gccggcttcg tgagatggct gccgcggtg agttgacctc   31680 ggagcagatc gttatcgcgc tgaggaagga acttccgaag ctccgcgagg agatggcttc  31740
gtttgcgccg gagatcggcg cggggttgaa ccggatcttt tccgaaaccc agaaatattg  31800
ggggcgcaga gcgaaggaaa caggcatcgt cgactgggtt gcgaaccagt tgaacgatgt  31860
```

```
tgccaagggg atcaacacgg cgaatacgct ggtgaaaaag ggcgagggca gcctcacggc    31920
caccctcgcc gccgagaagg cgcgtcaaga gcagatcgtg aagcgccaga acgatgccct    31980
gaagcgggct cgggatcaga acgtcgctga tctccagtct gaggttgttc ggaccaaggc    32040
cctacttgag cagtccacca agaacctcaa cgacgcgctt tcgcgccagg cagatgtccg    32100
caaggagttt gccgacctgg tgaagggcat ccaggcgacg cccacctccg gaacgcagac    32160
cttcggtgat gccactgcgg cccaggcctc ggctcgcaac gcgctgaccg ccggcaacaa    32220
ccaaaaggcg atcgaggagg cgcgccgcgc gctgcagatc cttcagcaac tgaaggacgc    32280
tggcgcgaac agctatggct tcgaaggcgt ggccaaagag gtggagcgca tcgccaacaa    32340
ggccgcagag gtcgaggctg gtaatgccaa ggctgcggat gacgtcaacc gcctgaacct    32400
ggccgacctc gaggagcgca tcaaggctgt gcaaaacgtc gaggtgtcgt tcggaatgga    32460
cttcgaaagc gcggagacct tgaagcaaca ggtcgccgac atcgccgccg gactggctga    32520
gcagctcgtg atacctatca cgctggttcc gcctccggag atgggcttgc ctggcgtgcc    32580
cagcatcacc cccaagatac ccgggtttgc cactggtacg cagagcgctc cccctggtat    32640
ggcgtgggtt ggggagcgtg ggccggagtt gatgatgatg cgcggaggag agcgcatctt    32700
caacgcggtg cagtcgctgc agatgtcgca gaggtatcaa cgaactctcc ccgagatacc    32760
cgagattccg actgcggcgc ttcagcaggc gaatccgccg gcagccatgc aaaacctggg    32820
atcgctgacc ctcaacctgg gtggagacga tgccggtttc accgttttcg ggacacacga    32880
cacgctccga gatatacgca aggccgcttc gaagttcggg cggacgcgcc caaaatgacc    32940
aagcccgcct cgcgcgggct ttttttatgg agttgggaat gatcattccg aacgtgatgc    33000
ttgggggcgt accgatcgtg atacacggcg gcgccccgca gtgtcagtac caggctgtag    33060
atggcggcgt cgagcgattg aggctcagcg gaggtgcggc agtacagatg acgcactggc    33120
gcaagacggc aatcaccatc agcggttcag gatggatcgg cacggggatg cttggactcg    33180
acttcgacaa cccgttggag ctgcgatgca atgcgtcgct tggcatttcc ggccgtactg    33240
ccgccgaccg agtattcaca atccctggag aggttcgccc cgatgccagt ccgtgggggc    33300
tggcgctggt cggccgtgag tgggtcagaa cggacgtgtc gtccgccggc caggtggtaa    33360
ccgtgtcgga gatcccaggc gcgcaactct accgcgtcga gtggtggccg ctgttccacg    33420
tcttcgcgtc ggtccctcct gaagcgcttg attcttcgaa caacagccgg acctggcaaa    33480
ttgtcgctga ggaaatctga tgctcaacgg tggaccgctc aatagcgctg agctgaactc    33540
ggccgctcaa tccgttgtgc ctggtcctga gccgatcatt ccaggctacg ctttcacctg    33600
gcgagcaatc gtgcgtgttg gcgatgacga cgttacaccg ctcctgaccg gggagatcga    33660
ggtcgatcgt gaagaggggg cggctggcgt cgcttccttt tcgatctatc tcggcgacgg    33720
ccctgttgtc cctacggact ggattggtcg aaccgtaacc atcgactacg caacggagac    33780
cgccggcgag ctgagtcagg gccggcggtt tacgggaagg gttacgcagc cagcctggaa    33840
tcctgttcgg cgcgtcctgg acgtcagttg cactgaccag ttgcagcagc gtgtagaggc    33900
catggagatt gcggccgttg acgccttggt cggcggcgcc tggtccgccg atgtgttcga    33960
gccggtcgat ggacgctcgc ggtgggacta cgcccaggag cgtttgacca gcgttaccgg    34020
gagcttggac tgttcgccat acggcgctct ccgcgtcacg tcatggcttt cggtggctcc    34080
tgccttcgag ttcggccaag gctctacggt atacgggtcg cttgcggtcg agttggccga    34140
cctgagttcg cagacgaaca ggatcgagat cgagtgcgac taccgattca gccggctctg    34200
gcagttgaac gcatcgtatg gatggcagca ccccgggacg ggtaacgctg ttggcgaggc    34260
```

```
ggggttctgt aattggcgcg gcgacgacac cgagctaccg gatgtcgaga tgatcacctc   34320
agcgaccgaa agcagcggcc agacgttgtt ctatgcgacc tggtatccac ttccgcccac   34380
gggcgtctac tgcaatccgc cggcggcatg gagaaatgac ttcaccgagc tgctgctcgg   34440
cggaaattgg atagctggcc ggcgctgggt gcagtccgtc acagagcgct accggctggt   34500
catggaagtt cagccgagcg ttgcggcgac cggtccgatt gtcggtcggc agcgcgcctc   34560
gttcgagatc gagtcggaca aggccgagcg ctgggaaagc gacccgatca ccggcggcag   34620
caccggccac gacgacgaga aggatggaag ccggcgtttg tccgcgctga actgcttgtt   34680
ggcccagggc gccacgacgc tcattgctgc gcatcgcggc acgaccgtga cctgggatgt   34740
gccgacgtcc atggtcctgc cgatcgatct tgtacatacg ctccgcctcg atgatcaggg   34800
cgcgcgtgcg gtgggcaagt gtcgacgcat tgtcgaccgg ctcgacctcg catccggaag   34860
cgcgctgacc acgatctcta tcgctgtgat gcgaggcggc ggtggcgcag cagaccccct   34920
tgttcctcct gctggctcgt ccggtcccgt cagcccaccg tcgggcgggg gacagctctc   34980
gacgcagctt ggaggccgca acggcagccc cccttatgac gatgatgcgg acggattctc   35040
cgggaactgg agcaaccgcg atcctggcgc cgagttgttc ccgcgcgcgct tttcgttgac   35100 cgcaaacgac attccggaga cctaccggga cgagcatgcg ccggagatcg cggccaccta   35160
ccgggtatct gtacctgatg acgtactgga gatgtagcga tggcgagagc ctggatcaac   35220
aactggaaga cgacgctgag cgccggcttg gcgcctggcg ccactagcct gacggttccg   35280
gatgccgccg ccgcgttact gcctctctcc ggcggtagct gggttctgtt gacgctggcg   35340
gatgccgctg gcgcgcagca tgaaatcgtg aaggcaaccg tccgcgcggg cggtgtgctg   35400
acgattgagc gccgacagga aggaacaact gatggcacct ggccggcggg aacggcgatc   35460
tatgcagccg tcacggccgg cgatctcatg gcactgcaag cgcgaatcgc ggcccttgag   35520
ggcggcactc ccgacggagc cctggtcgat gcgagcggtt cggccctcgt cgatggcgcc   35580
ggaaacaacc tgatcatgga gaacatttga tggcaactgt tacgcacgtc ctgtccggtg   35640
ctggcgctcc accctcggcc ccgcccagcg tgggcgctca ttacgtaaac acgacaaacg   35700
gtgaccaata ccttgccaag ggcacggcct ctgcggcgga ttgggtgaag cagggcgcg   35760 gcggtggaag cgctcccctcc gaagtactgc acataactgg cgcgggcagt ttctcgcttg   35820
ggccgcagca cgcagttgtc gaggcgcctc tgaataacat tcctgagaac gagatcgggg   35880
ctgtcgatat cgacacagcc tcttctcggc aatttgattt gcacgtcaag gggaacgcag   35940
attcagtgtt ttttgtcggg accgcgggtg gcgtcgactt gccgggtggg acgttcatcg   36000
tcgggatgca gaggaattgg gcttcaaccc gcgagtatgg attccagatc cgaggcatag   36060
acctagctgt tgaggcctgg gcgcgggtgt attacgacgc cggcgccgga actatgacca   36120
tgcttgtgct cgctgacgtg ccagcgccgg cataaggagg tggatcatgg ctctatcaga   36180
tgagcgccgc ggcatcggcg caaggaacga agcgatccgc cgcgccggcg ccagcgggt   36240 cgaagcggag cgacgcggtg accagggctt gacggcggcg ctcaaccggc tgatcgagcc   36300
ggagcgtcag gcgcgcgcac tgcgcaagat cgatccgcgc ggcgccctgg atgcaaagcg   36360
cgggcgggcg gactacaacc ccgccggaaa gcagctcggt gggggtggcg gtattgcgag   36420
ccccctgatc gaagaagatg ccgcccagcg cgaatactac gaactgcaga caatccccac   36480
cagcgatggc ctgcctggc tccggtatcg cagcgtgaag aagatcgtca tgaccgacgc   36540
gtcaggcgca gaagttgtga tggagtacgc gaacgatgtt tcccaatagc ccgctcgatg   36600
```

```
aagctccgca ggtatggggg tggccatggc acggcctaat acgacagcca atcaacgccg   36660
ttgattcgac attgacgtta ccaagcgggc gaacgatgaa gatgccggcg gtcaggacag   36720
caaatgatac tgcgctctgg agtgtaggta tgcctgtccc gaacgtcgaa accgatgacc   36780
ctgacgagcg ctggctcaac cgagcgatca tgcgcgaaac cggactagcc gaggcatacg   36840 gagggtatc actccagccg gcattcatcc gtgggtacac cgtccgttgc ggcgttgagg    36900
ttacgttcaa ttcatttctc ggaacagcct ccgcaatctg ctctattcgg gatggtgtaa   36960
caggattcgt tgggcagatt acaagcaaca ccattgcgcc ttctgcgctg ggtatccccg   37020
tccagccagc aggtatgtct tttcaagtcc tagatgtaaa tcacgacgga acgcgccgag   37080
tgttccgcgt cgactatcaa gaaactgttg acggaacggt gattgccggc ggcatggtgg   37140
aggtgcgcat tagcccaagc ggagcgtccg gatttcaagc tgagttggtt gtcgtggcta   37200
cgtggagtca ggtccagttt acaacgttgt ccagcagtaa gccggacgtt gacccggata   37260
ctcatacgcg gttctggtgg acagtgcga gcggctctta cgtttcggga acaagcgatc    37320
cccctggcat tcctgtggat acaagggtgc ttcaggggc atggacggcg actctgcggg    37380
cagagtcgat tgctgccgct tggtacggag tttcaggaga tcttgagttc gtacatatcg   37440
aggtatctgt ctctcattct ctccagccgcg cagcaagtgc ggcaggcgat catgttgcat   37500
tcaatcaaac ggacgattgg gtggttgact acagattgcg atctgcgtca ggagaggtgt   37560
tggagacgct gcgaaataaa gtcgaaatat cggggccaat atacaatgac ggtggccctg   37620
ggaccgcaaa cataaccgat agcatcagcg ggcaaacagt cgcaactggt acccggccga   37680
taactctgca agatcaaaat atctatacgc cagacgtggg agatacctac gcgagagggt   37740
tgaattgggg ctctcgctac catgtgtttc caatcgcggc cgacggatat ctttcgtcgt   37800
ttgctgccca atacgcatgg ccagtccagc gatactccaa caagatgttg ggcatcatag   37860
cggttcgaaa tagcgctatc ggaactccag atgagcgcta tcggcttgcc ggagttgcat   37920 tcacccccgca tggcgtacac ggaacccgtc aggttgacgt agatgttggt gcgtattcag   37980
gcatccagtt cgaggcttgg agtaagggcg catataaccc aatcaccggc gacgctatac   38040
gcaacgaccc gaacgccttc tattcctacg tttgattcct tccaaaggag aagccgcatg   38100
acgccggcct gtgtaccccct gcgcattgaa aaaggggcga cgttccgcga cacgatgcgg   38160
atcatgcaac cgagccttgt ctaccggccg atcacccaga tcgcgccggc tgctcccgtc   38220
cggctgacca tccctgggca cggattgcct ggcacgtggc tggcctggat cgatggtgtc   38280
cagggcatgc ccgaactgaa ccgcgctcga cttcggcaat gccccaccg gtcgcgtcc    38340 atcgacgaca acaccgtcga gatcaacctg ctttcagccg ttgggctggc gcctgtgggc   38400
gggcaattga tctaccagcc acccgttgac ctggctggcg ccgaggtacg gatgcagatc   38460
cgcgacgcgc caggcgggac tgtgctgatg acgctggcgc tcggctccgg ccttgagatc   38520
gctggcgccg gaacgatctc gcgcgagata tcggcatcgg ctaccgcggc gctgaatgg    38580 tcggcggcgg tctacgacgt ggacgtgaca tacccggatg gaacggtcca tcgctactac   38640
agcggtccga tcactgtgag ccgtgggga gggtgcgatg gatgacaccg ccgagccctg    38700
ggcgctggcg atcgaggttg attgcgagcc gcttgtgctc agcgagatgc aggaatacgc   38760
ggtcaccgtg acgccgccgg ccgatgtgct tgtggttgtt gcgggtgacc aagggcctcc   38820
cgggagggat ggcgtagacg gtgcccaatg gggcgcgact gattggtgat gacatggccc   38880
agattcgatt tttcaaagtg gcgaccctgc cgggtacgct ggaacccgat tcgttctact   38940
tcgtcgagaa cggcagctac tcggagtcct acctgacgaa cagcgccgga gtggcgcgct   39000
```

| | |
|---|---|
| cgatcggtaa cagcgcgatg atcaacgcgc tgatcaacga ggcgctgtcc agcctacccg | 39060 |
| gaaccggcgc gccgatcctg ttcgttgcgg atatcgccgc gcgcgacgct ctggagccgg | 39120 |
| agtcggcgat attcgttctg gttcaagacg cttccgccga ctcgacagtc gaatccggcg | 39180 |
| ctgcgttgta cgcatggaac cctgcgacca gcgcctggct gaaggtggcc gagtatgagt | 39240 |
| cgatggacgt cgagctcaac tgggacgcga tcaacgggcg cccgacgtcg acgccagcgc | 39300 |
| agatcgacac cgccgtttct caggcgcaca cgcacgcgaa caagtcgacg ctcgacaagt | 39360 |
| tcagcgaaga cggcggcctg gtgcgcttca acggccagcc gatcccggcc gagtggaatg | 39420 |
| ggacggcctg gtaatggccg tcctccagac ccacaaggtc gtggcgcaac tccccgcgtc | 39480 |
| cctggagccg aacgcgatct acttcgtccg gcgcagcacc ggctacgacc agttcgtcac | 39540 |
| caatggcgcg ggtgtggtgg tggcctatcc gatgaacgtc cgcatccctg cggctgtgcc | 39600 |
| gggctatctc gccgacggct ccatgcttcg gctcacgatg aaccctgacg gccaactgcc | 39660 |
| ggcgtacacc gccggcggcg caactctcaa cctgcaggtg cttttcaatg gctgatgtac | 39720 |
| gcccgacgaa actccaggcc gacggaaacg gctatggcag cctccgcgag ttctccgatg | 39780 |
| gcgacacggt gccgattgcc ctgggtggta ctggcgctgc aaccgctgct ggcgctcgca | 39840 |
| catcccttgg acttgggagt gctgcagtta gagctgccct gggttcaact ggggctttgt | 39900 |
| actgcgagaa cagcatcctt ggctcggttt cgcagtcgag cggggtgcca actgcgcag | 39960 |
| tgatccagcg gggtagtaat gcgaacggtg agttcgtgcg gttcgctgat ggaacgcaaa | 40020 |
| tatgcatagt cacgttgttg ggcgacggta gtcagcagcc aggtacgtct atatcactgc | 40080 |
| ccctgccggc tgcatttctg ggtaattgga ccaccggtgt cagcgtgagt tgggcgtcgc | 40140 |
| atgtgagcaa cccttctgtg gcaaacgggc tgaaagttgc ctatgcaaac ggctcgacat | 40200 |
| tgttcttcat ccttcaggac gcactggcca ccaatcgttt gattttcact ttggtaggga | 40260 |
| gatggttctg atgatcatca agttgtcacc gtacgcacca ctgccaggca gcgacgagca | 40320 |
| cctgtcgctg agcagggccg gcgatgtgct caccgtgaac ggccagtcgt tcgacttcac | 40380 |
| tccgctcccg gacggcggcg agttgccggc cgaggctatc gggtcggagt ggttcgctgg | 40440 |
| ttccgcagtg cgacgtggcg accggctgga gttgatcctg cggttcccgc ttgctgccga | 40500 |
| tgccagtggc gccgctcgct tccctgaacc gttgctgatc gaggccgatg gcccggtgga | 40560 |
| gttaccgcga tgatcgactg gagcaaggta aagaccactg aacagcaggc gcaagatcgc | 40620 |
| aggcaggctg agtacgatgc cgcagccgcg gcgcgggcaa atgcctaccg cctggaaagt | 40680 |
| gacccgctca agaccgaggc tgaattcgat gcgatcaagg caggcaccga gccggactac | 40740 |
| agcgcctgga tcgccaaggt cgaggagatc aaggccaggt ataagctgcc ggacgcgggc | 40800 |
| ggcgtgtaga ctaccatttt tgaatgggag catgaccgtg ctggtggtga gactcaagaa | 40860 |
| agggtggacg ctgaagcttg atcggaaagt gaacgatgcg aatcgggcgg gggtttggtc | 40920 |
| gttccattgc tccgagagca cgttcgtgcc gggcatggat aacttgctgc ggcacgcggc | 40980 |
| catccgtccg gctgagccgg cagaagggaa gagcaccgag gtagaggtgg ccatctgtcg | 41040 |
| gccaggtgat ccggaggaga agtggattcc ggtggggaag ggcgtggcgg tctacgaggc | 41100 |
| agagcgctga tttggtcttt ttttcctcca aaacgctacc gtaagcattt gattctgttg | 41160 |
| gcttgcgga | 41169 |

<210> SEQ ID NO 3
<211> LENGTH: 50657
<212> TYPE: DNA

<213> ORGANISM: Artificial Sequence
<220> FEATURE:
<223> OTHER INFORMATION: Synthetic construct

<400> SEQUENCE: 3

| | | | | | |
|---|---|---|---|---|---|
| aatcatccgg | ggtgggagat | ccctgttctt | cggctgcttc | ggccgcattt | caactcacct | 60 |
| tcgacagatc | cagcgtccac | ggttcctgta | cagcgaccgt | tccgttcggt | ttcactccgg | 120 |
| ccagccgcag | gcgggcatag | atccgcccga | cgacgggtcg | ctgcgcagca | ttcaattcgt | 180 |
| acttccagcc | atgagatgcc | agccactcga | cctgtttttt | cgatgacttg | gcgccgatca | 240 |
| tggcctccaa | ctcctccttc | gagaggaact | cagatgggt | ttccatgggc | aatgcctctc | 300 |
| cgcccaggcg | atcgcccggg | accgaaattg | agtgttagga | ttctcgcccc | agccgggact | 360 |
| ggcctcagga | gaggccgtg | gtggctcccg | gctggggact | ttgcgatatg | catgcccggt | 420 |
| cgagacgttc | gatctcggcc | agcgccaggg | cgcaggcctt | taccaggtcg | cgtcgtgcgg | 480 |
| tactcggctt | ccaccactgt | tcatcccagg | gccatgccag | cgacaccagc | agggcggcgg | 540 |
| ttccatcgtt | cggagcgctg | gagccggcca | gggcgtagca | ggcggcggcg | cgggccatct | 600 |
| gtccatcggc | gtgctcgtcg | tcgtgctccg | gcgtccagcc | ctcggcggtg | atctgccggc | 660 |
| ggcgctcggc | ctggacgtcg | agccacgcct | gcggcacttg | cccagccggg | gcagtgatgt | 720 |
| tcgcctccgc | gaccaggtcg | taacgacaac | cacactccgg | gcaagctgcc | gccatgcagt | 780 |
| tctcacccgc | gcaccctggg | cacttgtcct | catccggttc | tggtccagtc | caattgcagt | 840 |
| catggcaagc | ggcgtagtcg | gcggcgtcgt | tgatgccgat | gtgccggcag | ttcgcgcaca | 900 |
| ttctggcctc | ggcgtagccc | gcgctgtgct | gagcctgggt | gagcacgtcg | gcggatatgg | 960 |
| cgcgcaaaaa | gttctgaatt | gctcgcatat | cttcctcgct | gggttcgtta | cgcagataca | 1020 |
| gcactacagc | tctgggatgt | tcggcatcgc | gaccgatgcc | agatatttcc | ggcacgctgt | 1080 |
| gctgagcctg | ggctacaggg | gcggcgtaga | gtggaatcgt | gtaatgctcg | ctgacatcga | 1140 |
| gtgggcgata | gattcctcta | ctactgcccg | gcacgcgctg | tagcagatcc | ttgacgtctc | 1200 |
| gatggatgac | atcgacgcgg | tttggctgat | cgtgcatcca | tgccaccggc | tgctgcctct | 1260 |
| ccagctctgc | gacccggcc | agggcggcgt | catgtgcctc | gcacttttcc | agcatgtagc | 1320 |
| gcagcgaatc | cagcagttcg | cctttgtccg | ggttcatacc | gatgtcgtgg | ccgatggctt | 1380 |
| cccacgcctc | cagaacggtg | atcacctcgg | agcggaaccc | ggaataccag | agctttaccg | 1440 |
| cttcttcctt | gtgcagcggg | tagccgagcc | cggctgcttc | aagctcgtcc | tcggttggcc | 1500 |
| cctccggccg | ctccgcctct | gcctgctcag | gcctgagtgc | ttcatcggga | gcttcgttga | 1560 |
| acgcttccgc | atgcggggcg | aggttgagcg | ggtcgagctg | ctcgcgaaac | gcctggagcc | 1620 |
| gctcgatgcg | ctccgcctct | ttctccggag | tggactcgaa | ctcgttcagc | cgctgggcgg | 1680 |
| cttcgactac | cagccgcgac | gacacgccag | cgctgaagcg | gacgccacct | accttggctg | 1740 |
| gctgttccag | cttgggccag | tggttgaatg | ctcggcgggc | gagggtaatg | tcgcagaccg | 1800 |
| cagccggaac | aggctggccg | tcctcgccct | cgagttcgtt | ggccagccac | tcttcgaagc | 1860 |
| tggcttcata | ctgagactgg | gagggttgcg | ccagggcggc | gcggaactgc | cacgcttccc | 1920 |
| acgcccattg | agtttgcggc | atatagaggt | ctggtcgtag | cggctgccga | tccatcggta | 1980 |
| aatgcgtagc | ccacgcctcg | aacgccgccc | gctcatcccc | gcctgcctgc | tctaccggtg | 2040 |
| ccggcgggtc | acgaagcggt | gtgccggcca | agcccttggc | ggccaggtag | ttggtggcgc | 2100 |
| gcgccaccag | gttgctttcc | ggggcatgcc | gcttcaggga | agcggccagc | atgcgaacca | 2160 |
| gcattgccag | ttcctgggtg | cgttgtccct | cggcgcggcc | gatgtcgtag | aacggacgaa | 2220 |

-continued

```
gccagtgatc ctccgccggc ggctggctgg cctgggcgcc gaacgctagc gcgccggtga   2280
tggcgtctgc gatgacctgg cgctggtcga ttgccgactg ggctggcatg tcattgccgt   2340
gcgcattgca aatcgccgcc atgttgcgca gggaatccag cagttcgccc ttgctcgggt   2400
tcatgccgat atcgtggccg attgcctccc aggcctcgag cacagtgacc acttcggacc   2460
tgaagccggc gtaccagagc tgcacggcat cttccttggc gagcgggtag ctgaggcctg   2520
cggcgatcaa ctggtcttcg gacggcgcg cctggtcctt gatcatggcc agcaggctct    2580
cggctgagga atgaacctcg tcgaggtccg tcgaccagcg gtgcggggag cggtgctggg   2640
tgctgtcgtg gatgttgtcc agggcttcga cgatgccgcg taggcgggtg gcgcactgct   2700
cgatcagttg gtgttgggta gaggacattg tggtgtctcc ggttgctccg cgccggcgg    2760
ccggcagcgg aagcatttgc acaggcctat ccgttggccc gtggtgcggc agatggtggg   2820
gcggttcatt tcgtggcgtc ttgcttcatg gctttggcgt ggccgacgca ggtgcggact   2880
gggttgccct ggtcgtccag gtcggcgtgg cagtagaacc ggctgagttc ctgccggcag   2940
tagatggcat cggaggtggt gaccggcgag gtgttcgccg gggtgccgag tcgataggcg   3000
cagccggcgc acgtgccgcg agggttcacc gttgcggcca ggacaacgcc ctgcagcgct   3060
ccgaacatcg tcgggaggtt cgcctgctcc gcggtgtgcg gatgttcgcc gcgctcgatg   3120
aggatcaact cgaccatcgc tcggcagttc tcggcgacgg cgttggccat gcccagcacc   3180
tgggcgaaca ggtcgagcat ggtggccggg tcgcgctggg cggccatctt ctccagcacc   3240
tggcggcgca ggtccgccgg cagaagcacg gcgccggcca gttccttggc gtcggctgcg   3300
gtgattgagt agtcggtggc gggctcggtc atgctgccac tccgcttgcc tgagggccga   3360
agccagcctt cagccgcaac accagagggc cttgcggaa atcaccgtcg acggtaccgt    3420
gcaattccgc gcgctcctcc cgggtgaggt tcctccattt cgcgattccg tagtcgccct   3480
tcatcacgcc cactggtccg tcgcgacaag tgctgctgta gctgtaaccg ttggctgata   3540
gccactgttg gcatgcgtac agcgcctcga aggtgcctgt ctggtcgaag gtcttttgga   3600
atggctcact catggtctgc tcctggtcgc ggcggcgcac cggcatggtt tcgaagggaa   3660
gggaactgca gtcgtcgtga cgcgaggcgc aggcgcggca gcgcccgccc ttggggtagt   3720
agttgggcat ggttggctca ggtgaagagg gtgggctggg cgctcttgtc cagcgcctgc   3780
tggatcttgg tgaaggcctc ggggtgctgc tggtcgaacg ctggcatgcg ggcagactca   3840
acccacgtgc cgcgctcggc gcccttgtcg agccaggatc gtgtccagtt cgtcgcgctg   3900
acgccgcatt cggcgatctg cttcgtggtg atgaagccct ggcggcgaag cgtggcgatc   3960
accttcagcg cgccttcttt ccactcggtg aggcgcagcg gcgccggaac gccggcgggc   4020
acgtcgggga ccacgatcgg gacatggcag cgttccgcgg ggttcagtc gaacagttgc    4080
ggtccactgg agtgctggag ccagtagcgc aagtggaact cggggaagtc gacgaacttg   4140
ccgtcgcgcc gacggtgtcc gcgggacgga gcgagtactg cgatgccgca catttcaagc   4200
aggcgcttga tgccggcgct ggcctcggtg atccgcccga caatgaccag gcggtgatct   4260
ggccctggcg caccgtaccg gtcttgccag tactgcggca ggatctggtc ggctaccttg   4320
gcgttcaact gcaatttggc ctctacgccg atctgccggc catcctcatg gaccaccagg   4380
atgtcgaacc cggcagtctc cgggtagcag gtccagccgg ggactcggtt gaactcgtcg   4440
atgaacgccg cgcagagttc ggcctcgctc tgcaccagcg gcgcattgga tctggtcatg   4500
gcgttaccct cggcgcccaa ggctggagcg cttgatttcc aggcacgtac agagggtggc   4560
```

```
gcgggtgccc atccttcgtc gtgccaagac accagaggcg cccgccggcg gcggtcagga    4620
tgctggttac ggcttctact cgctcgggct tcgcattggc gccccaggcg cacacgatgt    4680
cggtgtactc tcgggcgatc gcgcgcaggc gccagtcgtt gtctgggcct actgggtcgc    4740
tgtgctgcca gaggtcggac gggttcgtcg cgcgcaaggc gtacagattg acgacggcga    4800
tcccgttaca gccccaggcc gaggcgaagt tgcggcagcg ccggatcgtt ggatcgtcga    4860
gcgcggcatc agcggtgctc ggattgagca tcaggaaaac cgctgtgcct ttgtcggcca    4920
ggcagtcgcc agggcgagtc agaaggtaac ggtactggcc gcattcgctg atgatggcgc    4980
tcatggcgtc acccgcttga actcgaccac ccagacccag gggttggatt cccagttgcc    5040
gccggtggag cgccagaggt gaacgaacga gtcaactgcg cttggcgccg ggcattcaca    5100
cccacagggc tcatggtttc cgcagttcga gcatcccccg tcggtgatac cttcggctcg    5160
cgcctggacc tcgctgatgt cctgcaggcg ctcgacgcgc accgcggtga tctccagtag    5220
gatgcggcag gcccaacggg gcatgtggat gctgggccga ccttttccag cccagtccgg    5280
cagcggttgg tcatctgggt aaatcggctc ctcgcgtcct gcaggcccga cgctctgcca    5340
gccgccggcg gtgtagagga cggtgatgcc tcgaccttcg gcgagcagcg gcgcaaggat    5400
gtccgctggc gcggtcttat cgtgaggctt gccaacgtgc caggtctccc gcacccacaa    5460
ccggtcgccg ggctcgccgt aggggcagat gatgcgtgcg tgcaggccgg catcaagcgc    5520
cttgaatggc gtattgggat cgaccattga gccgaggaag tcgggctgcg gcttcatcac    5580
tcgccgcgtg accgtcttcc taccttccag gatggcgcgg accatcggtc cagtgaacag    5640
gatcggacgt tctttcatgg ctgcacctgc ttctgcgaac ggttccaggg atgccggcgc    5700
ccgggcttgg gctgctggcg cggggagaga agtgcgtcgc gcaggctcat gccggcggcg    5760
acgcggcggc ggacggtcgt tgcgtggacc gggctctgga agtgctccac cagctcggcg    5820
atggtcccgg tcacgccgtc gacggtgaag cgtcggctct cgctccagcg ttcgtgcgcg    5880
cgctccagcg ctgcggcctg cgccggcgtg aacctgccgc gcgacgcttc gtaggccagg    5940
cggttgccga gcgtcgtgcc gttcttggcc cactcgatgg gccccatggc tccgatgatc    6000
aggtcgaact tccagcggcc caggccaagg gcctgcatcg ttgcgcggcg ggaaagcccg    6060
cgcgcggccg cgttgcgaat gaactgttcg gtgttcacgg gtttacctcc tgttgcgcga    6120
cgctcagcgc caccgcaacc gggcgcaccc agatcggcgt attgctgagc atgaaggttt    6180
cgccggcctc ggccagcagc agcgttgtac ccatcacgcc ggcgatggcc tcggccgcgg    6240
ccggcggtac ggcgttgccg atgcgctcgc gccagtcgct gtcgctcagg ccgtcgagga    6300
tcaactgttc ttccgggtcc accaggctct gcagcgcggc cagctccagg gtggtgaagg    6360
gccggtgcca ggtgccatcc agcgactgga tgatgcaggt cagccggtcg ttcgccttcg    6420
gcatgcgcgg atcggccacg ctccatcgac cgttgtcgtg ccgcgcactg ccgacaccg    6480
cgccggcgga ttggtcgaac ccaaccacgc cgtagtggcc gccagtgaga tacgggtctc    6540
ccttcgtccg gctgagcacg cgcgggtctt cgacgcactg gcctgtgcca tgggcactgg    6600
tgaccgcttg tgcgtggcgg tcccaaggca cgatgcggaa ctcgttagag tgtttggcag    6660
ggccacggtg gcgcgggtcc gcgacagcaa atgcaccctg gccggtagta ctggccgcaa    6720
tcacggtgcc ggctgggccg tcccagtcgg tgaccgggta cttgccgaaa ctctggccgc    6780
ggggatcggc gacggagtac gtgccttggc cgggcgactt gacgccgatg atggcgcccg    6840
aggtgtcggt ccagcggcgc acgccgtact gctggtattg cagggcgttt gccggcgcgc    6900
gcgggtccgc gacagagaat gcgccgttcg tggggctgct gcgaccggcg atgatgcccg    6960
```

```
tgctgtcgtt ccaaccgtgc acgcccatgt agccagcccg gtatttcggg acgatgatca    7020
gatcgcgcag gtagccgtcc tcgacggcga ggtcgttcag gctgcgccag tcgctgccgg    7080
ctcgcaccag tgccaggcga acccaggtct tccactgcag ggacggcaca cggtgcatcg    7140
ggccggcgga atcgatatca ccgggaagcg gcatgcggcc gaggatgtcg ccgacggcgc    7200
ggagcgattt cttctctggc tcgtacagga agggggcac tttctcgacg tgccgcgcga     7260
caagcaggaa gcgcttgcgc gactgggcca ggccgcccag ttcgccgcag tcgtgagttg    7320
tttccgccac ggcgtagccg aagccgccga gcaggctgtt gatctggtcc agcaggtgcc    7380
ggccgcggct ggctaggcgc gggacgttct cgaagacgat cagcggcacc gggtcatcag    7440
cccatgcctc gcccatgagc cagatgcagc gcagcgtcaa ctcgttcagc gcctggtact    7500
tcggggtcag gctcatcttc tccgacagca ggccgctggc gcctttgcag ggcgagctga    7560
tgaacacggc atccggtcgg cgcccgccgg cggcgcgtcg gatgtcctcc ggggttgcct    7620
ccctccaacc ggcgggcggc tccgttccat ggaagcggat gtattggtcg cgggtgaaca    7680
ggtccagcag ggtgcccggg acgccggcca ggcgctcgaa gtcgcgcaat ccggccgggt    7740
ccacgtcgat cccgccgagg cagaccccatt cggcctcgac gttgccgacc cgcgggcgcg    7800
cccggttgaa accggcggca ccgccgccca ggccgcagca gaagtggaag tggtagagag    7860
tgcgcttgat catgcggcgg gttccttatg gatgatgtca gcatcggcct cgagcagggc    7920
gaacaggtcg ggcatggcca tctcttcctc ggcagacttg caatagcccg caccgtccag    7980
gaagtagcgg gagttcagtt cgtgggcacg ggccctgcgc ttgagcttca gcgcgcagta    8040
cgggacggtc atgatcccgc cgaagggatc gaagaccagg tctccttcca tggagtactg    8100
cacgatggcc cggtcgacga tgtcgaactg cagcgggcac aggtgcattt cctgcccctt    8160
gctgtactgc tgggcgttga gcgtccgcat gcgggcgacg tcggtccaca cgtccgggtg    8220
ccaggactgc ggtggcagca gcatgaagcc ggtgggcagc ttcccggtga cctccagcga    8280
ttcgccgatg cggacgtggt gctcgaagtc gtagacggtg gacaggctgt agtcgcggta    8340
cagcttgaac atcacgtcgt gcgggatgcc ttcgaagtcc tcttcggtca gcggacggtt    8400
gccgctgctt cgggtgaacc cgtgggcgtc caactgccag cgtgcccggc tgtagccgtt    8460
gccgcgggtg acgtgagct tcttgtccat ggcgaaaggg acgatctggc cgtcttcgtc     8520
gatgcacagg ggcttggcct tgaccaccgg aatgtcgccg taggcgttgg agttgtcggt    8580 gggggcttg cggaagatca gcaggtactc gggcatgccg acacccatct tggtgccgtc     8640
cttgcactgt tccgtccacg agaggcggta ggtctgggcg ttctcgcgaa ccacgtcggt    8700
gacgatggtc ttcatgccca tgtaggccca gccgtgcttg acgaaggcgc gggtcacttc    8760
catgtggaac ggatagacgg tctggaagcc gaggccggtc atgccgccag gaacgatacg    8820
atccttcacg tggatgcaag ccaggcgccc gggaatggtc acgcgcagca tttccgggat    8880
cagatagtcc atctgctgga agaaatgcgc gttatcgtcg gtgtgcccga agtcggcgta    8940
gttcggcgag tactcgtact gggtactgaa ggggatactg gtgatggtca agccgacgct    9000
gttgttttcc atgcggcggg tttcgagcac agtgtcattg ttgacgatgg tgtagtcctt    9060
gcccttgatc tcgatgcgtt ccacacccat ggagcgggtg agtgtctgcg ccatggcggc    9120
gatggacagg ccgtattgct tgatgatctc ggtcatgcgc tgaaccatgg tgttgtgctg    9180
ctgccacttc cgttccaact ggcggcggat gtcgcgctcg gcctcggtgt agatcaggtc    9240
gatgcgcacg cggccggtct gcaggaagcg gtgcaggcgg tgaatggact ggatgaagtc    9300
```

```
gttgaacttg aagccgatgc ccaggtagat ggcccaagag cagtggcgct ggaagttgca    9360
gccgctgccg gcaatcaccg gtttggcggc cagctcctgg aactcgccgt cgctgaactg    9420
gacgatcgcg cgctcgcgct cttccagatc ctgggagccg tagacgctta cggcagtggg    9480
gacggcggcc tcgatcgcgt ggcgttccgc ctcgaggtca tgccagatga tccggtgagc    9540
atctggggcc tcggcgcgga tctccatcag tttggcgatc cgggcgggca ggctctcgcg    9600
tttctcggcg gcgcgtcct gcacgccaat agcggtatta cgaagcaggc gtccctggcc    9660
attgcgctcg tggccggcgt gcgagtggtc agacggtact tcgtgccagc ggatgtccag    9720
ttccggtagg gcgtagcctt cgtcactgaa cccgaggtcg ctgggcgct gaacgaagat     9780 cgcccaggac gccacccaca tccagaactc gccctccttg tgggcatgga tggtgagttg    9840
gtcggccttc tccgagttgc gtttgaagaa cctggtcttg gcctggccga catccatcac    9900
gccgaggaac gccgagtacg ccagcagctc gatgtattcg ttcgggctcg gcgtggccgt    9960
ggccacgtac cggtaccgta cgccatcgcc gcggatgccg gcggcgcgat cgtcacccgc   10020
gaacagggcc atgaactcgc ggaacgtctt gctgccgccg aagccgcgca ggcaactggc   10080
ttcgtccaaa ctggccacac tgaaccgtcg agggtcgagc ttgccatcgc ggacggtctc   10140
gtaattggtc aggtagatgg tgttggggtc gtctacctcg tcgaaacttc ggatgaaccg   10200
gacggtgatg ccgagcatcg cggcgtctcg gtagaactcc tggcgcacac ccagcgggat   10260
ggtgatgagc gcgtagcctc cggccagttc gcggtgacg cgccgcactt caagctgcat    10320
taccgacttg cccaggccga aggccgcgaa acaggccgcg cggccttggc gcaccagcca   10380
ggtggcgatg gctcgctggt gcggtttgag caggggatgg aaggccgatg gcttcacctc   10440
gaagcctttc ggctcggcga ggcggacctt ggctcgcaag aagtcttcat aggcggtcat   10500
gctgtttcct tggggaacgg cacgcactgg acgccgccct gcctgacagg gcggcccacg   10560
aggcatggtt gaatcgccca cagggcggcg tccggtgcgt gctttctggg agagaaagcg   10620 cccccggctgg ggcgctgtat cgagggtcag gccgcagcct gttgctgctg gtcggcgagt   10680
tgcccggcgt cgatccagac cgcttgtagc caggtcggcg tcttcgccat cgcctccttg   10740
agcgtgccgg cgacgatcac cgaatcgatt tccttgtcca tggtcacggc acgcagcagt   10800
gtcagggcct ggctacgact cggcaggtcc aacacatcga ggcgatccag cagcgccagg   10860
cgcaggccga agatcgtcgc gatggtcagg gccagcgtcg cgtcgcaccg ccagcgttcg   10920
gactcggaca gcaggccgta cagtcgaccg ccgaacgtga catcgatgtc ggcgctgatc   10980
tgtaccggcg accagccggc tgtgccggat aggcgctgca gcagttcgtt caccggtccg   11040
atcgcgtcgg ccaggatctc agccgggatt ccggtcggcg acagcgcgtc ggccatgccg   11100
gtccacgcca ccacatcccg gtgcgcggcc tgcgcttcg cgatcgaggc ctcacgctgg    11160
gcagccgctt ccatggcttc ctgaagggcc accagcttcg cgcggctcgc gtcgcgggcc   11220
tgccgcagtt cgttgatagc ctgctcgccg ttggcgatcg cttcggcgct gggcgcgtcg   11280
gcggactcgg tttccagggc cttgatctgc tcggcggcgg ccaggcactc gtccaggtcc   11340
cgctggctgt cgccacggc gcgctgagca ctggccagat actcgcggta ttccggcaga    11400
cgcttggctg cctcggcgtc agcgatcttc tcaggcggct gatgcaccac cagagcaccg   11460
gcctgcaggt cgaccgcgcc ctgacagtgg gggcaggtca gcggctggtg cggcacgctg   11520
ccggacgagg ccagctcggc ggccatgacc ttctcggacc actcgtcctg gttctgctcg   11580
tccgtgctca gcttgttgcg gcggcgcggc tccaggtcta ccagctcgcg cagattggct   11640
atgcgctggg cgcggccgtc ggcggcctgg cgggcctgct tgctggcgcc caaggtctgc   11700
```

```
tgggcttcag ccagatcgtc ctcgagcgcc tgcagggcgt tacgggcttc ctcgacctgg    11760
tcgttggtca ccgcggtggc caccagttcc ggcgcccagt caatggcctt ctcgctgccg    11820
tagttctcgc cggtgaccgc tttccaggcg ccgcgcgctt cgctggcgta gtcctttgcc    11880
tggccgacca tggcggagaa cccggaacgg agcaggggcg tcaccttctc gaacagcgcc    11940
aggtcgatgc ccttggcctt caggcgcttg ccgacctcgg ccgggctggc gctggcgccg    12000
gtcaggtcga acagcacccg gcggcgatct ttggcgtcca gagcggcaaa caggctggcg    12060
tcgagcacgt atggcaggaa cggcgagtcg gcgagcgggg agcctttgcc gctgggcagc    12120
gcgacccccg aggcctgcac ctcgccggcc tcgtccagcc actcgacgcg ggcctcgccc    12180
ttcttggcgc cctcggttac cagcttgtcc atctccttct tcagtgagac gcggcgcggc    12240
tggccgttga aggccatggc gatggcgtcc agcagcgaac tcttgccggc gccgttatgg    12300
ccggccacca gaagcactgg cgcagaaaca tcaagggccg catgacgcag cccttggaag    12360
ttggtgattt cgagtttcgt gatgcgcatg gctcactcca ggtcgagggc gatatccccc    12420
ggcttcttga cgacgcggta agtgttcaac tcgcgggatt cctcgttctc ctgctcgagc    12480
acgatgacgc cctggtccag cagttggaga atgacgcgct cggcttcctc ggtggtgaga    12540
gcgaagcgcg attgcagcca ggccgcgtcg aacacgtcct tcttggtggc gacgccgatg    12600
gcgatctcgc ccagggtgtg gccggcgaag cgctcgacgg tgagttgcgg cagttcttgg    12660
aactcggcat cgacgacgtc gctgtcgtct gctggttgca taccgcccca ggcgccgggg    12720
tcttccatgt catggtcgcc gccgttcagg tccagcgggt tctggtccgg atccgccttc    12780
acgtccttca tgccgtcgag gaactcagcg gcgccgccga tgatcagcag gcagtcctcg    12840
ttcaccgcgt ccagaaggtc gtgcttgttc gggctggagt gattcaccac gatgacggcc    12900
ttcatcttgt ccttggccgc gatggattcg agcttgccgt agacggtctc gcgctcggcg    12960
ccggcgatgg tgtgcaccgc gatggtggcg gcgttgcgta cctgctgctc caggcgctcg    13020
atcacatcgg tctgcttggc ttcggacagc ttctgccaca cgtccggcag gatgcggatt    13080
tcctggatca ggccctgcag caggctcttg ccgagcgtgt cggcggtcat gtggaggaag    13140
gcggcgttgt tctggctcat gggcgggttc ctactggttg gcgatgcgtt cgagggtggt    13200
gtgctgggac tcactgagga acatccgcgg gccgtagcgc tggaagttgg cgcgcaggtc    13260
ggcggtgaac tcttcttccc aggtggtggc ggcattcagc tccgccgcgc cgaggaggct    13320
attgaactcc tcgacacggt cgaactgctc ttcgatggtt cggctgggca tggccggtta    13380
ctcgagattg agcccgtcgt cgccggtgtc gccggtgtcc gactgctggc ccggggcggg    13440
ttcggtgatt tcgcccgtct cggtgttcac gccgtccggg acctggtcct gagactggtc    13500
gtcaacaacg ctgtattcgc cggtgaggat ggacgcgttg tcctggtcca atccggcgtc    13560
ggcgcgttcg tccagggtga ctgcggtctg caactcgatg ctgaccggca ggtacttgaa    13620
cagccggcgc atgacggtct tcttggccat ctcttcgtag tgggtgaccc aaggcccgtt    13680
tccggatgcc ttgctggtgg cgcgtacttt gtcgacgtcg gccttgctca tgacctcgaa    13740
ttgcacgccg ccgtccttca gcttggcgac cgcgtagacg tgggtcatga cgccgcgttc    13800
accttctccc ggaacgtgct ggacgtcttc gtcgaggcca tagcgatagc tgaactggtc    13860
gttctggtgc acggtgcgcg cggtgagcga acgatctgg ccggagcgcc gggcaaggtc    13920
aatcatcccg cggtagccga tgatcaactg gacgttcgac aggccatctt tcgccttgcc    13980
gttgccgaac ggcagcaggt aggcatggcc gagagcgtta cccggttcca ggccgagctg    14040
```

```
cgcgcattgc atcacggcgc cgaggaaact ctcctgattg catttcgcca gggccggtac    14100
tttgcggatc tcggtcagcg cgatgcgcgc gagtcggtcg gcggtcatgt gcttcggaag    14160
cgccagggcc atctgggctt tgatcttcgg gtcagtcatc aggtgggcca gcgttttcgg    14220
ctggccattg ttggcgacat tgccggtcgc ggcggctttc agggcggttg cggacatgct    14280
gggctccggt tacttgaggc ggaaaacgcg ggattcgctg gtcttcttga actgctcgaa    14340
cagcgcgggg tgagcttcct tgaaggcgga ttggtcgaag cggttggtgg tctgggactt    14400
ccacgtcagt accgacttgc cgttgaccgt gagttgggcg tggtcctgca tgaagagctt    14460
gatgcgctcc tctgcggact cgatctcgta ctccaggccc ttggccttgg ctttcagttc    14520
gcgcaggcgg ttgaacacct ccacgacctt gccatcggcc tcgatgctgg ttccggcgtc    14580
acgctcgaac agccggagga tgtcgctgac agcggttgct tcgggcggat ccaggcgctg    14640
gatgcgtccc cagaactcga cctccttctc gcgaatcgcc gcgatggttt cgtcgtcccg    14700
ctcgacgcgg tacacgcgga agtcgtcgcc gccgatcagc acgccgaaga tgcagacctg    14760
gcggccggtg accatcaggc cgtgcatggc ctgggcggtg tagtgactg gaatggcatc     14820 ggtctgaacc tcaccccagt cctttgcctt gaacgggctg accgtcttga tctcgatgtt    14880
ttcgccgctg gcggcctcgg cgtcgatctc ggcgccatg aaatcgtgct gctggtcgcg     14940
gtagcggtta ccgcggccga cgatcttcag gccggtctct tcggccagca ggtcgatgac    15000
gtagggctcc atccgctggc cacgggtgaa aatcttctgc ttcgccgggt cgacggcacc    15060
ggtgcgcggc tggaccttat ctaggtacac gtccaacgga gtgcgccagg gactgatgcc    15120
gaggatgccg cgcacatcgc tgccgcctag cagcttgctc ctgtcatgat gttcaggtgc    15180
gattttgagg agggacacag gcgtaatctc cgaggttctt caagaggccg tcgtacttgc    15240
aatggcatga tctgcaaaga cggatgtagt cgtttgggtc gtggtgcctt ccactaacgt    15300
tggcccactc gaacctggcc tttgggtcgg tggtcccgca gtgctcgcac ttcatggggc    15360
ggccccgcgc ggcatagacc ctgttgtggg ccggcttgta cttgaccgcc tcgcccccgcc   15420 agctactgtt cttcgctccg cgctgatctc gcttcgcagc tatgcgccgc tctatgccgc    15480
aacggatcat gaagagccga agggcacggc aggtacatcc gatctcggcg gatacttctt    15540
cgagcgtcat gcccgattcg tagagatggc gaaccaagcc ctcgttgagc agtggaacgc    15600
gcttactctg ttggccgcca aggtacttgg tgccggtcgag cgcgccgacc gatgcgagag   15660
ttgcagtcat ggggctggtc tcatttcagg gtgagggtgg ttgtcgcgtg aaggcgggag    15720
ctacgccgga agcgcagaac gcagaggtcg ccgcatatgt cggcgaagaa cgggttgttg    15780
tagccgtgac ggttggccaa ctcgacggcc tggcggatgc tctttccggc aaactcttcg    15840
atatcgtcga gctggtcgtc gatgatcgag cgaacggggc gggtggtcat aggtcgatgc    15900
tcctcagttc ttgctgtctc gcatccgctg cggcgtcgag ccggcggcgc atgtcgtcgt    15960
attgccgggt gccgatggcg tccagcgtgt aggccatctc gatctggccg cgccatacca    16020
actggtcgtg gcgcgggatc accgaccgac gcattgcgac gatcgcttcc tcgatcacgc    16080
cctcggcgcg ctcattcgcc caggccatcg tcgtcctcct gctcttcgtc ctcgtgctcc    16140
ggttccggct ccggctggtc ccagagcggg tctctggcga agtcccaggt gtgctgggcg    16200
ttgctgaaag ccgcgcggtt gcggcgctcg cggtatgtcc acatcgggat gctctccgtg    16260
gttcacctgc attcggcagc acccaggcac acggcagtcg tgcccggtgg gcgccgtggt    16320
gggtgctctc gaatggaggt tgaaaaaagc ccggccggag ccgggcgaag aggggaacg     16380 ctgcatgcgc agcggggagt gatcggcgcg tgggcgtccc ctctggctcc gtccgcgcca    16440
```

```
ccagccggcg gcgttgctcg ttggctcgcc tgcttacgag gcaggtgcct gactcggctg    16500
ccgatcactc tccgctgcgc cctggccgtg ccaggagcag gaaagagaag ggcgccgcca    16560
agcgccctgt ctccacttac atgcaccgcc ttatgtgaaa gcggttgggt acaggctcga    16620
ccgcatgttg gcgatctgcc gttggggttg ggctacatgg tgaggtcctc cgtatcgggg    16680
aagtccggcg ccgtgtcgag gaaccggata tggtgaaccg gcaggagttc aacggtgcct    16740
ccggggcgct caatgacagc cacggtgtag ttgcccgccc cagtctcgaa ctcttcgaag    16800
tcgacccccc actggtggaa gagtgcttcg ccactatctt ccaagcccgt gcgccgacca    16860
ttcctgtcgc acgtcacctt catagtcatg acacgtcgca tcgtggtctc ctgttcatat    16920
tgccgtgcag gcccgcaacg ccaccggcgc cgactggcct tcgatccaga taaccgccgc    16980
cccgccaagc gacacgctgg cccggccgac ggtgcgggtg cgctgtggtt cggcccctcg    17040
gtacgggcgg tactcgatca gcgctggcgc cgggtgctct cggttccagg cctcgaccag    17100
ctccgccggc ggcaccggcc ggacgttgcc gatctgctgg tagatctcgg agcggtgaat    17160
agcgacgtcg tccggggcgg tgatgccgag acgcacctgg tcgccttggc tgccgaggac    17220
cgtgacggtg atgttgtcgc cgatatgcag ggtttcgccg actcggcggg tgaggatcag    17280
catatgtgcc tccgttcagg atgctggacg tgcgggctca ggccggctcg cagtgggaaa    17340
gggcaacgca accggacact ccggcgagcc agacgcagc agtgtgtccg ccagcacct    17400 gggcttcggt tgtcgtccgg gtgcgcttcg gtgccgcggc gcgatggaat cggtagtcga    17460
cctcggtgcc gacggggtat gcggaattcc aggcagcaac ggtcgccgcc gggttggcgt    17520
ttcgcttcat cgtgtgtctc cggatagagt tcggtggggc tggtgatgcc ctgctactgg    17580
cagggcggcg ggttagcgca tagcgccctg cacgacgtgc agcagatgca gggccaactt    17640
catcgcctct tgcggcgtca tgaatgcagt gagggtgcgg ccatcgcagg aatcgctcgt    17700
ctggaagaac tcaaccgcga ctggatgtac ggcgccggcg atagtgcgaa cagttggttg    17760
tacgcactcc agcggcctcg cccccttctt gctgaatttc tcgtgaactc tcatgtcctt    17820
tcctcggtga tgccggcagg gcggcgggtt agaaccgctt cttggcattt tcattcactt    17880
cgcgcttcct gcgatttagc tcaacaatcc gatcaatttc atcgtcttcg gtgatctggg    17940
cgaatgccgc gaggactagg cgcgagtagt cacgcccgtc tcctttcaag cttgctggcc    18000
cagcttttgg tcttatcttc atgcgatacc ttcaaaagtt gtgctcgatg cggaaacacc    18060
aaagcgcgcc caattggacg gcgagtagaa ctgaacgact ttggcaattt tgatgatgtg    18120
ctcggcgcca aagcggaacg acttgccttt gtactggcgc ggctttgtca gcttcttgtc    18180
gaggcaggtg gccccaacca atcgcccatc gctaaggcga actccatgtt tcagggcgcg    18240
accacagtgc tcgcaattgc agtcgctttc gtagcccacg attgaaatct ggttcatctc    18300
tgaatcctcg gttgacttcc caatgccgcc tcatcgaagc ggcatcagtg aagtggtcaa    18360
atcggcatca ggtcgcgcgc cggaacagtt gcgcggatca gttcgccatc gcgggcaccc    18420
tggccccagt attcgatgcg gtagccgcgc gatgtcttgc ccagtacagt ggcgcgtgct    18480
cgaccgaggt agcaggcttt gtcacctgcc ttgtatgcgt tcatgtcttg ccctcttgac    18540
cggattcgtt gacttcctcg atgcgcctgt acccaagcgc atctgagaaa tcggatgccg    18600
cttacggcgg caagtcggtc agatcacgca cttccctcgt cgtacgacac aggcttatcc    18660
ccacttgggg cacccacaac gccggtccgg aaagccccag ccttacagga gcaaaacctt    18720
gggtagcgct ctgactggtt ccgttatgtc gccacggttt ccttggcttg ctcgttgact    18780
```

-continued

```
tcctcgatgc ccctcttgcg aagggcatct gagaaatcgt ttattcatgg gtttatgctg     18840
agtagagata ccaagggttt aaaccgtcct tgtgcctcca gatgaatcgg tcaagctcat     18900
gcgaacatgg cggtttgaaa atgcagatat tcccgtcgac tttctcgcac caaccgatca     18960
gctcgccggc tggcttggtc atgtgctgct cactggcgaa gatgcggcag ccccgcatcg     19020
gcttgaagaa ctggtacctc acgcgtgcat ccgcacggtg atgtagccgt tgctggcaac     19080
aacgtggtcc catcggttga accagatgag gtcgccgaac ttcttcatgg cggcctggcg     19140
taccttgatc agcacgtcat ccggtgtctc gttgccttcc ggcagggcaa tccagtccag     19200
gcgcttgccg ttgctcaggt gcgcatcgac attgaattga gccatttcag tctccttacc     19260
agggtttacc agcgttgatg tatgcgtttc ctgcgagttg cgtgagcgca actagctcca     19320
tcgaatcgat ctcaccgccg tagtacaggc cgcgcagcat tccaaccgtt tcgtggtact     19380
caatgcgcgc ctcgcgatcg tcttccgcct tgcggaggac ccgaagtgcc tggcgtacag     19440
cacgtgagga ttttttcattc atttctgct cctccagggc gtgttgactt cccgtctggc     19500
cctcggtgga gggccagcca gtgaaatcgg tgtttctccg cacctgcatg cggtcattc     19560 gctcggttca gcatttcgct tcgtccgccg tcgcagttgt ctgcgcgttg gcaggctttc     19620
gggcctgtcg gatcgccggt cgccgtagag gcaggcttgg ttgtttcccc tggatttctt     19680
tcgcccgcca ggaggcagct cgggctgacc taaccggcgg tgccgggtag tcgttcatgg     19740
cgcgggttgt taaagagcgg tcggctcggt ggcctggccg gcggtgtgtt gctggcgttg     19800
aagtgaaatt tagaaaacta aacgattaag gtcaagggat ttttttagaa atctaaactt     19860
ttggattgag cgggcacaaa aaagcccgcg ctaggcgggc tatgtccctc tggttaaggg     19920
tgttaccgtg tgagcatctc gcgaagcttc atgccatcag cgatgctcac gaccttggcc     19980
actacgcctc cttgaggcag gagtccgtat ttcgatggcg cttgccaagt gacggttgag     20040
ctgaggaagt agtcgcctgg cgggatgtcc gtgaatgtga agtttccgtt cccgtccgcc     20100
accgtagtga tggaccctg tcctgatcga ggatctggcg cctcaagcgc ttgtcctcct     20160
atgtagttca cttcgtacca ctgtttcgag taggacgtaa cggggactag gtaaactgtg     20220
ctccctgcac cgaatttcac atctccacca acggtcttca taaagacctg gccagtcaat     20280
gtgccagtcc ctttgtcgg aagagcggca aattcagcag cagggaatgg aattctcggg     20340
accggctttt gttgagatac ggcacaaacct gacagcatga tcattattgc tgctatggcg     20400
attaaacgca tgaaacctcc ttgattatca aaaagcccga gtgccggtca gcacctgact     20460
acatcgcgcc gccacgccaa acgatacgac cgataatgtc tacgccgcgc attccgtcat     20520
cagtgacagg ctggtctggg tatcgatttt tgtcctgatt atctgatcgg atcagccatc     20580
ctcctgatat ctctcggata aggcgcttga agatcacttc ttggtcggca tcatgcaggg     20640
cgaacatctt cccgttcgcg ggctccttgc aggaaacatc tatcaggacg acctctccgt     20700
cggagagggt aggccagttg ctgtctccct ggttgtaggc tacgcgaaga ttttcagcct     20760
tcagccccat gcgtcgaagc cagtcgcgct taaatgccaa tccacccttg acctcaacat     20820
gatcgtttag gtagccattt cccgacgaac ccttagcggt gagctgggga ataagagcgt     20880
agtcggcctc tgaaggagcc ccttcatgtg cgggaagctc cttttctccc ttcccggttt     20940
ccagccagga ggcgctgcat cgaagcacct tggccaaggc gatcaggttc tttcctctgg     21000
ccttgttggt gccattggtc cagtgggaga gagtcccctt ggagaccttg atctctctgg     21060
agatgtctgc ggcgctgatg cctaaggcat ccatgcgctg gttgagtctg tctgaaaagt     21120
ccatgtttag gattctaaat ccttgttggt ttagataact tgcatgcgac tgtttatttt     21180
```

```
tctaaactcc agcaaaacca ttgaggcagc cgtatgaatt acgaacaggc gctcacccac    21240
ttcggaacag ggcgagcgat tgcgaaggcc ctaggcgtaa gccctgggcg catttctcag    21300
tgcaaatcgg aaggtgggtt ttcctatcag catcagtgcg tcctggagaa ggcatcctct    21360
ggcgcgcttc aggctcgcga agaagacgag cctaagcggt tggcgtcgta accatgacag    21420
ccagccaatt aaaccccgag cgcgacgcaa gggcacggga gttcgagtcc ctagtcctga    21480
accggctttt gtcggttggg cagaagaccg tcgctgatgc aatcggcgtg agcgaatcta    21540
ctgtcagccg ctggaaagag ggcgagatag agcggtggtg caaggtgctt gcgcttctgg    21600
agcttcaggt cgtcccaatg tcggctcagt gtcatccatt cgagtacatt caggcgctca    21660
agacgctggc tgagttgggc cttcaggccg agaagaagcg gccgggaccg ctgggttggg    21720
actgaatgcc gtccttccag attggccagc cggacggcga agagctccgt ggtccggacg    21780
ctcgcccggt caccgaggta ctcgattgcg tgctgagcgg gctcggtaga gccgtaccag    21840
tcccggcggg aagcgtcgag tttcaccagc agatggctct gcaggccgcc cagcagatca    21900
agcagagcta cagccatatc gcgaaagaga atgctcgccg ggagtgcctt gcgcatctcc    21960
gggcatcgtt acgcaggccg aaggaggcct tccatgcaaa tccctgagcc acttgttccg    22020
ctcgagtgtg acgtgcggga ctcacccatt ccgaccgaca tgctcataga actggccatg    22080
accatatttg gcctcagcat ggaagaggcc gagagcaagg tccgcgctgc gatctccgac    22140
aaccccgtaa atctttcgga gattggccat ggctaaccaa tggttccgca tgtacgcgga    22200
gttcgccacc gacccgaagg tccagatgct gagcgaggtc gaccagcgcc gttacatcat    22260
gctgttgtgc ctgcgttgcg gaaacggcga tgtaacgttt catgatgatg aggtcgcgtt    22320
ccaactgcgc atcaattccg aggagtgggc gcgtcgaaa gggcgcctac tggggaaggg    22380
gctgatcacc gaagacaaca ttcccgccaa ctgggacaag cgccagtttt cctcggactc    22440
aagcacggcg cgggttgcag cccatcgtgc gcgaaagaaa caagaatgta acgtttcacg    22500
caacagcaat ggaacaaaag ctaacgccct agatacagat acagatacag aaagagatag    22560
tcctactgac gtaggactcg ttgacgcttc gcctcaaccg ggtcagtcga acgaccaaga    22620
cctgttcgaa cctgatcaac ccgaacacct caacggacac cagcacggaa tcaaaccgtg    22680
cccggcacag gccattgcag acctgtacca ccaggtgctg ccagagctcc cagcagtcgc    22740
cctgctgaac gacacccgac ggcgccacct gcaagcccga tggagggagc acgaagccca    22800
ccgctcgctg gacttctggc gagagctctt cgaaaccgtc aaggcctccc cgttcctgat    22860
gggcaatgtc cccggtcgca acggtgcgaa gccattccgc gccacgttcg actggatcat    22920
cgcgccgtcg aacttcgtga agatcgtcga gggaaattac catgcgtgac ccgttcagcc    22980
tggaagccga gcatgcgtt ctgggtgcca tgctcctgcg caacgagttg atcgacgtgc    23040
tgtcggcaga gctgaccccg gaggatttct actggccaga gaacggcgac ctgtaccgcg    23100
ccatcctggc tctgcacagc gacagccagc cggcagacat cgtgaccgtc ggtgaattcc    23160
tgggcgaccg gtaccaggtc caaaccactg acgggatgat caccgggctg gcctacatcg    23220
gccagatcat ccagaacact cccagcgtgg cgaacgctgg aacctactcg cggatcgttc    23280
gggagcgagc ggttgaccga gctctggcgg ctgcgggga cagacttcac gagttggcgc    23340
tcagcgaggc cgcccaggcc gacaaggtcg gcgccgccca ggccatggtc atggcgctgg    23400
actcgaagac ttcgacgcac gaggtgcgcc atgccgctga cgtgctgacc gaccacatcg    23460
aggagttgca gcgccgctcc gacctcggcg ggaagctgga tggtctggca accggcatcg    23520
```

```
gcgacctgga ccagaagctc atgggcctga agcctggcga catggtcgtg attgctggtc    23580
gtcctgcaat gggcaagacc gcgctggcga tcaacatcgc cgagcacgtc gcctgcgacc    23640
tgggtgaccc ggccctggtg gtctcgctgg agatgaccaa cggcgggctg atggatcgca    23700
tcctggcatc gcttggtcgg atcccgctca ccgcgatcaa ggacggctcc gcaccgtcca    23760
gccatggtgc cgagctggga tctgcctctc tgaaggtcaa gcgctcgaag ttgtacatgg    23820
ccgatcgccc cggctgaac gccgctcgac tgcgggccct ggcccggcgt cacaagcagc    23880
gccatgggtt gagcctgctg gtggtggact acctgcagct cctggagagc tccggcaagt    23940
cgactcgcac cgaggacgtc agcgacatgt cccgccagtg caagctgctg gctatggagc    24000
ttggtatccc tgtgatcgtc ctgtcgcagc tcaaccgatc gctggagcag cggccgaaca    24060
agcgtccgat gatgtccgac ctccgggagt ccggcgcgat cgagcaggac gccgacgtga    24120
tcatgttcgt gtaccgagac gaggtctatc acccggacac ccagtaccgc ggcgtggctg    24180
agttgatcat cgcgaagcac cgcaacggcg agccaagcac tgtccggtgc gcgttcctgg    24240
gtaagtactc gcgattcgag cagctcgctc cgggcgcgct ggacgagttc gatttcgacg    24300
agcctcagca ggcgccgaag gtcaccagca tggcggagcg ctaccgcggg atgaagggag    24360
ggcgcgccaa tggctgacct ccgtccagtg atgttcaccg tacccggcga gcctcagggg    24420
aaggggaggc cgcgtatcgg ccgcgtcggc gcccacgccc ggatgttcac tcccgcgaag    24480
accgtggcgt acgaaggcct ggtggccatg gccgcacagc aggcaatggc ggggcgcccg    24540
ctgataaccc ggccttgcct catcgagatc tggatgtacc accaagtgcc agcctcatgg    24600
tcgaaacgca agcgtgcaca ggctctggcc ggtgagatcg ccgccatgcg caaaccggat    24660
gcggacaact gcctcaaggc catctgcgat gcctgcaacg gcgtcgtatg gcgtgacgat    24720
gttcaggcca cccgcggcat attccagaag ctctggagcg aaacgccagg cgtgcgagtg    24780
aagatcgtcc ctctcctcga gggcgagcag tgactacagg aaactacagg ggagagtcga    24840
aatgagactg atcagcgcgc gccaggcttg cacgacgcc ttctacgaga gtcggagctc    24900
agtgctggcg gtggcggccg acaaggccgc gctgggcaag aaggggcggg tggccaacga    24960
gacgcacccc gaccgcaagg acaccaacgg gcgtagcgcc cacatgctgg ccgccggcct    25020
ggtgcaggct gccatccgct cgctgccgaa gccgctgcag cacttcggcc acacgctgta    25080
ctcgccgctg gccaccggtg acgacgtggc gatcgctcac ggcctggtct ggatcggcgc    25140
cggcctcggc caactgactc agcgccaggg cgagcgggct tactggatgg cgctggcggc    25200
gatcaactcg cataagcgcg ccgtcaatgg ccgcgacaca ctgcgcccgg ccgaggtctg    25260
cctcttcatc gaggagcgcc tcggctgccg gatcgacccc ggcaactggg cgcgggacta    25320
cgccagtacc tgggagcgcc tggcgcgcca catcgacaag ctcgacgctc aggcgctgag    25380
gccggtcgcc gaggtagtgg cgaagcagag cggcctgcgg aagggggccgg gctggcgctg    25440 gcaccaggtc gaccgcgatg tggtggcgtt gcagcgggcc gaggcctacg ccgagcgccg    25500
ggagcatcac cagcagcgct tggctgaacg gctgcgcggg atgtcggacc aggagctggc    25560
gcggtgggcg gcgaggatga agcggtacgg ggaggcatac cgggaggagt ggggcgagga    25620
catcctggaa tgccccagtg tccatcagcg ctaccatgac cgcgtggcgg cctactggac    25680
ccagcgggaa cgcctgaaac gggtcgcttg acgatttgaa gagcatttgg gtatcgtttt    25740
gccattgtgc acagttgcac ccgatcaaca gattcccccg aaaacccggc cctggcgccg    25800
ggttttttcg tttctggagt accccatggc tgaaccgacg agcagcggag cagtagcagc    25860
agccggcgcc gtcgggctca ctgccaccgc gatcattcct ggagttgatg tgaatgcagt    25920
```

```
gatcggcggc ttcgccggcg cgctgctgtt cgtgctctgg gctcacgacc tgaccatcgc   25980
aaggcgcgtc ggctacctgc tggcgtcctg ggtcggcggc tactacgccg ccaccgaggc   26040
tgtcgggcgg ggcgcgaccc agttctccgg gctgcccgca ctggtcaccg ccgcgctgat   26100
cgtcacgatc ctgatcggcg tgctcgactg gatgattggt ggccgcgcgc cggcatggct   26160
ccagatcgtt ctgcagcgca tcgtcggcat gatcggaggc cggaaagatg gttgatctgg   26220
tgaccctgac ggctgcggcc gtctgcgcg ctatcagttg ccgcatcttc acgtaccagc   26280
gccacggcgc cacgtaccgg ttcggcgtct cgctctgcgc gtacatcctc gccgctggga   26340
ccggcatgca ggcgctgtcg atcagcctgg ccgtgctgat ggcgcgccac gcaacgccga   26400
tatcgcccta cctgctggcg gtcctgctgg tgctgctggt gctggtctac cgcaacaagg   26460
gcaacatcgc gcccatcctg aggctcagtt gaggtgatcc atggcgctaa cagcaaaaca   26520
gcgccgcttc gtcgccgagt atctgctcga cctcaatgcg acccaggcgg caatcagggc   26580
cgggtacagc aagaatcgcg cgtccgagat cggttaccaa ctgctgcaga agccggacat   26640
cacatccgcc atccaggcgg ctatgaagga gcgcgccgag cgcaccaggt ctgacgccga   26700
ctacgtcgtc cggcgcctgg aggagatcga tcagatggac ctcctggaca ttgtcaacga   26760
tgacctgacc ctccgcccgc tcagccagtg gcccaaggcc tggcgccagt acctcagcgg   26820
cttcgacttg gccgagatgt tcgagggcaa gggcgattcc cgcgcggcgg tcggcatcct   26880
caagaagatc aaatggccgg acaaggtgaa gaacctggaa ctgctcggcc gccaccacgg   26940
cgtgttcacc gacaagttcg agcactcggg ccccggcggc ggcccgattc ccaccatgcc   27000
gaccatgatc gaactggtgg cgcctggtga agcacggat tgaactccca ccgaagctga   27060
ttccggtctt ctccgggccc gcgaggtaca ggggcgccta cggcgggcgc ggcagcggca   27120
agacccgcag ctttgccaag atggcggcga tccgggccta catgttcgcc gaggctggta   27180
tctccgggca gattctctgc ggccgggagt acatgaacag cctggaagac tcctctatgg   27240
aggaggtcaa gcaggcgatc cggtccgaac cctggctcaa cgcctacttc gagatcggcg   27300
agaagttcat ccgcacccgc aaccgacggg tgtggttctc gttctccggc ctacgccaca   27360
acctcgatag catcaagtcg aaggcgcgca tcctcatcgc atgggtcgat gaggccgaga   27420
acgtcagtga gatcgcctgg cagaagctgg tgccgacggt tcgcgagtgc gactccgaag   27480
tctggatcac ttggaacccg gagaaggacg gcagccctac cgacacccgg ttccggaaaa   27540
acatgccggc cggcgccaag atcgtcgaac tgaactacac ggacaatccc tggttccccg   27600
acgtcctcga tcaggagcgc ctgaacgaca gggagtcgct ggacgaccag acctacgctt   27660
ggatctggga tggcgcctac cgcgagaaca gcgacgcgca gatcctgtcc ggcaagtacc   27720
gggtggcgga gttcacgcct gaaccgggct gggatggccc ctactacggc ctggactggg   27780
ggttcagtca ggaccccaca gccggcgtga agctctgggt gcacgatcgc cggctctggg   27840
tcgagtacga agccagcaag gtcggcctcg aaaacgacga catcgcccag ttcatgatcg   27900
accgtctgcc tggcatcgaa ctgcacgccg tgcgggccga ttcagccagg ccggagacaa   27960
tcagccacgt caagagcaag gggcgagacc acaagcgcgc caacttgcca cgcatcgagc   28020
cggtggcgaa gtgcaaggc agcgtcgagg acggcatcgc gcatctgcgc agctacgtcg   28080
agattgtcat tcacgtgcgc tgtaccggct tcctgcgcga ggccaggctc tacagctaca   28140
aggtcgaccg cctgaccggt gacgtgctcg ccgagatcat cgacaagaac aaccacttca   28200
tggacgcgag ccggtacgcg ttgggcccgc tgatcaagcg ccgcggcgcg gtcggtatgc   28260
```

```
tgctacccgg agcccgctga tggccatctt catcctcaag gagcgcgcta ccagccgctc    28320
catggttgtc cgtgcgcgct gcactacatg cgcccgcacc gtggcggtcg aaaacgccgg    28380
tgccgaaggg acgatggtat ggcgtgaccc caacctctct tctgtcgaac tggtccgcga    28440
gacggacaag ccaggcctca tcctgaaatc ggactgacca tgactgacaa actcgacctc    28500
gcggtcaatc acgcgatgag cagtgccatc gcgcgtgccc gaatgagcct gctgaaccag    28560
ggcattggcc atgacgcgaa gcggccacag gcatggtgcg agtacggatt cccccaggaa    28620
atcacgttca acgacctgta caccatgtac cgccggggcg gcatcgccca tggcgcggtc    28680
gagaagatcg tcaccacttg ctggaagacg aatccgcagg tcatcgaggg tgacgaccag    28740
gaccgctcca aggacgaaac cgagtgggag aggaagaaca agccgttgat agcaggcggc    28800
aggttctggc gggctgtctc cgaagccgac cggcgccgcc ttgttggtcg ttattccggg    28860
ttgctcttgc acatcaggga tagccagccg tgggacaggc ctgtcacggg aaaggtcaat    28920
ggcctggcga aggtcacccc ggcctgggcc gggtgcctta agcccaagac gtttgacgag    28980
aaacaggata gcgagaccta cgggcagccc accatgtggg aatacaccga ggcctcccaa    29040
gccggtcgtc ccggtctggt gcgagatatc catccggacc gggtgttcat tctcggagac    29100
tggaccggcg atgcaatcgg attcctggag cctgcctaca actccttcat cagcttggag    29160
aaggtcgagg gaggcagtgg cgaatcgttc ctgaagaacg ccgcacgcca gctcctactg    29220
aacttcgaca aggaaatcga cctcaacaac atcgcctcga tgtacggcgt ctcgcttgac    29280
cagctgaacc agcggttcaa cgatgccaca cgccagctga accgcggcaa cgacgtgatg    29340
cttccgaccc aaggggcgac ggccactcag ctggtctctg cggtatccga ccctggcccg    29400
acctacaacg tcaacctgca aaccgccgcc gccggcgtcg acatcccgac caagatcctg    29460
gtgggcatgc agaccggcga aagggcgagc agtgaggatc agaagtacca caacgccaga    29520
tgccaggcgc gccgggtgca agaactgacg ttcgagatca cgacctgtt cgggcacctg    29580 atgcgcatcg cgctggtccc gctgaaggcc gagttcacgg caatctggga tgacctcacc    29640
gttccaacca aggccgagcg cctggccaac tccaagacca tgagcgagat caacagcgcc    29700
gcaatcggca ctggcgagcc ggtattcacc gcggaggaga tccgcgaaga ggctggctac    29760
gacccgctcg tgggcggtga cccgctgcct gatacctaac cggaggatga agatgccgcg    29820
cgcaccgatc ctaccggcga gcagcagtga cccgaccggg gtagatcgac tggaaagggg    29880
cgcaatgcgc gagttcgaca ggcgcatgcg gaaaatccgg gatggctatg tcgctgcctt    29940
ggaccgaatc ccgcccagc cggtggtgaa tgagcagtac acctaccgtc tcgaccaggc    30000
ccttctgtcc gcgatcttcg ccgacaccaa cctgatggtc gacgagatac tgcaggaggg    30060
cggggagcgc gacctctggt tcttcgaatc ctatgtcggg gttgcctaca tccgcggtac    30120
cgcacagacg catgccaacc tggcgcagca atcgcctgca taccgagccg gccgggaatc    30180
gctggatgtc ctgcttcgat ccgacgccta ccgcgcgcgg atggcactgc ttcgcgcccg    30240
agagttcgag gagatgaagg gcttgtccgg ccaagtcaag gccgacatgg cgcgcattct    30300
cgccgagggc atgggcgcg ggaagaatcc ccgcgagatc gcacgggacc tgaccgcaca    30360
gaccggcatc gaggcgcgtc gcggccatcg catcgcacgt accgaagtca caactgctct    30420
ccgaagggct cgctgggacg agaaagacgc tgctgaggcc gattacggcg ttcagtcgaa    30480
gctgatgcat atgtcggccc tgtcccccag caccagggca acccatgcgg ccaggcacgc    30540
caggctctac acctcggacg aggtgaggga ctggtacagc cgagacgaaa actcgatcaa    30600
ctgcaagtgc ggccaggtcg aggtcctggt cgatgacgaa gggaacccgg ttgtcccggc    30660
```

```
catcgtcgag cgcgcgcgcc gcaactacca agtcatgaaa gccaaagggc gcgggccctg    30720
ggcgaaagag gattgagcca tgcccatgca ggtcaacatc accacccagg tcaacagcgc    30780
cagcattcgg cgtgagacgc acaacgggcg cgaacatctg gttctgccga gctacaccct    30840
gccggccggc gtgatcatga acggtggtct ctacaccgcc gagcagatcg acaagcacta    30900
cccaggcctg gagggaacgc tggcgccgct cgggcacccg atggtcgacg gaagttcgt    30960 gtctgcgttc tccctgaag ggatcaacgc cgcccacgtc ggcgcctgga accgcaacgt    31020
gaagaaatcc ggcaaccggg tctacatgga gaagtgggtc gacgtcgagt tcgccaagtc    31080
cacggagggc ggccgtgaac tgttgcagcg cgtcgaagcg ctggagaagg gggaggacgc    31140 cccccgatc cataccagcg ttgccgcatt cctcaatcgc atcgagccga acgaaagcca    31200
gcgcgcccag ggcgcggagt gggtcgccga catccagagc atggaccacg acgcgatcct    31260
gctgcacgaa gtaggggcgg ccactcctga gcagggcgtc ggcctgatgg taaacgccga    31320
tcaggctgtc ccgcttcagc cgaattccgg cgctctggtt ggcgagtcct atcgggagcg    31380
ggagcagcgt ctcgatcgcg ccgcaaagga gcgattcgcc tccgggcccg atcagtacgc    31440
atgggttgcc gacttcaccg actctcaggc tgtgatcagc cgcaatggcg gtgtgaccga    31500
ggtgtacggc tacaagctcg aggcagggaa gatcgtcttc gacgaatccg ccagcccgt    31560 tgtcaggcaa gagtcctggg tcgccatggt ggccaacagc atcaagaaca ttttcaccca    31620
tcgtcaggct cggcctgatc aacctgagaa ggagggcgac atgccccctga ccccgaaga    31680 aaaggccgaa atcgtgaagg aaatcggcac caacacctcc agcgccatca aggaactggc    31740
ggacaccatc atcaagcccc tggccgacaa ggtcgacggc ctggtcgcca atcacaaggc    31800
gctggccgat acgctgaccg ccaaccagcg cgccgaggaa acagcatgc gcgaagcggt    31860 caaggccaag tttggcgagg tcatcgccaa cagcctggcc ggtgacgcgc tcaaggaaat    31920
gttcaagcag tgcggcgaat ccgctccgct gggcgccaat gctgccaccg acaaaggcgg    31980
actcaccgcc gatatcgcca acctgccgaa ggagtaagcc atgtctcgct atcgtcgagt    32040
gaacatcgac ggcaagtcgc tgttcaagac cgaaacccgc aagaccgccg cggaactcct    32100
gcccggcacg ttcgccgtga tcaatggcag cgacctgttc gcccaggcaa cgccagcgt    32160 tggccgcctc tacgtcatcg actgcgctca ccacgaaggg ctcaacatcc gcgatgaggt    32220
tcccgccggc cattcggccg tgggcaacta cgtcgaagag ggtcgcgagc tcgccgtgct    32280
gtgcccggcc ggcacctaca agaaggacac gccgatcaag ctcggcacca gcggccaggg    32340
tgccatcgcg tcgagcgata ccgacacggt cctcgggtac agccaggacg atgcagtcat    32400
cgcctccggc gaaaccgact tcatccgcat ccgcttccgt gtcggcagtg tcgccgcccc    32460
ggcgccctaa taggagtacg gacacatgtt cctcacccag caagcaatcg ccgcccatcc    32520
tcgcctgatg ggccactacc aggagttgca ggccaaccgc aacatctgga caaccagaa    32580 cgctgcgatg atcacccacc accgcggcgc catgacccc gaaatgctgg cctgcaacgc    32640
gctcgccggc ctgggtcgtg agttctgggc cgaggtcgac gcccagatca tccagtaccg    32700
caaccaggaa accggcatgg agatcgtcaa cgatctcctg caggtgcaga ccgtgctgcc    32760
gatcggcaag accgccaagc tctacaacgt ggccggcgac atcgccgatg atgtgtcggt    32820
gagcatcgac ggccaggccc cgtactcctt cgatcacacc gagtacaact ccgatggcga    32880
ccccattccg gtgttcaccg ccggctacgg tgtcaactgg cgccatgctg ccggcatgaa    32940
caccgtcggc atcgacctgg ttctggactc gcaggctgcg aagctccgca agttcagcaa    33000
```

```
gcggatcgtt gcctacaccc tggacggcgc caccaacatc caggtcgaga actaccggc    33060 tcagggtctg cgcaatcacc gcaacaccat caaggtcaac ctgggctccg cgccggcgg    33120 cgcgaacatc gacctgacca ccgccacgcc gcagcagatc atcgacttct tcaccaaagg   33180
cgcattcggc caagctgcgc gtgccaacaa ggtggacgcc tacgatgttc tctgggtttc   33240
cccggaaatc aacgccaacc tgtcccagcc ctacatgatc accatgggcg gcggtgccaa   33300
tgcggtggtg gccggcaccg tgctcgatgc ggtcatgcgc ttcatcccgg cgcgcgcggt   33360
tcgccagact ttcgccctgt cgggcaacga gttcctgggc taccagcgcc agcgcgacgt   33420
ggtcaccccg ctggtcggca tggctaccgg cgttgtgccg ctgccgcggc cgctgccgca   33480
ggtcaactac aacttccaga tcatgagcgc catgggcatc caggtgaaga aggacgacga   33540
aggtctgtcc ggcgtgatct acggcgccaa cctggcgtaa ggagaccgac atgcccaaat   33600
acgaggtgat caaaccctgg aacggcgttt ccaagggcca ggtgctggaa ctcgaatcac   33660
ttgccgctgc gctcctgccg aacgtgcgcg aggttggcgc actcaagaac ggaagcctga   33720
ccttggacgt ttcggcccag gttgacgaag cggccaggca agctctcgcc gaagcgcgtg   33780
catccgtcga tgccatgatc gacgaagcca aggcccaggc cgaaggcatc atcgccgcgg   33840
ccaacgcgga agcagcgagt atccgggagc aggccaaggc ccaggccggc accctgaccc   33900
cggcgatccc ggacggaagc gagcgccgcg agctgatcaa agcgcgcctg aaggaactga   33960
agatcgagtt cgatgccgcc cagggagagg aagcgcttgc cgccctgctg ccggagggcg   34020
aactggcgaa gctgttcccg gccaagtgac cggtgcgtga cgagaggccg cctgcgggcg   34080
gcctcgtcgt ttctggcctc agcgatgggg tcccttcttc tggagaatga atgtttggc    34140 aatcagaccg actcggacat cccggcgatt ccgaaggctc cgcccgctcc tatggggttc   34200
ccggcctcgt tcgggctag cgatgacttc aggctctgcg atgctatccg gaacaccgtg   34260
gatgctgcgc aagacgccca aggtatgacg cttcggattc ttcaacgaca cctcctccgt   34320
ctgtgcaacc tgcaggtcga gcaactggag ggatgtggtg atgatcacat ttgaacaggc   34380
ccggcagtac ctgcagagcc agggcatcga caacgtgccc gatttcatcc ttgcggcgtg   34440
gatcgagcaa ttgcagcaga tccaggactg cctggatgcc cattacccgg catcgacctc   34500
gctgctaatt caggcctacc tgctggcgct gttcgccctg gcacaggccg acaagtacat   34560
cagcagccag acggcaccat ccggcgcttc tcgatcgttc cgctaccagg cctttgctga   34620
tcgctggaag gcgcagttgg ccctgctgaa cgccctggac aagtacggat gtgcgacggg   34680
gctgattcca ccgaacccaa cccagaccgc acacggcggt cttggatcg cgcgcggtg    34740 ctgcatgtgt ggtgactcat gagcacgacg gcgaattgga gttacaccaa cacggcgacg   34800
gttcggccat tcctgcactt cgacctttcg acccaggagg ctgtttacgg tcccgagtac   34860
gagatcgcct gcacctgggt agcgaagggt gagcaggtcc gcgataacag cggcgccgaa   34920
ttcgtatcgc gccaccagat attcaccgag gaccgccggc cgaagtacct ggacctgatc   34980
cagttcgacg gatccaacgg ctgggaagag attcgctcgg tgacgaactg ggacatgtcc   35040
ttcttcggtg aacagccgga ctttctgctg gtgacctgac atggcaatcc aaggaatcga   35100
ccgcgtccgg cggaatcttc gtgtggctgt cgaaaacatc gccggcggtg tttccgagcg   35160
cgcagtttac gaggtactga gccagggcgc cgcaatggcg cagaccatga cgccgatcga   35220
cacatcgact ctcgtcaaca gtcaaacggc cccccagatc actgttggcc caacggggt    35280 cgaggggagc gtcggttaca ccgccgctta tgcggcggca gtccacgaag cgccaggcac   35340
tctcgccggc cagccgcgcg acgagaacga ccccagccgg ggagactact gggctccgaa   35400
```

```
tgcggagcct gagtttctca cgaaaggttt tgaccagatc attccagcta tcccggccat   35460
cctccgcagg acctaccgcg tatgacccc tacgacgcct tccaggactg gctggcttcg    35520
atcctgggcg agggctacca gtacagccgt gggatgtggg tcgaccaccc ctcgctcgac   35580
tcggcattca tcgcagcgat ccagcaaacc ggcggtccgc cgactcaggt cgacgtccgt   35640
cgcctgcggt tcaaggtgat cctcctcggc ccgaagggcg tccggaaaca cgttgtcgac   35700
gtcggcaact caatcgagac cctggcgcag gcagcgcttg cgacagcgt cccctgtggc    35760 gccgcatctg ttcgggcaat cggagagccg atcgggcccg atacaccac ggaaaaccgg    35820 gcctggtaca gcctggacct tgaagttctc tactaatcag gaggccagac atggcttgca   35880
agaagctcaa atttccgggc cgcgacgtcg tgctcgagta ttacatcggg tgcggcgatg   35940
cgctgccggc ggagaatgac tggcgccgtt cgggtcgct ccgcacgaag gagttcaccg    36000
tcgagtggga caccatcgac gcaaccgatt ccgactcggt cggcgcgctg cgcgagaacc   36060
tggccagctt ccagacgctg accatttccg gtgacggtac cgtaaaggcc tccggcgctg   36120
gcgcgcagaa cctgatcgac ctgacgaagc atgtcgtgaa acctgactcg actggcggac   36180
agcctgttgt ctggatgcgc atgactttcc cggacctgac cttcaccgca ttcatgctca   36240
tcagcaacct cagtcgatcc gcgccgtacg acgatgtcac cacctacagc ttcgaggctt   36300
cggcgaccgc ttccgacttc ggcctgatcg tcgaggatac ccccgatgcg gatgcgccgg   36360
accccaccag cattcaggtc gtgccggaga ccctctccct taccgttggc gagggcttca   36420
acttcgaagg cgtcgtgctg cctgttggcg ctccgcaagg cctgcgctgg acctcgaccg   36480
ctccgaccgt ggccgcagtg aacgcggtta ccggcgaggt cagcgcgctg tcggccggca   36540
gcgccacgat caccgctgcc tccagcgtcg tgccaggcgt taccgatacc gcaaccgtca   36600
cggtcatccc gctggtgcag gggattaccg tctcgccgac ctccgtatcg atcgctgaag   36660
gcgccaccca gcaactgacc gccgctgtat ccccgactgg cgcggctcct ggcctggtct   36720
acgaaagcgc ggcgccggcc attgccaccg tgagctcgag cggcctggtt accggcgttg   36780
atgtgggcac caccacggtg aaaatcacca gtgcggcacg tccctcggtc agcgtgaccg   36840
ttccggtaac catcactgca ccgtgatcct caccgagatc ggtgagatag gcgtacacac   36900
ggcctcgggg gagtgctttc tcctgcggcc gtccctgtac gccatgaccc agctcggtac   36960
gccggccgag attgtcgacg tcttcgcgcg agtcatgagc gacccgatca ccgagaagca   37020
ccaggcggac cagttcgccg acgccctggc cgtggtggtg gcctgtagtg agcaggacct   37080
gtccgacgtg tttggctact acgaccagga cctggtctac cggccaggaa ctgcggacgt   37140
cgagcacctt gtgcctctcg cgcgctgcct gctgaagcac ggcgtcacag gagcgcttcc   37200
gccactcccc cggcgccacg acgaagagcc gaactactcg ggggaattcg ttgcgcggga   37260
gtacgtcgcg acggcgatag cgcacctggg gctgagcgag cgcgaagctt ggtccatgac   37320
catgaccggc ctgatcggcg ctctgcgcgc gaaatatccc ccaaccgaat cgaacgctcc   37380
gggcgccaga gccccgaccg cggcagagca tgacgcgacg atggagtggt tcgacaagat   37440
cgaggccaag cgcaaggcgc gggcgaaagg agcaccctga tggctgagaa tgtcggcagc   37500
atctactaca ccgtcgaggc ggataccttc tggccttgtaa acggcacgaa tgctgctgac   37560
cgttcattgg atcagatgca ggcaaccatg cggcgtgctg atagcgaggc ggcacgtctc   37620
aacacgactg tcaccaagct ttcgtcggct attaagacga tcatcgcggc gtcagcgctc   37680
cgcgagatgg ccagcatggt ccagtcctat caggagatgg ctgacagggt tcgtctggcg   37740
```

```
tctgcaagcc aggaagagta tgaaaacgta caggccagac tgctccgtac cgccaacggg   37800
acataccgag cgctctccga ggcgcaggaa ctctacatcc gcacttctgc aggcctgaaa   37860
gctctcggat acgacacaac gtctgcactg gatgtgatgg attcgctgtc gtatgcattc   37920
gtgaccaatg cgaccaaggc ggatgcagca gaggcagcga tcagccagtt ctccaaggca   37980
atcaacaccg gcaaggtttc ggctgaccaa tgggaaacaa tctccagcgc agtcccgtct   38040
gttattgagg atatcggcgc cgctgcaggt aagacggggg cggaagtcag gagtcttggt   38100
gcgcaggggc aattaacggc gcaaatgctc accgagggtc tacgtaagtc cttagaagag   38160
aactccaagg cagccgccgg catgtccaat aacctgaccg atgcaggggt caggattcgc   38220
actgcattta ctcaagtcct tgtttcgttg gaagaccaga ctggtgccct tcaaacattc   38280
accaatggtc ttatttcggc tgctgatgcg cttcttgagt tcgggcttga ctcggaaaaa   38340
atggcagcat ttctcgacac tgcaacagtc gcagcagctt ctctggcctc tgttgtggct   38400
gggcgtctag ttacctccct gtatgcagca ggtgcggccc aagtgcaaag attgcgggca   38460
acgcttgagc agatagcagc tgatcggaat gctgctatag gtgcactgag gcgggcagag   38520
gcagagaagg ccgccgccgc cgcggctgtc gctctggctc aggcggactt gaatgctgcc   38580
aggggttcaa atgcccacgc aacagctcta acgcgctgc tggccgctaa agaacgcgac   38640
ttggccgcca caagagcgct aacggctgct caagcaacgc tgaatggtgt agcaaccacc   38700
gggacggtgg tgatgggtgg acttcgatcg gcaatggcgt tcctcggcgg accgcttggg   38760
gttgttctgc tggcagcaac cgcgatcgca acatttgcaa cgaatgcacg ggaggcgaaa   38820
gagcctacgg accttctaac cctgtccgtt gaaaaacttg acaggcaca gctgaaggtt   38880 gcacaactgg acatcgacaa gcgaatccaa gcagtgagcg ataagctcaa actgcttggg   38940
gaaaactatg cgttcgcggc aaaagaagcc caaggctctg gtcgaagggc caatcgatat   39000
gctgaagatg ccgtgcgtat ccagggcgcg gtcgaggagc ttacgcagga gcttgaccag   39060
ttacagaaaa agcgttcaga cgtcgacgca gccctagata aaaagagttc atccccatct   39120
ggtaatggcc cggatcgcca ggcaaacccg gaggatacaa aggctctcca gaatcttcgc   39180
gacgaggctg aactatctgc tctcgcgggt gaagaacggg cgaagcttgc cgcgcgcaaa   39240
aagctcagtg ctgatgccac aaaagaggag atcgcggagg cggagcgtct cgctgtccag   39300
atattccgca cagcgaagc gcggaagcaa gagaagaagt cagcctctga taccgcctct   39360
acggtcaaaa agtcgatgga ggatcagcgt cgcgctgcct tggacaatga aaagactatc   39420
ggagaccttt cccagcaact ggcacaggct ggactgaagg gaaaggaact ggcagaagct   39480
ggggcgcaat ctcgccttaa tccattcgcc acgccggagc aggtcgccca ggtccgcgcg   39540
ctcgccgcag ctctgtacga agcgcaacag gtcgaagcca acaagcagtt gctggggcag   39600
atggacccga tcgccggcga agaccagcgc taccagaccg aactggagaa tctgaaaaag   39660
ctgaacgagg ccaagttgct cgaggaccag cgctacctgg aactcaaggc gcaggcagag   39720
caacagcacg atgccacgat gaagcaactg gaggaggagc gattccgccg ccaggctgcc   39780
ggcaacgaga tgatcatggc aacgctggat caggtgcagc aggccggcac gaacgctctg   39840
acagggctga taaccggggc gaacaacggt gctgacgcca tgcggcaact ggccggcgcc   39900
atgctgaacc aggtcgtggg cgccctcgtc aaggtcggca tcgaacaggc gaagaacttc   39960
atcatgggcg aggcccagca ggcggctgcg gcgacgacag ccgcggcgac aggtgcagct   40020
atggcttctg cctacgcgcc agccgccgct gccgcctcgg ttgcgtcatt cggtggggcg   40080
gcaacggctg gcctgaccgc aatggcggct gccatcccgg cgatgcttgg catgttcggt   40140
```

```
ggtggccgac agtacggcgg ccccgtaggg gctggtggca tgtaccgcat caacgagaac   40200
ggcgcgccag aggtattcca ggctgcgaat ggccggcagt acatgctgcc gaacacgcga   40260
ggcgaggtga tcagcaacgg cgacgccacc gcgcagggct cgccgcagat cagcctgcag   40320
atcatcaaca acgtcctcc ggtttccgcc accgccacca tggacgggaa caacctgcgg    40380
gtaactctcg atgcggtcga gcaggacttt gccaacaagg tttcgtccgg ccagggcttt   40440
tacccgaaag caatcgaagg cgcctatgga ttcaagaggg cagggcgatg atcaaatggc   40500
ctgatggcct tcccttcccg ctcagggagg ggtacggctt caagacggta gagcctatgg   40560
ccaggacgtc cctccagagc ggccgggcac gctacaggcg gaacttcagc aatgtgccgg   40620
tcgcgctgga ggtttcctgg ctgttcactg ctgagcaggc tcggctgttc aaagggtggt   40680
accgagacgt cctgaaagac ggcgtcaagt ggttcgagtg cgatttgcgt acggaagagg   40740
gaatcgttcc gtgcaacctg cacttcgagg ggatctacga cggtggctat ctcgtcgggc   40800
gcgaccactg gcgtttcaac gcaaccgtcg tgatgcgaga gcgctcgatc atcgatccag   40860
ggtgggccga gattctgccc gagtacatcc tcctcgccga catcttcgac atcgcgatga   40920
acagggagtg gcctcgacat ggcgacggct cttgagcggt tctatgcatc ggatgggccg   40980
gatattccga ttgcaacgat cgagattact cggccctcca ggcccgatcc gatcctcatc   41040
tgtcaggggt tcaaagacct gacctgcatg acagaagacg gacggctact gacattcatc   41100
gctggcgcta tcgacgtttc gatcccgaag cgcgacaaca gcgggaacca gaatgttggc   41160
tttgcgatcg acaacgtgac tggctttgct cagcaatata ttgccgaggc catcgacgcc   41220
ggagagccgg tcacgcttgt cctgcgaatc tacctcggaa gcgacctgac tgcgcctgcc   41280
gagcggccgt atcggatgcg cgtgaaaggg gtcgacttcg aaagcctcac tgtccaggta   41340
gaagccggct actacgacct catcaacacc gccgcgctgc gccacatcta caacgttagc   41400
gagttccctg gcctcaaata ctggccctga tcccatgccg aacagatacc tcaccgccat   41460
ctataccgag ggcgggcggg ccctgccgtg ccttgactgc tggggcctga cgctcatcgc   41520
gcgggttgag ttgttcggtc tgccgatgct gaccgacttc ggcggtgtca cgcggcgcac   41580
cccggtttcg atgcaaaggg cgtgcgatgc ggagatccac cgcgcgctcg agcaatgcga   41640
gccaggacct gggtcatcg ccgcggccta cagagggcgg ctgctcgatc acgtaggtct    41700
gctggtcgaa gtggatggac gcctccgggt tctcgaaatc aacccgggaa gcggggtttc   41760
actcaccccg ctccagaagt ctccgacaa atactccaag gtggtcttct accgtgatcg    41820
aaatctaccc atcgctcctt gacgagaac cgctggagcg gcatccgatc ggccgcagga    41880
tgacgattca tgcctggctg accgcgaatt cgcccgggta ccgctgccac gacgtccacc   41940
cgttctctat cggtgttgtc cccgctgagg ttgcgctctg cgatgacctc accgacaagc   42000
agaaaaaggc ccatgaggat ttcatccatc ccggtgagtg ggccgagcgc atcatcgacc   42060
gcggcgacat tgtgaggatc tacaagctcc gcgcgggac tgatccgttc acgattactg    42120
cggccctttt caaggggggcg caatcggttt ttcggatgct catgcctcaa ttgcccggca   42180
tgccgacgaa ccccgggcag ggcgcgtcgc tctctgaaac tagcgcgcgc gggaacaagg   42240
taaaactcgg cgatgcgatc cgcgaagtcg ctggccgtcg tctgatttat ccagactaca   42300
tcctgccgcc ccggaagtac ttcgccggtc cgcgtgagca gtggaccgaa atgctcctgt   42360
gtattgccgg tggtcggttc cagatcgccg aaggggcagc gaaaatcggt gacacgtcgt   42420
tcctggcact gggcgctgat gcctctttcc agattttcga accagggcag aacgtcagcg   42480
```

```
ggcacccggc atcggtctgg tggcacctgg ttgaggaagt tggtgcgagc tcgactggta    42540
atgccggcct ggacctgacc gagagttcca atctcacccc gaacccgtcg gcaactacgt    42600
tcacgttttc cggaacgaac atcattattt ctgccggagc cgggtcgttc ccctctgact    42660
gggttgcggg gacgatcctg cggggttgag gcgatgtaccc ctattcggtg aacgatggcg    42720
gcggcacgaa tcgcgacgtc gtgacggggg atatcgctca gctcgggctg gatgttggcg    42780
atgagatcga ggtggtcggc accaacggcg gcctctacct ggtgaacgac atcacctcaa    42840
cgtcgatgac gctcaactac agcaacggtt cgccggccaa tgcgttgcag accggctccg    42900
gaaatgcagc aatcggcccg cgtgggctgc gctatcggat cacggcgtac agcgcgcagc    42960
aactcaccgt cgagcggctg accagtgcgg gcggtgtcga tgttgactgg ccaggattca    43020
ccgctctcaa ctcgtctacg tcccgagtca ccattgatcc gaccagccta aaggggggct    43080
ggcgcggtcc cttcccggcg tgcccagtat cggagaagac caacttcgtc gagatcgacg    43140
tattttgccc ggaagggctt tgcggtgtag gcagggaagg gcagatctac cagatccgca    43200
cctattacga catccagtgg cgagacatgg ccatcggcgg cgcatggacg acggtcagca    43260
agaaccatgc tggcagttct ctcgaccagc agggttttac ggacggcatc ccgctgccgt    43320
acatgatgcg gcccgagttt cgcatcagaa aagtgttcgt caaccagggc ggcaactcaa    43380
catccgagta ccgagaccgc acccagtggt acgggatgcg cgcgcgcctc caggctccat    43440
cgtcctacgc cggcgtcacg acaatggccg tcaggtatcg gtcgtctgac cgtatcgcag    43500
cgcagaccga aagccgcgtt tcggtggaag ctactcgcat gctaacgact cggcagaacg    43560
gtgcatggac gagcgagatc gctacgcgag acatcgtccc gttcctctgc tacatcgcga    43620
aggaacgcgg ctataccgat gcggatctcg atcttgagga actcgatcgg ctggacgcaa    43680
tctggaaggc ccgcggcgac aagtttgaca tgatctacga ggacggcaag gtcacggtcg    43740
cgcagatcat ggatgacgta cttgcagccg gatatgcgga gaagaccatt aagcgcggcg    43800
tgatctctgc tgcccgagac gagcctagga ccacgttcgg gcacatgtac tcgccgcaga    43860
acatggatgg tccgctgaag atcagcatca gtgcgccgtc tgaggacgac tacgacggcg    43920
tcgatgtcga gttcgtcaat gccaacggct ggatcgaaga taccgtccag tgccgcctcc    43980
ccggcgatgt cggcaggaag gtcgagaaga tcacggccgt cggcgtgaca gaccgaaacc    44040
gggcgtggcg atacgaatg cgccgccgga tggcacagcg ataccggaga accgagtatt    44100
cgttcgatac cggcctcgac gcgctgaaca gcgacttctg ggattacgtg gcccttgccg    44160
gcgatgttcc cggcccagga ctggcgcaga gcgcatacct gaaatcgttc gtgatctctg    44220
gaagctcggt cctgatcgag tccagcgagc cgctcgactg gtcactgctg aactcgccag    44280
cgctctacct gcgcgcccca gacggaacgg tttccggtgg atatccggcg tcgaggatcg    44340
acgactaccg gctgagcatt cccagcatcg atttcatccc tgatgtttct tgggagatcg    44400
aacctccaca cctgctgctg ggaaacccat acccggccct gatcagttcc atcgatccca    44460
acggcaatac ctcggcatcc gttcgtgcgg tgaactacga ccccagggtc tacacctacg    44520
acaacgccag cgcccaaaac tgaccgcaca cgaaaaacca tagcccgcca tagagcgggc    44580
tttttcatac ccgagaatt tgcatgacta catacgccac tggcaacccg cttggctcca    44640
aagacccgcg tgatctgtac gataacgccg agaacttcga cacggctatg aacgaccgcg    44700
agaatttggc atggagcgat cgattcggcg tttccagaaa aacctggttt ggacttgagc    44760
agcaagtcgc tgactttctt gccgctcagg gctacgagcc ggtgccgctg gagtatgtcg    44820
acggctctcc gctgaccgta gatcgtccga cccaactcat cgagcgtgat ggcaacctct    44880
```

```
acagcgtcaa gctgccggca tcgttcccgg ttgagctgac cggtaactgg gcgaccgatc    44940
agaatttact tgtcgcccag gtagaccgct cgctgcgtca gcaactgaga gattctggcg    45000
gatcagggat gctgggattc aatgcgtctg aatcttaccc atcagataca atcggctacg    45060
aggtaaatac ccttatggcg ctcaaggttg tcgtagttac taattacggt gccactggca    45120
acggaacgac tgatgacacg gcagcgattc aggctgccat tgcagcagca gggccgtatt    45180
cagatgttgt attcccgtct ggaacctacc tgatcacctc tacgctcacc tccctgactg    45240
gacagcgctg gcttggcagg ggcggacaac gagggaccac tatcaagaag gcgccaaca    45300 tcgacatggt ggtagtaggt acgctatcca ccattcttga tatcaacctg gaaggcgttg    45360
gtgctaccta tacaggtaag gggttccgta tcgtctctgg atttagccaa acgatcaccc    45420
ggtgtcgtgc ggtaaacatg ggtggtgagc ctctttactt cgacagtaac gcgggcggag    45480
gggctaacgt aacagtattc gaagggtacc ctgtcgatac ggatgcttat gctggctgcg    45540
ctattgcggg agatactgct cctcatcctc ggttttccg tggtatgtgg ctcagtggtg    45600
cgaattttgc gcttggacca ggggctggta acggcggatc tatgaccgaa ttctatattc    45660
gtgacttgag attcgacgcg acttctacac tgttccacat ttccaatggg cgctgcgcga    45720
cgcttggggc tacgacgacc cttaagggct ttgaccactc aattgatggg gttgcttttg    45780
caggccctgt tgcgctcgac tctgcccaag gcatcaacct tggtccgtcc tgctctgtac    45840
cgtcgctcac ggagaacgcg accaactcgc aatacaactc cgtctatgta cagcgtagga    45900 cctacaccc aacttggacg cagactagcg ccactcctgc aattggcaat ggtaccttga    45960
ctggtaacta tgttcgagct ggtcacatgt gtcatgtgca gattgagttg gtagcaggtt    46020
cgactacaac cttcggggat gcagcgtcag gttataggtt ctcccttccg ttccctggcc    46080
acctttcttt caaccagaga gggtttcctg tgcggatcta tgatacgagc gctggtgcgg    46140
atttcactgg gtgggcatcc attggcgcag gtcaggcta cattactatc tccgtgggag    46200
cgcagcaggt ccgcgccacg tcgcccatga cgtgggcgaa cggcgacacc ttacagtgtt    46260
cgttctccta tatgacacgc tagcgccgtt gtgccatgat cgccggtcct cacggcggcg    46320
atcatggaga actcgcggtg tcatcaatga aatacattcc aggggttgac ggactacgct    46380
cgattgctgt aatgagcgtc ctcctgttcc acgcagggtt tagctctcta gctggcggat    46440
tcgttggcgt tgatgtcttc tttgtgatca gcgggttctt gatcactcag ttgatttaca    46500
aggaaatatc gaccgctgga acctttgact accataggtt ctattcaagg cgcgtgagac    46560
gccttttccc tgctttattc gtaacagttt tagttagctt tatttgtgcc aacctttttt    46620
tcagtccaga gcatctaagt agattttctg gagaggttat ttactctcta ttctcgttgt    46680
ctaattttta cttctggagt gagagcggtt atttaacac cgcgtctgat ttcaagcctc    46740
ttctgcatac atggtctcta tctgtagagg agcagttta tatattctgg ccaatccttg    46800
tcgttttctt tggaaagaaa tttggttcca agggagtggg ttcgttccta ttgatttccg    46860
gtattgctag ccttctagga aacgtttcct ttattgatgg ctctagcgtc cttgtttcat    46920
gggctggaaa ggttgtatct gggtggttct ctgatggcgc atcgacaata ttttatctaa    46980
ctccatttcg cgtcttcgag ttttgtctag gtgctatcat tgtatttctt ccaaaggtta    47040
actcttcttc tgttcataac tttctgttcg catcaggcgt tgcgctgatt ggatattctg    47100
tttttgagtt caatgcactt actccattcc caacctataa cgcattgatt ccatgcgctg    47160
ggtctgctct tgtaatatat tcttccggct cttattttt caggttgaca atatctacgt    47220
```

| | |
|---|---|
| cgccatttgt attcctcggg aagattagtt attcgatata cttggttcat tggccgatta | 47280 |
| ttgtattcta taaatactat tattcagggg atgtatcgat atctgctaag gttgccattg | 47340 |
| tcatagtgtc tgttgtgctc ggatatctgc tgttcaggtt cgttgagact ccatttcgca | 47400 |
| gccagagtgg caagactata tctagtaacg gtttcaattt gtcctgcctg atgctttctt | 47460 |
| gtcttcttgt ggttccatct gcaaccgcat ggggaaattc aggctggacg tggcgagtat | 47520 |
| ccgaaccgcc aaaagggatt gctgctcaac tggctgattc taagaaattc cacatagacc | 47580 |
| agtatggagg aaacggatat caggagaggg gatggattag cggggaggt attgcggatg | 47640 |
| tggttgttat tggtgatagc catgcacgac agtatgcata cggactagat caagtcctcg | 47700 |
| gcacgccaga gaagctcaac atttacctta gctctgttag ctgcattctg cttcccggta | 47760 |
| tgaccaggtt gacgcccgga accgattggg attcgctgtg ctcggcagca ctcgatgatg | 47820 |
| cgcttgcggc tctggacaga aacccaaagg cggttcttgt gatagctcaa ctatgggttg | 47880 |
| accagttaac gatagctgcg acaaaccctg ggcacgtacc tgttccagat agtaaaggcg | 47940 |
| ctggtggata cagcctgctt atcgagaaga tacgtgaact caagagccgg atcggatcgc | 48000 |
| gaaaaatgat cgtgatcgga aatgtgcctg gtgctggctc tccggatatt gccgggtgct | 48060 |
| acaaccgacc gagctttgcg agaggctact gtctttcgaa aattggcatt ccctattcgg | 48120 |
| atgttaggtc tgtagcgatt aacaaggctc ttgccgacgt ctcaaaaata cctggcgtgc | 48180 |
| tcttcataaa tccgcatgat gttttctgtc atgatgggtt ctgcaaatct attgcgaacg | 48240 |
| acgcaatttt gtacagcgac agtaatcatc tttctaaagc tggttctgaa tattttgtgt | 48300 |
| caaaagagaa ggacaatatc ctgacgcata taaagagacc tccagaattg tccttgtcaa | 48360 |
| aaggtagcta gttagaagcc cgcattaagc gggcttttt atttcaggag agcgtatgcc | 48420 |
| tatcactgag cagcagttgc tgcatgtcct cccgaacgcc ggcctcgag ccggcgtttt | 48480 |
| tgttggtgcg ctgaaccgcg ggatgacgcg cttcggtatc acgtcgcctg tgcgagtcgc | 48540 |
| cgcgttcctc gcccaagttg gccacgaaag cggccagttg acccgcctgg tggagaacct | 48600 |
| caattacagc gcccaaggct tggcggcgac ctggccgagc cgatacctcg cgccgacgg | 48660 |
| ccagcccaac gccctggcgc agcgcctggc gcgcaactcc cgagccatcg ccaacaacgc | 48720 |
| ctacgcctcg cgcaacggca atggcgacga ggcatcgggc gatggctggc ggtaccgcgg | 48780 |
| gcgcgggctg ctgcaaatca ccggccgggc gaactaccgc gccgccggcg ccgggctggg | 48840 |
| ccagccactg gagcaggaac ccgagcttct cgagcaaccg gagtgggcgg cgatctcggc | 48900 |
| ggcctggtgg tgggccagtc acggcttgaa cgacctggcc gaccgcggcg aattcgccgc | 48960 |
| catcactcgg cgcatcaatg gcggcacgaa cggccaggcg gagcgcctgg cgctgtggga | 49020 |
| gcgggccaag gcggtgctgt cgtgatctcg gcccgcgtga tttcgatcgc gctggcctgc | 49080 |
| ctggtgctgg tcggcctcgg caccgctggc ggtgtctgga tcggcgcgcg gcactaccgg | 49140 |
| ccgcagctcg atgctgcgct ggcggatctg gctgcctgcc gttccgctcg tgggagcctg | 49200 |
| gaggccgcag tagtggagca gggcgggcag attgccgcgc tgcgtcaggc tggtgagcag | 49260 |
| cgcgcccggg atgccgcgca ggctgtggat cggggacggc agcaggccgc ggagcagtat | 49320 |
| gccgcggcac agcgcctgtt gcgtgagcgc tccgctggtg atcagtgctt ggcagccgaa | 49380 |
| gtggtcatcg atcaggagtt ggggctatga gggtggtgct gatgctggtg atggttgcgc | 49440 |
| tggcgggatg cgccggccgg caggaagccg agccgcgcac ggtgcgcgta gaagtgccgg | 49500 |
| tggcggtgcc gtgccgggtg ccggcggtgg aggtgccggc atgggcagcg gctgggctga | 49560 |
| agaagagcga cgacctacag accaaggtcc gtgcgctgct ggccgagcgg cggcagcgga | 49620 |

-continued

```
ttggttacga ggcgcagctc ctggctgcga atcaggcctg tcaggattag gagtagacta    49680
cggccttttc ctacgagggc agggcatgct ggtcattcga ttcaagggct ggtcggtgaa    49740
actcgaccac caggtgggca gcgctgggaa acatggcatc tggtcgttcc acggctcgga    49800
gagcagctac gtaccggaca tggagacgat tctccggcat gctgctattc ggcctgcgga    49860
gccgaaagaa ggcggggagg tcgaggtatt catctgtgat tcgcgtatgc cgcaggacga    49920
atggcgggcg gtaggaccgg gcgtcgcggc ttatgaggcc gagcgctgaa agtcaggcc    49980
accgccaggg ccggaagtca tcagggatct gctcggcgag ttgcagcgtg ccgccggcgt    50040
cgagttcgat ctccagaccg cgcacaacgc cggcgcgctc gagcgcctgg cccaggcgga    50100
ggtatgttat cccgtcgagc ggatcccggc tgatgtagcc caggcgctgt cgtgcgggtg    50160
cgggcccgtg gtagatcccc tcgctgtcca ccgtcccgac agcacggccg ccgtcgagca    50220
cgtcgtagca gcagtccgcg cagtagtgcg tctcgcgcgt tatgccgtgc tcgatcgccc    50280
aggagtacat gccgagcgcg tcggtgacca tgtcgtggcg gtcctgcagg ccaacgattc    50340
cgcactgata gagttcgttt gcctcggcca ccagatacag gtactgctca tccgcggcgt    50400
acagccaggc ggcatgctgc cgcatcgcgg cgagccattg ggtgacgcgc tggtggtggc    50460
aatgcctggg gtcggagtag gacatggaaa tctccggcag tcggttggc cggaaattat    50520
gctgtatgaa tatccagtat tcgagggcgg ccgacgagcg gagagttatg ctcgggcatg    50580
ccatggaggg ggctgaaatc atttccgcaa tttattcatt gacccaggca gcaagcggca    50640
tccagagaat gagaaat                                                   50657

<210> SEQ ID NO 4
<211> LENGTH: 39454
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6816)..(6917)
<223> OTHER INFORMATION: n is a, c, g, or t

<400> SEQUENCE: 4
gcgtcttcgg tgtagccaga ctcgctggcg aattttttaa cagtcaggta gcgcattcct      60
gaggcctagg cttgaatgca agcccctccc agcggccgga tgggccgcga atctcgcagc     120
gccgaacgta ggcccggcgt ttcttactgt cgaacagtgc ctggcaggca tccatttgct     180
caccgtcgtt cgtcattgcc agcagtctgg cgcggtcacc gctgttgacg aagacaaagc     240
cgtctttgac cttcccgaat ccactggtcc ggtataaggc ccagcgcgcc cctcctttct     300
tgccgccctt cgaccttcg gtcaggtaga acgcaaactc tccccctcatc acgcgaagca     360
gagttctagc catggcgacc cccaccatct ttcgccacta ccgaatacgc ctccggcttt     420
cgctcaaccg tacgggtcga tccgtccatg ctgtggacgg tgagtgccgg ccgccgaatc     480
tgcacagttc cgttcggcgc catttcctga cgcggggcgc cgtagaaagg gccacccggg     540
gcgaacgggt cagggatggc cgacggattt tcaagcaaga acttctggaa caggttctgg     600
accgctgcgg taagtggccc cgtgttccct cggttggagc ggccactctt gtggtccgcg     660
ctgtcctcga actccccacc aatccagagc aggccgccaa cgattccggc gtcgcccgcg     720
cagacctcgg cagcctcggc acggtgggca tgattcaccc ccaggaggtc gcacagatcg     780
tcgaacgaca gggcctgctc gatcatggct gagtttccga taagccaggc accgcactcc     840
```

```
tccatggctt gcgccgcaac tctggctcgc tcccgatatg ccatccgttc gcgctccagc    900
gcctgctcgg tgaacggcat gcccttgaga agtcgtcgcc acttctggcg atgtctgcg     960 aagctggcgt cgcgatcggc gtgcactgcc cggatgaaca tccggagagc tgctatacgg   1020
acgcgcaggt tacggctgct gtcgacgccg aggtcgatca gccgatgcat cgttgcgccc   1080
ttcatgcccg actctccttg ttcgtgtcgc agatccgcag gtcgacgccg caggcctgga   1140
ccagttcggt caactcgccg agcttggtgt tggggttctg catcgcctgg cccaggcgga   1200
ccaactgctg gccaagggtg gtgagcgggg tagggcgata ccctggtggt ggtggaatat   1260
cggagcctct catcactggc atacctccca gatgaacagg gtcttgaacg gctggagcgc   1320
tgcgccggcg gcaacagtgg ccaggccaaa cagcgcgacg agtgcgatag cggtcagagc   1380
cttgcgcatg gtcatcgctc acctccaggc gctggcgcag cggcaatgag gccccgatac   1440
acacgtgcta ggaaggcgcg aactgcatcc cgacccggga agtagtactc ggtatcctca   1500
acgagatagc cgtccattcc gtcctcgctg tcgcggcgcg cgtccagcat ttccggggtc   1560
ggctcaagcg gtaccagctt ccagcccttc ggaacgttag cctgagcctg tccgtcgatc   1620
agcgcgatga tgtggtcagg catggtcaag gcctcgtaac gcaccatcag attcgaggcc   1680
tcctctccgc tgagcagcgg gttcttgagc gcgacacaa ttcggcgtag ttcggcgtgc    1740
tcgcgggcta atcccggcgc ggggtgggtt tgctcgccgg tattacccgg tccggaaaca   1800
ggttcgccgc cagggttgcc cggctccgta ctcactccag ccccgctcag cgccgccagc   1860
gcgatctgcc gcatgttcgc cgccggcatg ttgtcctgct cgggacaggg gaactcggcg   1920
atggtgcgga gcgccaggac ggcgcgctcg agcggatgct cttctgcagc ctcggcgccg   1980
gccaggtgct tcgctaccgt ttcccggatg acgcgcagcg cgttcatggc ctggagcgag   2040
ctaccgtcct ggccgagctt ggcggtcaga tcgatctgtt taaacagggc atgggtcata   2100
gatcaccccc ttgctcggcg ctgcgcaccg cctggtaggc gagggcgtag caagccattt   2160
gcaccagcag gctcgaagcc gcgagtgcgg ggtgatccgt gagggccagg gccgccacgt   2220
gcagagcgcc ggtagggatg gagagccaag ggcgggcgag caggttcgcg gctccttgcc   2280
ccttgatgcc gccggcgaat atcagcagcc agcagagaac gttcatggcc gccgcgacat   2340
agaaggcgaa ctggtggatc gaccccctgac tgaagtacag gcacgcgctg agcagcaggc   2400
tgatcgcggt gccgatgagt gcttgcttca tgatcagcga cctccggcgg cagcggtcaa   2460
ggcgtcgagg agcgcatgct tccggcgctg accatgcagg tactcgcgca cggcgatgat   2520
gaccacgctg ttcatgctgc gttcatcgcg ctcggcctcg gcttcgacct cggccctcag   2580
gccgtcgggc agtcggacaa cgaacttgtc catatcccgg ctggtgctgg ccggcagttc   2640
ggttacaacg gttgctcgtt tcatggtatc tccagtggcg ccatcgctgg cgccggggcg   2700
aggatggcta cttgctgatg ccgatgaagg gcagcgggga gccgctggcc atgtaggtgg   2760
gcagcttgcc gtcccacttc tcgaccgcgt tgagggtcac gacgtcgggg ttcgagcgca   2820
gcgcctgggc gcggatctcg atcgccttcg catcggcggt ggccagggtc agcttcgcgt   2880
ccgcctcccc ttgggcccga gcgcgttcct tgtcggcttc tgccttggct tgggcgacct   2940
cgttacggcg ctgctcggcc atctgggtgg cctggatctt cgcgttcagg ctctgcgtaa   3000
cctgcggcgg gaggaccagg tcggatgcgt agtagatgcg ctcgatgttg atgccgatgg   3060
gcgccacctg gtcgcgcacg cgcttctcga cggccagcag caggtccgcc ttgccggcgc   3120
catagacgct ctcgactgga agcttcgagg caacatcgtt gaaggcgtcg cgcaccatgt   3180
tccgcaggaa cttgtttgtg atttcgtcga tacccgcccg gtacttctgg aacagcgtcg   3240
```

-continued

```
tcaccttgtc gggggatact gagtaggtga tgccgacggc gccgccaacc ttcataccct    3300
caacggtctg gaagctgatc gcttcctcgc cgccccaggt ctcggtctgc gtgaaggtgg    3360
ggaacaggta gagttcctcg ttcacgccta cccagtagcg cccagttcct acctcacgcg    3420
tctccacgcc cttctcggag ccgtagaggt tgacgatcac gccgacgttg ccggcaggca    3480
ccttcgaaca gcccgccagg acggcgagca ggcacagcat tgcagcagcg ggaatccgct    3540
tcattggtct ttctccttgc tggtggtggc cgcttgttcg cggcgggtgt tggcgaggtg    3600
gatgccgagg cagaccgagg cgatcaacca gacgccgggg atggcgaatc cgcgaaaac    3660 cagaacgtcg tcgcggctac tgaccagggc cggtccaatg ccacccacca gggcgacgga    3720
caaccctgca taggccagca gggcgataca gatcaggaag agcttccagg gcttgatgag    3780
aggcttgttg tccatgcttt tctccaggca agccgatggc ctgccgcggt tgttggcttt    3840
cgcgaaaatc tgttgggtgt cggtcagccc cgactgctca ccactgccca ggtgacgggc    3900
tttgcgctag gctgagcgct ctcacacaac acagccagca aaggagggcg gagccgtggc    3960
ggtttccgta attgcaaagt tcatcgcaga tgagtggttc aagatcatgg cgatcctgtg    4020
tttcctgctg ctggcggcct cgctcactct cgacctcaag gtcgacaacg gcatcgttgg    4080
gcttttcgct ttgtccggaa tgatctgggg gatcggcgag atggcttgcc gccccttcgt    4140
gtccaggatg gctccgcacc cataccaatt tggctcggtc gtcatcagtg gcaggcctcg    4200
ccggatgaac aagactggct tcgttctgtt cgtgctatcg atcatcgtgg cgatccttgg    4260
ctgccttagg gcatggccgt tcgtgttacc catgattgaa atagtccttc acccgaacac    4320
cctgtagcgg attcacgcca cccaggccgc gccatcgcgg cgagcagtca ggcgagtttc    4380
gatcttcctt tcgccgccac ggcggctgcg catcatgtgg tcatcgttga gcagtggctg    4440
accggagacg aggaaggcga gggcgatcac ggcgggtgag ataagcccgc ggcgcatggc    4500
ttcagctact agagccggcc tacggtaggc gttgagcttg tgcattgcgc gctcaattgc    4560 gccttcacg gtgcgaggtg ataccccgag ggaaagggcg gcctgtttgt cggtgcagcc    4620
accggctact gcaagcaggc attgaacctc tcgagcagca agctctgagt cggtgcgtcc    4680
actccagttt ccgaatgtga ttgctgccat gggggttagc tccaatgcct actcttggag    4740
ctaatagtgc tggcgggatt attttgtgtc aatccttgcg ggattatttt ttataggccg    4800 ggtactttg catctatcac ccgaccaatg atctcccagt cgtcatccat ctccagtgtc    4860
ctgtaggcct tgttcagcgg gaccaagtac ttgacccctg cgtcgtagac gtactgcttg    4920
aacgtggttt cgccatccga gtgcttggcc acatagtatt ttccgctgat caggtcgaac    4980
ccttctggct gcacgagaat cggcgttccc ggcgggaagc tgggcggggt tggggaggac    5040
attgagtctc caagaataat cagccaataa ccatttgccc ccgcgttttc ggtagatggc    5100
agccattcgt ccgctacacc cggcgggtgg agatcaggtg actcagccct ttctcctgca    5160
gctacccaac tgattacggg gtacctccga ggcgatctat gtggctggag tgcgagcgtg    5220
acgttactgg cctctctctc ttgacgccgg cctttggcgg ggagggccat tatcattcgt    5280
gtgatttctt cctccagcct tgggctgaag ctccccactg cgacctggag taactcggct    5340
atcttgacgg cgaattcggc attcagggcg ttccggccat tcaggtagtg actcagtgac    5400
ccctgcgtta tgccaagcct gcgggctatt ccttcttggg tgaggcccag ttcatgccgc    5460
ttctgttggt aaatggcttt cagggcgcg cattccgcct gttctctgg aggcagcggc    5520 ttcttcttca tttgcgatct cgaaaaaata atcccgcaag gattgatttg aaaaaatccc    5580
```

```
gctggcacta tccaaggcag aagaccagct tggacaagcc tgtggaacgc attcctctat    5640
ctgtatttgc ccgcaagcgt cacgcctgga cggcgaaatg ccttgggatg acgcaagggg    5700
ccctcagtaa agcgatccgt atggggcgcg caatctatgt catccaagag ggcgatggat    5760
caattcgcgc agttgaggag cgccccttcc catcatcgcg ccgacaggaa agtgatgtcc    5820
ttgattccga taataatccc aacggaacta ttttgcagcg taccaacgta cctgtgcagg    5880
catccagtgc cgaggtggcg ccatgagcat tcggtttgcg gtgcccgacc aagggctatc    5940
tagaggcctg gcaagcggat cagtttcgca tgctaaaccg ccacggtccg aatcattaaa    6000
cccggttaaa agcccagggg tttcctgctg gtggaagctc tgcacagaaa tccggggtga    6060
ctcgcccgaa aaagggcac tggctaccca ctattcctat gagagttcct gcgcggagtc    6120
tggtcagggt gttcatcgca agggcctctt cagggcctc gtttacatgg gcgcttggga    6180
tatttctaaa cgggtgcagg ctgtctgtgc cgttcaacga aattcgggag cttgcacttt    6240
gaaaagtctc atacgcgcgc tcgcgcccct tccactgaga agcgcgtcc gaaattcaga    6300 acgcgcaaac aaagccaccc tgacctgagt tgcgcttttc agaatgtgta gagagatagg    6360
agttacctgt ccccagacag caagaagccc cgctttcgcg aggcccttag tcggtagtcg    6420
ttgacgcgac tgcctggata tcaatttgtc tttcgaagga ccaattaact atgcaacaga    6480
aaactcaaag cgcgcaagtc ccctgcgccg ttaccactga ccaccgggtt tgcttcgatc    6540
ctctcaacgg ggatgagttc ttgttctccg ttgttgccga ccggccggtt gacgcggctc    6600
tggccgccgc cgaggacatc agcgaggcgg ttcacctgat tcttttgaga atgacccggg    6660
cgatggacga tgccggcgag ccgctgctct ctcaggaact caatactttc gccctgctgg    6720
ggagcatggc tggcgcattg ctcagagctt gccgggccgg tgtcgcgacc cactcacaga    6780
aatgctgaaa acgtgtcgcg acacgaaggc ggtgcnnnnn nnnnnnnnnn nnnnnnnnnn    6840
nnnnnnnnnn nnnnnnnnnn nnnnnnnnnn nnnnnnnnnn nnnnnnnnnn nnnnnnnnnn    6900
nnnnnnnnnn nnnnnnntcc gccgcgaaga ttcgcagcgg atcaaccgac cacgacgtcg    6960
aagagcgttg agcgaggcca tcgccgcctg acgctaagtg tttctagcat ctcggagcac    7020
tgaccacctc cgacgaagag cacgcgtgct tgtatgcctt ggagattgct gcagagatgg    7080
ctggcgattt ggttgacgcg cgctcgact ccctgcgtga ggagggccag caatgaacct    7140
cgcaaacctg atcagtaagc agtgttcccg cgacccgtct gaggtgctca cggaagagca    7200
ggcgatgtct cttggggg agcgtgaagt agcccggcag gctgctcaga acatggcgct    7260
tggtgtcgcc gcgtcggga atctgctggc gaacgttggc gctgaaggcg aagtgggcca    7320
ggaaacctca gagcgtctcg gctggttct ggaggagatc ggggggggca tcttccagtt    7380
ggtggagctc gaacaggtcc tctcggatcg catcaaccgg cagaaggagc ggaagcaatg    7440
agcgcctcaa tcaccatgct ccgccagggg attcgggcag agcgcgacct gacctcgcac    7500
ctctggacga tcctcaaaga aatgcggcta caaaggcaac tccccgagtg ggccgagcgc    7560
gccatcgatg gcacttcgca gcaggcggac gagatcagcg cgcatcgcaa gcaggtcgac    7620
agggctctgt tcgagttggt ccctgggctt cgcgaggatg tcgaaaggac tgatcgcgag    7680
agctacctcg aatggaaagc ccgtgagcgc gaggttaaag acgcgctggg aggtggtcat    7740
gtctgatctc tcgaaggcac aggcctctcg tcctccgctt cctgtcgacg gggaggtgat    7800
ggagcgggtc gagctcagtc gtaatgagtt cgatctattc aaccacgctc ggagcgatat    7860
gacgcaactt cgggctctgc tgatggactc ggtcgtacct gccctaggtg gtggagggca    7920
ccccgttgtg acggagattc atgacctgat cgagcggatc atcttgtgca ccgggaattt    7980
```

```
tctctaccgc tacaaccagc agatcggcgc cgcctatcgg gagcgtgacc tgtgaaccct    8040
gggagcttcg ataccggcga cgcgtttcag cgtgcgtcct caggcgatgg aattctgttc    8100
tggttcatct ccacaccggc cgttcagaag ggtgggattg cgatagccca gatggtcgcc    8160
ccgttctcga ccgaggaaga ggcccagcgt ggcgccgatc tgctgaacga ccgcttcccc    8220
ggcaaccgtt gctgggtagg ccgtggcgag tacgcgccgg aatacgccac ccctgatcgt    8280
ttggaccacg acgccaagcg agcacgcgcc gatctcgccg ggcttctgtc cggcattacc    8340
gggaggagcg gccatgactg agctcgatat caagaagtct ttgcgctcga ggagagggct    8400
ggtcccggac actccgtcaa ggctgtgcgg gacgtttagc tacggcttgc actaccacgg    8460
cccgcagcag gttctggacg attttcttgg tcgggtagag cgcgagcaag atcacaccaa    8520
gcgattaatg caggcacagc gcacgatcgg cgcgctgatg gcgttgtcgg cggcgaaggt    8580
cagtccggct tgcgcctggt acacacaccg cgacgtgttc cgacgcctcg ctgaccttac    8640
cggcgaaacg gaaaacgcac tggtgcagat ggcgggagta gagcgatgaa tctgactacc    8700
atcggcggcc aggccgccac catgaccagc cgcgagatcg cggatcttgt cgaggctcgc    8760
cacaacgacg ttgtcacgac catcgaacgt ctcttcgaca aggggctttt acgatcaagt    8820
cgtaaaactc gccgggagtc caccggtggc cgtccgatcg ctgtgtatga cctgatcgag    8880
agggatactc acctggtcgt tgctggttac agcgatgagc atcgtgcccg agtgatcgac    8940
cgctggcagc agcttgaggc tgagcgtagc ggtcgcgatt accagatccc gcgtacccga    9000
gccgaggccc tgcggctggc tgctgacctg gaggaacaga acgccgtcct gcaactggag    9060
aatcagcacc aggccgagac catctccagc cttgaatcgc tgttcatggt aggcgagacg    9120
cctactcagt tctgcaagcg cctgaacggg gtgaactgcg ccaaggtaaa cagcaccctg    9180
tgccaactcg gctggctctt caatgagcag cgcgaagagg agggcgcacc gcggtatcgc    9240
gtcgccagcc gtgtccgcga caagtacctc accgagcgcc cgcgcaagat cgcccccgag    9300
ggcggtgact ccttcatcaa gtacgacctg cagttgctgc tggccggcgc ccagcgcctg    9360
caccaactct acatgcagca aaagctggtc atgaaagcca cctgggacgg ccggttcacg    9420
caggccaagt acaccggggg gaccatccaa tgaccacaca accgaaaccg ggccggatca    9480
ccactggccc caacggccgc ccggtgatcg ccgggccctg gccgtcctac cgtcaattcc    9540
gcgacctgtg cgaaagcgac cggcttctga tgtaccgcca cgcgaagctg tgcagggcct    9600
cccttgaggt ccagggcttc gagatggctg aggactacga cgctttcgtg cggcgcgtca    9660
ccgaggagct cgacatatga gcgttcaggc catgacttgg gcacttgagc agcaggtcgt    9720
taccgatgcc gccatgaggc atgtgctgtt gtgcctggcg aactatgcca acgaggcggg    9780 aaaggggcg ttcccttcta tcgccacgct gagcagcgat acagggctat ccgagcggac    9840
tgtccagtac aagctccggt ccctcgagga ggctggtgtg attcgccgtg gaaaccaggc    9900
aatcgctgcc gcctacatct cgcacccgga tcgcctgccg atggtgtacg acctctcgat    9960
ggaacggggt gcaacggttg caccgggtgc aaatgacgac gtaacggggt gcaaaccacg    10020
acgtaacggg gtgcaactga cgacacaacg gggtgcaacg gttgcacccg atccgtcact    10080
taaccaccaa agaaccacca aagaacctaa agagcatgtc caaaccggcg aaaccggttc    10140
ggacgacgcg ggtgatcgga agggaaaacc ccagtctggg aagctgacgg ccaagcccaa    10200
tcctctggat ggtttcgagg agttttacca ggcctaccca aagcacaagg atcgagcgaa    10260
ggcggagaaa gcttggcgga agatcgaccc tgctctgcac ccagtgatca tggcggcgct    10320
```

-continued

```
tccgaagcac tgccgacaac gtgattggct gaaggacaac ggccagttcg ttccgctgcc    10380
ggccagttgg ctcaacgggc gacgatggga agacgagata gccccctgatg ctggcccggc   10440
atcgaacttc accaacctcc ccaaacacac ccccgacatg taccaggacc gcgacgatgg    10500
cagagcaaat ttttaacttc tggcgtaaac ccaaccgcaa gagcgaagaa agcccttctc    10560
ttcgctgccc ggttcacggt gactaccacg cgatccaggt ggagcagttt gatggcagct    10620
acttgacctg gtcttgctct cggtgtgttt gggatgggt gagtcacggg ccggggagcg     10680
aggagttttc ggtggccctg ctgagaaaa cccaacgcaa gatcaacgag ttgctggttg     10740
gctctggcat ccccgctcgc taccgggcca gcactttcga gacttaccgc accgatggca   10800
aggcggagaa ggcggcggtg ctggaagcat gccgggagta tgccgagcga ttcgtggaga    10860
acttccagga cggccgctgc ctcttgctcc tgggcaacct tgggacgggc aagacccatc    10920
tcgcgtgctc aatcgtccag tacgtcgtac ggaaccttca ggcccaagca gtgatcacct    10980
cggcgtcgga ataatccgt gtggctaagg gggcgatgaa tcgggcggcg aagtacaccg     11040
aacgggacgc tctcgaagag ctggcgggct tcgacctgtt ggtgatcgac gagctcggcg    11100
cgcagagcgg taccgagtac gaattggggc tgctccacga ggtgattgac gccggtatc    11160
gggagatgcg gcctacggtg gtggtttcga acatgagcgc gcaggaggtc gccaagtaca    11220
tcggtgatcg tgctgtggat cgtctccgcg agaacggcgg caaggctgtt ggcttcacct    11280
ggggctccgc tcgccgggag gttctggagt gagccgagag ctgtacagcg aagaggctga    11340
gttcggcgtg ctcggcgcta tcttgcagtc cgcgctccag caaaatcagg cgctggttga    11400
cgaggccttg tccagcgtga ccgctgccga tttctacttc gaggataacg ccgcgctgtt    11460
ccaggcgatc aaggattgct acgaggaagg gattcccgtc gatccggtga ccgtgggagt    11520
ggtccgcgat gtgctgccca gcggcgcgaa gctcattccc tatgctggga acattgcccg    11580
caatgtgcct tcggtggcga actggaggac gtacgtccgg cacgtccggg agcgggccat    11640
cctgcgttgc ttgatcgaca cggccgagtc ggtgaaggcc tccgccacgg atgaccgacc    11700
gttgcctgag atcatcgcca gagcgcagca ggcgatggcg gacctgcgcg accttgagga    11760
cgaggcgccg aagtacaagc ggctcgacga ggtgatgctc aaggttgtcg acgtcatcga    11820
cgacaagttc aacggccgcg cgccgcagtg gcccggtact ggcctgaccg atctcgacaa    11880
gctgggtacg cggcatccgc cctcgggaag ataaccgtga tcgccggcct tcccggcagt    11940
ggcaagacca cgcttgctct gcagattgcc cagcacaacg cctgcgaggc aagcgagcct    12000
tggctggtgt tcttcctgga aatgcccgag gaagaagttg ggtgtgcgcg gccatcgcct    12060
cgctgagcga agttgactga agcgcctgga cgatccgcag cagttgggtg acgacgactg    12120
gccacgcatc acgtcggcgg tggccaaggc caagggggcg cccctgttca tctgcgacga    12180
tcccaacgtg accgccagcc agatccgcag catcgcgcgg cgtgtcaagc gtgagcatgg    12240
tctggccggc atcgtcgtcg actacttggg cctgattccg ccggaggcga aggggcgcac    12300
gcgcagcgag gaggtgggca ggaccaacaa ggctctgctg cggctagcca aggaactcgg    12360
cgtgccggtc atcgaactgg cgcagctcaa ccgcgactcg accaagcggc ccgggaagcg    12420
cccgcagtcg agtgacctgc gcgattcggg ggagattgag gctgacgcca gttgcatcct    12480
gatggtccac cggacatgg acagcgaggc cggccagaac ggcatcaccg agatcctgat     12540
gaccaagtgc cgacacgcgc cgccgggcat gtgcctgctc cagcagcagg gcatgtacgg    12600
acgattcgtc aacttcgccg gctcacgcga gatgagccaa gaggaggtcg agatggggcg    12660
tagctacttc gccaacaaac acggcaagaa aaaggggagg gcggcatgag cagcgtacaa    12720
```

```
ccgatggcac cccgcaaggt catgaccaag ctggagcggg agtttctcaa ggtggccggc   12780
caggaactgg cgcaggtcaa ggtgggcggt gctgctgcct tggctgcgct gctggtcatg   12840
atcgccaact ggcacggtga ccgcggcact ctgggttttc acgactatgg ccggctctgg   12900
ctgcaggatg gcaatgcgaa gggcgcgcg gtggaaacgc tgctgcgcga tctgtttggc   12960
ctgaacggtc cgggggcggc atgagcagaa ctcgaaccta cgtggacaag ctgctgggcg   13020
ataccgagta cctcctcgag cagtgggggt ggtggcgaat ggatggaatg ggggttcccg   13080
gatatgtgtc gccggccgcc gctatcatga ccaagccat gccaatgtcg agccccaagg    13140
cctaccacgt cactgatgat atggccttgg ccgtcgaccg ggtcattgct cgactcatcg   13200
acagggcgcc gcaggccggc gacttcgtgt ggctctacta cggcgcgaag tggccggccc   13260
tgcgcatcgc gcgtgaacac cagatcggcg aggccaaggt gagggagacg ttgaagctgg   13320
cggtaggctg ggtcgatagc gccctggagc ggttccgcga gagcgcttga agaaatagtt   13380
ttacgcgcgg aatgaagggt gttttcatac cagcgtgaat tgctgtgaac gcagcgtgac   13440
gcactcgaaa cccggccctg gcgccgggtt ttttattgcg ttgtcaggtc tggcgcggca   13500
tcatcaggcc cccgccgatg ccgtggtttc cacctgggct attcctcgac agaggtggat   13560
ggcccggaag atccgctctc ccgggccttt tagtttccga aggtcgaaac tcggtagacg   13620
gcagtctcac ctgccacatc gggctgtaag caaagtgacg ggttaccgac ccacaaggcc   13680
ttcacccttt gcgataatga ccatcttgaa gccgagaggt ggtccaatga aagtccaga    13740 catcaaggtc gtgaagcttg agggtgacgc gttgccctgg tccatacgcg atgccggcca   13800
tgaggcctgt tttgtggtca tgcatggcct gacgctacgg agcgatttct tgtactccga   13860
ggaggaggct gaggcagtgg cagacgcggt gcacctagag atcatcgaag agatgaggtc   13920
gatgctggag tctgtccgag gacgataacc aatcaatgca ggtggagcgc aggatgcgca   13980
cggggtagtg gccctatcc accgcacct atttcagagc ccagcctag cgctgggctt     14040 tttcatttcc gccgcaaggc aagccaacac gcagctaggc ccgtacagcc gaaaggcgga   14100
tgtccgctca tccgtccgcc ccgctgcgct ccttttccag gtgagcggag tggatcagat   14160
gagtgagatt gatcttgatg aggccagcct gcgcgacctg gtgatggtca atgacggcca   14220
ggtcgtaacg acctcgctga aggtggccga gcgtttcgga aagcgccatg actcagtgct   14280
tcgtgctatc cgtcgcatgg cctgttcaaa ggcattccgt ctccgcaatt ttgtggagac   14340
ggtcgtgtgg cgagataacc ctagtggcgg ggagaagatc aagagcgcct gtttcgagat   14400
gaccaaggat gggttcatgt tccttgtgat gggtttcacg ggtaaagctg ccgctgcctg   14460
gaaagaagct ttcatccacg ccttcaactg gatggccgag cagttgttca agcgctcaat   14520
ggacttcaac acgttgcgca acgaactgat ggcggagtac cgacaggaga aagggattgc   14580
cagcctggcc ggtaagacct tgcgccgatg gcaggtcaag gctccggtca ttgagcagaa   14640
gatcatcgag gtcgagcgcg aagggcaact acaactgttt cacgcctgat ccactcgaa    14700 cccaccccga cgaacgaaag cccgccactg agcgggcttc gtcgttttag aacccctgcg   14760
aggggcagag actatgaaaa tgccagaacg ccctgaaact tgggctgcgc tgcttgcgtg   14820
gctgtctgcg cactatccgc agttgtacgc cgccggcctc tcctttgtgg tcgcgctgac   14880
ccgggtgatc tatggcggtg gaacgcggcg ccaggcgctg ctcgaggcaa cgctctgcac   14940
cttgattacc ttgggcctga ttccggtcct tgagtggttc ggcctgccac agaacatggc   15000
taccgctgct ggggtgttca ccggcttcct aggggtgaag aagatcgccg agttcgctga   15060
```

```
tcggatcgcc gactggaagt ttccgcgtcg gggggctggc gaatgaagat caccgcagat   15120
caactcgacc gcgctaccgg ctgcggtgct tctactgccg gcctctgggt cgagcacatc   15180
aacggcgcca tggcccggtt cgagatcaac acgcccgagc gtgcggcgat gtttctcgcc   15240
caggtcgggg acgaaagcca gagtctgcgc cgattggtcg agaacctgaa ctactccgcc   15300 gagggctgc tcaagacctg gccgaagcgg ttcgacccgg tagaggctcg ccagtatgcc   15360
cgccagcccg agcgcatcgc caaccgcgtc tacgcaaacc ggatgggcaa cggctcaccg   15420
gatacaggcg atgggtatcg ataccgtggt cgtggcctga tcatgatcac cggccacgac   15480
aactacgtcg aagccgcccg cgccctggcc ctgccactgg tggcgcaacc ggagctgctg   15540
gagcaacgga cctgggcagc catcgctgcg gggtggttct ggcagtctcg cggtttaaac   15600
gatatggctg atcaaggccg attcgagcgg atcacgctga agatcaatgg cggctacaaa   15660
gggtcaggcg accgcgcggt tcgcctcgaa tgggcgcgtg ctgcgctcaa gggggaatga   15720
tgctcgggtt cacgacgaaa gctgaggcgc gacgcatcgg cgcctcgcac acgggagct   15780 attacggcat tccgatgtgg ctaggggatg tcgatagcga ttgcccgcta gctttcgcaa   15840
agtgggcgcc gcttgagctg gtcgtctccc tgctctcggt cattgagggc atcgtcaact   15900
cgatgctcga tcaagagcag acgttcatgt tcaaggttgg tcgaggatc gaccagtgac   15960 ctggcggccc tggttggtgg tcgccctggt ggccgcgctg gtgttctggc gcctcgatca   16020
cgtgaccgcc cagcgtgatg acctgcaggc cgccgtcgag caatccgccg agacgatcac   16080
cgccatggcc cagcaggccc agcgcgacat ccaggcgcag gccggggctg atgccctggc   16140
ccgaacctac caagcagcac tgcaggcctc ccatgaagaa aaccaattgc gccgcgatgc   16200
tatcggcact ggtgctcgcg tcgtgtacgt caaagcccgc tgccccgcag acggagtgcg   16260
ccaggctccc ggagcctccg gcagcgctga tgcaggaaga gccgtccttg ctgccgctga   16320
tggacaagtt gtttctgatc tccgagccgg agtcgagcgg cgcgaactga tgatcgcggc   16380
gttgcgtaag cacatcgccg gcctgccgag gtattgcaga tgggttgcga aggatgcgcc   16440
gctcgccgag agcgcgccaa gcagatagcg aaggtgggat atgaccgaat catgcaagtg   16500
ctccagcgag cgtggcctgg atccggtggg cgttctggag tcgatgctgg ccgagcagag   16560
gaagaccaac catctgctgg ctctgctgat ccaggcgctg gccgatgagg gcgagataga   16620
tgccgacatg ccgcgcgtcg acctgagcgg caggccgatc tgatggccag actgaagact   16680
ctcgggttcc gcgtgtcgag ccagggcgac cggctgaaga ctgcggcgcc tggttcgtgg   16740
cggaccggca agacctcaac cgagcgaggc tatgactacc gttggcagca ggcacgggag   16800
cagtaccttc gcgatcatcc gttgtgcgtg tactgcgcgc gcaagggctt ggtcacggcg   16860
gccaacaccg ttgaccacat cgtggctcac cgaggtgatc gggacctgtt ctggatcag    16920 agcaactggc agtcgctctg cggaccctgt cactcctcgg tcaagcaggc cgaggaggcc   16980 gccgaggct gatgcacgcc attgacgtgc ttcagtcgat ttgaggcacg cctctggcgt    17040
gcaacaaggg tgggggggtg aaaatatccg gtttcgcctg aagctagacc gccccgcccc   17100
gcattcgcac atttttccg atctctagga attttgttaa tggcgttaac agacaaacag    17160
cgacggtttg ttgacgcgaa ggcccgagga gcatccaaca aagctgccgc cgaagccgct   17220
ggctacgcgc cttccagctc tgcggccgct ggcgctcgac ttgccaagca ccccgaaatc   17280
atcgccgccc tgaagatgtt aaaggggcgg cgagatgtta aagccaagga gccttcgccg   17340
aagcagggca aggaccatga agcgccgctc ggcgatgagc aggaacctga tggcgagtac   17400
ctggattgcc tgccgtttac ggaggacccg ctggtctggc tggtcaacct gatgaatgag   17460
```

```
ccgcgggcga aggtcttcga tcgccgcagc gcggctcaga aagctgtcga cttcttccat   17520
ggcaagaagg gcgagatggg caagaaggaa cagaaggccg aggccgcgaa gcaagccggc   17580
aaaggcaagt tcggccaggg caagcctcca ctatccgtcg tcaggggta aaccatgctc    17640 tggaccactg cctgccctga ctggtggcgg cgcttgagtg ctggtgaatc gatcattcca   17700
ccgccgctct ttcctgagga agccgaggag gggctcagcg tattccggga attgaagatc   17760
gtagacgctc ccggctcccc gacaatcgag gccgcatgcg cccctgggt gctcgacttc    17820 gccggcgcca tcttcggcag ctacaacaat gagaccggcc agcgactgat caccgagtac   17880
ttcctctgca tcccgaagaa gaactcgaag tcgaccatcg cagccgcgat catgctgacc   17940
gccttgatcc gcaactggcg gcttgaggcc gagttcatca tcctggcgcc gaccaaggag   18000
atcgccgaca cagcttcaa gccggcgcg gcgatggtga agcacgacga agagttgtcg     18060
gatctgcttc atgttcaacc gcacctgcgg ctgattaccc acaatcagac gggagccacc   18120
ctgaaggtag tggccgctga tagcgatgtg gtcggtggca agaaggccgt cggcgtgctg   18180
atcgatgagg cctggctgtt cggcaaaaac ccgaaggcac cggacatgat tcgggaggcc   18240 actggcggc tgctgtctcg ccctgaaggt ttcatcatct ggctcacgac ccagtcgaac     18300
gagccgcccg ccggggtgtt caggtcaaag ctgacctatg cccggggcgt ccgtgatgga   18360
cgcatcgaag acaaccggtt tctgccgatc atctacgagt tcccgaagga gatgatcgag   18420
agcggagagg cgcgccggcc agagaacttc cacctggtca acccgaacat gggctactcg   18480
gtggatcggc ctaccctcga gcgcctgttc atgcaggcag aactcgacgg tgaggccgag   18540
gtgcgcgggt tcctcgccaa gttcctgaac atcgagatcg ggctggcgct gatgtccgac   18600
agttgggtcg gcgccgcatt ctgggagccg caggcgctgc caggcctttc gctggatgcc   18660
ctgattgagc gctgcgaggt gattgttggc ggcgtcgacg gtggcggcct agacgacctg   18720
ctggcgctga cgctgttggg ccgtgagcga gggggcgcc ggtggtttca ctgggcgcat    18780
gcctgggcgc acccctcggt gctggatcgc cggaagtccg aggctccccg gctccatgac   18840
ctcgcggggg ctggtgatct gaccctggtt gagaaaatcg gcgatgacgt tgaggagttg   18900
gcggcgtacg tcgctcgggt caatgaggcc ggtctgctcg acaaggtcgg gctcgacccg   18960
gccggcattg gcgccgtgct cgatgcgcta ctggaggcgg ggatcaccga ggagcagacg   19020
gtcggcatct ctcagggctg gaagctgacc ggggcaatca agaccacgga aaggaagctg   19080
gccgagggtg tgttgatgca ctgcggtcag ccgcttatgg cctgggcctg cggcaacgcc   19140
aagggcgtgc cttccgccaa cgcttttcctg atcaccaagc aggcgtccgg caccgcgaag   19200
atcgacccgt tgatgtcgac gttcaacgcg gtatcgctgc tgtccctcaa tccggaggcg   19260
cgcggcggca tggatgacta cctcaacaac ggcttctttg gactcatagg ctgaccatga   19320
catttcgctg gtacaaccct cgcacgtggc ggatgttcgg ctacaccgac ccagccacgg   19380
gtgattacgt cgaggtggac cttgaggtcg gcggcaagag cacaaaggcc ggcgtgcgag   19440
tgaccaccaa gaccgcgctg tcgatcagca tggtctggtc gtgcgtgaag atcctttcgg   19500
agtcgctgtc gggcctgccg ctgaagctct acgaggattc ggacggcgcc tcgccgcgca   19560
cgttggtgcc gcgcaaggac ggggcgcaga agttgctgcg caaacccaac ccgttcatga   19620
cgatgctgaa cttcctcaag ttcgtcgtcg tgaacatggc gctgcgtggt aacgctttcg   19680
cactgatcga acgcaaccgc cacggcgagc cgatcggttt gattccgctc ggcatcgacc   19740
aggtgaccat cgacaccgac gaggaccttc tctactgggt gcagcccaag gatggggaac   19800
```

```
gattcccggt ttctccggag aacatgctgc atttcaagat attcagcatg gacggcatcg   19860
tcggcttgtc gcctatcgag taccaggcgg agaccatggg tctggccaag gcgggccagc   19920
aatggtctgc gcgcttcatg cgcaagggcg gatttactgg tggctacatc atcttcaagg   19980
agttcctgac cgagaagcag caggctcagg ttatggcgcg cttccccgac gtgcgcaagg   20040
gcgatgccga cgacctcggc aagatagcta tcttgcaggg cggcccaacc tttgtaccgg   20100
ccggtcttag ccagaaagat gcccaattca tcgagtccca gcagttccag gaggaggcac   20160
tggccggcat ctacggtgtg cctctctggc tggccaaccg ggccggcaag acgtcgatca   20220
tgggctccaa cctggagcag caactgatcg gcttcgtcac gttcggcctg aaaccctaca   20280
tcgacgcggt cgaggacgag ttcaacgaca agctgtatgg gcgcacctcg cgcttcgtcg   20340
agttcgcggt ggaggggctg ctgcgcgctg acagcgccgg tcgcgccact ctgttcgctg   20400
cggctcttgg tggctccggt ggttccggct ggatgaccat caacgaagtt cgccgcaaag   20460
aaaaccttcc gccacttgat ggccctgaat acgaccgggt ctcccggtgg agatgcaga   20520
ccaatgctca gcaaacttga ttgtcccttc gaggtgaagg ccgccgacga ggcgggcaac   20580
ttcgagggct acgccgcggt gttcgacaac gtcgacctcg gcgatgacgt gatcctcaag   20640
ggcgccttca ccaaggtgaa gaccgctcgc aacggccggt tgaagctggc gctgtaccac   20700
gacctgaccc ggctggtcgg aacctcggag ttctcccagg atgaccgagg gctgttcctc   20760
aagggccgag tgaacctggc agtcagctac gcacgcgacg cctacgagct gatgaaggac   20820
ggcagcctcg acagcatgtc catcgggttc aacaccatcg aagccaactt cgagcagcgc   20880
gcggggcggc aggtccgagt catcaaggcc gccgaactct gggaggcgtc gttcgttccg   20940
ttcggcatga accctgaggc cgaggtcctc agcgtcaagt cggacatccg gcttttcgag   21000
aacgccctgc gcgaacgcat gggtctctcg cagaaggaag cggcagcagt cgcttcgctc   21060
ggctaccccg cgctccgccg tgacggcggt agcgaggcca cggcgatcgt ggaagagctg   21120
aaagacattt caaccctgtt caccactcat tttggagtat cgccatgagc gaagtgaaag   21180
aactgaagga ctccctggag ctgcaactga agaacggttt cgacgggctc cagaagaaat   21240
acgacctggc catcaccgag gtcgagaagg caacgccgt cgccaccgaa ctgaagaagg   21300
atatccagaa gcagaaggac gaactgcaga aggtcatcga ccaggtgcag gaccttgagc   21360
agaagggcgt caagctgcgc ggcggccccg gcgaaggcaa gagcttcatc gatatggtga   21420
agtcgcacga cggctacaag gcgctgcaac agaagagtgc gaatgccgcc gacatcgagg   21480
tcaccaagtc ggacctggcg tcgatgaagg aaaccaaggt caccagcgcc ggcatcgttg   21540
tgccgaacta cgacccgacc atccagcccg gcatccgcca ggaactgcgc atccgcgacc   21600
tgctgaccag catcccggtc agtggccaga gctacaccta ctatcgagag ctgctgcaca   21660
cccgtggcgc ggggccggta ccgaaggtg cgctgaagcc caccagcaac gtgaccttcg   21720
agtcggtgac cgaccgcgtc aagaagctgg ccgtgtggat gccagtcact gacgaggccc   21780
tggacgacgt tccgcaactg ttcggctaca tccaggagct gctgcgctac gacctcaagc   21840
tggaggaaga agcgcagatc ctcaagggtg acggcaccgg cgagaacctg aacggcctga   21900
tgacccaggc gaccacctac gacaccgccc tgaacaaggc tggcgacacc tccatcgaca   21960
tcgtgcgccg cggcatctac caggtccgca agcagtcgaa gctgtctgcc gacggcgtgg   22020
tgatgaccga gctggactgg atgaacatcg agctgcagaa ggatggcgaa aaccgctacc   22080
tgttcgccaa cctgcagggc ctggtcaccc cggtgctctg ggggcgcccg gtgatcacct   22140
cggacagcat ggacgaaggc gcgccggcga acggtgaaga tccggccacc ggcggcgagt   22200
```

```
tcctgatcgc caacttcgcc cgctcctcga tcctcttcga ccgcatgtcg ttcctgttca    22260
agatgggcct gatcaacgat cagttcatcc ggaacgaacg ggcgctgctg gttgaggagc    22320
gtctcggtct gggcgtgcgt cgtcgcgagg cgttggtgaa aggccgcttc gcggcgtaac    22380
ccctgatgag gccggtcgta atgccggcct cttcgtttcc aggaggcaac atgaagatca    22440
aggcactttg gggtttcgta ggtgacgcga agaagctcgg ggcggagtcg gcccaggttc    22500
gcgcgggcca ggtgttcgag gaagtcgacg atgagtatgc acacgtcctg atcggcaagg    22560
ggctggctgc tgaggtcggg gaacagacca agccgaaaga gaccaagccg gcggcgccga    22620
aaggggccaa gtgatggaga tcgactggga tgccgatcca tccatcctgg cgaaggtgaa    22680
gcgtcaggca cgtatagacg ccgatatcac cgatgacgac gatctgctga aaggctatgt    22740
cgccgcggcg ctttcccacg tcgagcagca ctgtgactgc cgcctagtcg aaggcgagcc    22800
cacctctccg gatgaaatcg gcctgacgcc ggatgtgtgg caggctgtat acctgcttgt    22860
ggcgcactgg tacgccaatc gagagggagc cgtcgccgat ggttctgtaa ccgtggtccc    22920
gttggccgtt gagcgcttgc tctggtaccg gaagaggttc tgagacatgc aggctggtcg    22980
gttaaggcac ctggtcgcat tccaggtgaa ggagaaaatc cgtgatccgg atagcggtgc    23040
cgtcgactat acctgggtgg atcgttggcc aaaggtctat gccgccgtcg agccccttc    23100 tgctcgcgat ctgatcgctg cgcaagcggc ccagtcccag cttctgctc gcatcgtcat    23160 ccgctaccgg gaaggcgtct tgcccactat gcggatcgta caccgcggtg ttccgtacaa    23220
aatcgagggt aagccaatcc ctgataagag gtcgggacgc gagtatctga ccattctcgt    23280
gagcgagggg gtaaccgatg gctgatatag ctgagtcacg catccacgga ttggatggcg    23340
ttgtggagaa gatgcgatct cttgcgccaa ggctgcaacg caatggcctg agaaaggctg    23400
cgcgcaaggc tatgaacatt gtccgggatg ccgcgcgaga aaaggcgcga gttgtcgacg    23460
atcccgaaac gcccgagaag atttggaaga acatcatcac ccaggagtca gccaaggagg    23520
ggcggcgtga gggtggtgtg gtgatgaagg ttggcgtgcg cggcggtgcc agcagaaacc    23580
agcacagcaa ggatgcgagt gggaacccag gcggtgatac caggcactgg cgctatctgg    23640
agttcggcac caagtactcg ccggcgaagc cattcatgcg gcctgctcta ccagagaacg    23700
ttgcgaaggt cactgatcgg ttcgtgtccg aactgagcag cgagatcgac cgcgcggttg    23760
gggggcgttg atgtttgcgc caatctactc tgtcgtttca ggggacgcgg cctgccaggc    23820
gttgcttggg ggggcaccag acacgcgcat cttccgttc ggcgaggccg acgagcggac    23880
tctatatccc tatgcggttt ggcaggtggt cagcggttcg cccgagaact acctggcagg    23940
cctgccagac gccgatggtg taaccctgca ggtcgatatc tacgcgagca cgtccgcctc    24000
tgcattcgcg gtagcgaagg tcctgcgcaa cgtgatcgag aagagtgcct acatcgtgcg    24060
ctgggggcct cagcctcgcg accctcaaac caagtcgtat cgaatcagct tcgacgttga    24120
ttggctgata cccagatagc cagtcgccca aaccatcgcc cgctcagccg cgggctttt    24180 tacgcccgca ataggagaat gacctatgtc catgcttacc caagggacgc agctctacgc    24240
cctcgtgccg cccgcttcgg gcactggagc gctcaccgta atggaggtgg agtgcatcac    24300
ctccttcaac cccggcggaa acccggcgga ccagatcgag gacccgtgct tgagcgagac    24360
ctcgcgcaag tacaagaaag ggatgcgcac tcctggccag gctaccgttg gcctgaatgc    24420 cgatccgcg aatgcaagcc atttgcgcct ctaccaactg tccgaagatg acagcgtatac    24480 catgatccag ttcgccattg gctggtccga tggtgtcgac gtagccccca ctctcaacac    24540
```

```
cgaaggggat gccttcgtgc ttcctccgag ccgaacttgg ttcaccttcg agggttatgt    24600
cagcgatttc ccgttcgact tcgcagccaa caccttggtc gccacccagg ccacgatcca    24660
gcgctccggc aaagggcagt ggattccgaa accgcgtaa ggagcagaca tgaaactagc     24720
cgatctggtg gccgctggcg cggtcctggg cgatggactg gtgaagaaaa gcatcacctg    24780
gacgcacact ccgccgggca agaaaaaggc ggtcacggac accttcgacg tgttcatcaa    24840
gcgcagcagt ttcggtgcca tggaacgcct gttcgcccaa gacgacgaca agaagagcca    24900
gaatgcgcgc tacctggccg agagcgtaag actgggtgag ggtggtgaag aggcgattcc    24960
ctacgaaact gcgttcaacc tcgaccctgc gctgggcttc ctgctcttgc aggctgtcgc    25020
ggaggtcaat ggcactgcgc cgggtgacga aaaaaactga cgcccgccga tgaggtttgg    25080
catgaactcg tgctgaacgg catcggcggt tgcaccattc gcgaggcgaa ggagcgcatc    25140
gactacgatg agtacagggc gtgggttgcc tacctgaaaa agcgtggctc cctcaacggg    25200
agctatcgcc tggagtgggt gctggctcag ttagccgcga ttcaggccaa ggtaggggg     25260 gtgaagtgcg aacccgacga cttccgtccc catgttcggg ggccggtaga gccggtgggt    25320
atctcgctcg agcaagccat ggccgcatgg gtttgacctg gcaaggatgc tgggttcctg    25380
tgctggcgtt gtgatggtag attgtggcgc aaccactaag gagggagtat gaaaagggcg    25440
attttactat taccgttcct tgctctggta ggttgcaatc agtcaccgcc aaagcccgat    25500
atgccgattt ccgaagttca cccaacaccg gtgtgcgagg gtgcctcgca gtgctcggaa    25560
atgtggggta gagcgataga aggcgtgacc atggtaactg gaatgaaggt catgtctgca    25620
aatgaaacat ttattcaaac ctttccttct cggaaggttg gatacctaaa cgggcgagtc    25680
tacaagcaaa gtcttggtgg ggaaaaatac gaaataaaag gtacgtttga ttgcctgcca    25740
tacgattggt gtaataattt tagaaataag acgcaaagcg cttttaatat atatgtccag    25800
gggtatattc ctctgaagaa gtagagaatc ttctgttcaa accgcctccg ggcggttttt    25860
tattgtccgg agaaaagcta aatggcctct cgctcccttg gtgtgctgac gctcgacctc    25920
attgcgcgta ttgggggggtt tcagcagaac ctgagtcgcg ccgcccaaga cactgcgcgc    25980
agtatggggc agatcgagca gagcactcag agggctagtt ctacagcggt cagtgcaatc    26040
aaatctattg gcgttgcggc ggctgcttat ctgagcgccc gagaacttgt tggatattcg    26100
caagcctggg tctctattga gaaccgcatc aagcaggtca gcgaaagtca ggctcagttc    26160
agtcagtcga tggatgcagt gtattccgtc gctcagaatg cgcggtcatc cttggagggc    26220
actgcggagc tgtaccagag gattgccgct tcaactggcg acctcggggt aaatcaacag    26280
caagttgtcc aggtgaccca gaacatcagc aaggccatgt cggccagtgg tgtttccgct    26340
gccgctgcgg aagtgcgct ggtgcaactc ggacaggcct ttgcctctgg cgtgctccga     26400
ggacaggagt tgaactcggt actcgagcag gctccgggct tgcccaggc cgtcgcaaac     26460 ggtctcgggg ttgcggttgg agaccttcga aagcttggcg aacagggcaa gctaacttcc    26520
aagcaggtct ttgaggcgat cctgtctcaa acacgcgcta ttgatgacca gtttgcgcgc    26580
gcccagacca ccatcgctgg cgcgtttcaa gtgttggaga acagcgcgac caaagcgatc    26640
ggcagcctag atagcactct cggggtgtcc aaggcttta cggaagccat ggtttccctg     26700
tcgaaatcgc ttgactctac gggcgtgcag gccttcgtcc aggccctgaa tactgggctg    26760
tatctggcga tcggacgtac tgctggcgct ctggtaagcg cgacggctgc caagatcgca    26820
gacgtcaagg cgacccagga gcagacctat gctgcgtcgg ttgctgcggc cggagaggtg    26880
cgacgcgccc aggcggtgaa ggccgaggcc gttgctgagt tagatcgagc acgccaagcc    26940
```

```
gtggcttctg ctcgtgcaca ggtggctgct gatcgggagc ggcaagcctc cgaaatctct   27000
cgtttgcggg cggtacaggc atcgcttgtg gctgagcgcg aactcgaagg ccagcggctg   27060
aaggcccaaa tcacagagat tggccgacag cagtctgtcg ctcgaatggc cgagttacgg   27120
ctagcagaaa cggccatcat caagcagctt caggctgccg aggcgcaatt gacggccact   27180
acagtggcgg ggtcgcaggc gattactgcg gctcttaatc aacaatatgc tgcaaccgag   27240
agaaccgccg cagcgaccct acaattgaac gcaactcagg ctgcgtctac tgccgcaatg   27300
ggccgatggt tcgcggccag cacagctttg ggggcagggt taaatgccct gagaacagca   27360
ggcgcgggga ttctcaggat tgctgctgga tggccggggc tgatcatctc gctggggatg   27420
gtagccttgt ccttcgtcga cttcggggac aaggccgaga gcaatgctgg tcgtgcggcc   27480
aatgctttcg aggatgcctc cacgcgcatc cgtcaggccg ctcggtcgat gattccagag   27540
gacctttccg ggctcagcta tgaccagttg aagcagcagt tggcgggcct tcaggatcaa   27600
ttgaaggatg ccgaggcgct tcaggagcgg ttccagaagg gtgttgacga caataccgac   27660
attccgtttg gtccttcgct ggacgaggca aaggaaaaag cagagtcctt gcgccttgcc   27720
atccagaaga cacagcgaga actggacggt gcaaggttcg cttcggagaa ggctggcgcg   27780
agctatctgg ataatttgca gaagcagagc gttgtcgccg gcaagctgac cgaggtagag   27840
aagctccgcg cccagatcaa cgctggcatc ctgaagctaa gtcctgacga tgaaaagcgc   27900
gccctggcct atgccgcagc cgtggacaag gcgaatgcct cgaccaagtc ccagaaggac   27960
ctgttgaagg actctgcgaa ggggctgaag caggctgagg agcggtatcg ggacctcaag   28020
aaggagatcg cccctaccgc gactgcggcg gacgagtaca ggaaaaacat cgaggccctc   28080
aacaccctga aggacagggg gaagatcacg agccaggagt atgcgaaggg aatcgagtgg   28140
gcggccaagt cgttcaactc cgcagtggac gcggccaatc cgttcgtgaa gcggctcaga   28200
gagatcaagt ccgcgatgga cgagagcctg ggcaatctca agctcgaagg acagcgcgaa   28260
atcctcggga tggggatgag cgatagccag aggggggctgt tcgacaagct gaacgaggag   28320
aatgaccgtt acgccaaggc ccgcagggat cttgccgacc gctacgcaga cagatcggtc   28380
gggatgagcg acgacgagta ccagcaagaa ctccaggctc aacagaagca ccatgagcaa   28440
atgctggagc agttgcaggc aaactacgat gctcgacttg aggcccaggg ggactgggtg   28500
tccggagccc gctccgcatg ggaaacctac gtggaggatg cacagaatta ctcgaagcag   28560
gcctctgact tcgtgtctgg cgcacttggc gatgctacca acggattggg cgatgcaatc   28620
accgatatcg tcacgcggac caagagcctc ggagatgcgt tcggtgacat ggctgcggac   28680
ctggctaagt cggtcatcaa ggccctggct gacatggccg cccagtggct ggtctaccag   28740
gcggtgcagt tggtcgtagg gaagacggct caatcgactg cggcaatcgg gctggtcgcc   28800
aatgctcagg caacggcgtt tcaggcacag ctagcggcgt ttgcctcgac ggctgccatt   28860
ccggttgttg gccccggtct ggctgctggt gctgctgcgg cggcagccgc agctaccgcg   28920
ccaatggttg ctggagtttc ttcggcggcc ttcgcgggca tcgcgcacgg caggcatcga   28980
caacatcccg aaggagagta cctggctgct tgatgctggt gagcgggtgc tcagcctgaa   29040
cccaagacaa gagacctgac tgatttcctc agcaggcgg gcggcgcttc gggtggccgg   29100
aagtagccct tcgatcaaca tcaatacgaa tgtcactgta caggcccagc ctggcgcaag   29160
cgatgaggat gcgcgtcgcg taggtgatat ggtcggagcc tcactggacg atcgcatcgt   29220
cgaagtcttg cggcgagaaa cccagcaggg aggtgttcta tggcgtcgat gagcgaggac   29280
```

-continued

```
tttttgtcat ccttggttgg agaggtggtg aaggctgtct atatccacta caggctaaat    29340
gaaccgctgc cggaaccttt ggggtctcga aaggcgatgg ctgactgcca tgagatgctg    29400
gcgcgcgtga tcccggctat tacctggcag ggaggagatg tggacgccgg gtacttgatg   29460
tacgtgaaag ggtggaggct gaagatagga ccgttgttgg attctgcact ggaggcgatt    29520
aagcgatcac agattaatgc gatagaacca gaagagggcg gcggtgatgg ctgagaccct   29580
ttcttactgt acgcgccttg gagctaccgg cgagactgct caacgcacct ggcagaacga    29640
cttcggggat ggatacgttc agtccggcgg aacggggatc aacaccagat ccgagacatg    29700
ggatggaatg acgatcatcg ggcgcctgga ggctggtgat gatctcctgg gcgcccgcgc    29760
cttctggac cggcacgagg ggtataggtc gttcctatgg acgcctcctg ggggcgtgca     29820
gggtcgatac cggtgcaatg gatacaagct gaggccgttg ggtggagggc tgtacgaact    29880
gagtttcacg ttcgtccagg tcttctaccc gtaacaacca accatgagcg gctatgccgc    29940
gggagtaaag aatgattgag tctgaaaaga aagccgccaa tggtgattcg gtttggcgat    30000
tgagacaggg cggaactgtc gaaatcaatg aagcagatgt ttccgatgca gtggtctcgc    30060
ctctctccgt cattggtatc ggtctgccga aagagtttac agacgagtta gaaagaaaag    30120
ccgacctgct cgagcgccgg cttttcccgtg tcgaagcagt tctcggccta tctcctgtca    30180
gttaggaacc ttggcgctat caaaaaggat cgagagttgt tttgtattcg gtcttgcgcc    30240
gaaggttgag cccatgctct tagcgactga cagagccttg cctttcgccg agtcgacgcc    30300
agcattgcct tgcgtctcat tgagatgggc gatcaggccg aacaccgcag cagtaagagt    30360
ttggatctcc gaggcgtgag agttcaagac tttggtgagt tcgcggattt gttgatcgtt    30420
gctcatttcg acctcctagg cctttaaccg cgccgacatt ggcgcctccc gatccctggc    30480
cggaacgctc agggttggga aacccttaca tggtgatctt atgggtaagc cttgctcaga    30540
acgctggtca agaattcaat ggcatttgcc cggagctgct tggctgaatc gagattggaa    30600
gaaaccgatt gatgccaaac atcaacagac cagccaatca ggttctcatc tttcagccga    30660
actctatgta tctcaatggt gtatggatga gccatgtttt cgaatgtgtc gctatccgcc    30720
atgaagccaa gaatctcttt gtagtaggag gcgtgcgtga atattttgga tcgtctaagc    30780
agagctggac tgggggaact tgacatagcc tccgctcatc gaccttttcca cggctttaaa    30840
agcttcaaag agtccgtcga aagcagtgtg caggttgtcc caagcctccg tatcccgtt    30900
accataagcg ttgaagtaga tgcagaatcg tatccctgta cgctcgtcgt gcccgccggg    30960
aaggtcaagg tagtccgtag ggcaggcggc gatatcgaat atggccgcct ggaaatcggg    31020
cctttctacc tggaggtgga tgctcagcat ccgatatagc cagaggcatg cgtcatctag    31080
aagattgaac tccagttgac gcatgaagaa ctcgattctt ccccaggtct tcctgctgaa    31140
taggaattga tcgtctgggt tatcttcggg cggccgaagc aggcagtcat ttgtttcaag    31200
gctgccgtcc tttcggttga gccattcaat catttcataa aagagcctta ctgcctcttg    31260
cgattcgtgt ggtttgaaat cctccagaac ctttcggatt aatttcggat tgtctctgaa    31320
cgagtagtac tccccagcat tctccgtgta ggtggtcttg tcccatggat gggcgcggga    31380
tgcagactcc tgaggttggt aatgcgatac aaccagcatg atcggtcctt gaatgtggcg    31440
tgtgacggca cgacgctact accccggtag ggcggttgcc actggcatt catccacgct     31500
gtacaacctt ccagcccgcc tcgcgcgggc ttttttcatat ctggagaacg catggccttc    31560
aatgctgatg tgcagaagct tgagccgggg aacctgatcc ggctgtttga ggtggatgcg    31620
acgcgccttg gcggaaatct ctggcgattc catggccacg cccaagaagg ggaaatcatc    31680
```

```
tggcagggca atgtgtacga gccgatccaa atcaccgcaa aaggctttga tatccgcggc   31740
gatggtcgac ccgcgtcgcc gaccctccaa ctggcaaacg agctcgccgg cattcgagga   31800
gcgatatcgg ccatctgcct tcagttgcga gacctctgtg gcgccagggt gcgggtgatc   31860
gagacgtggc ggcactatct ggatgccgcg aacttccctg atggcaaccc cgatgcagcc   31920
gacgaggctc gggtggggat ctggttcatt gagcagaaga ccgaggaaac ccgggagcag   31980
gtcaccttcg cgctcagcag tcctatcgac atggaggggc agatgctacc ggcccagcag   32040
atcaccaagc tttgccggtg ggcgtgccga ggtcagtatc gaggagaggc ttgcgcctat   32100
accggcgccg ccctcttcac gaagaaggat gagcctaccg ataacccggc tctcgatcgg   32160
tgtggcggcc gctggagcag ttgcaagctg cgcggcaaca ccaaccgctt cggcggttcc   32220
ttgggggcca gtttgatcgt ttcgtcgagg taagcatgcg catcagtcaa aagctccagt   32280
gtcagatcct ggcgcacgcc gaaagcgtct acccgagcga ggcttgtggc gtattgctca   32340
agaccgatag cggccgagaa tacgtgcctt gtggcaacct ggcggtcagt gatcgcgaaa   32400
acttcgtcat ggatcaccgg gactacgcag cagcagagga ccgcggcgaa gtaattgccg   32460
tcatccatag ccatcctgac aaggctccga tcccgagcat ggccgaccgg gtcagttgtg   32520
agcttcacgg attaccgtgg ggaatcatcg ggctgccggg tggggaaatg acctggttca   32580
aaccatcagg ttatcgtgcc ccgttgcttg gccgagagtt ttcccacggc ttgctcgact   32640
gttggggcgc ctgcccggga ttggtacgag cgagaagctg ggttgacgct gccgaacttc   32700
gagcgcaagg acctttggtg ggaggtcaag gacggatcga gcctgtacga ggacaattac   32760
gagagtgcgg gtttctatcg cgttgaagac ctgcgccgcg gcgacatgct ggtgtttcag   32820
gtgccccact ccagagaggc cttgttatca cccgaaccat gccgcgatct atctcggtgc   32880
cgatccttgc ttgcgaagtg aagaggctcc agcgctgggc ggctcgggtc cgttcatcta   32940
tcaccacatg gcgggtcgcg cggccacacg cgaaatctac ggctggtcca tggccaacag   33000
ggtccggctg atcattcgcc acaaggactt cccccaatga agaccgtccg actgtatggc   33060
gcgttgcgcc gtgaatttgg ccgtgaatat gtgctcgatg tgtcaggtcc gcgagaggcc   33120
accattgccc tggccagcat ggtagatggt ttcgagaaat acatgcgaac cgcagaagag   33180
cgcgggatgc ggttcgcggt tttcgtaggg aggcgaaatc ttcgcgaaga ggagcttgac   33240
ctggccggag ccggcgagtc ggtcatccgc atcgtgccag tcatccaagg cagcaagagt   33300
tccggaattt ttcagacggt cctgggagcg gcgttggtcg ttgcgggcta tttcacgttc   33360
ggcaccacct cggcaatagg cgttgcaatg atggctggcg gcgctggcct ggcgcttggt   33420
ggcgttgccc agatgctggc cccttcaact caggcttccg ccgcgaagaa cgaggatggg   33480
aataacccga gctatggatt cggtggcgcc atgaccacta ttgctcaggg caacccatac   33540
ccagtgcttt acggcgagcg agagatcggc ggcgccgtcg agtcgggcgg ggtttacacg   33600
gaagaccagc tctagcacga ctgctgccag acccgcttc ggcgggttt cttgtttctg   33660 gagatcgaaa atgtctgttg tgaccaaaaa gcgccatcag cctttgcgtg gaagcaaggg   33720
gggcagctcc aagccgaagc agccgcacat cgcccagaac ggcgtcgcat cgctgtccac   33780
tgctcggatc gtgtatctcc tgagctgggg accgattgtt ggtccagtca atggacttaa   33840
gtcgatcaag cttgacggta ctccgatcca ggctgaagac ggcacgctga actaccccga   33900
cgtgaagtgg cagtttcgac cgggcgagtt aaatcaggag cgactggaag gtgtagcgga   33960
gtccagcaac gagattgcgg tgggccagac cttgctcagc acgcagccct acatctacac   34020
```

-continued

```
cgtcacgaac gccacggcgg atgcggtacg cgtgcgcctg tcctggccca acctgcaggc    34080
gcaggattcg tccgggaaca tcaatggggt gcgcattgag tacgcgatcg atgtcgccac    34140
ggatggcgct ccttaccaga ccgtactcag cacgtttgtc gaccggaaga acgttacgac    34200
ttactaccgt tctcatcgga tcaacctgcc ggcaggaggg cactgggcgg ttcgcgtgcg    34260
gcggatcacg ccggaggcga acagctctct ggtccaggac accatggtgc tgactgcgat    34320
agctgaagtt gtcgacagca accaggagtt tccgctcacc gccgttggct gcgtggagta    34380
tgacgcccaa cagttcgggg gcgactttcc gaagttctct gcgctcatgc gcgggcggat    34440
cgtgcgggtt ccgatgaact atgaccctga gactcggacc tattttaccg gcggccccgg    34500
taccacgaat ggcgtttggg acggcacctt caaggaggct tattccaaca atccggcctg    34560
ggtcttctat gacctggtgt tgaaccccta ttacggtctg ggtgagcgca tcgaccagag    34620
catggtcaac cgctgggccc tctatcgcat tgcgcagtac tgcgaccagt tggtgccaga    34680
cgggaaaggc ggtcaagagc ctcggttcac ttgcaacctc tatcttcaga agcaaggaga    34740
ggcgtatgcc gttcttcagg acctcgccgc aatctttcat gggttggcgt tctgggatgg    34800
tagccagatc actgtcaacg ccgacatgcc tcaggacccg gtttacacct acaccacttc    34860
gcagattctg aacgatggcg tggttgcgta ttcggggacg cggacgcgag accgccattc    34920
gctggcgatg gtctcttggg acaacccggc caatgcgttc gagacagaca aggagccggt    34980
cttcgacgag gatgcgatta tcgatcttgg cgggatcgtc agagaggtct cggtcggggc    35040
tcttggctgc accagtcagg gtcaggcgca gcggcgggg cagtgggcgc tgatgactga    35100
gcagttgcag acgcgtggcg ccgtctggaa ggttggcctg gatggattca tcccgcgccc    35160
tggacaggtg gtcgctctgg cagaccccat gcttgctggt cgtgcgaatg cggcaggat    35220 ctcggcggta tctggacgag aaatcaccgt agaccgagat gtggatatcc cggtcggcgc    35280
gcggctgcga gtcaacctgc ccagtgggcg ctcggaagcc agggcgattc aaggtcatga    35340
cggacgcgtc ataacggtgg tggccgactt cagtgaagag ccttcccccg agagcggttg    35400
ggcgatcgac tacgacgacc tggccctgat gcagttctac gtcaagaacg tgaccagacc    35460
aagttgggag caattccagc ttgaggttat ccagcacgag cccggcaagt ttgatgcgat    35520
cgatcacggg gcgatcatcg attctcggcc gatcagcgtc ctcccgtccg gggtgcagga    35580
tccacctgca cgcgtattga tctcgcagca catcgcggtc gagcaaggcc tggcggtcac    35640
gatcatgacc atcgcctggg acgcggcacc ggacgcggta gcgtacgacg tagagtggcg    35700
ctggggctcg cgcgagtggg tcagggttcc gcgtacgggg gagctgatgg tggaagtacg    35760
tggggtatac accggccagt accttgctcg cgtgcgggct gtgaactcca tgaacgtgtc    35820
gtcgatcccg gcgaactcgg tgttgaccaa catcaccggc aagaccgcg cgccgccggc    35880 gctggcgttc ctgcgtacca ccagcgggcc gtggaagatc ggcctggagt ggggattccc    35940
ggccagtggc gcggcggaca ccgcctacac cgagatccaa cagtcggtta ccccaggcgg    36000
cagcgaacag aacgcaactg ccctgggctt gtttgcctac ccgaccgaca cccatacgct    36060
gacctcgctg gcggccggtg ctcgccttgc cttccgcggg cggctgatcg accggaccgg    36120
caacgtcggc ccatggtcgg cctgggtcga cggcatcagc tcgacggatg cgagcgagta    36180
caacgagctg atcaccaagg agtacgtcga gtctgcgctg ggcgagcagt tcttcgccga    36240
catcgaccag atgcaggtcg atatcactgg cctgcaggac cagatcgaca atctgaccga    36300
tgtgctggcc tacgacccga cgaagaccta cgcgaagaac gatatcgtgc gggtcggcaa    36360
ccggctgtat caggcgaagc aggctgtgcc gctcaacgcc tctccgccga acgcgacata    36420
```

```
ctgggccgac atcgggcagt cgatcgagac ggccaacggt ctggcccagc aggtggccac   36480
caacaccgcg gatatcaccg agctcgacgg taaggtcgaa gccgccgctt cgagcctgga   36540
tgttctgcag gctgccgccc gccgggagcc ggcgaccgga gagaaggcgg atgcgctgaa   36600
gggctgggac accattgctc gagcagccac cgaagtcacc gtgcgggcga acgaggacga   36660
agcgcaggcg aagcggacga gcttgctgga ggcgcggacc gagacggcgg aaggcaggat   36720
cgcaactgtc gagtcggtcg ttgcgtcgaa caatgctgta accgtccagc ggctggacca   36780
gctcaccggc caggttgcga gcaacgcctc ggcgatcagc accgaacaga ccgtccgtgc   36840
caacgcggac agcgccctgg ggcagcgggt ggataccgtc agcgcgcgca ccgataccaa   36900
cgaggcgaac atccagaccg cctctcaagc ggttacctcg ctggatggca acgtcaaggc   36960
gctctacagc gtgaagctcc aggcgcatgc caacgggcag aagtacgccg ctggctggca   37020
actgggcttc gacagcggta cgagcgtgac gaccatggcg ttccaggctg atcggttcct   37080
ctggttcaac agttccagcg ggcagaccgt ggcgccggtc tcgatcgtcg gcgggcagat   37140
gttcatcaac aacgcgatga tccaggacgg ttcgatcacc aacgcgaaga ttggcaacgt   37200
gattcagtcg accgccctcg gtgccaacgg cgagccgctg tggaagttgg acaagtccgg   37260
ctcgctcacg atgaacagcg ctacgtctgg tggcttcatg cggcagacag cggaggccac   37320
caaggtctac gacgcgaatt tggtgctgcg agtacagata gggaatctcg acgtatgagc   37380
tacggcatcc gcctgagaaa tgcggccggc tccatcctga tggagctcac ccggccaatc   37440
ggcgcgtacg gtctaccggc agtcgctcgg cgccatcacc aacgggatga cggtgacggt   37500
gccgggtttt gatcctgcgc gcggcgttgt gttcatcatt gcgagcggaa acgcattcgc   37560
tgaagtgccc ctatacacaa tttccggaaa cgtggtgacg ttccactgga acggttcatc   37620
cggaacaacc tatgtactgc atgcggtgat gttctcatga gctatgggt attaattcgg   37680 gggaacagcg ggcagacaat tatcgatgac tcgaacccgt gtattcacat tgcggcatca   37740
ggaacatacg gtgtacagac cactagcgaa actatcgtaa gttatccaac tgcgatccag   37800
tccccgtacg agccgtatgt gtactttagg cctaatggtc cgcatcaaat ctacctgttc   37860
aggcatatcg gcagtccagg gaactggact ggattcgcct tctggcagag catctatcgg   37920
gacgtggacc ctccaatcta cggcggaaag tggaaagctg gcgcggtcat gttgccgaaa   37980
accggtgggt ggggaatgca ggttttcgac tcccagtcgc gtgtgatgtt cgacagtaac   38040
cgggaaatcg ttcgctatgt cggtggtgcg caggtttgga ataaatatgc gtacaacccg   38100
aactggcctg gcggcctggc gctgcagacg tggtatttgc cgttcccta cggaactgag   38160 gcttattttc aagtaagcca cttcaatgta agcgcattta tcactgctga ggctccgcgt   38220
attgggtttc ttgagaactc aatgagcttg atatttgtgt catcagttgt cgggtcgaa   38280 actaatcagc aattcaactg gccgctcatt gcagtagcgt aaatatatct ggaggactat   38340
atggcttggt attccacagg cacggtcgct gtcacgctga attcgccgac agtcaccggc   38400
actgggacca cattctccgc gaacgtccgg gtcggcgatg cttttcgcgg cccgatggt   38460 cgttggtacg aggtcacaaa cgtggccagt tcgacggtca tctcgatcaa acccaactac   38520
cagggcagca cggccagcgg ccagtcctat gcggtggcgc cgatcctggg ctacgacaag   38580
gacctgtcgg atcgattcaa cctgatcgcc aaccagtggg gggcaaccct ggcggggatc   38640
aagccctggg cgctttctgc aaatgcggct gcagcacggg gggatctcgg cctcggcagt   38700
gcggcggtac gggaggcact tggtggttcg ggtgcgctgt actcgcgaga cagcattctc   38760
```

-continued

| | |
|---|---:|
| ggcgcagtct ctcaggcgag cggcataccg tctggtgcga tcattgagcg cggcgcgaat | 38820 |
| gcaaatggcg attacgtgcg atatgccgac ggaacacaga tgtgttggtt caacgccagc | 38880 |
| gttactgatc aggcgattga tgtcccatat ggaagtctgt ttaccggaac ccgttcgtgg | 38940 |
| tcgtttccta tcgccttctc cggcagccca accgtgaacc ccggcctatt tcgctggggg | 39000 |
| actggagcag gctggggcac tgttggcggt atcgcaagcg cgacggcggc tacgttgcgc | 39060 |
| ggatttgaca ttgtgtcgcg cgcggttggg acagcgaccg tgatctcggc aagcgcagtg | 39120 |
| gggaggtggt tctgatgaac ttcttgcttg ttctttcgcc gcagtacggg cctgcggaat | 39180 |
| ttggcgacta cacaaccgtc tcagtttcgg gtggcgtgct cactgtggag gggcgtgact | 39240 |
| atgcgttccc cgatctcgcc gacggcgccg aactcacgat ggaggacttc gccgatccat | 39300 |
| atcccgtcta ccaggttcgg cggcgaggcg acacgatttc ggtctggatc atttacagat | 39360 |
| atccggcagg tgcgacccat gctgccagat accctgagcc tgttcccgtt ccgggggatt | 39420 |
| tcaacgggcc ggttgatctg ccgaggtgaa agcc | 39454 |

<210> SEQ ID NO 5
<211> LENGTH: 40016
<212> TYPE: DNA
<213> ORGANISM: Artificial Sequence
<220> FEATURE:
<223> OTHER INFORMATION: Synthetic construct

<400> SEQUENCE: 5

| | |
|---|---:|
| atataacccc gcacaacccc gccgctttgg tacaggaatt ggtacatgct gaccggcgcg | 60 |
| agatcagcgc tcggcttcgt aagccgcggc gcctgagccg acggcgatcc atccatccgg | 120 |
| cgagtgcgcg gtgtcgcaga tcgatacttc caccgtctgg ccttccttgg gctcggcagg | 180 |
| caggattgcc gcagtacgcc ggaggtcgtt tgaggacggc gcgaacgtgc tttccgagca | 240 |
| gtggaatgcc catatcccgt gttttccgga actgcctatc tgccgatcga gcttcagcgt | 300 |
| ccacttcccc gccaatcgaa tcaccagcat caccaagctc cgtaggaaaa ggccgtagtc | 360 |
| tactcctaat tcttacaggc cctgttggct gccagcagtt gcgcttcgta accgatccgc | 420 |
| cgccggcact cggcacggca cagcaacggg cacttctacg cgcaccgtgc gcggctcggc | 480 |
| ttcctgccgg ccggcgcatc ccgccagcga gaccgcgaaa ttcaaaatca tcgaacgcat | 540 |
| ggtcaactcc gacgaacggt tgttgtggtg tacgttgtta cccattacta taagcccatg | 600 |
| ccagccaaac ggcgaggcgc caacaaggag agacacatga aagtccccgc attcttcgct | 660 |
| gctaatatcc tgaccatcga gcaaatcatt gaagcgatca acaatgacgg aagcgctatg | 720 |
| accagcgcac cggaaatcgc cggctactac gcatgggatg ccgccactga cgcacttgaa | 780 |
| agcgagaatg accttgagca actgacggag gatgacttcg ttgctcatct ggaagttctg | 840 |
| gaagaaagag gcgccaagat cgaccgcgat gcagcaatcg cagttgcgct ccaattccag | 900 |
| gccgcagcag tgaacgacct gcattctggt gacgaatgaa accagattca gccaatcaca | 960 |
| accctgaccc gcgctacctg cgcgggctgg tcgacaaagc aggtgtcagc cagcgtcagg | 1020 |
| cagccgagtt gctcggcctg tcgtggcctg gcttccgcaa ttacctgcgc gacgagtccc | 1080 |
| accaactcta ccgggctgca ccgtacacgg ttcagttcgc gctagagtgc ctggctaacg | 1140 |
| agagctagcc ggatcctcga acgacgcaca cggaaacgga tacttggcct tgatctcctc | 1200 |
| gaccttagcc acccaagcgc ggtagtccgg ctcggtgccg gccttgatag cgtcgaactc | 1260 |
| ggcctcggtc ttgagcgggt cactctccag gcggtaggca tttgcccgag ccacggctgc | 1320 |
| agcatcgtac tcagcctgcc agcgctcttg cgcctgctgt tcggcggtct ttaccttgct | 1380 |

```
ccaatcgatc atcgcggcaa ctccaccggg ccatcggcct cgatcagcaa cggttcaggg    1440
aagcgagcgg cggcactggc atcgacggca agcgggaacc gcaggatcag ctccaaccgg    1500
ccggcacgtc gcagtacggg accagcgaac cattccgacc cgatagcctc ggccggcaac    1560
tcgccgccct cagggagcgg tgtgaagtcg aattcctggc cgtttacggt gagtacatca    1620
ccagttttgc tcagcgttag gcgctcgtca cttcccggca gcggaacata cggcgacaac    1680
ttgatgatca tcagaaccac ctccccgtag cgattgcaga aatcgccgtt gccgtgccag    1740
tcgcgcgcga agaaatgtcg aatatacgca acgtcacact cgttgtgctc gcgaccccac    1800
caacggtacc ccagcctgcg ccggtacccc agcgaaacaa accgacgcta acagtcgggc    1860
ttcctgcgaa cgtagcaggg aaagaccagc ctctagttcc ggtgaacaga ctaccgtagg    1920
gagagtcaac tgcctggtca gtaacggagg cgttgaacca acaaatctgc gtaccgtctg    1980
ccagcctaat gtattcccca ttcgcgttgc tgccgcgctc aagaaccgat ccgatcggcg    2040
agcctccaga ctgggctact gttccaagta actgagcatc ggacagcacg cggacccaag    2100
gctgccacgt actggccgcc ttacgacgga aatacagtat gtttgaagta cgcgggacga    2160
atagctgaac cgcagtcgca acgtcgtaag ggtggtgata gagcatcgat ccgatagggt    2220
tcagcgaatc gatgccgggc ggaaggttcg cccagggcga cgcgccgata ccatagaacc    2280
cgcactcgtc cggtaccgtg ttcgggtcag aaaccgctcg gttgaacgtc aagctcttgg    2340
ggacgccgcc gatgtagctc aaagcattcg cctgcgtaga cgctccgagc attccgcgcc    2400
ctacgctcgt cagcggtgtc tgcgcccagg tattcggtcc agtctggaac gggagctggt    2460
cagcgccacc gagcagaagg ctgaagttct gcagcctggc gtcgaacagg ctcaagcgcg    2520
cgccggcagc ggttgctgcc cctgttccgc cgagtgctac cggcaccgtg tcgccatcgg    2580
agaactcgcg gaggctgccg tagccgttgc cgtcggcctg gagtttcgtc gggcgtatat    2640
cagccattga acagcacctg taggttgaga gttgcgccgc cggcggtata ggccggcagt    2700
tggccgtcag ggttcatcgt gagccgaagc atggaaccat cggcgagata cccaggaaca    2760
gccgcgggga tgcggacgtt catcggatag gccaccacca ccccggcgcc gttggtgacg    2820
aactggtcgt agccggtgcc gcgccggacg aagtaaatcg cgttcggcgc aagggatca    2880 ggcaactgcg cgacgacctt atgggtctgg agcacagcca ttaccaggcc gtcccattcc    2940
actcggccgg gatcggctgg ccgttgaagc gcaccaggcc cgactcctca ctgaacttgt    3000
ccagcgtcga cttgttcgcg tgcgtgtgcg cctgggaaac ggcggtgtcg atctgcgccg    3060
gcgtcgacgt cgggcgcccg ttgatcgcgt cccagttgag ttcgacgtcc atcgactcat    3120
actcggccac cttcagccag gcgctggtag cagggttcca tgcgtacagc gcagctccgg    3180
attcgactgt cgggtccgcg ctcgcatctt gaaccaggac gaatattgcg ccctcaggct    3240
ccagggcatc gcgtgcagcg atatcggcta caaacaggat cggcgcgcct gtgccgggca    3300
ggctggccag cgcctcgttg atcagcgcat tgatcatcgc gctgttgccg atcgagcgcg    3360
ccacacccgc cgagttcgtc aaatacgatt cggcgaagtt gctgttctcc acgaagtaga    3420
agctgtccgg ctccagcgta cccggcaggg tcgccacttt gaaaaatcga atctgggcca    3480
tttcatcacc aatcagtcgc gccccattgg gcaccgtcta cgccatccct ccgggaggc    3540 ccttggtcac ccgcaacaac cacaagcaca tcggccggcg gcgtcacggt gaccgcgtat    3600
tcctgcatct cgctgagcac cagcggctcg ctatcgacct cgatcgccag cgcccatggc    3660
tcggcggcgt catccatcgc accctccccc acggctcaca gtgatcggcc cgctgtagta    3720
```

-continued

```
gcgatggacc gttccatccg ggtaggtcac gtccacgtcg tagaccgccg acgcccatgc  3780
caacgccgcg gtatcggagg ccgatatctc gcgcgagatc gttccggcgc cagcgatctc  3840
aaggccggag ccgagcgcca gcgtcatcag caccgtccca tctggcgcat cgcggatctg  3900
catccgtacc tcggcgccag ccaggtcaac aggtggctgg tagatcagtt gcccgccaat  3960
aggcgccagc ccaacggctg acagcaagtt gatctcgatc gtgtcgtcgt cgatggacgc  4020
gacgcggtga ggcagttgcc gaagccgagc gcggttcagt tcgggcatgc cctgacgcc   4080 atcgatccag gctaaccagg tgtcgggcaa cccgtggccg gggatggtca gccggacggg  4140
agcggtcgac gcgatctggg tgatcggccg gtagaccagg ctcggttgca tgatccgcat  4200
cgtgtcgcgg aacgtcgccc cgcgctccac gcgcaggggt acacaggccg gcgtcatgcg  4260
gcttctcctt ggagtagtag gaggggctaa acccaactgg tcaggtactg gatgcactcc  4320
gggccgcgag agatatctcc ggtgatcggg ttgcaactgg ctcgcaccca gcggtcggct  4380
ggctcccaga aaaagccgcg ccggtactca tgcgcgggct tgctcttttgt cagggtttcg  4440 gtaaccgttc cagaggtcac gccgccaagg cgaacgaccg gaccctggcg aacgctgacg  4500
gtcgttgtgg tctgcccctc gggatagtcg aacggatcgc ggatgtggca gatggctgcg  4560
ctgttgttgc tcaacgcggc gagccacact tggtgctggt cctggttggc cagcatgttc  4620
tcgtcgttca ccagccactg gtaggtcaca acggtgttga cgatatgcat gcccgggggg  4680
aatgtcgtcg taggcgggt gaccaccgga ccacccgtat ggtctgggtc ggtataagtc  4740
gtgacgtcat ccggctcccc cgtacacttc accgtccgag tgatctgcag tcctgtccca  4800
gggatgtaga tcgcctcgaa ctgctctgtc agtacagtgc tgtcgacaac tgatccggag  4860
ccgctcaaca gcgcaacctc gctgcttcgc tccgtcgctg ttcttgtcgt cacgccgggc  4920
tcgttgcggt actccttaag tgcatagtgg cgtcggttgt agcgcgcggt atggatgttt  4980
ccctgggcgt cataccaagc ggtcagcaac ccggaggtct ggttccattc ctctcgatag  5040
agcgtggttt cgattggatc gcccggctga ctgctctcgt cggtcacctg atgaaccgga  5100
ttaccgagcg cggcctggcg attctcgatc acgcctattg tgaccgtctg actgtgatcc  5160
gcctctggat ctcggatatc cggggcaatg gtcacctcga cgagaccata caaccctga   5220 ggggcgccag acggggacga accgctgacc accgacgttc cgggcggtgg gtcaatctgc  5280
cgcatccctt caccctgtgt caccaccacc cccagcagca accgattcg gtagaccccc   5340 agcagcttca ggtagtccag cttgacgttt tcaccaaaaa accagtagtc gaagttgctc  5400
ccgagcagat cttttaccgc acactccggc tgtcctgcgc cctgcccaac atcctcaagc  5460
gttatcttct tccgaagggc gtgaatcgtt ccgccctttg tccaaaaatc gaggtagtag  5520
ctgccctgct ccacattgag gtagatatcc acatacagcg ggcggcgcgg ctcctcgtcg  5580
ctagaccacc agagggggag cccctgaat ggggcgtcgc ctgtataggg ctgcccctcg   5640
gccgaggtcg tcgcgccgcc gtagtacaac tgatagccgt aattgccgcc acccgaagg   5700 atagtccgcc cccaccactt cccgccctgc tcctcgacct gcgggtcgtc atggtccggt  5760
aggcccatgt cgaacagatg cgtgtgattc atcgccagg tgccgtagta cgcaatcgct   5820
gggcgcgtcg ccccgttcgg cagggtgacg tagccgccca gatccttgtt cggctggcgg  5880
atctttccgt gccacggcca gcccatgcga acgacctcgc cgtcccaggg cataagctgg  5940
ttcatgcctt gaactccatg cggccaatat tctcgccgcc atcctgcatc tcgaagctgg  6000
tgacacgctt gaacacaacc accaccaggc catcggtgct cacgatctcc tcgtcggcca  6060
ccgtgcgctt cgacttgtcg gtctcggcca gcggccagga cacaccgccc ccgccgatct  6120
```

```
gcttgccggc ggggttgtag tcggccctgc cgcgcgcagc atccagggcg ccgcgcgggt   6180
cgattttccg tagcgaccgc gcctgacgct ccggctcgat cagccggttg agtgccgcgg   6240
tcaaccctg gtcgccacgc cgctccgctt caacccgttg ccgccggcg cggcggatcg     6300
cttcattcct cgcgccgagg ctgcggcgct catctgaaag agccatacgc tatctcctac   6360
gcgttcagca catcgctgaa caccagcatc gacagggtga gttcgtcagc atcgaaatag   6420
atgcgcgccc acacctcgcc gttgaggtca tttgcattga tcacgaaccc atacgactcc   6480
tgcgccgccc actgcctgga ggtgcccacg atcgacatac ctccgggcaa ttcacccgac   6540
gtaaccctga tttgcagttg ttgcccgctc ggagcccagg ttctgatgtt caggtcgaac   6600
tgtcgggatg tgctgggatc gattccaatt gcggcggtgc caagctcggg aattgcgaac   6660
agacgggcat caacaaatga gtgttgaggc ccgaggagga actggccgtc ggtattgaca   6720
tgcagcacct cgctcggagc gctgccaccg ccactaccca gcttcaccca atcggcaccg   6780
ctcgcggtgc ccttcgccat gtatagcgcg ccgttgttcg tgttcacgta gtgagcaccg   6840
atgcttggtg gcggatcgag cggctccccg gcgccggaca ggacgtgtgt aacagttgcc   6900
atcaaatgtt ctccatgatc aggttgttgc cggcgtcgtc gaccagcgtt gcgccggttt   6960
cgtcgacaag ggtgccgcca gacgccccgg attccagagc ctggatgcgc gcctggagcg   7020
tcatgaggtc gccggcggtg actgcggcgt agatcgccgt tcccgtcggc cagttgccgt   7080
cggaggttcc ttcctgggcg cgctcgatcg tcaccacccc accggcacgc gcggttgctt   7140
tcacgatttc atgctgcgcg ccagcgtcat ccgccagcgt caacagcacc cagctaccgc   7200
cggagagagg cagcagcgcg gcagcggcat ccggcaccgt caggctcaac gcgccaggcg   7260
acagccctac gctcagcgtc gtcttccagt tgttgatcca ggctctcgcc atcgctacat   7320
ctccagtacg tcatcaggta cagctacccg gtaagtggct gcgatctccg gcgcatgttc   7380
gtcccggtag gtctccggaa tatcgtttgc agtcaacgag aagcgccgcg ggaacagttc   7440
ggcgccggga tcgcgattgc tccagttgcc cgagaagcca tccgcctcat cgtcatacgc   7500
gggacttccg ttgcgacctc cgagctgcgt cgtaagttgg ccaccgcccg acggtgggct   7560
ggcgggatcg gacgagccag ccggcggaac aaggggatct gctgcgccag cgccgcctcg   7620
catcaccgcg atagagatcg tggtcagggc gcttccggat gcgaggtcga gccggtcgac   7680
aatgcgccga cacttgccca ccgcacgcgc gccctgatca tcgaggcgga gcgtatgcac   7740
aagatcgatc ggcaagacca tggatgtcgg aacatcccag gtcacggtcg tgccacggtg   7800
cgcagcaatg agcgtcgtgg cgccctgggc caacaagcag ttcagcgcgg acaaacgccg   7860
gttgccatcc ttctcgtcgt cgtggccggt gctgccgccg gtgatcggct cgctttccca   7920
gcgctcggcc ctgtccgact cgatctcgaa cgaggcacgc tgccgaccga caatcgggcc   7980
ggtcgccgcc acgctcggct gaacctccat gaccagccgg tagcgctcgg tgacggcttg   8040
cgtccagcgc ctcccagcga tccagtttcc gcccaacagc aggtcggtga aactattgac   8100
ccaggccgct ggcggattgc agtagacccc ggttggcggc agtggatacc aggtggcata   8160
gaacaacgtc tgaccgctgc tctcggtcgc gaggtgatc atctccacat caggtagctc    8220
ggtgtcgtcg ccgcgccagt tgcaaaaccc tgcctcgccg accgcgttcc ccgtgccggg   8280
gtgctgccaa ccatacgagg cgttcaactg ccagagccgg ctgaatcggt agtcgcactc   8340
gatctcgacc ctgttcgtct gcgaactcag gtcggccagc tcgactgcaa gcgttccgta   8400
caccgtagag cctgggccga actcgaaggc aggcgccaca gcaagccatg atgtgacgcg   8460
```

```
gagagcacca tatggcgagc agtccaagct cccggtaacg ctggtcaaac gctcctgggc    8520
gtagtcccac cgcgagcgtc catcgaccgg ctcgaacaca tctgcggacc aggcgccgcc    8580
gaccagggcg tcgacggccg caatctccat ggcctctaca cgctgctgca actggtccgt    8640
gcaactgacg tccaggacgc gccgaacagg attccaggct ggctgtgtaa ctctccccgt    8700
aaaccgtcgc ccctgactca gttcacccgc ggtctccgtt gcgtagtcga tggttacggt    8760
tcgaccgatc cagtccgtag ggacaacagg tccgtcgccg agatagatcg aaaaggacgc    8820
gacgccagcc gccccctctt cacgatcgac ctcgatctcc ccggtcagga gcggcgtaac    8880
gtcgtcatcg ccaacgcgca cgattgggcg ccatgtgaaa gctagccag ggatgatcgg     8940
ctcaggacca ggcacagcgg agtgagcggc cgagttcagc gcaacgctat tgagcgatcc    9000
accgttgagc atcagatttc ctcagcgaca atttgccagg tccggctgtt gttcgaagaa    9060
tcaagcgcct caggagggat ggacgcgaag acgtggaaca gcgccacca ctcgacgcgg     9120
tagagttgcg cgcctgggat ctccgacaca gttaccacct ggccggcgga cgacacgtcc    9180
gttctgaccc actcacgtcc gaccagcgcc agccccacg gactggcatc ggggcgaacc     9240
tctccgggga ttgtgaatac tcggtcggcg gcagtacggc cggaaatgcc aagcgacgca    9300
ttgcatcgca gctccaacgg gttgtcgaag tcgagtccaa gcatccccgt gccgatccat    9360
cctgaaccgc tgatggtgat tgccgtcttg cgccagtgcg tcatctgtac tgccgcacct    9420
ccgctgagcc tcaatcgctc gacgccgcca tctacagcct ggtactgaca ctgcggggcg    9480
ccgccgtgta tcacgatcgg tacgccccca agcatcacgt tcggaatgat cattcccaac    9540
tccataaaaa agcccgcgct tggcgggctc ggtcattttg ggcgtgtccg cccgaacttc    9600
gaggcggcct tgcgtatatc tcggagcgtg tcgtgtgtcc cgaaaacggt gaaaccggca    9660
tcgtccccac ccaggttgag ggtcagcgag cccaggtttt gcatagctgc cgacggattc    9720
gcctgctgaa gcgccgcggt cggaatctcg ggtatctcgg ggagagttcg ttgataccct    9780
tgcgacatct gcagcgactg caccgcgttg aagatgcgct ctcctccgcg catcatcatc    9840
aactccggcc cacgctcccc aacccacgcc atgccagggg gagcgctctg cgtaccagtg    9900
gcaaacccgg gtatcttggg ggtgatgctg ggcacgcccg gcaagcccat ctccggaggc    9960
ggaaccagcg tgataggtat cacgagctgc tcagccagtc cggcggcgat gtcggcgacc    10020
tgctgcttca aggtctccgc gctttcgaag tccattccga acgataccc gacgttttgc     10080
acagccttga tgcgctcctc gaggtcggcc aggttcaggc ggttgacgtc atccgcggcc    10140
ttggcattac cagcctcgac ctctgcagct ttgttggcga tgcgctccac ctccttggcc    10200
acgccttcga agccgtagct gttcgcgcca gcgtccttca gttgctgaag gatctgaagc    10260
gcgcggcgcg cctcctcgat cgccttttgg ttgttgccag cggtcagggc gttgcgagcc    10320
gaggcctggg ccgcagtggc atcaccgaag gtctgcgttc cggaagtggg cggcgcctgg    10380
atgctcttca ccagatcggc aaactccttg cggacatctg cctgccgcga aagcgcgtcg    10440
ttgaggttct tggtggactg ctcaaggagg gccttggtcc gaacaacctc agactggaga    10500
tcggcgacgt tctgttcccg agcccgcttc agggcatcgt tctggcgctt cacgatctgc    10560
tcttgtcgag cctctcggc ggcgagggtg ctgtgaggc tgccctcccc ctttttttacc     10620
agcgtattcg ccgtgttgat tcccttggca acatcgttca actggttcgc tacccagtcg    10680
acgacgcctg tttccttcgc gcgacgcccc cagtatttct gggtttcgga aaagatccgg    10740
ttcagccccg caccaatctc cggggcaaac gacgccatct cctcgcggag cttcggcagt    10800
tccttccgca acgcgatgac gatctgctcc gaagtcagtt caccggcggc agccatctcg    10860
```

```
cgaagccggc cgacagtcac cccgaaggag tccgccaggg cgccagcaat gcgatccgag   10920
gactccagaa cggtattgaa ctcttcgccc gcagaacac  cactggcgat ggcctggag    10980 aactgggtaa tgaccgaggc cgactcctcg gcagatgccc caccgatttt caggccgagc   11040
gataccgcct ctacggtttc gagggcggct cgctgatcca tgcccgcatc ccggagcggg   11100
cgctgcaacc gcgaataaag gccgatgagg tcgccgacat cgccctggac atcatcagcg   11160
atacggtcga gttcgatctg cgcggtgttg aactcttcct gcgagcgggt tgccaggcga   11220
agcctggaat caagccggcc aacagtgtcg gccccgttcg ctagcttcgc cgttgcagcg   11280
cctaccgcgg cggcgagacc tgcaaccgcc agtgccgggc cgctcccgcg agagagccg   11340 atgctcgaga gccgcgagcc ggcaccaagc gagccgagtt cgctcttggt ctccgcgatc   11400
tgcttcttga gcgcccgctg cgcaacggca agctcccttg tggatagcgt tccgctggac   11460
cgaagcaagc gatattgctg gttcaactgc ccgatggcag cctgcagttc gcgcaccctg   11520
gcgactccca gggtgctacg cgcttgctcc aagttgtagc ggcgctgctc gatcgcgctc   11580
tgcttgatcg ctgcggcctg ttgccggagg ctggtggtgg ccgcatcatt ccggccagcc   11640
tggaggtttc gatccagctc ccgctggagc cgctgccgtt cggatgtcag gctcctcgta   11700
tccagcccgg cctgcttcaa ctcccggcgc atcgcggaaa gccgagctat ctggaccgtc   11760
tctgcccgct ccaggcttcg caagtccgaa atggagtccc ggtaagcctg ctgcaattcg   11820
cggctcggcc tgatcgtcga tgccagttcg ttgccgagcg tgcggatctg ctcgcgcgcc   11880
gagcgcgctt ggcgttgcgt gtcctcaagg gtgctttcga gagcagtgaa atcgtttaaa   11940
cgccgaagag gttgcgcgac ctgcctgacc agttcggcgt attccttgcg gaaacctgac   12000
acctcgcgca gcgcatcatc gaggtcagca gtcagccgga tctttacgtc agccatttca   12060
ttcagccttc agcgcggtca agaacagcga ccagggatat tcaaggacgt ggtgatgccc   12120
aagcctcacc agaacgcaaa tggcgcgctc caaactcctc aaggcttgtc gcggagtttc   12180
gagagacggc ccagcattcc gaaaaaatgc gggttcacct ctttacatgc atcccgcaac   12240
ttggcgagtt ggctcggccg gagatcgtta atttggctct cagtaaccga cgtcatcagg   12300
cacagatcgg aaagcctgat atcttcgaag agagcattac tgacgatgtc ttggtcactg   12360
acctcttgca ttagttttcg aacatccgca acgctaagct cacgcacggt caactcaacg   12420
ccatcaatat caacaactct acttgcagta acgtgacca  tttcagtact ccaaaaagca   12480
caaaccccgc cataaggcgg ggtcgttgga aaataagagc tgtcctagca gtcaaaagta   12540
tcccaggatt cctctcctgt taggtccgcc cctttaggct tcaccgtata gtgtccagca   12600
ctgttgaata taatctgcca ctctgggtct gtagcaccat cagacttacc gaagaacccg   12660
ttcgtatata caaatgaact gagcccgcca cttgtgttgc atttcccatc ctgccctatc   12720
ggtggtttct tcacctttc  tagcgccgga attgttccat tggaagcaaa cacgacacag   12780
ccagagtcaa gcccgttaga gccaatgcta ttatattcgc gagaggaaag cttacttaca   12840
gtttcccact catacttaaa cccgtatttg actaagcccc cgcctttact cgtgcttgct   12900
atgactctct cggccttacg tgcattgctg atagttattg tcccatcagc tacgcagacc   12960 tgcgcccgg  tcttatttgt catggccatc gcgcgcgcat aatcgagact cttttgcaaa   13020
tcattgcgcg ccgaggccgt gctgttgcct tttatgagat tcacaaaaga cggaatggcg   13080
aaagcgacca tgcacccaa  aaggacgaca atcaccatca gttcgacaag ggtaaatccg   13140
cgcgacctag agtacatttc aaccccctccc taaatggcgc cactgtagca ccacgcgggc   13200
```

```
gcgcccacat ccggcgtccc tgccgggcat gaacggcgtc acaccgtcgc caattccttc  13260
ttgatgttga agtacttcga ttttccagcg ccgaccttgg tcgggtccat cagcaccttg  13320
gcagtggcct cggcggccag gaagtcttcg gtgttgatcc aatcctgctg gctcgacggg  13380
ttcaagcggc agaggaagta gcgcgcctgg attcggcgct gggtaccggc ggcgttctcg  13440
ccctcgaaga ggaattcgaa cgtcttgccg ctgttggtca gcgcctcgat cacatcgacg  13500
gtggcagact tgtaggtcac cttgatcggt gtggccgcag agatcgcgcc cccttcaacg  13560
atttcgaggc cggctccggt catgttccag tcgtcgaact cttcgtagtt cgtggtgccg  13620
tcctcgctct tcacgctggt gatctccagc ggcatgaagt cgagcgcgat cgtgcctccc  13680
ggaacggctg tgtgcgcttc gtcggtgtgg gtggcagaag gaacgttggt ggcgtcgccc  13740
cacatcaggg ccgccagcat cgaggtatgc agttcgcgga agttgatccc caggccgacc  13800
gaggagatgc gcgataccga gtcgtactcg ccgccctgcg gagtggtggt gtcggggagc  13860
gtgatctcac tgctctcgat ggtctgctga atggtggata ccagacctac tttcttgaaa  13920
ggccctgtag tccctgcctc gcgtgccttc agccagccgc cgatcacgta cgtctctttc  13980
tcgatagcca tatcaggcct ccttcttgat cacgccttcg cggcgcagga attcaacctg  14040
gtcagggctg acgttgatct tttcgccggc cgccttctcc ttgccctggt gccaatgcac  14100
cttgaccagg gtgacctcga cggccttgtt cagcgcagcc ggcggcgcgg cgtcgaccga  14160
ggccggcacc tggggatcgc tcttcatggg ttacgcctcg atgatggttt tcagatacac  14220
agggattcga atcacggcag cggccactcc atcacccggc gggtacggct caggcgcccc  14280
caacgtcagc ccggtaatac cgcgatctcg ggcagccag cgcaggaatt gccccttggg  14340
ggcaggcatc aggcacgcca gaatatctag ctgcaggtcc tccagagcct ccgcatagtg  14400
gtcatacccg ccacgcaccg cgcctaccac gtcgaagccg cgatgaaagc gaacggcggc  14460
atcaagatgc tccggcggct gctccttgcc cggctggacg acaatcagcg gaaagccctc  14520
atgccgctcc ttgaccagct cgttaaacca cccagagagc acgcgagtgc ccgcgtccgt  14580
ccggtatccc tggtttggcg tgatggtgtg caggcgcgcc aacaaggcca agcggccgat  14640
cgtgagcacg ttcggcttca tgcttcctcc tcgatcgttg ctgccgtcag caaccaaccg  14700
tcgttcgcaa tgagctttc cacgagatag cgcgacgacc cgatgacgaa gaggtcgcca  14760
cgcgatgccg tgggaacgtc cttcgccagc caactgatcc caaccttgtc cgtgatgaaa  14820
accccatcag gcccctcgta ggtgaggttt cggtcgacct gcagcggtat ccccttgatc  14880
gggggggcgac cgatgccgcg gaactcgccc acggcatcag ataaacgctg ttgcccacgt  14940
tcgtggagcc gttggatcag ccggccaaaa cggcccggcg cgctcattgc tggatcagca  15000
tcgccgacgc gaagccgtca acggtgggct cggtgatctt gccgaacgcc actgagtcgg  15060
cagtggcagc agctaccagc cccccatcga gcacgctgca cttggcaccc tgggtcaggc  15120
cagcggcagc cggagccgc cagacgccgc cagtcttccc agcgaaaggt tctccctcgg  15180
cagcgttgac cagcgacacc accaccatgt caccgactac cgccggcaca ccggactgaa  15240
cgccgccagg gggcgcgatg agagtcagga cgttgccgtc ctccacatag ttcttcgcca  15300
tggttgattc tcctaatggc agaaacagaa agccccgcta ggtgcgggc tcgggagttg  15360
gcaccgatca ggcgccgttg gatttctgca ggccgcggaa gtccagcggc gcgacgccag  15420
cgtcgatgcg caccttggtt gctgcaccgt cgacggtgaa gccctgctgc tgctccatgt  15480
agggcagttc gttgccatcg aggtacgcaa cctcgatggt gtccgagccc tggcgagcgg  15540
ccaggtagta ggcagtagcc gagttgtcgt ccagccgcgg ctcgccgatc acctcagcga  15600
```

```
agttgcggat cgggttctca atgccggagt tcgactctgc gccgggcacc gaggccgagc    15660
ggatgatctg cttggcctta tcctccagag ccacaggggt cagcacgaag gccggccgga    15720
tgttgagcgt gcgaggctta ccaccttcca cctcggtctt ctgagtagcc atctgagtct    15780
tagccttgct cagcgactcg atggacagcg cagagcttgc gccggtctgc aggttcttgt    15840
gatcggcatg gaacagagcc ttgccgtccg acagcaccgg gttgctggtc aggatggcgt    15900
agaccagatc gccgatggtt gccttggccg ccatgcccat cttgcgcggg atgtcggtga    15960
gcaggttcat gtcgtcgttg atgatggcct ggcgggtaat gctgaagatc tcgccgtagg    16020
tggccagggc gatcggctgg gagcgactac cgacggtaac gtacttgtac tcggcgcctt    16080
cgcgcacttg gcgcagggac ggaaactcgc cgaggccaac gcggtgcacc gttttgaagt    16140
cggacaacat gcccttcttc gtccacagtt ggaaggtctc ctcggcctcg tcccagccgg    16200
ccaacatgga gcggttggcc acgtcgatca ggatcgtgcc gaagtcgctg gtggtatgag    16260
tgaaagccag gccaaccatt tgcatcggac tgtaggaggc aacaccaata ccacggtcga    16320
ccagcgaagc acgcgccagt tcgcgcaggc tcatgaagtt gtagcggttg tcgctctgct    16380
gttcttccag gccggcacgg gccataacgg aggcgcggac ggagtcacca accagattgc    16440
cgttgccagc gtacacgtgg ctgtttgcgc cctgactgcc ggaagggccg gcgctgggag    16500
tggctccaga ggccagcgag gccaggagct tggcttgagc ctgctcgatg gtgacgctgc    16560
tgtcgagcag cacctcgttg agcatttcgc cgtgggaggc ggcgaacggc tggaacacgg    16620
cgcggatgcc ttcccggcgg gtgttctcgg cggcgttgat ctgggcacgc acggcggctt    16680
catccggtgc ggcgggagcc ggctgcgagg taggtgcggc cggagatggg gtcggagcag    16740
cggcggcagg ggtagacgcg cgcggctgca tcagggcttt cagtgcttcg ggcatgtggg    16800
caaactcctt catgcgtttt gaggtcagtt gagcagcagc ggcgagcggc tcggtaagtt    16860
ggtcggcaaa gccggcctcg acggcctcgc ggccatccat ccaggtctca gccttgagca    16920
aagccttgat gtcttcctcg gacttcccgg tcttcgccat gtaggcggca accatggtgc    16980
cctcgatctt ttccagcagg tcagcgtagc ggcgcatgtc gtccgcctcg cccccctgga    17040
ttccccatgg gcgatgcacc atcatcattg cgttctcggg gatgtggatc acatcgcagg    17100
acatgagaac aacagtggcc atggatgcag ccaagccatc aacgtagcct tcaactctgg    17160
ccggatgatg cttgagcagg ttgtagatcg cagttccctc aaagacatct ccgcccggcg    17220
agtgaacccg caggctgatc agtgacaagt caccaagcgc cttcagctct cgggcaaact    17280
gctgggcggt gatgccccaa gcgccgatct cgtcgtacag cagaatctcg gcaacgcctc    17340
gggaaagcgc cttgatgctg taccagcttt ccgccggctt ggtgtcgttg gtcaatgcgc    17400
acgccatggc ctgtggggcc agcagcggcg cgctactcat cttccgttgg ctgcccatcg    17460
gcgcctcctg tcggtttctc ttcctcggtg aagtcggggc ctgggatctc cagatcggcg    17520
ccgtactggt tgaccaggcg tcgcgcctcg tcgctggtga gtactttccc aaccccccaaa   17580 taggctttct ggatcgcctc gacggcggtc aattgccgat ccttggtcag gctgtgcgct    17640
gcgtccgaac tgaacaccaa gcccaactcg cggttctgcg ctatctcgga ggcgcgggac    17700
ttcttcaact cctgcgggtt gcgtcctctg gctcgagcca cctcggcttc atcgcgaaa     17760 ccacccttga ccaaggtttc ccaggcattg gcctcatgaa ccggattgat ccaggcatc     17820 accggacctt ggtaaacggc cgacaacagg gttctcacat ccacatcggg cggcacccga    17880
agcacgcctg aggcaatcgc taaaggcacc caggtgcggt ataccggacg gcaccagtcg    17940
```

```
tcgatgaagt cgtgttgcag caggtcgtag ccctcttgcg cctcgaccaa ctcctggcgc   18000
tgcgacgaat agttaccgtc gtaggagcgc gcgatggtcg aataagcgct tcgaccagca   18060
gcggcaaccg cgcggagcat gccgttgcgg tatccctcta gcatcgggtt tggtcggttg   18120
ctttcgaaca tctccaggtc ttcacctggc tgcaggtcgt cgaagatcat tcctggcgca   18180
atcgggaatg atccgcgctt gtcggcagga gcctggttta cgccgtagtc ggctgcttcc   18240
cccttcttga tgtagaaggc catcgccgcc gaaatacgcg cggcaatgcg ctcgctctcc   18300
tcgtagtcct tcaggtctgc caaacgaacc agtgcggcat gtagcagcgg tacgccacgg   18360
ttctggccga tgcgcttgcg attggcaacg tgaataactc gctcagcctc cacgcgcttg   18420
gtctgctgga agatcccgct tccaatgtct cctggatgcg ccttgagcaa atggaaggct   18480
cggatgcggc gccaggcatc gcgctcgacc ccctgaatga ttcccttgcc agtgtcgttc   18540
aactcaaagg gcagatagtc cggctccagc agttccagag cgaaggggac ggcggtaagg   18600
tgcttgtagt tcgccaccgg ccccatgact ttctgggcca gagattcacc gtccctcagc   18660
caagttcggc aaaccagccg ctccatctgc ggcctagtca actcacccgc cgtctccggc   18720
ctcaaagacc actcggccca agcgctcttg atctgagcgc aaaactccag atgcacctcg   18780
ccagcctggt ccaacaccag gggctcaacc ccaatgccgc taccgccaac cactcgctcc   18840
tccaggcgt cgaacaaccc agtaacgatg tcgtggttct cgtccagcca ccggcactgc   18900
tctcgcagag accggccggc ggattgcaag gcggcgtcag cagaacgcgt ctctcccttg   18960
gccttgtggg tgcgcgaagg cctcgcagct tcatacgcac ggatcaccgc ctgatggcgc   19020
atgcgttgag cgacaaaacc cggtgccaga ggcgccagca gccgatcaat ccagttcatt   19080
cgaagaccgc cagcttgtag ggacgagact gcccaccggc gaggcgctcc aaagctgcca   19140
ccttgcgctc ccactcctgg cgaccgcgcc gaatctcgcc cagatcgacc atggtcaaga   19200
cgcgactgtt gaacgagacg gttttcccca gaagaacatc ctgctctgct tcgatgtagc   19260
gctgcagaat ctcgcgcgat tgctcaaggt tcatagccat ggactgccac ctgttgtacc   19320
caggaacgcg ttggtcacgt cctgcgcaga ttgattggag gtatgtttct ctaccacttc   19380
ggcgaccgcc ggcctggcaa cgacctggcg ggctgcctcc atctgatcga ggtcgaggcc   19440
gaagcgctgc tggctgatgc gcagcgcggc aagggcgtac acgaagcaat ccaacgcctc   19500
gtttcggcgc ccgccggaat cccagcgcag gacgcgaaca cccttcgcca tcaccggctt   19560
cttcttctcg gcggtgatct gcttcagttc gtcttcgtcg cagatgtcgc tgtcgatcgg   19620
aaagtgcaca cagccgggcg tcggctgcca cggaatgggc acatcaatgc gcaggcggct   19680
gtagatcagc tccttcgcgt tgtcggtgcc cagttcagtc ttgtagacct tgcgcttgcg   19740
acgcttcggg aagttcgcga tgggcttgcc gtaggcgctg gccccgaagg tcgggatcac   19800
ccaatgcacg ccgtgtttga tgctctcggc ctccacctcg tcggcgtagt ggccgccagc   19860
atcccagcac caccgctcga cacgcatcgg cacgccgtct acccgggtga actgccggtg   19920
aatctccagc cccaccttgc gccgcaactc ctcgctggcg ggatcgccgg tcaggatgaa   19980
gcgatgcacc agccaggcct cctcgcccaa tccgaaggcc cagacgcggc cctcgtagcg   20040
gtcgtcctgg gtgtcgatgc cgcccatcag gaccagcgcc tggggtggca ccttcgggta   20100
gttctcgcgg cgagcgtaga gcgtctgcca ctccacacgc tcgccctggt cctcctccca   20160
cacctctccg cgcgtggtgt tgatgaaggc gatcagcttc tcgcggtcgc ctttgacctt   20220
gagccactca tcgccagcg acacccagtc tttccaggtg ctgtagatgg cccagcagta   20280
gaagctgacc gagcgcggcg tgcggatcgg ctcgttgtcc gggccgaacc agtccatgct   20340
```

```
gtcgcgcgtc cagatgccgg tctccgaaca gatccagcgc ccgttctcct gggctgccac   20400
catgtcgcga tggatgaagc aggcattgca gtgctcgcag gagtaccagg cctcctcggc   20460
ctcgcccagc gcgttcttcc gccacttcag accgaatgcg caatccttgc cgccccactt   20520
cagggactgc tcttggtggc aatgcggaca ggcgacgtgg aagtgcagcc ggtagggcga   20580
ctcctcggcc gccttggtga tctggcagct accagccgtc ttgggcgtcg agccgcggat   20640
ggacttcggg tagatcgcac cgtccaagcg cttgtcgccg aggaaggtcg gcgagccctc   20700
cccctcgacg tcagcgtcga acttcgacaa ctcgtcgtag atcacctcgt cgggcgattt   20760
ctcgcggtag ttcctggcgg ccttcccgcc gagaatccag aggttccgcc ggttcgagaa   20820
caccttgttg tccagggtgt tgtcgctgtg cttcttgcca taccagggcg cgagggccag   20880
catcacgtcg acgtcgcgca ccatccccat cacgtgcttc ttgctgatgg actcggcatc   20940
cgggtccgtc gggctccaca tcatgatgtt gcggcgcttg tgctggatct tgtagccgat   21000
gttggccatc agcagcttcg tgtagccgat cctggccgac ttcacgaagt tgaccacccg   21060
gatcaggtcg ttgcccatcg cgttcaggat cgcgacctgg aacggggccg tcttccaatc   21120
gccctcgttg tacgaggact cggccgacat atagaagtta tcgtcggccc attggaccgc   21180
cgtcatcggc aggtctttga acatggcctg caagcccagc ttgaccgcat tgcgcaggtc   21240
attcatccag ggttgcaagg tactcatcga gatatcccgg aaggtcgtcg ccgaagtcgg   21300
ccgagaggtt gcgcgccagg gcgatctccc gctcgaaggc ttccaggatt aagggggtcca  21360 tctctgggtg gcgttggctc acggtcttc cgaccgtctc cagcttcgaa cctatcctgg   21420
cggcgatctt ggccagcgcg taggtggcaa atgggacggg gaccaggagc ttgtcattca   21480
cctggttctt ctgttcctgg gcgtaggttt gagcgcgtgt aagttcgagc gcgcctgca    21540 tcagtttcgc ttcgacgtag ggatcaacac cttccggtag ctcccctca ggttgttgtt    21600 tccgagcggc gtgctggatg cggttttcga ccacatccgc caccgtgtag aaggcctctc   21660
gacctattcg ctcgattggt tgaacgcccc atttatcaaa ggcttgcgga gaaatcccga   21720
ggctcgaggc catctcggac ttgttcaacc atccgcgctg cttggttgtt tcgttttgc    21780 tcatgactaa acaacaacca acctccgaaa aaaggtcata catatttggc gcgcgggct    21840 cgaattaccc tctgaccggg gcaccccgg gaggacccgc gacgcaccac tttggtgcat   21900
tcatcagcgc ctcgcagcga accgagcagc aacgccgcgc atcgccgcct cgaactcacg   21960
cggcaggttc tcgtcggcgt actgctgcgc gatctcgaag aagctcagcc ggcggcgata   22020
cgaagggcgt gacacgaagg ccatgatgat cgagacggca tcccggcctc ggcctgtgcg   22080
ctcagcaata cctataggct ggcccttgcg tgtcatgacg aagtagcggc gagcattacc   22140
cttcgctctg ctccgtctgc tatcggtggc gttcgcgttg tacccggctt ggctgaagcc   22200
gcgaatgccg ctcaatgctc tggtgacctg cccgcgcttg atgttcccgt agcgatcaag   22260
atcagcaccg gcaccaggca ccacgtactt accttcgggc aggatcccct ggccctgag    22320 ctgaagctcg gccggcttgt tccgacgagg cccaccgtag acctcggggg caatccacac   22380
cgatgcaggc tgggcaccgt ccgcttcgtc cttgaaccaa acccgcgctt cgagccggtc   22440
tttcctggct ggcaccatgc gcaggctgtt cagggtgtac ggggtcgggc ggtcgaacac   22500
gacacgcatc tcatcgcgca atcgatccat caggccttgc gcggtccgcg taagcgcagt   22560
ggctgtcgcg taaggaatct gccgctgctc aagctcagtc aggtctgcga gctgctgctg   22620
gaacccttct ggcttgatgc tgatcatctt cggcaatacc tcggcaggcc ggcgatatgc   22680
```

```
ttacgcaacg ccgcgatcat cagttcgcgc cgctcgactc cggctcggag atcagaaaca    22740
acctgtccat cagcggcagc aaggacggct cttcctgcat cagcgctgcc ggtggctccg    22800
ggagcctggt gcactccgcc tgtggggcag cgggctttga cgtacacgac gcgagcacca    22860
gtgccgatag catcgcggcg caattggttt tcttcatggg aagcctgtag tgctgcttgg    22920
tatgtgcggg ccattgcgtc ggtctgagcc tgtgcctggc tatcgcgctg ggcctgctgg    22980
gccatagcgg tgatcgtctc ggcggattgc tcgacggcgg cctgcaggtc atcacgctga    23040
gcggtcacgt gatcgaggcg ccagaacacc agcgcagcta ccagggcgac caccaaccac    23100
ggggaccacc tcatcacgca cccgccagcg ctgcgcgcgc ccattcgaga cgcgccactc    23160
gatcctcagc accgttgtag ccgccgttga tcttcagagt gatccgctcg aatcggcctt    23220
ggtccgccag gtcgtttaaa ccccgcgact tccaccacca ccccgaggcg atggctgccc    23280
aggtccgttg ctccagcaac tccggttgcg ctaccagtgg cagcgccagg gcgcgggcgg    23340
cttcggcgta gttgtcgtgg ccggtgatca tgatcaggcc ccggcccggg tatcgatacc    23400
catcacccgt atccggcgcc ccattgccca tccggtttgc gtagacgcgg ttcgcgatgc    23460
gctcaggctg gcgtgcgtac tgcttcgcct ctgccggcgt gaaccgcttc ggccaagtac    23520
ggagcaacaa ttcggcggag tagttcaggt tctcgatcag gcgattgagg ctctggcttt    23580
cgtgtccgac ctgagcaagg aacatcgcca cacgctcggg cgtgttgatc tcgaaccgcg    23640
ccatggcacc gttgaggtgc tccagccatg tcgttgcagt agcagcaccg cagccggtag    23700
cgcggtcgag ttgatcggcg gagatcttca tcagcccacc ttcctttccg cccagcgcgc    23760
gcccagcttt tgcacggtgc ttaccccgag gacaccaacg aagccggcgg caaaaaactg    23820
ccaggcagga ctccagccaa actccttggc ggtgagaccg acaaccatga ccagcatcgc    23880
gccaagagcg gcttcgatca gttgccgaac tatgctcggc tccttcccct cgtactgggt    23940
acggagccag gtaaggatga aggcgagccc catcgccagc ccttgctcgc gcagcgcgag    24000
cagcaccgtg gcccagaatg acgggtcctt ctctggcatc ttcatagtct cgatatcccc    24060
tcggcgggc gaaaatgaaa accccgcgt gaggcgggt ctgtgagtgg gtgcgggcac    24120
gtcttttcaa gggtctcgca ctctccgcag cgctaagcgc cgtccgcaaa aataaatacc    24180
acttttttgt tgtatcacca caaatttgtt gtataatgaa cccatctaaa cacagagacg    24240
agtgatgaag ttcagcgaat tcagacgatg gttgaaggcc caaggggtga ctttcgaagc    24300
cggcaaagag agccacttca agatcaccgc cccgaacggc aaacagacca ccttcgcgga    24360
ccacggagct aaggaaatgc cagaaccgac ccgcaaggcg atcatcaagc aactggggct    24420
caaatgagcc ccctcgcctg caagcgctga acgatcaccc cggaggagtg accatgtacg    24480
actatgcaat ccgtttcgaa caggacgata gcgctcctgg cgttgccgtt ttctgcagag    24540
acttgccgga gctgaacagc tatggcgacg acaaggtcca cgcaatcggc gaggcagtcg    24600
acgccatcga gtcgaccctc tcgctatacg ttgatcagcg ccgagaaatc cccgcggcca    24660
gccaggcgca accaggcgag cgcgttatcc atctgccggc agttaccgtt gcgaagatcg    24720
cgctctggaa cgaaatggtc cgtcgagata tgcgaaaggc tgacctctgc cggcttctcg    24780
ggatcgcaca gacccagggc gacaggctcg tcgacttcct ccacaacact aagatggagg    24840
ccatggagaa cgctctatcc gccctcggac tccgcctctc agtgaatatc gaggcagcat    24900
gacccagaaa cgaaaagcc cagctcggtg gctgggctat tttctgtggc gttccgctct    24960
gcggcagttc gcctaagcgg caaaaccgca atgtatgtcg aaaggtacag gccgcgatta    25020
tcactgtcaa tacgtccagc ctgtacattt cttcaggcag cctttttctc ctccatcacg    25080
```

```
aagcacgcca gcagagctga caggcccgcg cgaaccagca tgcgagcgtc cgcgtagctg   25140
atccccatcc ggtcctgtat atctcgatac gacatgccat ggatgaagta gaggatcagg   25200
ctgcggatgg catccgggtc ttcgtcgtag aggcgtgcga gaaaccggtc tacttgcagc   25260
gcccgatcat cactgatgca gggggccaca gcagcaaacc gttttcgtt cgccgggttc    25320 cgtttcatca gcgccagcat cggcgaagag ccgcgaggcg tgccattgtc ggaccaaacc   25380
cacagcccgt attgctccat cagaaattcc aacgccttga tgttcatttc agtcgcctct   25440
gaagtgggag ccgccggcgc cccgctggtt gttctcttct cgcgccagac tgctcgcctg   25500
gcgtcgctgc tcttccacca gccgctttac ccacatccgc agttgcacca ccgcatcccg   25560
ctgatcgagc gccagccccg tcaccccgtc aacgaagcca gcggcaccgc acgcgtcgca   25620
atcaatgtcg tagaacactc cccggcgctg accgtggcca ttgcatgcgg ggcacggaac   25680
aaggtgacgc ggtttgttcg taagatccgg accatgcttc ttcatgcggc agccctcttc   25740
gcatccctgg ctttggctcg gtagagggcc ttgatcgcct tgatctcctc aaccgtccac   25800
ttcctggcat cgtgcggccc ctccagtcgc gctacagcct cagcgccgat cttcgccacc   25860
aggttgatcc ggtagttcac gacgtccccc gacttgtggt tgttgcacgg ggcgcattgc   25920
ttgtggacgt tgttctcgtc gaacctcaac tcgggatggg atccgacaga gcggtaatga   25980
ccggcgtgat actgcccatc atgaaagcgt ccacaactga tgcaggggcg gtcccagtcg   26040
cgccagcgga tgaactcgtt gaatgcggcc tgagcctccc tcaagtggtc tgcacggctc   26100
ttcaatttct ctttccgaac cgcgatctcg cgccgctcgc gttgctgaag ggacttgcgc   26160
tccttctcct gcttctgccg agcgatgacg atgccgcact cagggctgca ccacgtctga   26220
aacgacttca ccgggacgaa gcgggcgcgg cacgtcgata ctgcgcactt cttcggccgg   26280
ggcttccgtg ccgacaacgt catgccacct cccgcgcata ggtgatctgg tgatggcgtt   26340
cgcaaacacc gcacgtctcc ttcgcagtcg caaccggggt gcaaatgaat tcaccctgta   26400
cgctggcccg gtagtgagcc tcgccggcca caagaagctt gcaaaccttg tagggcggct   26460
gggtatcgct aaccattaga tagtcgttga gtacgctcca catcatgagc gatctcctcc   26520
tttgagttgt tttcgaagct gttcgagggc agcaattcca acggattggg ttcgcgcctt   26580
ctggtgggtg acctctccct ccggaacctt tccgagcgcc tccccgcgcg ccaacttctt   26640
gatgatctgt cggtaggaga cctccagcgc cgccagccca tcctttctgg ccagagcctg   26700
cagccggctg aatccagcgc cagcggccgc ccaatacact gcagggcaac tccatttcgc   26760
ggctccgacc atggctgggt gggtgttggc cagcgcctcg cgatacgcgt catcgagggt   26820
tggtaggccg aagacctcgg gagcccagca ccaggcgcaa aactggcctg cagacggaac   26880
aagcggcctg gctgcgcgc tcaacgctct taccccggcc tgcagttgct ctcggcgcgt    26940
aacctgttgc cggacgatct ctgccaacca ctcagccttc gcggcactct cgacctcttc   27000
gcttggccag gaacttcgcc atccaggaca gatcgcttg atccgcaaga acaaccggtc    27060
aacctcgcct ctcgtctggg gatcgacctt caccgccggc tgggacaaag ggcgcagacc   27120
cgtgccctga ttcacatgcg ccagcacagc accgaccgat tgcggctcga actgcctgcg   27180
agtcatagct gcacctgctc ggtccaatcg gtcgacggca cggaaccggc tgttgcccac   27240
ttcgtgcggt aagcgccagc cttggccagc agcaacccga actcatggca actgtcgacc   27300
aggaacttgt catccagccc gacgaagaac gccgccaccg caggcgcctc ggcgccgagg   27360
gcggccacca gttgcttcac ctgggaattg acctttgcgt ttcgcaccgg ctgaacactc   27420
```

```
cagcgcgcct cgtaggcagc ccggtacgcc gcccacacac tccggcaagc ctcctgcagc    27480
gcttcgccag ccgccggccc ggaacgggtc ggcaaaggtg acggttcccc tgatggttcc    27540
cttgtaggtt ctattacggt tctgggtgca gcatctgcgg gggtggggtg catttcctgc    27600
gggggttggg gtgcagcatc tgcggggtg ggtgcagatc ctgcggggt gcatttcctg     27660 cgggggtgaa ccttctgcgg gggtgcaaat gctgcggggg ttacggtgaa catcgtcgag    27720 cgccctggc gcgcttcaat gctcagcgcc ctgcactcgt tcagcacctt gatggcctgc    27780
tgcacggcac gttcggacag gcaggtgcgc tcggcgatct tcgccaccga aggccagcac    27840
acgccctcgt cgttcgcgtt gtccgccagg ctgatcagca cagccttctg cgccggcgtc    27900
agaccctgca gcggccagca ggcagacatg atgatcgtgc tcacctgcgc gccctccgcg    27960
acactttctt gcgaatcgct atttcgtgtc gcgacacgct ctcttgttgg atggtggata    28020
cctgtgtcat attcggctcc gttggatgtt cggcaccgcc ttccggtgcc tcctcagaaa    28080
gcccggttgc agccgggctt tttgctgtct gctctactgg atgcctgaac aggggtcgta    28140
gggatctgac cagcgccagc acaagccagt agcattcgaa tctctgctaa gcggcctgga    28200
cgccagttcg cggcgaagcc ctgagctcag cgggagagag atcgaaaccc ttccctctag    28260
ccaacccaca gatccgctcc gcgtaatccg tttcgccggt gtagtcagtt cgcggaaggc    28320
ggccgcttgc cagccacttg taaacggctc gaggacttac ctcgcagctc gcagccacct    28380
gacttacgcc gccggctttc tcgacggctt gcttgagttc gcgcatgcgg cctccggcca    28440
atatgaacat taggtacata ttaggcagga actgaaagta catgcaagga cgtgagaaag    28500
tgaacgaatg gttcaagaca tgcagacaat ccgcgcagcg ttcatcgccc gcctgaagga    28560
ggccgcatct gatgcaggct ttcaggagtg ggggcttggc gctcgactgg caaaaatcac    28620
aaagcgcacg ccaaaagctg tcagcaaatg gatgaatttg gagagcatgc ccgagcgcga    28680
tgccatgctg tcgatcgccg atgcgttcgg cgtgcgcgtc gactggcttg agcatggcca    28740
gggtgataag aacagccgat atatgacgtc caatcggaca gaagaagcgg tgcgcaacct    28800
ggttgcgggg cgggctggcg attatggcaa cgtgcaaccc acagctcagc cctcaaggaa    28860
gaagaagggg tatccattga tcagttgggt agctgctggc gcctgggcgg aaagccatga    28920
caacttccaa cccggcgatg ccgaggagtg gattgagtcc gaagcaaagg ccggcgagaa    28980
cggatactgg ctggaagtcc atggcgactc gatgctgccc tcgttcccgg aaggaacgag    29040
gattctcgtc cagccggagg gtttcgatct ggtgagcggc aagttctatg tcgctctact    29100
gtatgagcca ggcaagcaac gcgagaccac cttcaagcag tacgtgcggg acgcaggtcg    29160
cgagtacctg atgccgttga caaggactac caagcccta caagtgaccg agaatgttcg    29220
agtaatcgga cgggtcatcg atctgaagcc tccaaagtct ctcctctgat cccctccccc    29280
aagcccgcct agcgcgggct ttttcgtgcc tatcaaaaaa atatgtactt ttggttcttg    29340
accttaagtg aaccaatggt acatatttga ttcacggcag cgatgccgag gccaccgagc    29400
cgaccgctct ttaacaactc acgcaaaagg ccgctggcca agccaagcat tgacgtaccc    29460
ggcgtgggcg aatcccacct gagtacgccg tattgcctaa gccaccagcg gctgaaccag    29520
aaaacgtatg gaaagaaatc atcgcccaag cacaggtggc gggtaacggt gctcaagact    29580
gcggcgcgcg gcatgccggc gacacggtca accctgacag caatgacgaa agaccgcgg    29640 gttgtagaag cccagcaggc gaacgcggga gaaacaccga tttcactggc tggccctcca    29700
ccgagggcca gacgggaagt caacacgccc tggagggcaa gacgatgaac accaagctga    29760
acgccaccaa gaccaaaaag gtgaaagcgg tagtcgctca gaccggagtc accgaagcgg    29820
```

-continued

```
aagccgttga ggcactggaa gctgaggagt ggctggagtc agaagccgtg ttcaacatcc    29880
gcgccgagtt caacgccaac atgcgcgaac ggggcttgct gtgatggccc gatctacccc    29940
tgaacaggcc cgcaacaagc tgggcctagt ggccgcaaag aagctggaaa ccgcagccga    30000
agcactgcac gcctaccgca tggcctgtct caactgcgac gaccacgcag cccagcatga    30060
ccgccgcaag tcgctggtag gcgagcttca ggagatggcg gcgtggcttg aaggctgctg    30120
caagtagccg ccccggcgaa ccggggcatc accgaggaaa ggacatgaac agcaagcaac    30180
gccgacaagc ctaccgcgcc atgcccaaga ccggcgccgt cgtccgctgg aagtcggcca    30240
tcactggcaa ggtgcgcgaa ggcgtgatgg tcgggccgtc cgatatctac acgaacgaac    30300
acccgaacgc cttcgaaagc aggccgacac cgagccccca ccgcgtggcc gtcaggatgg    30360
ccggcggcag caagtgccac atcctggttc gccaactgat ccgctgaaca ccgccgccct    30420
gccagtagca gggtaccacc cgcgcctgcc gggttcccca acgcaggccc gatccacctg    30480
gctccccatc gccaggctgt atcggagagt ggtctggccg cacagcgcta ggggtatagc    30540
gtgtgctgcg ggtactacct gattcagttc agagtcactc cgccagatga cccaatccag    30600
ccggacagag actcagcacc ggccagacca ctcccccata cagccaccac gcaatcacaa    30660
cagacggagg cctcatggcg gccaaatcgt tcaagcaaat ggtttcaacg aaggagatcc    30720
ggcgcgccga tgcatacaag gtccgcctcg aagacctcca cgaagagcca ggtctcaact    30780
ggcggcgtta caccgatgcg ttccacaagt ctgttgagga gctcgcggaa ctcatcgccg    30840
gcgggatgga ggtagatccc ctcgaggtgc gccctcgcga gagggaggc gtctggatcg     30900
ttacaggtca tcgccgtaca agagcttggc gcctgctcga tctctctggg cgcctccagc    30960
gtgatccgaa gaccggcgag ttcctcgtca gcgtagttcc ttcgaaggca aggaccggc     31020
gccagcgcct ggcgcgcgta agcaccagcc aggaccagtt cgagctcacc cctctcgact    31080
atgccgaagg ctgtcgccga atgcatgaag aggaaggcat gacacccgcg gagatcgcag    31140
cggaaatcaa aaagacgcgc cagcgagtcg agcagttctt gaagctcgcg acagcgagcg    31200
aggggggtgaa ggctctcatc gacgcggga aagtatcggc gtcgacggtg accagattgg    31260
tccgcaagca cggcccagat gttgagggga tcattttgga gaaactggag gcggcgaagg    31320
cgcgcggcaa gaagaaggtg actccggcgg ccatggctga cgctccggct tcggaagctg    31380
cggccgtacc gcatagctcc gctctggcag cgccagcctc tgctccagct caagctcaag    31440
gcccacacga cgaactgatg aaggtagttc gcgagatcgt ccgatccttc cctacagagg    31500
ttcgcgcagg tctcgccgag ggcgccgaag cgatcactct caccttccgg gcgtcgcaga    31560
tcgagcggtt gaccgagatc ctcgcccagg tagacgaagc ctagaggaaa cccatgttca    31620
tccttccatt cctcatcggc ctggtgctcc acgaccagcg gccgaaccg ctgcgcgcgc     31680
tcgatagcac cagcgccgat cttgacctgg gcgcctcggc tccagcaggc cgagaacgat    31740
gtacccgcgg ggcgtccgga gttcgggctc caggcgtccc gcccaaaatg cttcaaacca    31800
taaggcggtt tgtaagtaga ggcggggcgg tgggcgcccc gcttcacccc tctctcgact    31860
tcatgcgcga gcactccacg caatgccgag tgctgaccca tgcagccaag gaatcaacca    31920
tgcacgcaac catcaactgc ggcggatgga tcggccgcca gggcctcggc ctggctcccc    31980
gcgaactcga agctaccgcc tggagcgcca gcgaacttac cgcgaaagag gtcgcgcgca    32040
ggatgggcat agccccagga accgtcgaga agcgcctcga cgacgccaaa ttcaagctcg    32100
gcgtgcgcag cgtgcgcgga ttggtgcttg aggcgttccg tcgcggaatc atctcgccgg    32160
```

```
cagtcttcgt gctcgcattc ctcgtcgctg gccacccgct gatcgatgac gaccacatga   32220
acaggacccg caggccgagc aacgagcgac gactcaccga agcccgcacc attcgccgga   32280
tcgaagaaat caccatcaac gcgtaggaga accatcatgc tcaagcacca ggaacaaacc   32340
gaagttctca ccggcctgct ctcccagacc gccctcgccc gctggcgtt cgctcagcgg    32400 atcatggctc ctgcggtggc ggaaccctac caggtcgtgc ctcaggggcg cggtttcttc   32460
cacatcgtcg aaacggccac tggcgcggtg cgcggattcc gccggagcca caacgaggca   32520
tgcgcatacg cagagcactt gaagcgcgag caggccgcca agtgaccaga cgtcgagcaa   32580
ttcgaaccgg cggcatcggt gcggccctgg gcttcatcgt gcttgtgttc gtgctccccg   32640
cggctgttcg gcaacagcca cccaggacgc cgccgtccgc cgtcgcgcca gcagttcaag   32700
aggcgaagcc tcgaacggtc tcctaccgct ccagcgccag ccgccaacag tcttttgtct   32760
tctgaggtcc acatggcaaa gaccaacgcc cagcgccagc gggagaagcg ccagcgccag   32820
cgagaggcag gcatccccga gcgcaagctt ccatccccgc cggcgatcga cgctgcgttc   32880
gagcgcctgc aggcggccgg cgatttcgag gactggcgag aagcgttctc gacgctgcta   32940
ctcaacgcct cagccctgcc cgatgccgat ctcctgcctc ttctcgtcgt gtcgcgacac   33000
gaatacacgc aagcgaaaa cgtgtcgcga caactactag ccgccggact ctccgtagcc    33060
gacgacgaac agtaactcac caccagatca ccgacgctag ccgcaggcca gcgcgatcct   33120
acacgccctg gagaaactat ggccgagcac aacatcacca gcttgtccgg aggaaaggac   33180
agcctggcaa ccgccttgct catgaaagaa cgagaggtag agaacggcat gctggtgttc   33240
gcagacaccg gcaacgagca cgacctcacc tatgaatatc tcgattatct ggagcaggtc   33300
ctgcccttcc cgctccggcg agttcgcgct gactttaccg aagcgatcgc cgctcgccgc   33360
cagatgatgc tgaacgtgat agctggcacc cacaaggaga gggccaacgc ggcatatcac   33420
tggacgccag agactgcgga acgggccctg tccgtattgc accccaccgg catcccctt    33480 ctcgacatgt gccttgtcca tggccggttc ccctcaacca aagtcaagtt ctgcaccatc   33540
gaactcaaga ttcagccaat ggagcaacag gtgcaaaacc cgctgctggc tgaaggccac   33600
gacattgttt cgtggcaagg agttagggct gacgagtctc cggcgcgcgc gaatctggtg   33660
gaacaggaat ggatgctcac ccatccggac agtggcgccg agctgtggca ctaccgcccc   33720
atccacaaat ggaccgcaga gcaagtgttc gccattgcaa agcgccatgg ggtcaagcca   33780 aacccctct acctcatggg catggggcga gtcgggtgca tgccgtgcat caacgccggc    33840
aaggacgaaa tcctagagat cagccgccgc tttccgcagg tgatcgacca gaaggaagca   33900
tgggaggcca acgtttcaat ggccagtaaa acctgtgcag ccacgttttt cccagcacgc   33960
gaccttggcg cagggaatgc ctctgcgatt gatccagcaa agcacggcat tcgcggtcgg   34020
gtcgagtggt cgatgaccctc ccgcggcggg cggcagtacg acatcacccg cgtgatgcct   34080
gctgaacctg caaccgcctg ctcgtccgta tacggactct gcgaatgagg aactgaaggt   34140
atgaagcacc gcgtctactt gtccggcccc atgaccggca tcgcagattt caactacccc   34200
gcgttctacg ccgaggagaa gcggatccgc gccctcggct atatcgtcga gaacccagcg   34260
gtcaacatgg tctaccgcgg ggcgacgtgg gagacattca tgcgcgacgg gatcaagcgg   34320
ctgatggact gcgacatcct ggccctgctt ccagggtggg agcggtcccg cggcgcgaac   34380
atcgagcgca acctgcaat aacactcggc atgcacgtcg tcgacgccga ggccatcccg    34440
gagcctgatt tcgtctgcaa gtgccgggca atccaattca cctgctgctc gataccaagc   34500
gacaacgatc cgttcgtgtg ccggcgcctg gcaggcatgc ccgcctacaa gtccccagag   34560
```

```
gaccaactgg caaccgcacg taaagccctc gagcagatcg cagcgctcac cgacgtctct    34620
accggaggca tcgggatgga cgtgctcaag atcgccaagc aagcccttc caactgatca    34680
gcgccagcaa gcgagaggta ttccctatgc ccgcagaaaa gccgcgggag cggccaatcc    34740
tgttcaagga ccagatggtc cgcgccatcc tggaaggtag gaagacggtc acgcggcgag    34800
tgatgaagcc gcaacccatg cccagcaaaa gcggcggcca ccattggccg tgcaaggtcc    34860
accagtcgat gcttcatgtt gagcgagagc ttcagaatgg cgagggctgt tggtgtggtc    34920
tggcagaggc tgcctgccct tacggccagc caggcgaccg gctgtgggtg cgggaagcat    34980
ggcaagggcc gctgatttcc gatgaggaac aggccgccaa ccagtcatgg tggaaggaca    35040
tgacgaagtt ccaaaaccca gggcactgcg cctatcgcgc cagcggcgac gacaacgaat    35100
acgtcgatcc cgacggctac ttccactgca aatggaagcc aagtatccac atgccccgct    35160
gggcctcccg catcctgctg gagatcaccg ccgttcgcgt agagcgcctg caggacatca    35220
gcgaggagca ggcacgggcc gagggatatc ccgccgagcg cgaatgcgaa accgcggta    35280
gtggcttgga tgcctggctc tggttccgct cccttttgggg agagatcaac ggtccagagg    35340
ctttcaccgc caatccctgg gtctgggtca tcgaattcaa gcgggtgaca ccatgagcgc    35400
catcatcagc gaatgcggcc agtaccgtta ccttctgact cgccctggcg actgcctggc    35460
cgacaaaggc acagcggttt tcctaatgct caatccgagc accgctgatg ccgcgctcga    35520
cgatccaacg atccggcgct gccgcaactt cgcctcggcc tggggctgca acgggatcgc    35580
cgtcgtcaat ctgtacgcct tgcgcgcgac gaacccggcc gacctctggc agcacaacga    35640
cccagtaggc ccagacaacg actggcgcct gcgcgcgatc gcccgagagt acaccgacat    35700
cgtgtgcgcc tggggcgcca atgcgaagcc cgagcgagta gaagccgtaa ccagcatctt    35760
gaccgccgcc ggcgggcgcc tctggtgtct tggcacgacg aaggatggcc acccgcgcca    35820
ccctctgtac gtgcctggaa atcaagcgct ccagccttgg gcgccagggg taacgccatg    35880
accagatcca atgccgcct gtgcagcagc gaggccgaac tctgcgcggc gttcatcgac    35940
gagttcaacc gagtccccgg ctggacctgc taccccgaga ctgccgggtt cgacatcctg    36000
gtggtccatg aggatggccg gcagatcggc gtagaggcca aattgcagtt gaacgccaag    36060
gtagccgacc agatcctgcc gcagtactgg caagaccggt acggtgcgcc agggccagat    36120
caccgcctgg tcattgtcgg gcggatcacc gaggccagcg ccggcatcaa gcgtctgctt    36180
gaaatgtgcg gcatcgcagt gctcgcgccg tcccgcggtc accgtcggcg cgacggcaag    36240
ttcgtcgact cccccgagtt ccacttgcgc tactggctcc agcacttgag cgggccgcaa    36300
ctgttcgact ggaaccccgc tgaacgctgc cacgtcccga tcgtggtccc cgacgtgccc    36360
gccggcgttc cggcgccgct gcgcctcacc gagtggaagg aaggcgcgct gaaggtgatc    36420
gccacgcttc gccgccaggg cttcatcaca acgaagcaga tcgccgaatg cggcgtcagc    36480
gcgacgaact ggacacgatc ctggctcgac aagggcgccg agcgcggcac ctgggttgag    36540
tctgcccgca tgccagcgtt cgaccagcag caccccgagg ccttcaccaa gatccagcag    36600
gcgctggaca agagcgccca gcccaccctc ttcacctgag caccgcaatg aaccgcccca    36660
tctactgccg cacaacaggc cagcgcatcg ggcaatgcaa ctgcatccgg tgccggcctc    36720
ccgaggaaac gccatgcaca ccctcaacct gaccgcgctg ttcctggacg gcgaggatgg    36780
ccagcgcctg gccgaggtca acggcctccc acgcctcggc gccctgctct cctcatctca    36840
actgcgccag ctcgcgcgcc agctcaacga gatcgcaaac gacgcagacc agggcgccag    36900
```

```
cggtgagcac tgctacacgg caccaccttta cggagcctgc ccatcatgcc tttcgacgaa   36960
agccccgcag tccgccgcat aaacgccctc tgctctcccg cgccagcacg ctacctgcac   37020
attcccaccg gcattcactg ggtcgtcatc gacagcctgg gaaatgtcct gcaactcgag   37080
aacatcgagc gccggcgccg actgataacc gtttctgacc tcgaaaccga ggcctggaga   37140
aagctcccat gaccgaatca aagatttgca cctgcccttc cggcgacggc tccctcgtcc   37200
atccgtgcca ggcacatcct gcagagcagg cagaggcgga gcggccggag gttgtggcgt   37260
acttcgaccg aaactatcca agcaccggcg atgccttcat ctggtcgaac tatgagggaa   37320
gcccatacga gccagtgatg accgtcgccc agcacgaccg catcgtcggg gcgctgcggg   37380
ctaaggctga tcaacttcgc gaagcactcg aatggcgcaa ggagaatcag gcaggtcagc   37440
gcgaactact gcgttcagtg acagcagagc gcgacgccgc cctggccagg gtagctgaat   37500
tcgaagccca gtctcagcac agcgcgggct atgccgaagc tcgccagtgc gtgaactgcc   37560
ggcacatcgg tatcaacgat gccgccgact acgccgcttg ccacgattgc cgatggactg   37620
gaccggaacc cgatgaggac aagtgcccag gttgcgcggg cgagaactgc atggcggcag   37680
cttgcccaga gtgtgggggc cgttacgagc tggtcgctga ggcgaacatc gccaccccag   37740
tcgcccaggg tgggcaggtg ccgcaggcat ggctcgacgt gcaggcagag cgccgccggc   37800
agatcaccgc cgagggatgg acgccggagc acgacgacga gcacgacagc ggcgagttgg   37860
cggcagcagg cgcggcatat gcactgcatg ccgccgatca cttgaaccca tacagtcagg   37920
gcgatggtgg agatgaggca cccagttgtt ggccatggca tgacggaatt gcagggcgtg   37980
gagaaggccc ggagaaaacc gagccggcat ggtggaagcc gagcaccccg cgccgcgatt   38040
tggtcaaggc ctgcgccctg gcgctggccg agatcgagcg cctggaccga gcagcgcccg   38100
gcaaggaggt aggtcatgag taactgctcg cacgaagctt gggatttcgg cgcgctgcaa   38160
tgcccggact gcggcgctgt gaagggtcac gtcgcggatg ccgactacgc caagctcgaa   38220
gccgaggcta aggcgctaag ggaggaagtc gatcagcaga agttcctgat caaagtcgag   38280
aacgacgcgc tgcagatgat gacggccaag gccaatgagc ttaagtctga agtcgagcaa   38340
ctggaggaag agctggaagc cctgcgcgca cgggtggctg ttgtgccgga tgcgagcacg   38400
gtgtatgcgg cgctcgatgc tcgtgagcgg ttattcacaa gtcctgagaa cattcaggta   38460
gcgctggaag ctcaatcgcg cctcaacggc ctgacggtca gcgaggggct ggtgcagggg   38520
atggccaagt tcgcgcgcga gatcatctgc ggagccctcg atggcggaag cttcgatggg   38580
gcagacatac aggaaagcgc tgaacgccat ggactgatcg ccaagcaggt gatgaacgag   38640
ccgtgccgcg gcccagaaga gtactgcgcc tgcgcctggt ctacctcgtt cccggctgaa   38700
tgctaccggg taactccgaa gcttcgcgcc ctactcaacg aggacaagga gaacagcaat   38760
ggctgaagaa ctaaagccgt gcccgttctg cggatgctcg atgcgcctag agagcaaccg   38820
cgactggcat aggatcgtag gcgatcacgc tttagagtgc gccttcacgg acagcgaaac   38880
aatggtggtg ccgcaacaa aagagcagcg tgatattgct gtctccgact ggaacgcccg   38940
agccgtaccc gcagggcatg tggtggtaag cgaggggctg ttgcggcgtg tctgcgcgga   39000
acagccagcc acgtgctgta tggacgacga gatgagttgg cggcgggatc gcgactcggc   39060
gttgatcgaa ctccacgccc tgctgagcga gcaggaggga gggaagcaat gagagaggta   39120
actgaactgg atttttcgccg gccggagttt cgtgacgcca aggtcgaaga ttacgagttc   39180
cgccaggacg gcgcgctagt acgaaaggat cggtgggagc gcggggttcg cgcgatcgtc   39240
gctgcactag gctggtctcg aagggatttc gaagtggaag atgttgtgtc cgaggttgag   39300
```

-continued

| | |
|---|---|
| cggcatgtcg gagggtggat ggatgcagat cctgaagatt ttaccgatat gcttctacaa | 39360 |
| cccgttgata tcaagatgcc gtgcggctct gtattagctg agtgcgatgc aattgacgga | 39420 |
| tgccttgtct ggaaattcag cggggcaacg ttcacccagg aagatatagg gcaagcggtt | 39480 |
| cagaagtggc gacgcacgaa gatccatcag gacgttgcgt agccaccat cgacaaccac | 39540 |
| tgtacgcata tacagcaatt cggataatgg gctacccact acccggattg aatatgcgca | 39600 |
| cgaaaacctt ccgcccgccg cgccggcatg agatcgccgg cctccgctac taccgcaccg | 39660 |
| cgtcggctta caactggctc ggcgtagcga tggcacatcc gactcgcgca atccagttgc | 39720 |
| tgctcgaaca gtgtgagcca gacgtgcttt cgccgatgtt cgagattgag atcgacgcga | 39780 |
| tcctgcgtca ggccgatgag tacgcaaaga ccggccaggt gctcgagcgc gagcaactgc | 39840 |
| gcgaaatgct catgcacctg atctcgaagg ccgcgggcga ctgatccgga accaccatga | 39900 |
| agaaagccct ttcccgactg gcggcagtag ccgtcattgg cgccagcctg gtcgcgctac | 39960 |
| acgcagtgat cgagctagcg ccagcattcg cagccctgca atggggctgc tcgttc | 40016 |

<210> SEQ ID NO 6
<211> LENGTH: 50084
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (11033)..(11350)
<223> OTHER INFORMATION: n is a, c, g, or t

<400> SEQUENCE: 6

| | |
|---|---|
| tttctgcttg ttgcggcgag cgatgatcag ttgcttggat gccgtggcaa ctcccttac | 60 |
| acgtctccag agtagcgctc atgcagtgtg ggcaaagcag agccatcttc gtgctgcgcc | 120 |
| cacgcttcgt cgatcacctt ggctgcccgg ctgcggaatt gcaaactgct ctgcctcatg | 180 |
| aagctcacag cgagcgcctg ttcaagtcct tcaaaccgcc gtcgaatacc tgtaccaggt | 240 |
| gcatgaaggc atcgaacggc tcgacctccg tttcacaatc gctgcaccag atgcggcgct | 300 |
| ccttttcgtc gtagaccatt ttcctgtgac ggcatgaaga aaccgggcgc ctggtcaatc | 360 |
| ctcgggcaac tcgaagatcc tcgatctgga cgacctttac gccgtagagg tattcatggg | 420 |
| gttcaattgg tgcgtcgctc actccccacc tccttccttc ctgtgtagtg gtctactgat | 480 |
| cccggacacc gatttaggcg agaatcctcg ccgtgagaga ggtgtctgat gagcaagcaa | 540 |
| cgacgtacgt tttccgccga gttcaaacga gaggccgcgg ccctggtgtt ggaccaaggc | 600 |
| tacagccata tcgacgcctg ccgttcgctg ggggtggtgg attcggcctt gcgccgttgg | 660 |
| gtgaagcagc tcgaggcgga gcgccagggt gtgaccccga agagcaaggc gttgacgcct | 720 |
| gagcagcaaa agatccagga gctggaagcc cggatcaacc gattggagcg ggagaaagcg | 780 |
| atattaaaaa aggctaccgc tctcttgatg tcggacgaac tcgatcgtac gcgctgatag | 840 |
| accagttgag tgagcaggag tcggtggaag tggtctgttc agctttcgat gtggcgcggt | 900 |
| cttgctacta cgtccaccgt cttcgacggc ggcgtgtcga tgctcgccgc gtggcgctac | 960 |
| gcagccaagt caaccagttg ttcagccaga gtcgggctc ggccggcagc cgcagcattc | 1020 |
| tgggcatgct gcgcgaagag ggcgtgacca tcggccgttt ccgagtgcgt cggttgatgc | 1080 |
| gtgagctggg cctggtcagc aagcaaccgg gctcgcacgc ctacaaacag gccacggttg | 1140 |
| agcggccgga tatcccgaat cggctgaacc gcgaattcgc gaccgagcat cccaatcagg | 1200 |

```
tgtggtgtgg cgacatcacc tacgtctggg cgcaaggccg ttggcactac ctggccgcgg    1260
tgctggatct gcatacccgg cgggtgatcg gctgggcgtt ctcggccaag ccggatgccg    1320
aactggtgat caaggccctg acatggcct  acgaacagcg cggcaggcca cagcaggtgc    1380
tgttccattc agaccagggc agccagtacg ccagccgcct gtttcggcaa cggctctggc    1440
gctatcggat gcagcagagc atgagtcgcc gagggaattg ctgggataac tcgccgatgg    1500
agcgcctgtt ccgcagtctg aagtcggagt gggtcccgtc aacgggttac ctgacgcgc     1560
aggaggccca acgggacatc agtcattact tgatgcaccg ctacaactgg atcaggccgc    1620
atcaattcaa cgacgggtta ccacctgcgg tggccgaaga aaaactcaac ccactgtccg    1680
ggatgggttg accactacac tggcctttag catggcgtcg gcgtatcgat aagcaaccct    1740
cggtatgtca gcaagaggat tgctatgggg cttgcttacg cttgactcta tgtacgtcgg    1800
atgaagcaag gcctgcatcg ccttggccgc gaagtagtcg cgcagggtca ttcccgcttc    1860
ggacgtgtac atcgattccg agggaaacgc ttgtccgccg ttgtctttca tcactcccca    1920
cctcccatag actttccgat ctcggctgcg gcgcgagtga ttgctcgccg agttgccgca    1980
tacggatttt ccgtgaacac ttcctgacta gggttcatcc cgtcaccatt tgatggctcg    2040
gcggctactt cctgaaagcc gttgtagaac gttatgtcca ggcgaagctt cacagccagc    2100
ctcagcgcgt cgccgtcgtc ggtgagcggg ccccactgtc gccaccgccc agtctctgcc    2160
aggattaccg gtaccgccgg gctggagagg gaccggtacg agtatgaaaa ctgatacccc    2220
gccgcccgcg ccgccagttc gagtagcgtg cggtcgttca ttgcgttgct cctttgaggg    2280
ctgcgtcgat ttcagcgtct aggtcttcct ggttgagtac gatgttctcc ggggtcatcc    2340
cggcgaatac gccgccttgt ctgatcgttt cgaggtctcg ctctcgcagc caccggtagc    2400
gcgcggcgtc cttcgccatg cgccgaatct gctctggaat gctgacattg ccgccgtctg    2460
gagggtccat gtagtaagta ccgggcagaa cgcttgcgca ctccttcaag tcctgcgcca    2520
accactcgca gtgtttctgc gtgtccttgt gggcgcagtt ctccgccttg agccggtcga    2580
tctcgtccag cagggcgagg atggtcttgg ggttggcgga tgcgatgtat ttcaaattct    2640
ctgcgggcgc tactatgtca ggccagccat catgcgggtg cgtgcatgga cgaagtacat    2700
ctccatcacc gctgtcggtt ccgatgcggc gccaactgca cccggtttga acacgccacg    2760
gtccaggcgt tgccgcctta gccagcctcc gcagctctgc gtggtcggtc atgtcttttc    2820
tccccatttc acttcgagcc acaggtcaac gaactggcgt tcttcggctc gcacagcgca    2880
gacgtaaccg agtccgcgca gttccttcag gatcgcgatg cagagcttcg ggtaatcgca    2940
ttcgttgcag taggtgctgg tgccgaaccc atagtcacgg gtggtgtaca cgtacttgcc    3000
ttcggcggct gcttttgcga tgcctgcaag gatggtatct acggcgaacg cagggtcttg    3060
ttcgcgagct atatcacgcg cttgctcagc ggtcagtcgg ctcatggttg ctcctagata    3120
gcggttgcgg aacaggctgg ccgtcctcgc cctcgagttc gttggccagc cactcttcga    3180
agctggcttc atactgagac tgggagggtt gcgccagggc ggcgcgggct ttccaccct    3240
cccatgcatc attggtgaac ttggcgtccc agttcacagc gatatgctcc ggcatgccgc    3300
agtgcttgcg aacgaagaat tcgaaaaccg cgcgctcatc cacgcctgcc tgctctaccg    3360
atgccggtga gtcacgaagc gctgtgccgg ccaggccctg gcatcttgc  gtcggcgcct    3420
ggtcattgat cagggcaagc aggctctcgg ctgaggagtg cacctcgtcg aggtccgtcg    3480
accagcggtc cgggctggtg tcgtggatgt tgtccaaggc ttcgacgatg ccgcgcaggc    3540
gcgtagcgca ctgcttgatc agttggtgtt gggtagagga catggcggtg tctcctgttg    3600
```

```
ctccggcgcc ggcggccggc agcggaagca tttgcacagg cctatccgtt ggcccgtggt    3660
gcggcagatg gtggggcggt tcatttcgtg gcgtcttgct tcatggcttt ggcgtggccg    3720
acgcaggtgc ggaccgggtt tccctggtcg tccaggtcgg cgtggcagta gaaccggctg    3780
agttcctgcc ggcagtggat ggcatcggag gtggtgaccg gcgaggtgtt cgccggggtg    3840
ccgaggcgat aggcacagcc ggcgcacgtg ccgcgtgggt ccacagtggc ggccaggaca    3900
acgccttgca gcgctccgaa catcgtcggc aggttcgcct gctccgcggt gtgcgggtgt    3960
tcgccgcgct cgatgaggat caactccacc atcgcacggc agttctcggc gacggcgttg    4020
gccatgccca gcacctgggc gaacaggtcg agcatggcgg ccaggttgcg ctgggcggcc    4080
attttctcca cacctggccg gcgcaggtcc gccggcagaa gaacggcgcc ggccagttcg    4140
tgcgcgtcag cggcactgat ctggtagtcg atagggggct cagccatagt tcctcctggg    4200
gtttattcgt agggaccggt catggttgag ctgtcggaac tcggtacaga tgacgatcac    4260
gtcgggaccg tcacgcggt ggaccggcat cgtgctgaag tcgaagctcg aacagtcgtc    4320
caggcgtcgc tcgcaggcgc ggcagcgccc gcccttgggg tagtagttgg gcatggttgg    4380
ctcaggtgaa gagggtgggc tgggcgctct tgtccagcgc ctgctggatc ttggtgaagg    4440
cctcggggtg ctgctggtcg aacgctggca tgcgggcaga ctcaacccac gtgccgcgct    4500
cggcgccctt gtcgagccag gatcgcgtcc agttcgtggc gctgacgccg cattcggcga    4560
tctgcctcat tgtgatgaag ccctggcggc gtagcgtggc gatcaccttc agcgcgcctt    4620
ccttccattg ggtgagccgc agcggagccg gaacgccggc aggcacgtcg gggaccacga    4680
tcgggacatg gcagcgttcc gcggggttcc agtcgaacag ttgcggtcca ctggagtgct    4740
ggagccagta acgcaccaac gcttaggagt gtgaagctgg cggcttttgg gtaggaacgg    4800
gatggactcg attgagccgc cgagcgcgta cttcacatta caggggaaaa gtttccatat    4860
aataaagaat acgggagttg cggctcttcc tatagtgatg cttcctcttt gttcttttcg    4920
aagctaaata tggatctgaa gcgacttaga ataaaatcgc tcattatttc gtgaagatca    4980
atcgtctttt tgtttacgag cattattttt cgtcttcgtt gcatctggtc gacatcgtta    5040
gtttgttctg aatctaacgt ggccagatcc ctaagctccg ctattagagt aatagccttt    5100
gtttcgaaag tatcaaagtt cccgtcccac ataatacggt tgctgcactt tattcttaag    5160
gcctttatgc gtagttctat aaaattgcac ctgaatgtaa tgtaggattg aaagagttgg    5220
catttcattg tgtgctcttg gtcggaagag tctgcatcgc gccaaaattt gtaattctcg    5280
tccgaaattt cttgcagcat tttgtctacg gtcgcgacaa tagcattagc tcagccttgc    5340
ttcgctaagg ctctagaatt taaataagtg aatgcccagc ccgccatggc taaccaaaat    5400
ggtaatgaca tagtcgtctc cattagctcg ctggtttagc atcttcaata tattttctta    5460
tggttctcac tatgctgtca tatctgtaaa ttatttcgac cctttctagt acttcttctg    5520
gcttaaaacc ttcatatgct accaggccac caaaggcttc atctgtgaag gatgatccgc    5580
agcctaatgt accatttaag tcaacctta ccttctggta ttcgctgagt ttctcaacca    5640
gaagttttct aaatgcgaat ccgttaaatt ttccatcttt ttcgttcctg ccgtaaggca    5700
tgtcagaaaa acttttggca acatcaattg tgatttcgct tttcataaat tatcctagcc    5760
ggatattcca ctgtatgaat gtgcccggca ttctgtctgg cagaggttct atgctgtcta    5820
tgttaggtgt catagcgttg aattcgtaag agccaagccc actatatatt agcatttgtc    5880
cttcagggtt cgcggtgaca aagtcctgcg cttcggccag tccttttcct ctgcctcccg    5940
```

```
tcttaaacct cgaattacca tactcaaccg ctgctctaat tgctaagctg tcgttagagc    6000
tggggaagcc aagtgaaccc aatagatgat caattatatc gctgtaccaa ggttttttg     6060 aaagtgttgc tggtatgccg actcctgagt cgtacactgc aatgaataat tggttttcaa    6120
ttttctcgac aactatccac caattttttt catcatctgg cagaggtttt ggatagaaat    6180
cgtcatcata tgcgtgttgc cagacgttac taaaagactc agttattgct gcaaatgcct    6240 ttacccctc ttcttcattc attcccgagg ttttgattgc ctcttgaaca tacgttattg     6300
cgcgcctgag ttgagaggtg tcgccactct gttggtcttt gtaggaggtt gagcaaacct    6360
caaatcccat ggagagattt tttcgaatat gcttgctttc tttcgtaagt ctccagaggc    6420
cgatgcgttg tagtccattt gcgacgccgg agtgcctgca cactgttgtt ttaacaggat    6480
cttttctttt ttgttttttt tgaataattt ctactgttgc gtagagaatt aatgcggcgg    6540
aaatttttat gtcttttgtt ttttgtagat ctattattat tttcgacctt gatgatgtga    6600
tgtgcagttt cttatgaac tcaaagaatt ttttgtaatt ctcttttccg aagaaagaga     6660
tgctgcttgg agctggcacc acttctctgt caagtattct cttggcatga gtggctttgt    6720
ttggattgta ttttctggtc gatctgctag ccttcagaga ccttctgtcg gcaatgctct    6780
gatatatctc gtccgttgga tgtcttttcc tcatatctct tactgaatgc tccttttcagg   6840 cggcagtttg ccaagcagat catcctcata accttaccgt tctacgtagg tttatgctac    6900
tagacctgtg tggcggcgcc gctagggcg atactctctt gacggaggcg attgccgctt     6960
atcttgacaa cctacgttgg gacagttagt ggctatcatt ctggcaatac gacactcagc    7020
gccaccgcaa ccgggcgcac ccagatcggc gtattgctga gcatgaaggt ttcgccggcc    7080
tcggccagca gcagggtggt gcccatcacg ccggcgatgg cctcggcggc ggccggcggt    7140
acggcgttgc cgatgcgctc gcgccagtcg ctgtcgctca ggccgtcgag gaccaactgc    7200
tcttcggggt cgaccaagct ctgcagcgcg gcgagttcca gggtggtaaa cggcctgtgc    7260
caggtgccgt ccaggctgcg gatgatgcag gtcagacggt cattcgcggc cggcatgcgc    7320
ggatcggcaa cgctccaccg gccattgtcg tgcctggcgc tggccgacac tgcgccggcg    7380
gactggtcga agcccaccac gccgtagtgg ccgccggtga ggtaggagtc tcccttcgtc    7440
cggttgagca cccgcgggtc ttcgacgcat tgccctgtgc cgtgggcact ggtaaccgct    7500
tgtgcatggc ggctccaagg cacgatgcgg aactcattcg agtgtttggc agggccgctg    7560
tggcgcgggt ccgcgacagc aaatgcaccc tggccggtag tactggccgc gatcacggtg    7620
ccggctgggc cgtcccagtc ggtgaccgga tacttgccga aactctggcc gcggggatcg    7680
gcgacggagt acgtgccttg gccgggcgac ttgacgccga tgatggcgcc cgaggtgtcg    7740
gtccagcggc gcacgccgta ctgctggtat tgcaggcgt ttgccggcgc gcgaggatcc      7800
gcgactgaga accgccgtt catcgggcgg ctcgcgccgg cgacaacgcc acacgaatcg      7860
ccccagtgat tcacgcccag gacgcccgg tggtactccg gcacgatgat cagatcgcgc      7920
aggtagccgt cctcgacggc caggtcgttc aggctgcgcc agtcgctgcc ggctcgcacc     7980
agagcgaggc gcacccaggt cttccactgc agggatggca cacggtgcat cgggccggcg    8040
gcctcgatgt cgccgggaag cggcatgcga ccgaggatgt cgccgacggc gcggagcgac    8100
ttcttctctg gctcgtacag gaagggcggc actttctcga cgtgccgcgc gaccagcagg    8160
aaccttttcc gggactgagc caggccgccc agtcgccgca gtcgtgagt agtttccgcc      8220 acggcgtagc cgaacccgcc gagcaactgg ccgatctggt caagcaggtg ccggccgcgg    8280
ctggcgaggc gtgggacgtt ctcgaagacg atcagcggca ccgggtcatc agcccatgcc    8340
```

```
tcgcccatga gccagatgca gcgcagcgtc aactcgttca gcgcctggta cttcggggtc    8400
aggctcatct tctcggagag gaggccagag gcgcccttgc agggcgaact gatgaacacc    8460
gcatccggtc ggcgcccgcc ggcggcgcgc cgaatatctt ccggggtcgc ctcccgccag    8520
cctgccggcg gctccgtgcc gtggaaccgc acgtactggt cgcgggtgaa gaggtccagc    8580
agggtgcccg ggacaccagc caggcgctcg aagtcgcgca gtccggctgg gtccacgtcg    8640
atcccgccga ggcagaccca ttcggcctcg acgttgccga cccgcggccg cgcccggttg    8700
aaaccggcgg caccgccgcc caggccgcag cagaagtgga agtggtagag ggtgcgcttg    8760
atgatcatgc ggcgggttcc ttatggatga tgtcggcctc ggcgagctcg cagaagaagc    8820
tgcacgccgg aatggcttcg ttgcggcgga tcggcccgga gggaaggtcg cggagcgagt    8880
agcgttcctg ggtctggcgg ttgcggaaga ggtacgaacc cgggccgagc tcgtcctgca    8940
ccatgcacaa ggcttcgaac tgctcgggaa agtcctcccg gatcgcccgg aagtagcctt    9000
ctccgccttt cacgcagccg atgcagttcg cgttctcgta gcccaggcgg tacatggccg    9060
gcagttcgat gccggcgcgg gcgatgatgg cttttgcagtc ctccttgccc aggccacgct    9120
caatcagcgg cgcgatcacc ggacggtcgg ggttccgctc gcggaagtcg tccagccggt    9180
gctcttcttc cgcagtgaag ccgagcacca tcacgtcgcc gggacgcttc caggtgtcca    9240
gcaggcgacg cttcagcagc ttggtgcagg gcgcgccagt gcggcccttc atgtagcgct    9300
cgcggcggaa gacgttgagc acgtcggcgc cgtacttctc gtcgcgcagc accgtgaatt    9360
tccgccagt ccatgcctcg cagtcggcaa ggaagcgccg gttgtcctga tgctcgttgg    9420
ccagataggc attgaggaac tggacgtcgt gggtatcgcc gtactgcgcc agggccagct    9480
tgccggcgac cgcagaggcc gcgccgcaac tgaactggac cacgatgcgc gattcgggct    9540
tgatgatgtc gacctgactg ctcatacggc gggttccttt tcgcgaacgt gacgatgcac    9600
tgcgctatgc gtgatggcgc agtgatgtcg ttggagttag atttggaagg cccggcatgg    9660
ggccggatca aggaggagag atgcctgact tcagaatcgt cgagatcgtg ttcgatgaca    9720
ccaaggtcta ttaccggtat gagacggtgg gtgcatcaac aatcggtgga gagcaaacac    9780
ctgcttatca acaagacatc atcctcaatc attttcgatc tgccgcaggc tatcggggtt    9840
ctccgaccaa ggttgaaagc gctgcacttg ttgcatcgaa ggccgtggga cgagtggtcc    9900
aaactttgag cggatccaag gctcaagcca ggtcgacaaa gaacacttgg gtaaccaagg    9960
cgcatgcaga tcgtaactat gaggttctca acacccagag tcgttaggct gtacgcgacc   10020
cgctagaagt acgtcagtac tccgtgaaca ggcactggac gccgccctgc ctgacagggc   10080
ggcccacgag gcatggttga atcgcccaca gggcggcgtc cggtgcgtgc tggaagagaa   10140
agcgccccag gtggggcgct gtatcgaggg tcaggccgca gcctggagct ggtgaccacg   10200
acctagagga ataaactgag cttgaaatgc agatcgattg ccctaaaact cgatggtgaa   10260
gtcacggtgc tattacttga ccaactaggg ggatctatgc ctatcaagat gaatctgtct   10320
ggcctgaagc gtctgcagca aaacctcaag caactcgatg gcacgcatca agtgccgttt   10380
agcgagatca tgagtcccag ctttatttcg tctaacagca agtttgcgaa tttcgacgag   10440
tttgctcgtg gtgccggtta taaggttgaa actgcggaag atctacgggc gattccagac   10500
gagccatggg acgcttatgt ccgtagtgag actccttttcg agagttgggc agaaatgctc   10560
aaggccggca tagtcgcgca tgccaagcgc tcacttcaaa aggggttgta actgccgtc   10620
tctactgaaa ccgaatgctg cacgtgtggc ctttctccgc ccagaacgct cggatgtgcc   10680
```

```
cgagcgtttc gttctgcatc gtcgatgggg gcgacttcac gacagaacct cgcgagatcc   10740
gtctccctgc atcggcccga cgatatccag caattccatt tcctctacca ggcgtgccgc   10800
gcggttgtag ccgatcttga gtttgcgctg gatggcggag atcgaagcgc ggcgcgtctc   10860
gcggacgaag cggatggcct ccttcagcag cgggtcgtca ccgggcccgt tgacctgggg   10920
gatatggagg gtcgcggtga taccgtcgcg catccctagc gccttggtta cgtcgatgcc   10980
ggcgccaggc gctggctcgg gctcatcgta cgcaccgtcg attccctgcg ggnnnnnnnn   11040
nnnnnnnnnn nnnnnnnnnn nnnnnnnnnn nnnnnnnnnn nnnnnnnnnn nnnnnnnnnn   11100
nnnnnnnnnn nnnnnnnnnn nnnnnnnnnn nnnnnnnnnn nnnnnnnnnn nnnnnnnnnn   11160
nnnnnnnnnn nnnnnnnnnn nnnnnnnnnn nnnnnnnnnn nnnnnnnnnn nnnnnnnnnn   11220
nnnnnnnnnn nnnnnnnnnn nnnnnnnnnn nnnnnnnnnn nnnnnnnnnn nnnnnnnnnn   11280
nnnnnnnnnn nnnnnnnnnn nnnnnnnnnn nnnnnnnnnn nnnnnnnnnn nnnnnnnnnn   11340
nnnnnnnnnn gtctctcgct gacgatgaca gcgcgctcgc tacaccgtcg ctgtcgctgc   11400
cgtagttctc gccggtgatt gccttccagg cgccgcgcgc ctcgctggcg tagtcctttg   11460
cctggccgac catggcggag aacccggagc ggagcagggg cttcaccttc tcgaacagcg   11520
ccaggtcgat gcccttggcc ttcaggcgct gccgacctc ggccgggctg gcgctggcgc   11580
cggtcaggtc gaacagcacc cggcggcgat ctttggcgtc cagagcggcg aagcggctgg   11640
cgtcgagcac gaacggcagg aacggcgagt cggcgagcgg ggagcctttg ccgctaggca   11700
gcgcgacccc gcaggcctga acctcgccgg cctcgtccag ccactcgaca cgggcctcgc   11760
ccttcttggc gccctcggtg atcagttggc cgatatgctg cttctgcgca acgcggccgg   11820
gcttaccggt gaatgcgtgg ctgatggcgt cgagcagcga actcttgccg gcgccgttgt   11880
ggccggccac caggagcacc ggcgcagaaa catcaagggc cgcatgacgc agcccttgga   11940
agttggtgat ttcgattttc gtgatgcgca tggctcactc cagggtgatg ggctcttcgg   12000
ccggggcctt ggtggcaacg gcgacgcggt aggtgttgag gtcaggcgat tcgccttcgg   12060
tggcgagcgt gatcacaccg tcgtcgagca gcttcatggc gacagccaag gactcgtcgg   12120
tgctcagcgc gaagcgcgac tgcagccagc ccggggtgat ctcgtctttg cgcagcacca   12180
ggacggtgat gtcgtcgatg tgtggccgc cgtaggttgt ggcgccgggc tcggcggcac   12240
tgctcagcag gtcttttccc ggttccggcg gcgattgcag gatcacctcg cgctcgccgt   12300
tggagttcgg tgccgataca acgccggcgg cttccatttc ctcgacgatg cgcgcggcgc   12360
ggttgtagcc gatcttcagg tgcctctgga tggaactgat ggttgcctgg cgggtgtcgc   12420
ggacatgtgc gacagcctcg aggtacaact gatcttcact gccatcgccc agcagcccct   12480
ctgcgacgtt gccagcgtgc agcggcattt cgtgctggtc gcggtcgggc cggacgtcgt   12540
ccagccctc gtcgtaatcg ctcggtgcca tgaccagcaa gcacaacttg ccggcggcgt   12600
cggtcaattc gtgcttgttc ggctctgcgc cgtctacctt cgccgtgatc gtcatggtct   12660
tggcttcgac cttgatcgct ttcatatcga ctggaacgga gactgcgccg cgggaagcaa   12720
tgatgctgat ggccacccct gtcacttcgc ttacgctttc cgctatgcga tcgatcactt   12780
cctgctgctc gtctaaatgc agcaggtgga aggcacacg gacactgcgc agttcggtga   12840
ccaccgtgtt gaccaggtcg cgctccagca actcgtgcgc gatggtgctt gggtagtagc   12900
cgtgtagttt ggcgcggtcg atgatctcgc ggtgttcggc tttcatccgg tggagctcct   12960
attcgttggc gatccgctcc aactgctcga gttgggcgtc gctgaggtag gtgtgtgcgc   13020
cgtagcgctg gaagttgctg cggaggtcgg ccaggaactg ctcgtcccag tccgtagcgg   13080
```

```
cgttgagctc agccgcgccg agtagcgcgg cgaactcccc gacttggccg taccgctcaa   13140
ggacagtgag gctgggcatg gccggttact cgagattgag ctcgtcggtg ccggtgtccg   13200
gctgctggcc cggggcgggt tcggtgattt cgcccgtctc ggtgttcacg ccgtccggcg   13260
gagagggctc gtctccatcg tcttcggcgg cgacagccgg cggcgccggt tctttgtctc   13320
ggagatcatc gacatgcacc gtcacggttt caccctggat atcggtgtcc cgcggttcga   13380
tgaagtcgtt gacctcttcg acggtctgca ggcccatcag cagctcaggc gcatacaggc   13440
ggcccagtag gctggcagcg cggtagcgca acatcacctc gggcatggtc tgccacttgc   13500
tgccgttctt ggtgagccag ccctcgtcga gcgccatttg aatcgacact tcggggcttt   13560
cgatcacggg cactccgtac tcgcggcaca actggagcat cgacttttcg cgaagctcct   13620
cggggctgaa ggtcgggatt tgaacgcccc tctcggtggt ccaggccgtg caggtctgat   13680
ggcgaacctt gatggtcttc gtctcctcga ccttctgctt gttcttccag gtagtcgcct   13740
tataggaaac ctcctgctct ttgcccggct ggctgaggtc gtagcggagc gggttgaaac   13800
ggccgcaact gttgatcgag gcgatgatga actggctgga ccagctcggc cggccctcga   13860
tcacgtacag gttctgcatc accatcagcg gatcggcgcc catacgctgc gccatgttca   13920
gagcgacgat gcagttcggc agcccggcgc cgttcggggt gtagccggtg accttgccgt   13980
actctttcac ctcggcgaag gcgcggtact gcaccggcac tagggtagac gcgctgagcg   14040
cctttgcgac gcgctggatc tggtcgaagc cggcgccggt gaggagggac atcggcgcat   14100
cgttggttga cctcgcgacg gcgctggtct tcaactgctc cagttgggtg ggttcgctca   14160
tgctgctgtc tccttgtaac ccatgaattt ccggtactcg gcctcggtcg caacgctcac   14220
gacgcggtgc tcgtcgggct tgtccggctt gttgtgctgc ttgcgctggg cctcgaggaa   14280
ctggccgcga tcccagacgc ggtggtggtt gattacctcg cggcgcttgc cggccgggtc   14340
ggtgaggcgg acgtacaaat cttcggattt catggcgatc ctcattcgtg gtatgggcag   14400
gtccgccagc gcggacagta cttcgggctg caaagtgggc tttgcgggtt cggggggaag   14460
aggccggagc ggaacatgtc ggcggcgaac ttgatcaggc cgtggtgctc ggcagtgccg   14520
gccatcatct ggcgcgcacc gacgatctcg ccgaccgccg cctcgggctt gcccttggtc   14580
ttcaggccga tgatctcggc cggcgcggtg atcgggtcgc cggtggtgtg ctcgtaaagc   14640
agttcgtagg tcccgatctg ggctttgtgg cccttggtct tggccacgcc ctggctcacc   14700
gcggcgccgc cggtcttcac gtcggcgatg ccgacgccgc agctatcgcg cttgatgcgg   14760 gccccggtcga gttggccggt caggcggaca aggatgccgc caccgcagtc gatctccatc   14820
ggcttggtcg tcagctccac ggccacgaac gtgtagcgcg ggctgatgtc gttgcagtac   14880
ttcgtgtgca gcgtcagtcc ggtggactcg gcttcgcgcg ggctgatgtc ggagccgcgc   14940
cagtcgacct cgaactccgg ctgctgcagc gtgtgcacca gcagttccga ggcgtcgtag   15000
gcgctgatcg gctcgccgtt gaccgtgccg gcatcgaacg cggcggtgct ggcgtggatt   15060
gcggtaccga gcagcgcccg gggggatgaa gggctacgca tcttcaggat gtgtacgcct   15120
tcccagcgga acgcgcagtc gaacagcgcg ccccaggacg aggcgcgcac ggtgatggtt   15180
tgcatggttg gctcacttcc cggcgatggg cgccgtggcg ggttgttcgg cggtgatcag   15240
gccgccccag gcaggggcga agatgagcag gatgtagaag gcggtcatgg ccagggcgcc   15300
gaggagggtg gctttacgct tggcattcat ggcgcatgcc tcccggcccc attgcacctc   15360
cagcaggagg agtaggcaga atggtgcggg ccgtgcgata cggtgttacc ggtgccttga   15420
```

```
cataccoggc aaacaacctt tcccgctcc ttctcaagtt ccttgcgaag cgagtcggtt    15480
tcgcgtgccc ttggatcttc cggggaatag aaggcttgtc caatgttctc tgcgaacaag    15540
acaacgtccc tggcaatcgc cttgatctgt tcgctggtgg ccaccacgcc atgctcctcc    15600
agcgactccc caagcccttc ggcgaagtag tcttcccgtg agtagctcat cgccgcaccc    15660
ccaggcactt ccggccgcgc ttgatggtca gcgccatgcg gcgcgggaga ttcaccacca    15720
gggtctcgcg gggcaggccg agtaccgcgc gatgtcggc gccggcaggc ataccaggt    15780 cgtcgagctg gtcgtcgatg atcgagcgaa cggggcgggt ggtcatgtgt tcgtgctcct    15840
gagttctgcc cagcgcgaat ccgctgcggc gtcgagccgg cggcgcatgt cgtcgtagag    15900
gcgggtgtcg atgaagtcca ctgcgtaggc cagttcgatc tggccgtgga ggaagctctg    15960
ttcggggcgc gggaagtggg accggcgcat ggccgtgatg ccttcctcaa tcatccgaac    16020
cgcgcgttca ttgctgaagg ccatcgtcgt cctcctgctc ttcgtcctcg ggctccggtt    16080
ccggctccgg ctggtcccag agcgggtcga cggcacggtc gtaagcgagt tgcgcgttgc    16140
taaaagccgc gcggttgcgg cgctcgcggt atgtccacat cgggatgctc tccgtggttc    16200
acctgcattc ggcagcaccc aggcacacgg cagtcgtgcc cggtggggcg ccgtagtggg    16260
tgctctcgaa tgggggttga aaaaagcccg gccggagccg ggcgaagagg gggaacgctg    16320
catgcgcagc ggggagtgat ctggccggtc gcgactccgg ctctggcatc agtgcgcttc    16380
tcgggtgttt gccgctgctg cggtgactgt gctgatgccc ggaacttcat cggccatggc    16440
cgcccacgtg cgcgcttgtt ccgcgcttc ccgcgtgtct ccagggagct ttcggctccc    16500
agcttccacg cctcaaatca ctctccgctg cgccctggcc gcgccaggag caggaaagag    16560
aagggcgccg ccaagcgccc tgtctccact tacatgcacc gccctatgtg aaagcggttg    16620
ggtacaggct cgaccgcatg ttggcgatct gccgattgag gctgggctac atggtgaggt    16680
cctccgttgt gcgcgccgtt ggaccggcgg gcgctcgccg tgggttaaac gcccggcaat    16740
gggccaggcc ccgaagtcag gagatcgcgc tgcaggcccg caacgccacc ggcgccgact    16800
ggccttcgat ccagataacc gccgccccgc caagcgacac gctggcccgg ccgacggtgc    16860
gggtgcgctg cggttcggcc ccgcggtacg gccggtactc gatcagcgct ggcgccgggt    16920
gctctcggtt ccaggcctcg accagctccg ccggaggcac cggtcggacg ttgccgatct    16980
gctggtagat ctcggagcgg tggatggcga cgtcgtccgg ggcggtgatg ccgaggcgca    17040
cctggtcgcc ttggctgcca aggaccgtga cggtgatgtt gtcgccgata tgcagggttt    17100
ggccgactcg gcgagtgagg atcagcatgt gtgcctccgt tcggggtggt ggggccgtc    17160 agcccaagcg atccgggacg accttcattg cctcggcgac gagcttgtgg gccccttcgg    17220
agtccaccgt ggcgaacccc ttttcggcgt ggtcccactg ctcatcctcg ccgcggggga    17280
aactgctgca cgccactgaa cagacgccaa gcccgtcggg cttgaagtag aggcgcacct    17340
ccgggccgtc atccccgcga tcaagcatca cgagcacctg gcccaggtct tcgaactcga    17400
aaagcttcgc gaactgcttc attggaattc ctctggttgg tttccctgat gcccctcggg    17460
ggaagggcat cgaggaaatc ggtgttgctc ccgcgttcgc ctactgggct tctacaaccc    17520
gcgggtggtc ctcattgctg tcattcccct gactgcggcg ccgattgccg cacggcacag    17580
ccaggttcct gcccattacc gccggggtgg cggggcgcat tgctttccgg gtcattcgct    17640
cggttcggtc tggtcctcgt ccgccgcagg ttcttcctgc gttgcccagg cccgcattgc    17700
ctgagcgcgc atcgccggtc gccggtagag gcaatgcgat ctgttgttga tgtgttgtgc    17760 tgtcggggttg ttaaagagcg cggctcggtg gcctggccgg cggtgttgtg ctggcgttgg    17820
```

```
atgaattatg catcagcgca tatgcatgtc aatgcattga tgcaattttt tatgcgcacg   17880
gatatgcatg aacgaaaaaa cccgcgctta ggcgggcttc aagaggggag ggagggacta   17940
gtggtggagt tggcgaagca gggcgtcagg cccaccgtgg aggtcgatga agcgaccgaa   18000
ggagtggcca tcctcaccca agaagaatgc ggaacggtgg attaggttga ccttgtcggt   18060
atcgctcaac gggcaggcca tgatccgctt tacaaacaag agaaatcgca ggtaatcacc   18120
gccgtttctc ggccagggtg tagcacctct gcccatgcat cgcaggcgta actcctcgaa   18180
gttcggcatt gtgcgcggta gccacgtacc ctggcggcca tctttcagac ctggtacgag   18240
cggagggtaa gtgaagtccg ttgtgatgcg accatgctgc tccaaaacgg aaagtggagt   18300
agctatggca agcacagcga agaactcttg agcgcggaga aaggattcgt cgcggcattc   18360
gcccttcgtt tcgtacgccg ccaggtcctt gaatggagag tagctgccga tcaccgcgcg   18420
gccggggtag gaatgatcca tgacgagcag ttggattgtc tcggggccat cgtagatcag   18480
gccatcagca cggtgcccg gcggcgagcg aaagattgcc cagtccagaa aatcctggtc   18540
ggggccggcg gtcgcctcgg cgtctcggtc gtagatgacc tgaccgcctt tggtgagtgt   18600
ggcgatcgcg ccggcgccgt gctgctggac cgtcacgagg atgtcgatct tttcctggta   18660
gagcaggcgc tggcggatga cgctctcacg ctcgtcgagg acctcaacgg ccaggagcag   18720
agcggtcagt tgttcatcat ccatccggcc tgccactggg cgcgcaagcg ccttcagaag   18780
aacatcgcgc cccagaacac acggccgatg atctcgatct cttgagcgac aatttcatcc   18840
tttgagtatt cctcatcggg atgttcgtcg cggttgaagc tgcgaagtcg gatgcctccg   18900
cccggcagcc ggtaagtctg tttgacgcgg agtaggccgc cgtgattgat cgcgtagagg   18960
tctccatcaa cgatccgggt attgccgaca tcgaccccga cagttgcgcc gttacggagt   19020
actggctcca tgctgttgcc cgtaatagtc acgcatcgtg cattggcagg gtctaccccc   19080
tgcttcttca gactgtactt cccgaagcgc aggctacgcc tcgaattcat ctcgaccgac   19140
atcttgccac ttcctgcggc caactctacc tccttaagga atgggactag cacctcatca   19200
gaagggagag gcgtgctgtc gtcccagacc tcaatcggac cgtccatcgt cgcctcaggc   19260
tctcgaacga ctgcggggat aggcgcagtg ccaattgaca ccctgccgcg caattggtct   19320
gtgctcaaac cgaagtattc ggcgattggg tagacctgtt catccttggg cgtggcgatc   19380
ttgccgttaa ggattcggga aatggtggat tgcccgacgc cagtgcggcg actgagctcc   19440
gttggggata ttccatgctc cgccagaagg gcggccagga tgtgctggat cgtacttttt   19500
tgcatggatg caatgctgcc aatgccttgt gcataggggga agagtccatt tatgcgttga   19560
cagttatgcg gcaatgcata gactgtgcat atctccagag gagcatgcac atgactaccc   19620
ccaccctggc cacgaaggtc aaagacctcc tggccgcccg caagacctac cgcgccatcg   19680
cggaacgagc tggctgcgat ccctccacga tctttcgcat cagtaagggc gccatcgaga   19740 acccagcta ctccgtgggt tccgcaattg acctcatgca tgccgagttg acgcctgagc   19800
agcagctcgc gcacctccaa gaggccggct gatcgcaaag agcgacggtt ttcgttgaag   19860
gtcatccatg acggggactt cctgctggtt gatcggatgc caatagcttc gcccaggagg   19920
gccaccatgc atacgtcgaa tcctcgacac gaaacccgcg atgccgtgct gatcgccatc   19980
gccgaggaca tgatcgcccg gaccagcatg tcgcaggacg ggttcgccga acgcttgaac   20040
atcgaactga acctgcgggc gccggaacgc tgccgggcca aggattaccc ggacctgaag   20100
gccctggaag gggcggccac cagtcacgtc gactacgccc ggatctacaa gaactggagc   20160
```

```
aagcgggtgg aacgctggct cgacggcgac gtcgagatcc cagcctggat tgaagagtcc   20220
tgggtacagg cactggagca accctggcgc gagcgcgcgc tgttggagtt gtccggtcgg   20280
tacggcctgc tcccggtgcg tccggtcgtg gcagagggca tggatgccat gaaggtgttc   20340
ggcgcactga tgcgtcgcct cggtgatgtc gccggcgtcg gcaccagggt cttcgacgac   20400
atgatcctcg atgcgcggga tggccagttc cttccggacc tgatcaacgc cctggactcc   20460
actgcggcga aatgcacgac gctgagccga atggctaagt cggttctggc gggcgaaggg   20520
tgatccgtgc cgtccttcca gatcaacgac gaggagtggg atgcgctctt cgacgagccg   20580
catcagctgc tgaaggtgta ctgcgcgatc cggatgttca tggactacag gaccggcatc   20640
gctggcgaaa cccgccgcct gagcgagcag atgctgatcg aggttttgag catctcggca   20700
tcacctgggc gtcctgcgca caaggcgacc cgcaaggagg cgcgctacac catcgatgcg   20760
ctggtgcgcc gcggcatggt cgagcctatg cccagcatcg gtcctttcgt tttccacctg   20820
ccgaaggctt cgcgggatca atccgtttcg gagaggtggg gccagaggtt tgaccaaggt   20880
ggggccagac ctggggccct aggtgggcc aaggatttag atccagaagc cccggaaata   20940
ctgggctaca gcgaagaggc tggagcaggt ggggccagag gtagggccgg aggttatcca   21000 gaggtgggc cagaggtggg gcctacatcc ggtcttcctc cgatacctcc tccgtcacgt   21060
aacgcgcgcg aggcagagcc ggtatctggt gctgaccgat tctcgatgca tgaggcctgg   21120
gtgccgagtg cgaaggggtg ggcggaaacg ctggtctgca acggaattgg gacctaccaa   21180
ctacgcgacg acgagcttct cgagttccgc agctactgga tcaaccgccc cgagaaatac   21240
cagtcccaag gccagtggga gcacgaactg gcacagaaaa tccgccgcaa ccagcgcttc   21300
gaccagaaca ggagcagcca tggaaaccaa gcaggaaacg ccgaaggcca gccggccat   21360 cgtgccgcaa agcgcggcct ctcacatcga cagggccctc gctcagccgt cgaccgcgtc   21420
aacgccatcg tcgcagccaa cgaggctgcc cgacaggctg ctggaacggc tctgggtgaa   21480
gatgaccgag atgtacgggc accgctggac gtcgagtttt ggcgacaacc cgaaccctga   21540
cggtgcctgg gctaccgtgc tccagggct gaccggccag caactcgccc acgggctcaa   21600
catgctgacg ttcatgggca gccggttcga ttggccgccg gcggcgccga cattccggga   21660
gctctgcttg agcgtccagc cggagtcgct cggtctcccg gaccacgaca ccgcgttcca   21720
tcaggccctg gcgtgccgct accgccacca ggtggtcaag gccgccgccg aggccaccgg   21780
cgttttcgat ctgcgcaccg gtgaggtgaa cgacgatcgc ctccgaaagc gcttcggttt   21840
ccactacgcc gagatggtcc ggcgctgggc gaacaacatc ccgttgagcc agcccgtcgt   21900
ccacgcgatc gaacatgaca ccgggaagag cttgctggac ctggccgagg atgaagccga   21960
gcagcagctc cgccggcgga tgcaggccca gggcctggat gggctcagtg gcgcccaggc   22020
ccgggaactg ctgctggcca agatgcgccg gaaagcgccg gaggtgcgcc gtgatgcatg   22080
acctccgacc ggtgatgttc actgtgcccg gcgagccggt ggggaagggg agaccgcgta   22140
tcggccgcgt cggagcccac gccaggatgt tcacgccggc gaagacggcg aactacgagg   22200
ggctgatcgc acacagcgga cagcaggcca tggcaggccg cgcgctgttc gagggcccag   22260
tgctggtcga gctcgacatc gcgctcagca tccctcaatc gatgtcgaaa agcggaagt   22320 cgctggccct ggcggcggc ctgtacccga ccaagaagcc cgacatggac aacgtgatca   22380
aagcgatcta cgacgcctc aacgcgtgg tctggaagga cgacgtccag gtcgtgaagg   22440
cggtggtggg gaagcgctac ggcgaaacgc cgggcgttcg agtgaaagtc gtccctctcc   22500
tcgagggcga gcagtgacta caggaaacta caggggagag tcgaaatgag actgatcagc   22560
```

```
gcgcgccagg cttggcagga cgcgtaccac atcccgggcg cgtcggtgat ggcgaaagcc   22620
atcgaagatg ccgaagaggc gacacggaag accagggcga agcgccgcaa gaaactggtg   22680
gcccgcttcc ccgaggggta ccagggcgag agcaaggagc cggagggcct gttccccatc   22740
gactcccaga tcatcgccgc ctacgagacg cggaccgggc gggccgcggg aaacctgaac   22800
cgctgccagc acatgctcgc cgccggcaag gtgatgcatg cgatcagcac ccttccggcg   22860
ccgctgcagc acctcggcca cttcctgtac tcgccgctgg cgaacggggt cgaccagaac   22920
cgcgcgcagt ccttcctgta cttctcggcg gatctcccga agatgaacaa gccccgccag   22980
gaggtcgctt actgggtggc cttggcgcg atgcactcgt ggaaggacat ggtgaacggc   23040
cgggaggagt ggtggccggg taaggtgatc cagttcctgg cggactggcc ggggttcgta   23100
ctgtacgccg cgaattggga gcgtgactgg gcggcgatct gggagatttt catgcaggag   23160
ctcaaccggc tggacgccca ggctctggtg ccggtggcgc aggtggttgc ggcccaacga   23220
gacgccgctt gacattttga taagagattt gggagtattt tcccagtttg cgaagtagca   23280
cccaatcaaa agattccccc gaaaacccgg ccctgaagcc gggttttttc gtttctggag   23340
caccccatgg ctgaaccgac gagcagcgga gcagtagcag cagccggcgc cgtcgggctc   23400
actgccaccg cgatcatccc cggagtcgac gtcaatgcgg tgatcggcgg cttttgccggc   23460 gcgctgctgt tcgtgctctg ggctcacgac ctgaccatgg ccaggcgcct cggctacctg   23520
ctggcgtcct gggtcggcgg ctactacgcc gccaccgagg ctgtcgggcg gggcgcgacc   23580
cagttctccg gacttcccgc actggtcacc gccgcgctga tcgtcacgat cctgatcggc   23640
gtgctcgact ggatgatcgg tggccgcgcg ccggcatggc ttcagatcgt tctgcagcgc   23700
atcgtcggca tgatcggagg ccggaaagat ggttgatctg gtgaccctga cggctgcggc   23760
cgtctgcggc gctatcagtt gccgcatctt cacgtaccag cgccacggtg caacgtaccg   23820
gttcggcgtc tcgctctgcg cgtacatcct tgccgctggg accggcatgc aggcgctgtc   23880
catcaccctg gccgtgctga tggcgcgcca cgcaacgccg atatcgccct acctgctggc   23940
ggtcctgctg gtgctgctgg tgctggtcta ccgcaacaag ggcaacatcg cgcccatcct   24000
gaggctcagt tgaggtgatc catggcgctg accaagaaac agcgcctgtt cgtcgacgag   24060
tacctgatag acctcaacgc gacgcaggcc gcgattcggg ccggctacag caccgggcgc   24120
gcgacggaga tcggctatca actgctccag cggccggagg tcgcccaggc catccaggcc   24180
gccatggccg agcgctcgaa gcgcaccgag gtcgaagccg actatgtgat ccgccgcctg   24240
cgcgagatcg acgagatgga cgtgctcgac atcctcgagg acgacggatc gttccggtct   24300
atccgcgact ggcccagggc gtggcgccag ttcctgtccg gcatcgagat cgccgagttg   24360
ttcgagggcc gcggagacga ccgccgcatc gccggcgtgc tccgcaaggt caagtggccg   24420
gacaagctac gcaacctgga actgctgagc cggcatgtcg gcaccgagtc tgccgcgctc   24480
gacttggagc tcaagcgcct ggatgttgcg aagaagcgcg ccgagctgaa gctgctggag   24540
aatcccgagg acgatgcgcc gccgaccagc gtcgcggtga ccatcatcga tgcgagggtg   24600
cgcgatgccg acgctgaata ggccccaggc gaagttcctg gcgcttccgc acaagttctg   24660
cggcttcgtg gccgggttcg gctccggcaa gacctgggtc ggctgctcag gcctcgccca   24720
gcacgcttgg gagtggccgc gcatcaacgc cggctacttc gcgccgacct acgcccagat   24780
ccgcgacatc ttctacccaa cgatggagga ggtggctttc gactgggggc tgcggaccag   24840
gatcaaccag gcgaaccacg aggttcacct cttcagcggc agcgcctacc gcacgacgat   24900
```

```
catctgtcgc tccatggaga agccgcagac catcgttggc ttcaaggtcg gccgatccct   24960
ggtggacgag ctcgacgtcc tgtcgctggt caaggcccag caggcctggc gcaagatcat   25020
cgcgcggatg cgctacaagg tggacggcct gcgcaaccgt gtcgacgtca ccaccacccc   25080
ggaaggcttc aagttcgtct tccagcagtt cgtgaagcag ttgcgcgaga agccgcacct   25140
gcaggacctg tatggactgg tccaggccag cacctacgac aacgaggcga acctgccgga   25200
cgactacatc gattcgctga tggagtcgta cccgccgcaa ctgatcgcgg cgtacctgcg   25260
cggccagttc gtcaacctga cgtcgggcac catctacacc gcctacgacc gcactctcaa   25320
cgcctcgccc gagacggttc agccaggcga gccgatatac gtgggtatgg acttcaacgt   25380
cggcaagatg gccgccgtcg tgcatgtgaa gcgcctgggc ctgccgcacg cggtcgacga   25440
gatcgtcaac gggtacgaca ccccggacat gatccgccag atcaaggagc ggttctggct   25500
atacgccgac ggcgaatatc ggccgacccg ccagatcagg atctatcccg acgcctccgg   25560
cgactcgcgc aagtcggtac gggccagcga gaccgacatc gcgctgctca agcaggccgg   25620
cttcgtcgtc tcggcgcccg ccgccaaccc gccggtcaag gaccggatca actccatgaa   25680
cgccatgttc tgcaacgcca aggcgagcg ccggtatcgg gtcaaccccg accggtgccc   25740
gacctatgcc gacgccctgg aacagcaggt gtggggcaca aacggcgagc cggacaagtc   25800
cgccgacatc gaccacccca atgatgcggg tggctatttc atccacaagg aatacccgat   25860
cacgaagtat tccctcgcag gtgtttccta atgggcgtaa ggcgcttcct cactgacaag   25920
ctggtcaact tcgtggccaa cttgggcacg gagcgagaca aggccgccgg cagcttctac   25980
gcgccggtcg tgctcaccga tgagcagttg cacaacgcgt atcgcggcgc ctggttcccg   26040
cgcaaggtcg tcgatatccc ggcgaaggat gcgaccaggc gttggcgggc atggcaagcc   26100
agcaaggcgc agatcgagaa gatcgaggcc gaggagaagc gccttcaggt ccaggcccgc   26160
accatggagg ctctaatcaa ggcgcggctc tggggcggcg cagcgatctt catcggtacc   26220
ggcgaaactg acaccagcaa gcctctggta cccgagcgcg tccaggccgg cggcatcaag   26280
tatctgacgg tgatgagccg gcgcgacctg tcggcaaccg agcaggatcg tgacgtcatg   26340
tcaccgaact acggcaagcc caaggcctac cggctcggcg gcagcgcgat cgagattcac   26400
ccgtcccggc tggtgatctt caccggcgcc gacatccctg accaggacct ggccagcggc   26460
aatcagttcg gctggggaga ctcggtcctg caggccgtgt tcgaggccat ccaacagatc   26520
gacagcacca tggccaacgt ggccagcctc atcttcgaag cgaaggtcga cgtgatccgt   26580
atccccgact tcatgcaggg gatgcaggac ccgaagtacg agaagctggt gctggagcgc   26640
atgcgtctgg cggccatggc gaagggaatc aatggcaccc tgatgctgga caaggacgag   26700
gagtacgaca gcaaatcggc gaacttcggc acgctgccgg acatcatgga ccgcttcatg   26760
caagcgggct gcggcgctgc cgatattccg gctacgcgca tgctcagcca gtcacccgcc   26820
ggcatgaact ccactggtga ggccgacctg cgtaactact acgaccgcat ccagtccagc   26880
caggagctcg acatcacgcc ggctatgtcg gtgctggacg agtgcctggt gcggtccgcg   26940
ctgggcagcc gaccgccgga gatccattac gtctggaaca gcctctggca gaccacggcg   27000
aaggagcggg cggacatcgg gaagatcacc gccgagacta tcaagaccat cgccgagaca   27060
aggctcttcc ccgaggaggc gctcagcaag gctgccgaga ccctgctggt cgagaacagc   27120
gtgatgcccg gtctggagtc ggcgctggag gagttcggct ccgaagtacc cgaggacgag   27180
caggacgagg agggcggcaa ccggtcgtcc agccaggcgc tgaacgacgc ggcacctcgc   27240
acgctgtacg tctcgcgccg ggtgctgaac gccggcgcga tcattgactg ggcgaaggac   27300
```

```
cagggcttcg agaccacgct cccggccgac gacctgcacg tcaccatcgc ctacagccgg    27360
acgcccgtcg actggatgaa ggtcacccag gcctggacgg tcaagccgaa cggaaacctg    27420
acctgttccg ccggcggccc gcgcctggtc gagcagttcg gcaaaggggc tgtggttctg    27480
ctgttcaact cctctgacct gacctggcgg cacgtcgaaa ttcgcgatgc cggtgccagt    27540
tgggactggc cggactacca gccccacatc accttcacct accagcccgg cagcgtcgac    27600
cttgaccagg ttgagccgta ccgcggcgtc atcgagctcg gcccggaggt cttcgaggag    27660
atcgacgagg gctgggcgga tcgcctcgac gaggaataac gatgcttctc catgactccg    27720
tgtcggtgtc cggcgttcgc cggaccgctg acggctacct cgtggccgat gcccgggtag    27780
cgcgcactgg catccaggaa tacctgggtt ccgaggtcgg caagcccgac atacccattg    27840
tccgcgtgta ccgccgccg gaatcggttt tcgccgagga cgccatgcgc tcctacgcct    27900
accgcccat gaccaacggc caccacggcg aggtcaccgc tgagaactgg aagcagctcg    27960
ccatcggcca gaccggctcg gaggtcctgc gagacgcga cttcgtgcgc gtgcctctgg    28020
tgttgatgga tgccgatgcg atccgcgact acgaggcagg aaagcgcgag ctatccatgg    28080
ggctcgaggc agaggtcatt ttcgaggatg gggtgacccc caccggcgag acctacgacg    28140
cccggcttgg cccgatgcga atgaaccacc tcgccctggt cgatcacgcc aggggcggcg    28200
agcaactgcg catcggggat tcgcgcaccc ccggcgccaa gaaacctgcg caaacaaccc    28260
ccacaggagg ccatgacatg gctgatgcac tccgcaaaac cctggtcgat ggcctcacga    28320
tcgagaccac cgagcagggc gcccaggtcg tcgagaagct gcagaagcaa ctcggcgacg    28380
ccggggcgaa cctcaagacc atccaagacg cccacgccac cgcgatggca gcgaaagacg    28440
ccgaactggc gaagaaggac gccgaaatcg atgggctgaa ggccaaggta ctgagcgacg    28500
ccgacatcga caaactggtg cgagagcgcg ccgacctgat cgccagcgcg atgctgatcg    28560
ctgacgcga ctatgccggc aagtccgccg ccgagatccg caaagcggcc gtcgtggcca    28620
agctgggcga cgccgccatc aaggacaagc cggaggccta catcgccgcc cgcttcgaca    28680
tcctgctcga ggatgccgcc agtaacgacc cggtgcgtgt ccacctgaaa cagcaagaca    28740
gcaaaccgtc gaacccggct gacaacggtc aggcggccta cgaggcgcgc gtcaacggcg    28800
cctggaaagg aggtgacaaa taatgcccgc cgttcaaacc acctacagcg cgaacatccg    28860
ccccggcctg ccgggcatga tcgtcgacga agtcccgaag accctgatct cacgcaccgt    28920
cgaggccgct ggcggcctgg cgttcggcat cccggtcatg cagggcaccg ccgacaaggc    28980
cggccgtgcg ccgactactg gcgataccgc cgcgaagttc gtcggcatca gcgtccgcga    29040
ccgctccgtc aaggccgagg ctaaccagta cagccagtac gagtcggccc gcgtcatgac    29100
cgagggcgcc atctgggtga ccgcttccgt gcagggttgc cgcaggcgat ccggtctact    29160
tcgtgccggc caccggcgcc tggaccaacg tcgcgaccga caacgtgcag gtcgccgggg    29220
cgcgcttcga caccagcacc actggcacca atcaactcgc tcaagtccgc ctgggctaag    29280
gagaaaccat gagccgattc aagctgctcg acgcccaggc cgccctgggc ttcgtggtct    29340
cgcagaccac ctacatcgag cgccaggtca acgagatcgt ctaccgggat atccagtatc    29400
cgcaactgat cccggtcgac acctcggcgc ccgagtggat caagaccgtc accttctact    29460
ccgccgacaa ggtcgggaag gccgactggg tcaacggcaa cgccgacgac ctgccgctgg    29520
ccagcaccga gcgctcgaag ttcgagtcga cgtgcacat ggctgccatc ggctatggct    29580
atggtctgga agagatcagc caggcgcaga tgctcggcat caacctgacc ggtgacgatg    29640
```

```
ccgccgccgc gcgtcgcgcc tacgaggagt tcgtggaccg cgtagccctg gcgggtgacg    29700
cgcccaaggg cttcagtggc ctcttcaact acccgggtgt taccgcgggc tccgccgtca    29760
ccgggaactg ggaaaccgcc accgccgacc agatcctggc cgacgtgaac accgcgctga    29820
ccctccagac gcaaggcacg ctgttcaccg cgttctccga caccctgctg ctgccttacg    29880
cgaagttcct gctgatcgcc acccgcaagg tgaacgaaca gggtctggag acgatcctca    29940
cctatctgca gaagaacaac gtctacaccg ccaccactgg tcgcccgctc accatccgcg    30000
gcctgaacgg cctggatgcc gcaggcgccg gcggcaccgc acgcatggtc agctaccgcc    30060
gcgatccgtc ggtgctgaag atgcatatcc cgatgccgca ccgcttcctg ccggtgtacc    30120
aggccggtcc gatccgctgg gaagttcccg gcatcttccg cctcggtggc gtggatatcc    30180
gtcgtccggc ggaagttcgc tacaccgacg gcatctgacg ggggtggacc atggcgctca    30240
tcaccaatac caaccgcatc accccatcg gcctgccgag cggtgccgtc atcccgccgg    30300
gcgcgtctgt tgacgtgccc gagtgggacg atatcaagga ccgcaagaac ctcgccttct    30360
acgtggtcac cggcgtgctg gtggtcgatg gcggcgtgca gagcgacggc cagggcggcg    30420
aagaggcgta ccgccagcaa ctgttcgccg agctgaaggc cctgggcgtg aatgccggcg    30480
ccaacagcaa gaccgagacc ctggtttcga aactggcaga ggtcaaggcc aaggccacgc    30540
cgcccgctga cgaagcggct cagaaacaag cgctgatcga gcaactggcc accctcggag    30600
tgccggctgg tcctgatgcc tccctggaag aactccagaa ggccctggcc gacaagcagg    30660
ccgagcagca gtaatacccg cctcacggat ggtcgaccgg gccaggatgg cccacctatt    30720
cgaggattct gcatgagccc catctactgg cacttcggac cgctgcagtt caccaagtcc    30780
ggctctctct gggttctctc cgttagcggt ttcggtctct gcggcatcgg gctgcgcatg    30840
gggctgtacc gtggctgacg cctactacgg caccgtggct ggtgctgatg cctaccacca    30900
ggcccggggc aatgccgcct gggcggctgc tgctgaggcc gacaaggaag cagcgctggc    30960
ccgggcatca gcctacatcg acggcctcgg cacccaacag ccggtctctg aatgcgtgct    31020
ggtctttcct ggcaagaaag ccggagggcg agcccaagca ctgcaatggc cgcgcgtagg    31080
cgccgttgac cgtgacgggg agcccgttcc ggctgatgag gtgccgcggg aggtcgagca    31140
ggccacctac gaggccgcgc tgcgcgaact gttgaagccc ggcagcctga atccggacta    31200
cgttgcgacc accgcggtga aacgcgccaa ggtcgggccg ctcgaaaccg agttcttcgg    31260
cccagccgaa ggcgacgagc agcccaacaa gcccttcgtg ggggtcatca acgatctctt    31320
ggcgccgatc atggtgttgc ggtgcccgat gccagcggta ttcacggtat gaccgaagcc    31380
gagatcctgc gcgcaatcga gggaaaggag ccggcgttgc agagggcgta cctggaccgg    31440
gtcaggtcgg tgacggatgc cgctgtcgtg gctgagatcg agcgctacat caacgagcag    31500
gatgaggatt ccattgtctc ggtgctgtcg ctggggttgc tggcggtgtt cctggagcaa    31560
ctgcggtcca cctatctggc cggcgcgacc ctcgaaatca gttttttccc gggacggccg    31620
gtcccggagt tcgaccctgt aggccgcggg ccgtcgacct ggttatcgga gcatgccgc    31680 gtcctgcagc gcgacatcga tgatgctacg cgcctggctg tccgccacac gatccagatg    31740
gccgacctcc tggggcgccc gccgcgcgcg acagcactcg atatcgtcgg ccggcgaagc    31800
ccgcagaccg ggcagcgaac cggtggaatc actggactct caggcaacta cgcccaggca    31860
gtggccaacg cccgcgccca gttgctcagc ggggaccctg cgcagatgcg ccagtacctg    31920
acacgcactc gcagggatcg gcggttcgac aggttggtcg agcgagccgt cgaggcgcgt    31980
cgcccggtcc cgtcggcgga tgtcgatcgc atcgtaggcc gctattccga gcgactgctg    32040
```

```
cggacccgtg ccgagcagat cgccgcgact gaggcacacg acgccttcag cgccggacgg   32100
gatcaggtct acgagcaact cgtcgccaat ggactggagc gcagcagagt cctgaagacc   32160
tggcacaacg tcggcgacaa ccgcgttcgg cacactcatt cgccgatgca gggccagcga   32220
cagcaactcg gtagtccgtt cgtgacgggc ggtggcgcgc tgctgatgtt ccccggtgac   32280
cagacgcttg ggccggcga caacgaaacc gccggctgcc ggtgctgggt cgagtacgaa   32340
atcggaggta tccgtgcgtg acgaaatgca ggctattttc ggccagatgt tcgacagcgt   32400
gttcagcgag tcggtgacct cgttcgctgg cgagtatccg gggccgggcg tcttcgatcc   32460
ggtcaccgag accaccacca gccaacccgt gcggtactcc gggcgcgggg tcttccacaa   32520
ctacgaggcc aaccgcatcg acggaatcaa catcctggtc ggcgacatcc aactgatcgc   32580
tctgatcaac gaggtgtcgg accagcccgc cgtcggccat gaactgagca ctaccgacgt   32640
ggtgccgatc cttggtgggc cgttggcggg ctatcgcatc gtgcgcgttg gcggtgatcc   32700
cgccggcgtg catcacgatc tgcagttgag gaaagcgtga tggcaaaggg gaagggagga   32760
aggtcctgga gcatccctcc gtcggctttc gccgagaatg tcgggcaggc cgtggccaac   32820
caccagcggc ggctgaccat cgaaatgctc gagcagatca ccatccgcgc accggtactc   32880
accggccggt tcaaggccaa taacctggtc agcgtcggcg agccggtctt ctattcggtg   32940
aaccgctacg acaaggacgg gaacgagacc ttggcttatg cgaggcggc cctgccggc    33000 ctggctccgt actcggtggt ctacatccag aacaacctga tctatgcgcc gccgttggag   33060
gatggtcact ccggccaggc cccggcgggc atatatggcg tcagtttcca tagcgtcacg   33120
gcgagacatt catgacctcg aacagatccg ggcagtcatc atcacgcgca tgaccgaatg   33180
ggccgcgatc ccgggcgatg acgtcgatta cccgaacaac ccaaagggcc cgttcaagcc   33240
ggacgggagg ccgatctggg cgcgcctggc ggatatccct ggcgcctctg cggctaccga   33300
gatcggcaac ggccctgtg ttcgccgcag cggcctgatc atcgtgcagc tcttcgtgcc   33360
gacctacaaa ggcacgctgc tgctgacccg gaccgccgat acgctgcgcg agcacttcga   33420
gttctatagc gacccggtcc tgccgttcga gtgctttgcc gtctcccaag ccgttcccgg   33480
cgatgatggg cacggctggt accaggccaa cctgacgatc ccctaccggg ctggttgagc   33540
ccgactcacc caccgccgca cggcggtttt ttttcgccta tcacaggaga acgcccca    33600 tgagtagcgg cgcgaaggtc cagcttgcct ggatcaaaga ggtaaccccc gacgtcaccc   33660
cgccgggcga ctggcacacg ctcacccgta tcagcaacgg ggtgacaccg acctacaact   33720
ccgaggccaa caacgagatc ggtgccgacc gtatggctca gggtaccgcc atgaccaccg   33780
tcgacgttgg cggtgacatc gagagcaaat ggcgctacgg ggcgctggat gaattcatgg   33840
cctcctgctt cggcaagaac tgggtcgcga acgtcctgac catgggtaac gaccgcatct   33900
ccttctccct ggccacctat gccgcggata tcggcgtcgc cggtatcgcc cgtggcgccc   33960
aggttgcgac gatggcgttc gacttcccgg gcgacaacga gatcaccgtc accaccacgt   34020
tcgctgccac aagttggagc gataaggccg atgacacctc gttcatcgtc aacgcccagc   34080
cggagccggc gcagcgccgc tactcgttca aggacatcag cggcctaaag ctcaacgacc   34140
agcaggtggg agagggcaat gcctgcgtcg acagcttcaa cctgcagttc gacaacgcgg   34200
tacagaccca gcgctgtatc ggcaacggca accctttccc gggcaacatc atcccccacga   34260 cgttcactcc gtcgggctcg atcacgatca gttggtcgaa gatggcctat cagctctgga   34320
aggcacagca gaccggtgac gccatcagct tggagttcac cgtcagcaat gccgacggcg   34380
```

```
gctatcgcat cagcctcccg gagatggagg tcaacgggtc ctggccggat gccggcgccg    34440
aggaaatcgt ccaggtcgaa ctgaactaca ccgcgcgccg tatcccgccg accatcaccc    34500
gcctgccggc gccgatcgtg attgcaagtg tcaccgtcac gccggatacc gcctcggtcg    34560
ccgccggtga aaccgtagac ctggaagccg aggttctacc ggccggcgcc agccagaccg    34620
tcacctggtc cacctccgat gcagcgatcg ccaccgtgaa cgacaccggc ctggtcaccg    34680
gcgtggccgt aggcaccgca acgatcaccg ctaccagcac cgcggacccg gccaagaccg    34740
atacctgcgc gatcaccgta accgcgtaac cccttgcctg acgcgccctg cggtgcgcgc    34800 cgggccttt taccgcagag gaacaccatg gccatcaccc tgaagaaaaa gcccgaaatc    34860
gacctgtacg gcacccgctg gctgcatctc aaactggacg agcaggggca tctgtcgcct    34920
tgcgaggtag aagcggaggc cgacctttcg ctgttggtgg cgtcgactgg cgatccgctt    34980
ttccaatccc accacgcgat gatcaaccgc cacatgcagg cgatcgatgc tcaggccggc    35040
gtcggaacca gccagttcag cccgctgact ctggccgatg ttcagttcga caatatcgac    35100
gacctgctga ttggcctggt ggccaggcac atcatcaagg actggaaggg tgtgcaggac    35160
gaggcggcgc ccgtgtgcc cgccgactac acgccggagc gcggccaggc gctcatgcgc    35220
cagcaccctg atgcctactg gcttgcgctc aagaccggcg ccgacatcgc ggttcgcgcg    35280
gatctgcgta cccaggagac cgtgggaaag tcctgagcgc gtatcgctgg gctcgggact    35340
gggcgggacc cgacaacgag aagaagcgat ggaagcatga acggttcggg ctcccggtcc    35400
ccgcggagcc caccatagac gccgtctgcg ccgaggtgtt cgaggcctac caccggatca    35460
gcaggggccg gcagttcatc ggcatgatcg gcgcgccggc cccgctttct caccgcgata    35520
ttgacgccta cctcctgcgt taccccaccg ccatccccat cgccgagttc gaggcggcgg    35580
tcctcgcgat cgacgacgag taccgcgtcc agtgggccgc ggcgcaatca gaacctgctg    35640
aacaagaacc cggagaccgc catggcggaa gaaagtcgcc tctcaataat catcgactcc    35700
cggggcgctg agaagaacgc gactagtctt agcgacgcac tggaccgagt tgagcgcagc    35760
ggggacgaag ccgccggcag cacctctcgc ctcagtgagg tgactgtccg cctgggctcg    35820
aacatgagca aggctgcggc cgctaccgtt gcgtcgctgt cgcgtatcga gcgcgcgacg    35880
gagtcgacca gttcgcagat gacggcgctt gtctcccgcg ctgtcgccct ggaaaacgcg    35940
atgtcgtcgg tgggccaggg tatcggtcgg ctcgacaccg gcatcaccca gtcgaacgcg    36000
caacttggac agttgaacac ccagatgtcg catctggtgt cgacgttcag cacgtttttcc    36060 caggggcaga gcgcgatcaa cgcgcagtta tcgcgcatcg cggcgaacat gtcgcgggca    36120
gcggacgaga cccagaacct ggaccagtcc accagccgtg cgggccgcgg cgcgcgcgaa    36180
gccgcgagtg acctcgacgc agaacgcgcc ggcctggcgc gcctgctggg gcagatcaat    36240
cccactgtcg cggcgctcga ccgcctcgac gacatgcagc aacggctcac tcgctacaag    36300
aacttgcgcc tggtcgatgc tgagacggtg gcggagtaca ccgagcggct gaaggcaatg    36360
cgcaatgccc ttggcgacgc cgagggcggc atgaaccgcg ccgggatgtc ggccaaagcg    36420
ctgtcggcga acatgcggat gctgccggct cagatcacgg acatcgttgt cggcctgtcc    36480
tctggccagg ccccctgac cgtgctgctc cagcagggcg ccaactcaa ggacatgttc    36540 ggcggaatcg ggccggctgc gcgcgccgtc gggggctaca tcgctggact ggtaaacccc    36600
tacaccatcg ccgccgccgc cgctggtgtg ctggcgttgg ctttctacca gggttcggtg    36660
gagtcgtcgc gcttgaccaa cgccctggtc aagaacggca acgccgccgg aaccactgcc    36720
ggccaactct cggtcttcgc gcagcaggtc ggagcaggga acgcaacggt agcccaagca    36780
```

```
gccagtgcgt tgacgcaact ggctggcgcc ggcaaccagc tgaccatcct ctacccgaag    36840
atcgccgccg cggcgatcag ttggtcgaag gtcaccgacc agtctgtcga ggaggtggtc    36900
gacagcttca atgacctggc caaaaaccca gtcgatgcgg tgaagaagct cgacgaccag    36960
ctcaacttcc tgaccgcaag ccagtacgcg aacatccagt cgctgcagga gcaggggcgc    37020
acaatggatg ctgcccgcat tgcgaccgag gcatacgcca acgcgctggc gagccgctcc    37080
acggagatgg agcagaacct gggggtggta gagcaggctt ggaacggact gaagagtgcc    37140
gcgaagtcag catgggatgc catgctcgat gttggccgca ccgagtcgcc ggaacagcaa    37200
cttcagaagg tctacaagca gattgagaat gcccagaagg gcattgggcg aggtggccgg    37260
gccgcgtttg gcctgggtat cagccagccc agcctcgatg cgctgtataa gcgcgccgct    37320
gaccttcagg cgaagatcgc cgccgatggc gcgaagaacc tggagcaggc aacgaacaac    37380
gcgatccagg cggccggcaa gaaaggcatc gatacgatca acactacgtt cgccgccgcg    37440
cagacgcaga ccgagaagct ccagaagcaa ctggtggaac tcgacaaggc tcgaaaggct    37500
gccatggagg cgggcggatt cacagccgag gaggagacca agttcgcggt cgcacgcaag    37560
aacatcgagc agcagatcgc cgacatcaag gcgcgtgagg cgaagaagag cgcgccgaag    37620
acccgcggcc agaatgtcgg cgtgcgtgag gctgacaata ccgcctcccg cttgctggcc    37680
cagtacgacc cggccggcca ggctgtgcgt accctgacca aggaggaaac tcagcttcaa    37740
ctggcgctct ccagaggcaa gatcactcgc gaggagtaca gcaaggcgct ggctcaggcc    37800
tcgctgaact acgccgcggc aatcaagggg gcccagggcc tcaccgcagc cgagcagtac    37860
caggcgcagc ttgagcggca gttgttgctc cagcgtgagc aatacgctgc gcaggcggcc    37920
gccgtaggta tgggcggtct tgaagcagag cgctatcagc agcgcattca gcttgagcag    37980
caatcgaatg accgtgtcct gcaactgcag acggagctgg cccaggctac gaccgagaag    38040
cagcgtcagg agcttcaggc gcagatcgat ctggagcgtg aataccttcc caagcggatt    38100
caagcgcaga aagagggcta ccagcagatg gataaggccc ggcaggactg gctggctggt    38160
gcagcttctg gggctcggac ctggttcgaa cagatcgatg acacggcgag ccaaacccgt    38220
tcggcgatga tgcgcggcct ggatggggttg aacgatgagc tccataccct cgttacgaca    38280
gggaaggcct cgttccgtag cctcaccact tcggtgctga gcgacttggc gagaatcgcg    38340
cagaacaagt tcattacgtc gctcatctcg tccatgtctg ggagcagcaa cggtgtgatc    38400
agtgcgatcg gcagttattt caccgcgaat gccaaaggcg gtgtctacag ttcgccaagc    38460
ctctcggcat tcagtaacgg ggtgtacaac agcccgcagt tcttcgcctt cgcgaaaggg    38520
gcgggcgtgt ttggcgaggc cgggccggag gcgattatgc cgctcaccag ggcggcagat    38580
ggcagtctcg gagttagggc tattgggagt ggtggcgcga agagtgctgg tggcaatacg    38640
ttccagatca acaccaatgt cacggtgact gcaggcacga cttcgcagtc cgtcacttcg    38700
gacaccaatg acaactacgc catgcagcta tcgaagatga tcgccgatgt ggcgcgtggc    38760
gtgatagccc aagaatctca acccggcggc atcatctgga gaatgcagaa tggccgttga    38820 gaccttact tggtgcgttc actcacagtc ttctggaaca acggactatg cgacgctgaa    38880
cagaaagttc ggcgatggtt acgagcaggt ggccgagaac gggctgaaca acgtcgcgca    38940
gtcctggaat atttccatca gcgggaccgg caccaagatc aaggaaatca ggagcttcct    39000
tgatcgacac gctggtgcaa aatcgttcct ttggacgcct ccgcttggcg aacttggttt    39060
ctaccgggga accgcacctt cgatcagcgg aggaggggt gactactaca ccctgaccgc    39120
```

```
cacctttacc caggcatacc acccatgagc atcaacaccc agattcagaa actggagccg    39180
ggcgccgaga tcatgctctt cgagctcgac ggtagcgagt tcggtgccga ggtgctgcgt    39240
ttccatggcc acgccatccc tcacactccg caggagctag cagccgctgg cgcaaacgca    39300
gaccaactac ctgcgaagtc gatctggtgg cagggacagg agtactccgc ctggcccgtc    39360
caaatcagcg gcatcgaggc gaacggcaac ggcacggcag tacgcccgaa gttctcagca    39420
ggcaacgtga cgggcagcat caccgctctc tgcctggcgt tcgacgatct ggcgaacttc    39480
caactcacca ttcgagagac gctggcggaa tatctggatg cggagaactt ccccgacggt    39540
aacccagatg ctgaccctac tcaggaatcc atcagcgtct ggtatatcga ccagaaatcc    39600
gccgaggaca acgaggctgt tacctgggat ttggcaagcc cgggagatgt cggcaacgag    39660
gctgtcggca gacagatgac tacgctgtgc cactggtgca tgaccggcgg ctaccgtggc    39720
cctgactgcg gctacacagg cccgtatttc gacattgacg acaacccgac cgacgacccc    39780
gcgaaggacc agtgcgcagg cctctatcgg tcctgcaaca agcgttgggg gcagggcaac    39840
cagttaccca tcggcggctt cccggccgtg tccctgatcg cacggagctg accatgcgca    39900
agcagatact gagtgccatt cgggcgcacg cggccgagga gtaccgcgc gaggcctgcg    39960
gagtgatcgt cggtgccggc aaggcgcagc aatacgtccg gtgccgtaac acggccggac    40020
agccgcagga agagttccgg atgcatccgg gggactacgc tgcggcggag gacctgggcg    40080
aggtggtggc catcgtgcac agccatccgg acgcgaccag ccgaccgtcg ccgcacgacc    40140
tggccatgtg cgaagcgtct ggcctgccgt ggcacatcct cagttggccg gaaggcgacc    40200
tgcggacgat cgcgccggcg ggcaacatcc cgctgctggg acggccctt gttcatggcg    40260
tctgggattg ctggcaggtc tgcgccgact ggtacaagcg ggagtggggt atcgaattcc    40320
cgcacttcga gcgttccgac ggctggtggg agcgggcaga cggtccgagc ctctacgagc    40380
agcagttcga ggccgcagga ttcgtccggg tggaacggcc gcagcgcggc gacatgatcg    40440
tgatggaggt ggggcgtacc gcgcacccga accatgcggg gatctacctg gcgacgatc    40500
cgtcgctgcc gggcgaggag accaaagttt cggcgctgg cccgttcctg ttgcaccacc    40560
tgtacgaaaa gccagcgag atcatcgtct acggcggtaa ctggcacgag cgggctcgcc    40620
tagtgcttcg gcatcgccaa gccaggcaat aggttgtgct aacctccagc gatctgtaag    40680
gagggaatca tgaagaagtt gatcgggtg ccgcgctta tggcgatggc agggtgctcg    40740
tcgatgagtg agttgcgaca ggagaagccc taccggtcgt tttccagcac caaggggggtt    40800
gagcaggcgg cagagtgcgt tctgtttgcc tggcaaaatc aatccttagc aggcgttcat    40860
tatgacgttt cgctgcagcc gctacttggc ggcgggcgca ctgttgtctc gcaaggacag    40920
actgagttcg tcgacgtggt ttccaccgac agagggtcag atatcagcat ttacttcag    40980
tccgggataa tgggctggcg aaagaacagt cgaatcgagg cagtcaaggg ctgcctgtaa    41040
accaagccgc cttcgggcgg cttttcatg tctggaggaa gcatgtccgc gagtgtcctg    41100
aaataccgac agatgaccat catcaaatta tctgggccac tgatccggga gttcggtcgt    41160
gaacatcgcc ggcaactcga caccggaagc gtccaagaag ccttcagcgc cctgcgcaac    41220
acgctccctg gcttcaagga ggcaatcatg cgcctccagc gcttgggtat gcgattcgcc    41280
atctaccgga accgcaggaa cgtcggagaa gacgagttct ccacctatgg tgccagggag    41340
gtgcggattg tccgattat cgccggcagc aagcgcgccg gcctggttca gaccatcatc    41400
ggtattgcaa tggtcgcggt agcgactatc gccaccggcg gcatcggcgg atttgctgct    41460
ggcggtgcct ggggatttgt aggcgctact ggtgcctctt tggctctcgg tggtgtcgtc    41520
```

```
caaatgctca gccccaagc acagggcctg aagcagagtg cggcgccgga gaaccttccc    41580
agctacgcct tcggtagcgc cagaaacacc accgccagcg ggaacccggt tccgatctgc    41640
tatgggaagc gccgctgggg cggggcgatt atctcggctt cgatttacgc cgaggacaag    41700
gtgtaacaac caaccatgag cggcgaggcc gcggagaaa attatgagca gagaagcagg    41760
aaaaaccgaa aaggatggca aagaaaagaa gcttcaatat cgcatccttt tcgataagtc    41820
agggagatat atggccggta ttaagcttat ctctcaatag cttctatgaa gttgtcgatt    41880
agttggttgt aatgctcttg gcttccgcct tcgatgctta ccgatcgagc atcaagcagc    41940
cccttcttaa atgatgccgc ctcgaatcct ggaatttcct tcacggcact gatgagttcg    42000
ataatcgcat tagtgttggc tgaggcatgc gtggaaaaaa cggcttcaat tgctgctata    42060
cgttgttcca gattaacgct catttcgacc tcctaggtct ttaaccgcgc cgacattggc    42120
gcctcccgat ccctgggccg gcacgctcag ggtcgggaca cccttgcatg aaggcacgac    42180
gctactaccc cggtagagcg gttgccactg gcatttcatc cacgctgtac aaccttccag    42240
cccgcctcgc gcgggctttt tcatgcccgg aggaaagcat gggcgcagtt caccagcacc    42300
tggccggccg caagggcggc agtagcaagc cgaaacagcc ggtcgaggca cccgacagcc    42360
tgcgctcggt cgcgatggcc aagatcctgc tcgccgtggg cgaaggcgag ttcgccggcg    42420
ttccgagcga gcgcgacatc tacctcgaca cacccgct gatggacccg agcggtaacc    42480
tgaacttccc gaacgttaag tgggagtggc gcgcggggc ggtggaccag gactacatcc    42540
cgggcatccc tgccgttgag aacgaaacca gcgtcaacgt cgagttgcgc agcgatacgc    42600
cctgggtgcg ctcgctgagc aatacccagc tttccgcagt gcgtctgcgc ttcgcctggc    42660
cggcgcttca gcagcaggac accaacggca acatcggcgg gtaccggatc gaatacgccg    42720
tagatctggc caccgacggc ggcgcctatc aggaggtgct gcgcgaggcc gtcgatggca    42780
agaccaccac ccgctacgag cgctcccgcc ggatcgacct gccggcggcc accagtggct    42840
ggcagttgcg cgtgcggcgc ctgacgccga accagaacaa caaccgtatc gccgacacca    42900
tgctgatcgc tggctacacc gaggtgatcg acgcgaagct cgctacccg aacacggccc    42960 tgctgtatgt cgagttcagc gcagagcagt tcagcaacat tccggccgtc acagtcgact    43020
gccgcgggcg gaaggttcaa gtgccgagca attacgatcc ggagacccgg gcctacctcg    43080
gcatctggga cggcacgatg aaacaggcat ggaccaacaa cccggcatgg gtcacctacg    43140
acatcagtac caatgcgcgt tcggcctgg gcaagcggat caagccctgg atggtggaca    43200
agtgggagat gtacaagatc gcccagtact gcgaccagtt ggtgccggat gggaagggtg    43260
gccaggagcc gcgctttctg tgcgatctga acctgcagtc tcgcgcccaa gcctggacgc    43320
tgctgaggga cattgcggcg atctaccggg ggatgagcta ctgggcgcag ggcaattgg    43380 tgtcccaggc tgatatgccg cgcagcgctg acttcgacta cgtctttacc cgggcgaacg    43440
tgattgacgg gaagatgacc tacgcgcgcc cctcggctcg cgccagatac agccgcgccc    43500
tggtcagcta cgacaacccg gcgaacaact acgacaccga cgtgacgggc tattccgaca    43560
cgacgttgct acgccgctat ggcgacaacc cggtggaaat ttctgccatt ggttgcactc    43620
gcgagagcga ggcgcagcgc cgcgcgaagt gggtggtgct gacaagcgtg caggatcgga    43680
caatctcctt caccactggg acggagggcc ggatccccct gccgggctac atcatccctg    43740
tggccgattc gctgctggct ggtcgcgaga ttggcggccg gatctcgggt gttgctggcc    43800
gcgtggtaac gctcgatcgc gtcactcaag ccaaggccgg tgatcgcctg atcatcaacc    43860
```

```
taccgagcgg gcgcgccgag ggccggacgg tgcagtcggt caacggcaag gccgtcaccg   43920
tcactgctgc ctactcggag acgccggagc cggaactgtg ctgggcgctc gacgccgatg   43980
acctggctgt ccagctctat cgagtgatga gcaccaagcg tgacgacaac ggccaatgga   44040
ccatcaacgg cctgcagtac gagccaagca agttcgacca catcgatacc ggcgcacgcc   44100
tggaagatcg cccgatcagc gttatcccga tcaccacagt tgcgccgccg gcgagcgtta   44160
cgctgacctc gcactaccag ttcgatcagg ggttggcggt cagcacgatg accatcgcct   44220
ggcctgctgt agaaggggcg gtggcatacg acgtcgagtg gaagaaggat agcggcaact   44280
ggatccgcct gccgcgtgcc ggcacgacca cgtcgatgt gaccggcatc tacgcaggtg    44340
gctatctggc gcgagtgcgt gcggtgtcgg ccttcgacat cacgtcggtc tggaagagtt   44400
cgatcctgac acaactcagc ggcaagaccg gcgcgccgcc ggcgctggcg ttcctgcgta   44460
ccaccagcgg accgtggaag atcggcctgg agtggggatt cccggccagt ggcgcggcgg   44520
acaccgccta caccgagatc caacagtcgg ttaccccgg cggcagcgaa cagaacgcaa    44580
ctgccctggg cttgtttgcc tacccgaccg acacccacac gctgacctcg ctcgcggccg   44640
gcgctcgctt ggccttccgc gggcggctga tcgacaggac cggcaacgtc ggcccctggt   44700
cggcctgggt cgacggtata agctcgacgg atgcgagcga gtacaacgaa ctgatcacca   44760
aggagtacgt cgagtccgcc ctgggcgagc agttcttcgc cgacatcgat cagatgcagg   44820
tcgatatcag tggcctgcag gaccagatcg acaatctgac cgatgtgctg gcctacgacc   44880
cgacgaagac ctacgcgcag aacgatatcg tgcgggtcgg caaccggctg tatcaagcga   44940
agcaggcggt gccgctcaac gcctcgccgc cgaacgcgac ctactgggcc gacatcggac   45000
agtcgatcga gacggccaac ggcctggccc agcaggtggc caccaacacc gcggatatca   45060
ccgagctcga cggtaaggtc gaagcggcgg cttcgagcct ggatgttctg caggctgccg   45120
cccgccggga gccggcgacc ggagagaagg ccgatgcgct gaagggctgg gacaccattg   45180
ctcgagccgc caccgaagtc accgtgcggg cgaacgagga cgaagcgcag gcgaagcgga   45240
cgagcttgct tgaagcgcgc accgggaccg cggagggcag gatcgccacc gtcgagtcgg   45300
tcgttgcgtc gaacaatgct gtaaccgtcc agcgattgga tcagctcacc ggccaggttg   45360
cgagcaacgc ctcggcgatc agcaccgaac agaccgtccg cgccaacgcg gacagcgcac   45420
tggggcagcg ggtggatacc gtcagcgcgc gcaccgatac caacgaggcg aacatccaaa   45480
ccacatctca agcggttacc tcgctggatg gcaacgtcaa ggcgctctac agcgtgaagc   45540
tccaggcgca tgccaatggc cagaagtacg ccgctggctg gcaactgggc ttcgacagcg   45600
gtacgagcgt gacgaccatg gcgttccagg ctgatcggtt cctctggttc aacagttcca   45660
gcgggcagac cgtggcgccg gtctcgatcg tcggcgggca gatgttcatc aacaacgcga   45720
tgatccagga cggttcgatc accaacgcga agataggcaa cgtgattcag tcgaccgccc   45780
tcggtgccaa cggcgagccg ctgtggaagc ttgataaagc agggagtttg acgatgaaca   45840
gcgcaacgtc cggaggcttc atgaggcaga cagcggaggc cgttaaagtc tacgacgcga   45900
acctggtgtt acgggtacag atcgggaatc tcgacgtatg agctacggca tccgcctgag   45960
aaatgcggcc ggctccatcc tgatggagct caccggccaa tcgcgcgcta cggtctaccg   46020
gcagtcgctc ggcgccatca ccaacgggat gacggtgacg gtgccgggtt tgatcctgc    46080
gcgcggtgtt gtgttcatca ttgcgagcgg aaacgcattc ggtgaagtgc ccctatacac   46140
aatttccgga aacgtggtga cgttccactg gaacggttca tccggaacaa cttatgtact   46200
gcatgcggtg atgttctcat gagctatggg gtattaattc gggggaatag cggcagaca    46260
```

```
attatcgatg actcgaaccc gtgtattcac attgcggcat caggaacata cggcgtacag   46320
accactagcg aaactatcgt aagttatcca tctgcgatcc agtccccgta cgagccgtat   46380
gtgtacttta ggcctaatgg tccgcatcag atatacctgt tcaggcatat cggcagtcca   46440
gggaactgga ctggattcgc cttctggcag agcatctatc gagacgtgga tcctcctgtc   46500
tacggcggaa agtggaaagc tggcgcggtc atgttgccga aaaccggtgg gtggggaatg   46560
caggttttcg acaccagtc gcgggtgatg ttcgacagta accgggacat cgttcgctat    46620
ctcggtggtg cgcaggtttg aataaaatat gcgtataacc gaactggcc tggcggtttg    46680
gcgctgcaga cgtggtattt gccgttcccc tacggaactg aggcttactt tcaagtaagc   46740
cacttcaatg taagcgcatt tatcactgct gaggctccgc gtattgggtt tcttgagaac   46800
tcaatgagct tgatatttgt ttcatcaatt gttcagacgg aaactaatca gcaattcaac   46860
tggccgctca ttgcagtagc gtaaatatat ctggaggact atatggcttg gtattccacc   46920
ggcacggtcg ctgtcacgct gaattcgccg acagtcaccg gcactgggac cacattctcc   46980
gcgaacgtcc gggtcggcga tgcttttcgc ggccccgatg gtcgttggta cgaggtcaca   47040
aacgtggcca gttcgacggt catctcgatc aaacccaact accagggcag cacggccagc   47100
ggccaggcct atgcggtggc gccgatcctg ggctacgaca aggacctgtc agatcgattc   47160
aacctgatcg ccaaccagtg gggggcaacc ctggcgggga tcaagccctg ggcgctttct   47220
gcaaatgcgg cggcagcgcg gggggatctc ggcctcggca gtgcggcggt acgggaggca   47280
cttggtggtt cgggcgcgct gtactcgcga gatagcatcc tcggtgctgt ggctcaggct   47340
gggggcgtgc cgactggtgc gatcattgag cgcggcgcga atgcaaatgg cgattacgtg   47400
cgatatgccg acggaacaca gatgtgttgg ttcaacgcca gcgttactga tcaggcgatt   47460
gatgtcccat atggaagtct gtttaccgga acccgttcgt ggtcgtttcc tatcgccttc   47520
tcgggcagcc caaccgtgaa ccccggccta tttcgctggg ggactggagc aggctggggc   47580
actgttggcg gtatcgcaag cgcgacggtg gctacgttgc gcggatttga cattgtgtcg   47640
cgcgcggctg aacagcgac agtgatctcg gcatccgcga tggggaggtg gttctgatga    47700
acttcttgct tgttctttcg ccgcagtacg ggcctgcgga atttggcgac tacacaaccg   47760
tctcggtttc gggtggcgtg ctcactgtgg aggggcgtga ctatgcgttc cccgatctcg   47820
aagacggcgc cgaactcacg atggaggact tcgccgatcc atatcccgtc taccaggttc   47880
ggcggcgagg cgacacgatt tcggtgtgga tcatctacag atatccggcg ggtgcgaccc   47940
atgctgccag ataccctgag cctgttcccg ttccggggga tttcgacggg cctgttgatc   48000
tgccgacctg acaaacctat cgacgaacga aagcccgccc tgcgcgggct tcgccgtttc   48060
tggagctcac atgcctatca ctgagcagca actgctgcag atactcccga acgccggccc   48120
tcgagccggc gttttgttg gtgcgctgaa tcgcgggatg acgcggttcg gtatcacgtc    48180
acctgtgcga gtcgccgcgt tcctcgccca agttggccac gaaagcggcc agttgaccca   48240
cctggtggag aacctcaact acagcgcccg cggcctggct tcgacctggc cgagccggta   48300
cctcggcgcc gacggccagc ccaacgccct ggcgcagcgc ctggcgcgca accccgagc    48360
catcgccaac aacgcctacg cctcgcgcaa cggcaatggc gacgaggcgt ccggcgacgg   48420
ctggcgcttc cgcgggcgcg ggctgctgca gatcaccggc cggtcgaact accgcgccgc   48480
cggcgccggg ctgggccagc cgctggagca ggaaccagag ctgctcgagc agccggagtt   48540
cgctgcgctg tcggcggcct ggtggtgggc cagtcacggc ttgaacgacc tggccgaccg   48600
```

```
cggcgagttc gccgccatca ctcggcgcat caacggcggg ctcaacggcc aggcggagcg    48660
cctggcgctg tgggagcggg cgaagagggt attggcatga gcgccttcgt tcgagtgtcg    48720
ccgatcctgg agaaggctga cggtaaactt ttcttcgagt gtccgggttg caagatgctg    48780
cacggcgtca acgtcgaggt cgacggtcag ccccgctgga cctggaacgg cagcgtcgac    48840
aacccgactt ccagccgtc gatcctggtt cggtatccgt ggcgcctcct ggagagcgga     48900
gagcgtgagc aggttgtctg ccactccttc gtcaccgatg ggcgcatcca gtacttgagc    48960
gactgcacgc accgcctggc tggccagacg gttgatcttc cgccgcaggg ggatgacgaa    49020
tgacaggctt ccagtggaag gcggccggct tggttctggc ctgcctgctt ctggtcggcc    49080
tcggcgccgc cggcggtgtc tggctcggcg cgcgacacta ccggccgcag ttggatgccg    49140
cgagcgcgga tctggctgcc tgccgtgcct cccggggaga gttggagtcc gcagtggcgg    49200
agcaggtccg gcaggttgcc gcgctgcgcc tggccgacga gcagcgcgcc cgggatgccg    49260
cgcaggctgt ggatcgggga cggcagcagg ccgcggagca gtatgtcgaa gcccagcgcc    49320
tggtacgtga gcgaaccgcc ggtgagcagt gtgcggccac cgaggcggtc atcgatcagg    49380
agttgggcct atgaaactgc aggcgtggcg aaagactgca ggtgcagcga ttttcggcag    49440
gtgcagccga aggcgcagg tggtgcaggt gctgggggttg tgttcgcgc tggcgggatg      49500 cgccggccgg caggaagccg agccgcgcac ggtgcgcgta gaggtgccgg tggcggtgcc    49560
gtgccgagtg ccggtggtag agatgccagt ctgggccacg gcggggctgc ggaaaggcca    49620
cgacttacag accaaggtcc gtgcgttgct cgccgaacgc ttgcagagga tcggatacga    49680
ggcgcagctc ctggctgcga accaggcctg ccaggattag gagtagacta cggccttttc    49740
ctacgagggc agggcatgct ggtcattcga ttcaagggtt ggtcggtgaa actcgaccac    49800
caggtgggca cgctgggaa gttcggcatc tggtcattcc acggctcgga gagcagctac    49860
gtcccagaca tgcagacgat tctccggcat gcagcgatcc ggccggcgga gccgaaagaa    49920
ggcggggagg tcgaggtatt catctgtgat tcgcgcatgc cgcaagatga atggcggcct    49980
gtcggcagcg gtgtcgcggc ctatgagtcg gaccgctgac cctgtaccag ttttttgtacc    50040 aatcgatgcg aattctggcg aataatggtg cctgaaagcc gtga                     50084

<210> SEQ ID NO 7
<211> LENGTH: 61080
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9947)..(10668)
<223> OTHER INFORMATION: n is a, c, g, or t
<220> FEATURE:
<221> NAME/KEY: misc_feature
<222> LOCATION: (13676)..(15030)
<223> OTHER INFORMATION: n is a, c, g, or t
<220> FEATURE:
<221> NAME/KEY: misc_feature
<222> LOCATION: (28261)..(29351)
<223> OTHER INFORMATION: n is a, c, g, or t

<400> SEQUENCE: 7
tcactccgcg gcctcttctt cgtttgccgg tgccggcgga gtccaggtgc cattgcagta      60
ctggtcgatt tcagcctctg cccagcgggt ggcgcggccg aacttgcgcc ctttcgggaa     120 gtccccttc ttcatgtgat cgtagatgaa cgtggtgccc attccggttc tcatcttgac      180
catgttcaag tcgatgaagc gggggatgtc ttggtgctgt tgcgtattgc gcatagaaat     240
```

```
acctccctgg tccgtctata tggaccgggt gaaagttgga gggcggcgag gtgcagctag    300
tcgggcgagg cctctacctt gcgggtgcgt ggtttagaat ttgcggcgga ctcggtcgaa    360
tggactacct gcatcgggca aatggggata gctcattcgg tcgggttctt ctgttaggat    420
tgcgcggctc accggtgacg ggaccagcct tggcgggcat gtgcccctga tccggtgggc    480
agtctctgtc agaaggagct gagcatggga atgaatcgtc cgagccagaa gctacggcaa    540
gagttgctgg atatggcggc tacaggcgac gagttggtga ctgaggtcag cagaatcgcc    600
gagcgatgcg acgagatggc ggcattcctc ttgcgcgggc tgcttggaag gatgtacgac    660
aatatcgtcc aactcgaatc ccttgcagaa gaagttcgcg ccggccggat cgtccggaag    720
agcccggacg agtcctgagc gcggcctcta tccgaagcac cccgcctgcc aggccgccag    780
cgtgcggata tcgggaata tctccaccag ccctaccacg gccaggccga gggcagcgat    840
gatgccgagg gcggtcagcg ctctacgcat cgcttggccc tccctgactc gccgctgccc    900
ggtcaaggcg ctcgatctca gccagcgcca gggcacaggc cttgaccata tcgcgtcgag    960
cagtgctcgg cttccaccac tgttcatccc acggccatgc cagcgacacc agcagggcgg   1020
cggttccatc gttcggagcg ctggagccgg ccagggcgta gcaggcggcg gctcgggcca   1080
tctggccgtg gctgtgcgca tcgtcatgct ccggcgtcca gccctcgacc tcgacctgcc   1140
gcttccgctc tgcctgcacg tcgagccatg cttgcggcac ttccgtgccg ggcgcggcgg   1200
cgagcagatc cgcagccaac aggtacagga ccgattctgc gattccgctt tcaccatcgc   1260
gggcggcggc gtaaccagcg ccgttgttca ggttcatgac gacgatgcgc tctgctgagc   1320
gttcgatgcg ccacccctcc ggcacgctgt gctgagcctg tgcgaccggg tgcgcgtaga   1380
gcttgatgcc ggggccatac aggccggcag cggcctccgt ccacttcacc cagaaggcat   1440
gaattccgcg attggcgaga gccaccggct cctgcttctc cagctcagcg accctgacca   1500
aggcagcgtc gcgctcttgc tctgccgttg cgcaggccgt tgctacttcg tgcagccggg   1560
cgttggcagc gtcgcgctcg ttgatgcacg cggtgaaagc gcggtccatc tgctggcgtt   1620
cgaaccgcag ctcaccgacg atgcgctcat gctgggcgac ggtcatcagc ggcgtctgga   1680
ccttggcgca cacctcaagc gcggttccgc aatcctcggc cgacagaatg gtcccgtcct   1740
cgtagcggac gccaaccacc tccggccgct ccgcctctgc ctgctcggcc tgctttgcga   1800
aattctcatt cttttgcatc acagttcacc cttgccgcgc atggcgttca gttggttgtg   1860
gtcgggatgc cggtagttga gaagccacgg aggcgtgctg ataaaccggt tgttctgctt   1920
gatctggacg tgggcggtga tatccggctg gttcggccag tggtcgtccc actcgtccat   1980
cagttcagcg aatcgggcct gccagtcatc cggcatcgcg tgcatcatca cgcgcggaag   2040
gactgcgtat gcgctgcggc tcaggccaaa ccagccccaa agctggtcgt agccggaagt   2100
ggtcggcgcc gggagggt tcgccagggc ggcgcgggct ttccacccct cccatgcatc   2160
attggtgaac ttggcgtccc agttcacagc gatatgctcc ggcatgccgc agtgcttgcg   2220
aacgaagaat tcgaaaaccg cgcgctcatc cacgcctgcc tgctctaccg atgccggtga   2280
gtcacgaagc gctgtgccgg ccaggccctg gcatcttgc gtcggcgcct ggtcattgat   2340
cagggcaagc aggctctcgg ctgaggagtg cacctcgtcg aggtccgtcg accagcggtg   2400
cgggctggtg tcgtggatgt tgtccaaggc ttcgacgatg ccgcgcaggc gcgtagcgca   2460
ctgcttgatc agttggtgtt gggtagagga catggcggtg tctcctgttg ctccggcgcc   2520
ggcggccggc agcggaagca tttgcacagg cctatccgtt ggcccgtggt gcggcagatg   2580
```

```
gtggggcggt tcatttcgtg gcgtcttgct tcatggcttt ggcgtggccg acgcaggtgc   2640
ggaccgggtt tccctggtcg tccaggtcgg cgtggcagta gaaccggctg agttcctgcc   2700
ggcagtggat ggcatcggag gtggtgaccg gcgaggtgtt cgccggggtg ccgaggcgat   2760
aggcacagcc ggcgcacgtg ccgcgtgggt ccacagtggc ggccaggaca acgccttgca   2820
gcgctccgaa catcgtcggc aggttcgcct gctccgcggt gtgcgggtgt tcgccgcgct   2880
cgatgaggat caactccacc atcgcacggc agttctcggc gacggcgttg gccatgccca   2940
gcacctgggc gaacaggtcg agcatggcgg ccaggttgcg ctgggcggcc attttctcca   3000
acacctggcg gcgcaggtcc gccggcagaa gaacggcgcc ggccagttcg tgcgcgtcag   3060
cggcactgat ctggtagtcg atagggggct cagccatagt tcctcctggg gtttattcgt   3120
agggaccggt catggttgag ctgtcggaac tcggtacaga tgacgatcac gtcgggaccg   3180
tcacggcggt ggaccggcat cgtgctgaag tcgaagctcg aacagtcgtc caggcgtcgc   3240
tcgcaggcgc ggcagcgccc gcccttgggg tagtagttgg gcatggttgg ctcaggtgaa   3300
gagggtgggc tgggcgctct tgtccagcgc ctgctggatc ttggtgaagg cctcggggtg   3360
ctgctggtcg aacgctggca tgcgggcaga ctcaacccac gtgccgcgct cggcgccctt   3420
gtcgagccag gatcgcgtcc agttcgtggc gctgacgccg cattcggcga tctgcctcat   3480
tgtgatgaag ccctggcggc gtagcgtggc gatcaccttc agcgcgcctt ccttccattg   3540
ggtgagccga gcggagccg gaacgccggc aggcacgtcg ggaccacga tcgggacatg   3600 gcagcgttcc gcggggttcc agtcgaacag ttgcggtcca ctggagtgct ggagccagta   3660
acgcaccaac gcttaggagt gtgaagctgg cggcttttgg gtaggaacgg gatggactcg   3720
attgagccgc cgagcgcgta cttcacatta caggggaaaa gtttccatat aataaagaat   3780
acgggagttg cggctcttcc tatagtgatg cttcctcttt gttcttttcg aagctaaata   3840
tggatctgaa gcgacttaga ataaaatcgc tcattatttc gtgaagatca atcgtctttt   3900
tgtttacgag cattattttt cgtcttcgtt gcatctggtc gacatcgtta gtttgttctg   3960
aatctaacgt ggccagatcc ctaagctccg ctattagagt aatagccttt gtttcgaaag   4020
tatcaaagtt cccgtcccac ataatacggt tgctgcactt tattcttaag gcctttatgc   4080
gtagttctat aaaattgcac ctgaatgtaa tgtaggattg aaagagttgg catttcattg   4140
tgtgctcttg gtcggaagag tctgcatcgc gccaaaattt gtaattctcg tccgaaattt   4200
cttgcagcat tttgtctacg gtcgcgacaa tagcattagc ctcagcttgc ttcgctaagg   4260
ctctagaatt taaataagtg aatgcccagc ccgccatggc taaccaaaat ggtaatgaca   4320
tagtcgtctc cattagctcg ctggtttagc atcttcaata tattttctta tggttctcac   4380
tatgctgtca tatctgtaaa ttatttcgac cctttctagt acttcttctg gcttaaaacc   4440
ttcatatgct accaggccac caaaggcttc atctgtgaag gatgatccgc agcctaatgt   4500
accatttaag tcaacccttta ccttctggta ttcgctgagt ttctcaacca gaagttttct   4560
aaatgcgaat ccgttaaatt ttccatcttt ttcgttcctg ccgtaaggca tgtcagaaaa   4620
acttttggca acatcaattg tgatttcgct tttcataaat tatcctagcc ggatattcca   4680
ctgtatgaat gtgcccggca ttctgtctgg cagaggttct atgctgtcta tgttaggtgt   4740
catagcgttg aattcgtaag agccaagccc actatatatt agcatttgtc cttcagggtt   4800
cgcggtgaca aagtcctgcg cttcggccag tccttttcct ctgcctcccg tcttaaacct   4860
cgaattacca tactcaaccg ctgctctaat tgctaagctg tcgttagagc tggggaagcc   4920
aagtgaaccc aatagatgat caattatatc gctgtaccaa ggttttttttg aaagtgttgc   4980
```

```
tggtatgccg actcctgagt cgtacactgc aatgaataat tggttttcaa ttttctcgac   5040
aactatccac caatttttt  catcatctgg cagaggtttt ggatagaaat cgtcatcata   5100
tgcgtgttgc cagacgttac taaaagactc agttattgct gcaaatgcct ttaccccctc   5160
ttcttcattc attcccgagg ttttgattgc ctcttgaaca tacgttattg cgcgcctgag   5220
ttgagaggtg tcgccactct gttggtcttt gtaggaggtt gagcaaacct caaatcccat   5280
ggagagattt tttcgaatat gcttgctttc tttcgtaagt ctccagaggc cgatgcgttg   5340
tagtccattt gcgacgccgg agtgcctgca cactgttgtt ttaacaggat cttcttttt   5400
ttgttttttt tgaataattt ctactgttgc gtagagaatt aatgcggcgg aaattttat   5460
gtcttttgtt ttttgtagat ctattattat tttcgacctt gatgatgtga tgtgcagttt   5520
ctttatgaac tcaaagaatt ttttgtaatt ctcttttccg aagaaagaga tgctgcttgg   5580
agctggcacc acttctctgt caagtattct cttggcatga gtggctttgt ttggattgta   5640
ttttctggtc gatctgctag ccttcagaga ccttctgtcg gcaatgctct gatatatctc   5700
gtccgttgga tgtcttttcc tcatatctct tactgaatgc tccttcagg  cggcagtttg   5760
ccaagcagat catcctcata accttaccgt tctacgtagg tttatgctac tagacctgtg   5820
tggcggcgcc gctaggggcg atactctctt gacggaggcg attgccgctt atcttgacaa   5880
cctacgttgg gacagttagt ggctatcatt ctggcaatac gacactcagc gccaccgcaa   5940
ccgggcgcac ccagatcggc gtattgctga gcatgaaggt ttcgccggcc tcggccagca   6000
gcagggtggt gcccatcacg ccggcgatgg cctcggcggc ggccggcggt acggcgttgc   6060
cgatgcgctc gcgccagtcg ctgtcgctca ggccgtcgag gaccaactgc tcttcgggt   6120
cgaccaagct ctgcagcgcg gcgagttcca gggtggtaaa cggcctgtgc caggtgccgt   6180
ccaggctgcg gatgatgcag gtcagacggt cattcgcggc cggcatgcgc ggatcggcaa   6240
cgctccaccg gccattgtcg tgcctggcgc tggccgacac tgccgccgcg gactggtcga   6300
agcccaccac gccgtagtgg ccgccggtga ggtaggagtc tcccttcgtc cggttgagca   6360
cccgcgggtc ttcgacgcat tgccctgtgc cgtgggcact ggtaaccgct tgtgcatggc   6420
ggctccaagg cacgatgcgg aactcattcg agtgtttggc agggccgctg tggcgcgggt   6480
ccgcgacagc aaatgcaccc tggccggtag tactggccgc gatcacggtg ccggctgggc   6540
cgtcccagtc ggtgaccgga tacttgccga aactctggcc gcggggatcg cgacggagt   6600
acgtgccttg gccgggcgac ttgacgccga tgatggcgcc cgaggtgtcg gtccagcggc   6660
gcacgccgta ctgctggtat tgcagggcgt ttgccggcgc gcgaggatcc gcgactgaga   6720
accgcccgtt catcgggcgg ctcgcgccgg cgacaacgcc acacgaatcg ccccagtgat   6780
tcacgcccag gacgccccgg tggtactccg gcacgatgat cagatcgcgc aggtagccgt   6840
cctcgacggc caggtcgttc aggctgcgcc agtcgctgcc ggctcgcacc agagcgaggc   6900
gcacccaggt cttccactgc agggatggca cacggtgcat cgggcggcg  gcctcgatgt   6960
cgccgggaag cggcatgcga ccgaggatgt cgccgacggc gcggagcgac ttcttctctg   7020
gctcgtacag gaagggcggc actttctcga cgtgccgcgc gaccagcagg aaccttttcc   7080
gggactgagc caggccgccc agctcgccgc agtcgtgagt agtttccgcc acggcgtagc   7140
cgaacccgcc gagcaactgg ccgatctggt caagcaggtg ccggccgcgg ctggcgaggc   7200
gtgggacgtt ctcgaagacg atcagcggca ccgggtcatc agcccatgcc tcgcccatga   7260
gccagatgca gcgcagcgtc aactcgttca gcgcctggta cttcggggtc aggctcatct   7320
```

```
tctcggagag gaggccagag gcgcccttgc agggcgaact gatgaacacc gcatccggtc    7380
ggcgcccgcc ggcggcgcgc cgaatatctt ccggggtcgc ctcccgccag cctgccggcg    7440
gctccgtgcc gtggaaccgc acgtactggt cgcgggtgaa gaggtccagc agggtgcccg    7500
ggacaccagc caggcgctcg aagtcgcgca gtccggctgg gtccacgtcg atcccgccga    7560
ggcagaccca ttcggcctcg acgttgccga cccgcggccg cgcccggttg aaaccggcgg    7620
caccgccgcc caggccgcag cagaagtgga agtggtagag ggtgcgcttg atgatcatgc    7680
ggcgggttcc ttatggatga tgtcggcctc ggcgagctcg cagaagaagc tgcacgcccg    7740
gatatggctt cgttgcggcg gatcggcccg gagggaaggt cgcggagcga gtagcgttcc    7800
tgggtctggc ggttgcggaa gaggtacgaa cccgggccga gctcgtcctg caccatgcac    7860
aaggcttcga actgctcggg aaagtcctcc cggatcgccc ggaagtagcc ttctccgcct    7920
ttcacgcagc cgatgcagtt cgcgttctcg tagcccaggc ggtacatggc cggcagttcg    7980 atgccgcgc gggcgatgat ggcttttgcag tcctccttgc ccaggccacg ctcaatcagc    8040
ggcgcgatca ccgacggtc gggtttccg ctcgcgaag tcgtccagcc cggtgctctt    8100
cttccgcagt gaagccgagc accatcacgt cgccgggacg cttccaggtg tccagcaggc    8160
gacgcttcag cagcttggtg cagggcgcgc cagtgcggcc cttcatgtag cgctcgcggc    8220
ggaagacgtt gagcacgtcg gcgccgtact tctcgtcgcg cagcaccgtg aatttccggc    8280
cagtccatgc ctcgcagtcg gcaaggaagc gccggttgtc ctgatgctcg ttggccagat    8340
aggcattgag gaactggacg tcgtgggtat cgccgtactg cgccagggcc agcttgccgg    8400
cgaccgcaga ggccgcgccg caactgaact gggaccacga tgcgcgattc gggcttgatg    8460
atgtcgacct gactgctcat acggcggggt ttcctttttc gcgaacgtga ggacgcactg    8520
cgctatgcgt gatggcgcag tgatgtcgtt ggggctagag ttggatggcc ggcatgggg    8580 ccggatcagg gaggagagat gcctgacttc agaatcgtcg agatcgtgtt cgatgacacc    8640
aaggtctatt accggtatga cacgtgggt gcatcaacaa tcggtggaga gcaaacacct    8700
gcttatcagc aagacatcat cctcaatcat tttcggtctg ccgcaggcta tcggggttc    8760 tccgacaaag gttgaaagcg ctgcacttgt tgcatcgaag gccgtgggac gagtggtcca    8820
aactttgagc ggatccaagg ctcaagccag gtcgacaaag aacacttggg taaccaaggc    8880
gcatgcagat cgtaactatg aggttctcaa cacccagagt cgttaggctg tacgcgaccc    8940
gctagaagta cgtcagtact ccgtgaacag gcactggacg ccgccctgcc tgacagggcg    9000
gcccacgagg catggttgaa tcgcccacag ggcggcgtcc ggtgcgtgct ggaagagaaa    9060
gcgccccagg tggggcgctg tatcgagggt caggccgcag cctggagctg gtgaccacga    9120
cctagaggaa taaactgagc ttgaaatgca gatcgattgc cctaaaactc gatggtgaag    9180
tcacggtgct attacttgac caactagggg gatctatgcc tatcaagatg aatctgtctg    9240
gcctgaagcg tctgcagcaa aacctcaagc aactcgatgg cacgcatcaa gtgccgttta    9300
gcgagatcat gagtcccagc tttatttcgt ctaacagcaa gtttgcgaat tcgacgagt    9360 ttgctcgtgg tgccggttat aaggttgaaa ctgcggaaga tctacgggcg attccagacg    9420
agccatggga cgcttatgtc cgtagtgaga ctcctttcga gagttgggca gaaatgctca    9480
aggccggcat agtcgcgcat gccaagcgct cacttcaaaa ggggttgtaa ctcgccgtct    9540
ctactgaaac cgaatgctgc acgtgtggcc tttctccgcc cagaacgctc ggatgtgccc    9600
gagcgtttcg ttctgcatcg tcgatggggg cgacttcacg acagaacctc gcgagatccg    9660
tctccctgca tcggcccgac gatatccagc aattccattt cctctaccag gcgtgccgcg    9720
```

```
cggttgtagc cgatctttga gttttgcgctg atggcggag atcgaagcgc ggcgcgtctc   9780
gcggacgaag cggatggcct ccttcagcag cgggtcgtca ccgggcccgt tgacctgggg   9840
gatatggagg gtcgcggtga taccgtcgcg catccctagc gccttggtta cgtcgatgcc   9900
ggcgccaggc gctggctcgg gctcatcgta cgcaccgtcg attcccnnnn nnnnnnnnnn   9960
nnnnnnnnnn nnnnnnnnnn nnnnnnnnnn nnnnnnnnnn nnnnnnnnnn nnnnnnnnnn  10020
nnnnnnnnnn nnnnnnnnnn nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
nnnnnnnnnn nnnnnnnnnn nnnnnnnnnn nnnnnnnnnn nnnnnnnnnn nnnnnnnnnn  10260
nnnnnnnnnn nnnnnnnnnn nnnnnnnnnn nnnnnnnnnn nnnnnnnnnn nnnnnnnnnn  10320
nnnnnnnnnn nnnnnnnnnn nnnnnnnnnn nnnnnnnnnn nnnnnnnnnn nnnnnnnnnn  10380
nnnnnnnnnn nnnnnnnnnn nnnnnnnnnn nnnnnnnnnn nnnnnnnnnn nnnnnnnnnn  10440
nnnnnnnnnn nnnnnnnnnn nnnnnnnnnn nnnnnnnnnn nnnnnnnnnn nnnnnnnnnn  10500
nnnnnnnnnn nnnnnnnnnn nnnnnnnnnn nnnnnnnnnn nnnnnnnnnn nnnnnnnnnn  10560
nnnnnnnnnn nnnnnnnnnn nnnnnnnnnn nnnnnnnnnn nnnnnnnnnn nnnnnnnnnn  10620
nnnnnnnnnn nnnnnnnnnn nnnnnnnnnn nnnnnnnnnn nnnnnnnngg cttgctggcc  10680
agggcctgct ccagcgccgc ggcgtcgatt tgcaggtttt gggtgaggcg gtagatttgc  10740
aggttgcgga accacatggg gtgtctcctg ggtggcctgg cgcttacacg agacgccaga  10800
gcaggcgata ggggtcatcg aacggaatgt cgtcgtcgta gctgtcgtag tcggttgccg  10860
gttgcggctg gtggtgagtg gtcggccgcg gtggcggctc gcggccaggg ccacgcgact  10920
ggcctgcctg ctcaggcttg ccgccgagca gttgcatgtt gccgttgatg tcgaccacta  10980
cctcggtgct gtagtggtcc tggccgtcct ggccctgcca cttgcgggtg cgtaggctgc  11040
cttcgatgta gacctgggag ccctttcgca ggtattgcgc tgcgatttcg accagccggc  11100
caaagagcac gacccggtgc cacgtcggtg cgctcctgct gctggccggt ctgcttgtct  11160
ttccagcttt cgctagtggc cagactgagg gaggtgaccg cctttccgcc cggggtagat  11220
cttgcgtctg gatcctggcc cagatggccg accaggatta ccttgttcac tccgcgtgcc  11280
atggctcagg cctccgcctc agccggcggc accgaactgg ccggcgccac atcgactccc  11340
tgcaaagcga agtagatgcg ggcgcaggct tgggcgtccg gcatcgcgcg gtgagcctcc  11400
accaggtcct ccccggtgaa gtgcttgtat gcctcggcca aggtcggcag cttgttgcgg  11460
ggaagcgcga cctgtgcgcg ggagcgatag caggtgcaga acttctcacc cgattccttg  11520
aaggcgttgg ccgcatcctc gtcctggtag cgcatcagcg cgatgcgagt gatacggtcg  11580
tcgaagctga tgttgtgcgc cgcgcggcgg gctgcgcggc cgttgatcgc aagaaagccc  11640
tccagagcct cggcctcgct gatgccaaca tccatcgcct gttcgtggct gatgccgtgg  11700
atcgctgtca tttcgggggt gatttcccag ccgttgggtc gcacgatcgc ctcaaagcga  11760
tcgatggtgt tgccggcggc atcgcagagc agagcggcaa cttctacgat gtggggctgg  11820
cacgggtctt cactgggcaa cttccactcg ggaatacccg tcgtttcgaa gtcgaaaatg  11880
ttggtgagca tggtctgtcc tcagtggttg ggcatcaggc tgcgcgctcg atgaacgcgc  11940
acccggatgc cgcaccggcg gcgggcgccg gcgcaggcgg ttcgagggag agggggcagg  12000
cggagggat ggtcaggccg ctttcgcggg tgccttctcg acgatcacgc ccggtaggtt   12060
```

```
cagcgtttgg ccattgctgt tggccaggct gtccagggcc ggctggttga tgatcagcag   12120
gtcctcggtg gtgtggcccg cggcaatcgc tgcgatgagc gcggacttgt cggtgacgcg   12180
ggcgatccat tgggtggtcg gtgcagtcgc agtgcgagag cgtccggcgg cgcgggcagg   12240
ggccggtgca gcgggaactg gctccggctc ggctacggga tccggttgct gcgcggtagc   12300
ggcttcctgc tgctcgagtt ccaggcgctg gcgctcctct tcgcggatgc gttcgcgttc   12360
ggcctcgagg cggcgctcct cttccgcctg gtgctcggcg atgcgcgcgt tgatcagcag   12420
catcaggtcg tcgttggcct tcagcaccaa ctgctgcgca tcgctgaaca ggaaggcgtg   12480
gtcggtcgcc agttcgcgca ggctggccag gttctgctcg atgagcgtgg cccacttgtc   12540
ggcctcgatc ttcgctcggg ccaactcgcc gttggcgcca tcctgcagtc cggtgatcgt   12600
cttcttgccc ttgatggcgt tggcgaagtc gacagggatg accggcagtt gcaccttgcc   12660
caggcgctgg ttgatggccg ccacgtagtc gcagaagtcc tgctcggcct tgcccttgat   12720
cttcaagcgg atggcttcct tctgagtatc gaccagcttc ttcagcgtca gacgcttgtt   12780 ccgcgttttcc gcggcgatct cgtcgatggt gcggaacagc tcgtcgatcg aggccgtctg   12840
actcagcgca tgctgcttcg ccgcctccag gcgctcctcg acgttctcgc accacttcac   12900
ggtcagcgcc gcgtcggcga agtgctgatc ggtggtcagg tcggtgttga tcttggccag   12960
cacgcccagg gcggtggcct tgaattctgc caggttgctg gcctcgacca tgccggtgac   13020
cttgatgcgc agggccggca ggtgctccgg cgcgcggacc cacggcttcg gccttgggcg   13080
cctcgacttc gaaggcctcg aggtcggcgg cgaactggcg ccagccagcc tgcagcgctt   13140
cggcgcggcc ggcgaccggg cggtattcca tgtgaacgaa gttggcgcgg gtgccgtcgg   13200
agcagacgaa gatcacgcgc tcggcggcgc tgaccagcaa ctgctgttcc aactgccagt   13260
agtagtgcgg ctccagttcg ccagcgcgga cctgggcgac gaggttggca ttccacagct   13320
tgtgctcgaa caggacggtc tcggccatgt ccatgccgtc catgctcgcc agcaagttgc   13380
cctcggttgc ggtgaccggg tacagctcct cgccgatcat ctcctcgacg atcagccggg   13440
cggcagcttc agcggcatga ccgcggttga acagcgcctg ctggtgctgg ctgacctcgg   13500
cggccaggcc ggtcttcttc tgctttagta ggtcgctgcg cgactggtac ttcgaggcgc   13560
ccatcatgga ccggagcctc ggaagcggtg aagtgctggg cacgcagcgc gtgccattcc   13620
ggcgagcctt ggactacgtg tggatgatca tgcggatgct cctacggtga ccaggnnnnn   13680
nnnnnnnnnn nnnnnnnnnn nnnnnnnnnn nnnnnnnnnn nnnnnnnnnn nnnnnnnnnn   13740
nnnnnnnnnn nnnnnnnnnn nnnnnnnnnn nnnnnnnnnn nnnnnnnnnn nnnnnnnnnn   13800
nnnnnnnnnn nnnnnnnnnn nnnnnnnnnn nnnnnnnnnn nnnnnnnnnn nnnnnnnnnn   13860
nnnnnnnnnn nnnnnnnnnn nnnnnnnnnn nnnnnnnnnn nnnnnnnnnn nnnnnnnnnn   13920
nnnnnnnnnn nnnnnnnnnn nnnnnnnnnn nnnnnnnnnn nnnnnnnnnn nnnnnnnnnn   13980
nnnnnnnnnn nnnnnnnnnn nnnnnnnnnn nnnnnnnnnn nnnnnnnnnn nnnnnnnnnn   14040
nnnnnnnnnn nnnnnnnnnn nnnnnnnnnn nnnnnnnnnn nnnnnnnnnn nnnnnnnnnn   14100
nnnnnnnnnn nnnnnnnnnn nnnnnnnnnn nnnnnnnnnn nnnnnnnnnn nnnnnnnnnn   14160
nnnnnnnnnn nnnnnnnnnn nnnnnnnnnn nnnnnnnnnn nnnnnnnnnn nnnnnnnnnn   14220
nnnnnnnnnn nnnnnnnnnn nnnnnnnnnn nnnnnnnnnn nnnnnnnnnn nnnnnnnnnn   14280
nnnnnnnnnn nnnnnnnnnn nnnnnnnnnn nnnnnnnnnn nnnnnnnnnn nnnnnnnnnn   14340
nnnnnnnnnn nnnnnnnnnn nnnnnnnnnn nnnnnnnnnn nnnnnnnnnn nnnnnnnnnn   14400
nnnnnnnnnn nnnnnnnnnn nnnnnnnnnn nnnnnnnnnn nnnnnnnnnn nnnnnnnnnn   14460
```

```
nnnnnnnnnn nnnnnnnnnn nnnnnnnnnn nnnnnnnnnn nnnnnnnnnn nnnnnnnnnn   14520
nnnnnnnnnn nnnnnnnnnn nnnnnnnnnn nnnnnnnnnn nnnnnnnnnn nnnnnnnnnn   14580
nnnnnnnnnn nnnnnnnnnn nnnnnnnnnn nnnnnnnnnn nnnnnnnnnn nnnnnnnnnn   14640
nnnnnnnnnn nnnnnnnnnn nnnnnnnnnn nnnnnnnnnn nnnnnnnnnn nnnnnnnnnn   14700
nnnnnnnnnn nnnnnnnnnn nnnnnnnnnn nnnnnnnnnn nnnnnnnnnn nnnnnnnnnn   14760
nnnnnnnnnn nnnnnnnnnn nnnnnnnnnn nnnnnnnnnn nnnnnnnnnn nnnnnnnnnn   14820
nnnnnnnnnn nnnnnnnnnn nnnnnnnnnn nnnnnnnnnn nnnnnnnnnn nnnnnnnnnn   14880
nnnnnnnnnn nnnnnnnnnn nnnnnnnnnn nnnnnnnnnn nnnnnnnnnn nnnnnnnnnn   14940
nnnnnnnnnn nnnnnnnnnn nnnnnnnnnn nnnnnnnnnn nnnnnnnnnn nnnnnnnnnn   15000
nnnnnnnnnn nnnnnnnnnn nnnnnnnnnn gtcgtcgtaa atacgagtgt cgatgaagcc   15060
gaccgcatag gccagttcaa tttggccgtg gacgaacttc tggtccgagc gcgagaatcg   15120
gtgatcggcg catcgccgta atgccttcct cgatcatcag caccgcgcgt tcattcgccc   15180
aggccatcgt cgtcctatgc tcgtcctcgg gctccggttc cggctggtcc cagagcgggt   15240
cgacggcacg tcgtaagcg agttgcgcgt tgctgaaagc cgcgcggttg cggcgctcgc    15300
ggtatgtcca catcgggatg ctctccgtgg ttcacctgca ttcggctgaa cgctcgcgcc   15360
gccgggctgg cccgatgggg aggcggggag cgttcatgcg aatgcgggcg gagaaagtgc   15420
tatataaatt agaaaaacac aggagttact tgttatggat gggaagactg gagttaaggt   15480
tgtcggagtt gggcttttt tggttgttgt ggcgattata tttatggttg cagctgatgg    15540
aggtacaaac tctgtcgcgg cagcctgggt tcaggctatc ggttcggtgc tggcaatctg   15600
ttatgcgttt tatatagctg atacacagca taggcagtcg gagttagatc gtgaggagga   15660
gcaagagaac aggcttagga agatggtctc aattgcccat tatgcagaga gaatcattgt   15720
tcaggtcgtt gaagaacatc gtgaatatgt ctatgaagaa caaataaaaa atcaggtgaa   15780
tatgcttagg aatgccagag agctgttcaa gtttgttgac ctggataaat tgagaaattg   15840
cgaggattta gctgatttct tagacgtttt tcaactgact aaagatcttg aagattacat   15900
agctcccaag gctggaaaga tatattacaa aattgatggt gagggtctct taagaattgt   15960
ttctaaagct gaaacagcaa gaaagcgaat ggagtccaga tgtaagtcgt tagtttccca   16020
ataagaacct tcttgatcac ttcccattgt gccctggcgc cggagcgcca ggggagcgga   16080
tcaagagaca gcggtgcagt tgcgcagcag caccggcgtg gcttggccct cgacccacac   16140
gaccgccatg ccggcggcgg atagccgcgc cagcccgagc gtgcgagttc gaacgggtgt   16200
ggcgtcccgg tacgcgcaat agtcgacagt ggccgggccg gaatgcctgc tgttccaggc   16260
ctcgaccagc tccgccggcg gcaccggacg gacgttgccg atctgctggt agatctcgga   16320
gcggtgaatg gcgacgttgt ccggggcggt gatgccgagg cgcacctggt cgccttggct   16380
gccgaggacc gtgacggtga tgttgtcgcc gatatgcagg gtttcgccga ctcggcgggt   16440
gaggatcagc atgtgtgcct ccgatcagga tgctgggcgc gcgggctcag gccggctcgc   16500
agtgggaaag ggcaacgcaa ccggacacgc cggcgagcca gacgacagca gtgtggccgc   16560
cgaggagctg ggcttcggtt gtcgtcttgg tgcgcttcgg cgccgcgccg cgatggaatc   16620
ggtagtcgac ctcggtgccg acgcggtatg cggaattcca ggcagcaacg gtcgccgccg   16680
ggttggcgtt tcgcttcatc gggtgtctcc ggatagagtt cggtggggct ggtgtgcagt   16740
cccggcgaac cggggcgggt tgcttagcag ggccgcagtt ctgtgcagtc cgtagaaggg   16800
```

```
gcgcctacca tgatgcggcg ggaaatttca ccgtaggcct gggggaagtg ctggaacagc  16860
tcgttggcct cctcttgggt ctcagcttcg aaagccggat gccaatagga cgggctatcg  16920
ccatacttga cttcgatcat gaggtggaat gcttgagctt gagtgctcat cgtcttgccc  16980
tccagtgcgg taaagccccg gcgaaccggg gcatgctcct tatgcggctt tcaccttgca  17040
ggcgcgggcc tgcagctctt tgccgttcac ttcgacgacc aggtactcac cgccaccgcg  17100
gccggtgccc ttgttgatgg tgcgcaggaa cttgccttcc ttcgcgacgc cacgcgggtt  17160
ggtcaggatc acggactggc cttcttgaa catcggtgtt tcctctcgtt gtggtttccc   17220
gtatgcccct cccgtactgg cgaggggcat ctaggaaatc ggtattgctg ccggcgtta   17280
cgcgccacct ccggctgggc gaatgctttc tcggggacc tgagatcccg acagccggcc   17340
acgctttgct gccgactctc gcttgcgtg ctcgaagctg cacacccggg gcgaggcgtc   17400
ccctgaatcc cgttctgcct gtcggcaagg ccttggctcg ctgtggcctg ttctgtcgtc  17460
acgatgttct gtgccgacgg catgaaaatt atcagcggtc atattattgg tcaagacctg  17520
cggtattaaa aaatcaaaa tagcgctctt gaaaagtagg ggttctggta atactgtatg   17580
gatatacagc ttgtggaggt gcttatggcc aagcaaaaga aaaagcagga agcccaggtt  17640
ctcaccgcgg gtgagaagct aggggttgcgg gtgacccaga tgatcaactc gccgaaggcc  17700
caagagcttc ggacagtaac tattcaccgt ctggacacgg atgcagacga ggcctgggaa  17760
gggattatgg aagtgttggc cgagacggac ggcattgatc tgactttcaa cgatgacggc  17820
agcgtcacgt tgaggtggga ggagcaggag aggggcgagc aggcctggta gccccggacg  17880
gggctggcca ggcgggtggg agcgggctca gtgttttcta cgtctcatga cggaccacca  17940
gaagacccaa ccgatgatgc tgaggttact ctcacgcatt tggtccctgg tgtactcctc  18000
gtctgggtat tcgtcacggt taaagctgcg caggcggatg cctccgccgg gtaggcgata  18060
gacgaacttc actcgcagca tatcgtcatg cttcagggca tagatctcgc cgtcagtgat  18120
tgtgctgact gatagatcga ctccgatgat cgcgccgtct gcgatcagcg gttccataga  18180
gttccccgta acgttcacgc agaccgagtt cttggggtct actcccgact cccggaggac  18240
tgtgcgaggg aaccgaattt tgcgcttcgc ctgctccaga tcaggcaagc gaccatcccc  18300
cgctgcaatc tgaatttcgt tgaaatagggg aatctcgact tcattggcat ccagtggatc  18360
gccgtcatcc cagacgggga tcggttcgag gtcgcccctg gtatttgcaa ccggcttggg  18420
gcgtaccgtc gttgccatgc gctctatctc ctcggccagg cgcgggctga agtccctgac  18480
ctgaatctca agatagcgag cgaaaaccgc tgctgcctct gcgttcagcg cgttcttccc  18540
agtgaggtaa tgacttgccg cactctgggt ggtggcgcca agcccctcga gggcgatctt  18600
ctcttgagtg atgccgagtt ctcttttctt cgccttgtaa atggcattga gagcttggca  18660
ctcctgcttt tcttcggccg tgagcggccg cttcttcgat ttcatgttca tccactcatg  18720
atattaccag tgttcatatt tctctaagat cgccggtctt gtaaaattaa agaccgcaag  18780
taataattcg gaatgaccgc gtaggagggc atatgcagat cattcccatt aacgaatttg  18840
tggccgagca agggcaggcg aaggcagcgg agctgctcgg cgtgacccag ggggccatca  18900
gtaaggcgct tcgagcgggg aggaagatca atgtctaccg ctgcgaagat ggttcgtact  18960
ctgctgagga ggtgcgcgcc ttcccggccc aaaaggtgcg catggcttcg tgacatgcag  19020
ttcaccgtga cgatcaatca agcgaaagcg ctcgagtggg ggctgaactc gcagcaggcg  19080
ctgctgttcg ccttcgtcta cgagtgcccg agttgggcgc gcctggttca gacgcccgca  19140
ggtgatttct acgccctgag caaagcgaag atcctcgagg agttgccgct gctgacggac  19200
```

```
aagccggaca cggcgtaccg cttgctgaag cagatcgctg cggccggtgt gatcgatctg   19260
tcgagcacag caaccatcac actcgtgcgg ctaactgcga aggggcagga gtggaatcgg   19320
aaactggacg ggtcggaaaa atatccgacc caggtcggag aaaaatccga ggtcggaaat   19380
tcttccgagg tcggagaaaa atccgatgca ggtaggtcgg aaaaatctcc gaccaagatc   19440
ggaaaaaaat ccggggtagg tcggaaaaaa atccgttcag ggtcggaaaa atctccgaca   19500
aatcaggtaa ccagtaatca gggtaccaat caggatattg ccggggaggc tgcgccggcc   19560
ccgggcgggg aattcgtcgg cgccgagcaa gagcccgggc cgcgctgcca gataccggcc   19620
gacatgccag gcccgaaaga cccgaactgc aaggcgtacc gcacatgggc caactacgcc   19680
atggcctatc gcactcgata caccgcttgg ccggtttgga acgcgtcggt tgccggcaag   19740
ctttcgaagc tgatcgatcg tgtgggccag gccgacgcgc caaaggtggc cgcgttctac   19800
gtcaagtgca tccacgatgc tcgactgatt gctcagcacc atcccctcgg cctgttgctg   19860
gcgaacgctg agggctacca cacgatgtgg ttgaccaatc gcccgaccac cggaacgcag   19920
gcacgccagc aggagaacac cgcatcgaac ttgtccgccg ctgagcaggc cctggccgag   19980
cagagagcga ggagggctgc ccatgctgac gcctgagcaa caagacgaac tgctgctttc   20040
ccttttcggc accgccgagg caatgggtca gcaactcacg ccggccgctg cccaactcat   20100
ggttcaagac ctggctgcct acgacgagcc agtgctgacc gccgcattgc aggccgttcg   20160
ccgggagggc ggacgattca ctgttgccgc tgtactccgg catgtcgagt ccgccgacgg   20220
tcggcccgag ccgaacgagg cctggccgat cgccctacag agcttcgacg aggctgaaac   20280
ggtgcttatg acgccggaaa tccagcaggc ggctgtggta gccgcaccgc ttatgaaggg   20340
gcgtggtgac cgggtgggcg cgcgcatggc gttcattgcc gcctacgagc gcctgctcac   20400
tcgtgccagg cagcaggcgc tgcccgccag gtggtcgctg tcgttgggca gcgatgcggg   20460
ccgccgagct gctgcgatcg aggaagcgga acgcctgggg cgtctgctgg cgccggcagc   20520
gcagttgctg ctcgaacagc acgtactcga accggtttcg ccggccggca gcgcaatcgc   20580
cgggctgctg actggaccct ccgaccggct gctggcactg acgaatgacc cactgacccg   20640
cgaagccctt gcgagggagg ctgctggtgg ggggatgtg ccagacgact ttcgccggcg   20700
gcttgaagac atcaagaagc gcttggtccg cagggaaaag gcgaaggtcc gactgcgtga   20760
tcgccacctg cgccacgagc gcgaagacat ggaccgtcgg cgcgccgcgg ttcttcaaac   20820
catcgatcag ctacagagcc aggaggttca acatggctga agcactatca acccaggcgc   20880
cggccaagag cgcggcggcg aagaggaagc gcgccgggcg gccgatctac ctggagttca   20940
agcgcatggt cgaccccggac accggcgagg ttcgcctggc cctggtcgcc gacagcggca   21000
tcgacaagtt cctgctgaag gagcgcgggt ataaggctgg cgcaaaagtg cgcgcggagc   21060
tgaagcagcc gcgggacgtt cgcaagcacc gcctggtcca ccgcctgggc cagttagtcg   21120
cgcgcaatgt ggatgggttc caggggtgg atgcgcactc ggtgatcaag aagctacagg   21180
gagacgccgg ggtctgctgt agctcggagt attcgacct gggcgggctg gggcgcgtgt   21240
cgcgcctggt gccggagtcg ttggcgttcg acgaaatgcc cgaggagcgg ttccttgagt   21300
tctggcgagg catctgccag cacctgatcg agcactactg gacgggcatg agcgaagagc   21360
agatcggcga catgatcaac atgatgcccg aggaggtggt atgacccgga gccgcgacga   21420
ctactgggga ttcgtcgacc ctaccgcgga ggtggtgtga tgctggtcgc cgcgaagaag   21480
cctcgcaaga agacgtgcaa ggcgtgccgg gaggtattca ccccggagcg atcgctacag   21540
```

```
tcagtgtgca gtccgaagtg cggattggcg ttggcggctg ccaagcgaga gagagagcgg    21600
aagtctctgg cgaagataga gcgccgcgag atccgtgcgg ccaaggaacg cttcaagacc    21660
cgttcggacc atatgcgtga ggcgcaggcc gctttcaacg agtggattcg cctacgcgac    21720
gccgacaagc catgtatcag ttgcgattcc acggcctatg acgcagggct gatcaccggc    21780
agtcgctggg atgcagggca ttaccgctcc gtcggtgctt gtcaggctct gcgcttcgag    21840
ccgctgaacg tgcatcggca gtgcgtgcgt tgcaacaggg acatgtccgg caacgtggtg    21900
gagtaccgca tacgcttggt ccagcgcatc ggcgccgaga aagtcgaatg gctagagggg    21960
ccgcacgagc cccggcggtt tcctatcgat gaactgaagg agatcaaggc caagtatcga    22020
gcgctgtctc gggagctgaa gcgcaagatg gggaggggag tagggcatgg ctgaccctca    22080
gttcaaggag tggctgcagg agcagtggcg cattctgcgt caacacgggc tcatcgctga    22140
aggggagagc agatgaagaa atcttcgacc caggttgtac tcgacgccgt tcgggaactg    22200
cacagccagc agcagatcgt tactcgccag accctggtcg aactcacggg gctgaagccc    22260
ggcgttgtcg atgaccgcct gtccgttctg gtggacgact tgctggtgct gcgcgtcgag    22320
cgcggagtgt tcgtaccggc accgcagttc gatccgccca ggccgatcac tatcacgcag    22380
ataccaggtg gctgggcgaa ggtcgagatc agcgatgatc acgtcatcac gcttacgcca    22440
gcggagaagc ggatgctcgg cgaactgttg gcgggtgctg ctcagcagtt cgcagcgatc    22500
gatatcgggc attcgaacca gatactggcc gcagagctgg cgatcaagat acggaagctg    22560
gaaagagaag tggcagcatt gcgcgcagac aggaccgatg gtgggcaact caccttagcc    22620
atgagtgatg ccgctgctgt gcaatagact cagcataggg cgacgatatc accagcagcc    22680
actcgctcag acagagccgt cagcctgccg attccttctt gcaggaatcg gctcagttgc    22740
tcgatgcact cgtgctgatc ctgagtgagg cgaaactccg actccatggc tgccatcaag    22800
tccaggcagc actgattgag gaaacctacc tctagcagtt ctgcccgtaa tcgacgcctc    22860
agtatctcgt ccattccaat gtccatctac ttcgcataag cagttgggga ccgtagcaaa    22920
aacgagatgc cagtcacaat tatcagaacg attagggttt tcgccaacct gcatgatccc    22980
cctgtagggt tcgacccatc ccctctggcc cggacaattc cgggtcatga ctcagaagcc    23040
cagcacaaaa ccgaagaagg ccccggtagc gaagaagcgc gctactgggg cttccgcacg    23100
tcccccagcc aagaccgcag cgaaacggcc accgggtcgc ccgagcagat atacgcccac    23160
tgtcggcctg gctgtctgta ccgcgcttgc cgagggcatg agcctacgga aggtatgcca    23220
gttaccgggt atgccagcga tgtccacgtt cctccggtgg ctggccgacg agcagcatgc    23280
ggatttgcga gagcagtacg cgcgcgcgcg cgaggcacag gccgacacac tcgctgaaga    23340
gatcctgcag atcgccgacg acggctcgaa cgacacatac acggacgatg aaggccgcac    23400
gcatgtcgac tacgaccata tctccaggtc gaagctgcgc gtagatgctc gaaagtggtt    23460
ggcgtcgaag atggcgccca agaagtatgg cgaccgcatc accaacgagc acactggcgc    23520
gaatggtggc gccatagagg tcaagagcac agtcaccttc gtgcagccca agccacgagg    23580
tgacgacgag tgaccacctt cgtcgctgcg cctctcaacc tgaacatcac gctcccttc     23640 aaactggcgc cactgtacga ggcgcgccgg tacaaggtca tgcgtggtgg gcgcggcggc    23700
ggtaagtccc atggcgtggc ccaggtgctg ctcgacatgg gcgcgcgcaa cccctgcgc     23760 atcctctgcg cgcgggaaat ccagaagtct atgcgcgact cggttcaccg gctgctgcgc    23820
gactacatcg tcaagctcgg cctgaccgag ttctacgagg tgctggacac cgagattcgt    23880
ggccgcaacg gcacgctgtt cctgttctcc ggcctgcaag ggcacaccgt cgattccatc    23940
```

```
aagtcctttg agggcgtaga catcgtatgg gtggaagaag cccagggcgt gtgcaagaag   24000
tcctgggacg tgctgatccc gacaatccgc aaggacggat cggagatatg gctgacgctc   24060
aaccctgcga tggacaccga cgacacctac gtgcggttct gcgccgcgcc ggatgacgac   24120
gtgtggctct gcgaaatcaa ctggcgcgac aacccgtggt tccctgatgt cctcaaccag   24180
gagcgcctgc gcgccaagcg ctccatgtcg caggaggact acgagcacat ctgggaaggc   24240
aagccgcgca ccgtggccga gggtgccatc taccgccatg aaatcctgga cctgatggaa   24300
agcgggcgcg ttcgcccggt gccatacgac cctctgctac ccgtccacac ggtatgggac   24360
ttgggctgga acgacgctat gaccatcggc tttgtccagc gcgggccgat ggacgtgcga   24420
atcatcgact acatcgagga cagccatcgc acgctggatt ggtacgtggc gcagatcgag   24480
aaacgctcgt atcgctgggg catcgactac cttgctgcac gactgtcgta cccgcaacta   24540
cccagaccgg caagagcacc gaggaacagc tacaggcgat gggccgcaag gtccacgtcc   24600
tggccgccac cagcatagag gaaggcatca aggccgtccg catgctgttc ccgcgctgct   24660
acttcgacaa ggacaagacc gggcgcctgg tggagtgcct gaagcgctac cgccgtgccc   24720
tacaccagca gaccggagag gccatggcgc ccctgcacga cgaatacagc cacggctccg   24780
acatgttccg ctacgtcggc caggccgtgg aaatcatgcc caacgaaatg gaacgcacct   24840
acgaggaagc ggaagcgcct gactggcgac tgtgaggaca cgacatgcag atcactgaga   24900
atgaccgcca gtacatgaat ggcctgccac cggccggcga cacgccgctg accgtggacg   24960
agtacgccga catcaactac gaaatcgagg accagcccgc gtggcgcgcc gtcgccgaca   25020
aggaaatgga ttacgcggac gggaaccagc tcgacaccga cctgctgcgt cgccagcagg   25080
cactgggcat cccgcccgcg gtagaagacc tgattggccc ggccctgctg tccctgcaag   25140
gctacgaggc cgtcactcgc accgactggc gcgtgacgcc gaacggcgac gtgggtggcc   25200
aggacgtggc cgacgccctg aactaccggc tgaacacggc agagcgccag tctggtgccg   25260
accgcgcatg ctccgaagcg ttccggccgc agatcgcgtg cggtatcggc tgggtagagg   25320
tcagccgcga gtcggacccg ttcaagttcc cgtaccgctg ccggcctatc cgccgcgacg   25380
aaattcactg ggacatgaag tgcggcgacg actgggaggc ttgccgcttc ctgcgccggc   25440
agcgctggct gtcacctgat cgcattgccc tggtgttccc ggagcatgcc gaactgatcg   25500
gcatggtagg taagtacggc agcacatggt ggggccagcc cgatctcgga atgatgaag   25560 gcggcacatc caccggtctg cacaacgcat ggagcgaggc gcgggcatgg accgtgcagg   25620
aggaccgctg gtacaaccca agcagcaagg aaatctgcct ggtggaactc tggtatcgcc   25680
gctgggtgca ggtccacgtc ctgaaatcac ccgatggccg agtcgtcgag tacgacccga   25740
acaacctggc gcacaacatc gcgctggcgt ccggccgcat ttcaccgaag aaggtgacgg   25800
tatcccgcgt gcgccgctcc tactggctcg ggccgcactg cctgcacgat gggccaagcc   25860
catacacaca tcgtcacttc ccctacgtgc cgttcttcgg cttccgcgag gatgccaccg   25920
gaattccata cgggtacgtg cgcggcatga aatacgccca ggacagcctg aatagcggta   25980
tgtccaagct ccgctggggc atgagcgtca ctcgagtgga gcgtaccaag ggcgcgggtag   26040 acatgaccga cgcccaacta cgccggcaga tcgcacgtcc ggatgccgac atcgtgctga   26100
acgctgagca cttcgcaagc aacaggggcg ctcgcttcga ggtaaagcgc gactacaccc   26160
tgaccgacca gcatttccag atgctccagg acaaccgcgc caccatcgag cgcgtaagca   26220
acatcacggc cggtttccag gggcgcaaag gcacggcaac cagcggcatc caggagcagc   26280
```

```
agcagatcga gcagagcaac cagtccattg gccggatcat ggacaacttc cgcgccggcc    26340
ggaccctggt gggcgaactg ctgctggcaa tgatcgtcga ggacatcggc caggagcgca    26400
ccgaggttgt tatcgaaggc gatgccgtaa ccgccgatcg tgtcgtggtg ctcaacgagc    26460
cgcagcgcga tccgcagacc ggcgccgcct acctgtccaa tgatctgctg cgcactcgga    26520
tcaaggtcgc cctcgaggac gttcccagca ccaacagcta ccgcggccag cagctcaatg    26580
cgatgtccga ggccgtcaag agcatgccgc cgcagtacca ggccgctgtc ctgccgttcc    26640
tggtcagcct catggacgtg ccgttcaagc gcgacgtggt ggaggccatc cgagccgttg    26700
atcaacagca gaccccggag cagatccagc agcagatcga ccaggccgtg caggacgccc    26760
tggccaaggc cggaaacgac atcaagctgc gcgaactgga gatcaaggag cgcaaggcgg    26820
atagcgaaat cagtgggctg aacgccaagg cagtgcagat cggggtgcag gccgcattca    26880
gtgccatgca ggccggcgcc cagattgcgc agatgccgat gatcgcgcca atcgccgacg    26940
ccgtgatgca gagcgcggga taccagcgcc cgaaccctgc tggtgacgac ccgaactacc    27000
ctgtagctga ccagactgct gccatgaaca tcaagtcgcc ctacatccaa ggacaggggc    27060
cggcagcaga agcggaggca gagagcgtcc cggtacgtag aaacactagt ccgacctatc    27120
caccagtgcc agaagaagca ccaacggggc tgcgcggtat cgaaactccg agcacggcag    27180
acaacctatc agttcgaggt ggctaggggg gggagggcag tggaattggc caacggccct    27240
gcgtatagtg atggcatttt ggactgaatt cctcacggaa agagcatggc taaaaaatac    27300
gcacatataa agaatccgtt aacagtaatc gctatattcg caacatttgt tgagcttggc    27360
ggaacagtag ttctgcctct attagaaggt gaagtacagg atcaatatgt ttggttcttg    27420
atgggctttc cttctttctt ggttttacta ttctttggtg tgttgtggtt taaacatgaa    27480
gtgctttatg ctcctaaaga ctatcgcaat gatgatacat tcttcatgc gcgtggaatt    27540
gcccaggctt cgcaggcttc agttctcgac aaaataatag aagaggttga cgaaacacgc    27600
gtgcatacag attgcgaacc tgtcgtagac tcattgccag gcaagttaga gatcagtgtg    27660
tcgaacgttc cggcctctca ggacgctagc ggtggcagcg cgtccggtca agatgaagag    27720
caggagggac tatcgttaga agctatggag cagccacctg agcgtgcgcc tgagccgact    27780
gacttggttc ggtctgttca agatatattt aagcaagaaa atgatgcact tgatcttctc    27840
tccagagaaa agaaaacttt cttccaaaga aatgttgctc ttgaagggggg tgcatacatc    27900
tttagtggtg cgtcaattac gccaaaagaa actctgttgg tagaggtttt tagaccttgg    27960
cagatattta acgggaaaaa ggttgggatg atccaagaga ccgtcagtca atattatcat    28020
aattatcacc ttggatctga ccatgttcgg tttaagttta ttgttttagt agtggggcg    28080
gatcgctcct gcgttgtttg ctcaagagcg ttgtgcgcct taaagaaatg tttacggggt    28140
tatggtgtgc cgcatgaggt ctatgctgta aatagcattc aaactctcaa caaagtttga    28200
atcactgagt gcattacaag cttggactct gtccgggctt tcttttgtgc gttagttgac    28260
nnnnnnnnnn nnnnnnnnnn nnnnnnnnnn nnnnnnnnnn nnnnnnnnnn nnnnnnnnnn    28320
nnnnnnnnnn nnnnnnnnnn nnnnnnnnnn nnnnnnnnnn nnnnnnnnnn nnnnnnnnnn    28380
nnnnnnnnnn nnnnnnnnnn nnnnnnnnnn nnnnnnnnnn nnnnnnnnnn nnnnnnnnnn    28440
nnnnnnnnnn nnnnnnnnnn nnnnnnnnnn nnnnnnnnnn nnnnnnnnnn nnnnnnnnnn    28500
nnnnnnnnnn nnnnnnnnnn nnnnnnnnnn nnnnnnnnnn nnnnnnnnnn nnnnnnnnnn    28560
nnnnnnnnnn nnnnnnnnnn nnnnnnnnnn nnnnnnnnnn nnnnnnnnnn nnnnnnnnnn    28620
nnnnnnnnnn nnnnnnnnnn nnnnnnnnnn nnnnnnnnnn nnnnnnnnnn nnnnnnnnnn    28680
```

```
nnnnnnnnnn nnnnnnnnnn nnnnnnnnnn nnnnnnnnnn nnnnnnnnnn nnnnnnnnnn    28740
nnnnnnnnnn nnnnnnnnnn nnnnnnnnnn nnnnnnnnnn nnnnnnnnnn nnnnnnnnnn    28800
nnnnnnnnnn nnnnnnnnnn nnnnnnnnnn nnnnnnnnnn nnnnnnnnnn nnnnnnnnnn    28860
nnnnnnnnnn nnnnnnnnnn nnnnnnnnnn nnnnnnnnnn nnnnnnnnnn nnnnnnnnnn    28920
nnnnnnnnnn nnnnnnnnnn nnnnnnnnnn nnnnnnnnnn nnnnnnnnnn nnnnnnnnnn    28980
nnnnnnnnnn nnnnnnnnnn nnnnnnnnnn nnnnnnnnnn nnnnnnnnnn nnnnnnnnnn    29040
nnnnnnnnnn nnnnnnnnnn nnnnnnnnnn nnnnnnnnnn nnnnnnnnnn nnnnnnnnnn    29100
nnnnnnnnnn nnnnnnnnnn nnnnnnnnnn nnnnnnnnnn nnnnnnnnnn nnnnnnnnnn    29160
nnnnnnnnnn nnnnnnnnnn nnnnnnnnnn nnnnnnnnnn nnnnnnnnnn nnnnnnnnnn    29220
nnnnnnnnnn nnnnnnnnnn nnnnnnnnnn nnnnnnnnnn nnnnnnnnnn nnnnnnnnnn    29280
nnnnnnnnnn nnnnnnnnnn nnnnnnnnnn nnnnnnnnnn nnnnnnnnnn nnnnnnnnnn    29340
nnnnnnnnnn ncgaggccat cgccgcaatg gatccggcat ccatgtcggc cgtcctgggc    29400
ggcatgagcc ccgatcaggt cgaggcattc ctgaaccgga acatgtaagg gagctacccc    29460
atgaccgcaa gcaaaaccac catgcgttac ggtgatccga acgcgatgat ccaacaggcc    29520
gccggcttgt tcgcgctctg ccagggccgc aactcgaccc tgaaccgtct gaccggcaag    29580
atgccgagcg gcaccagcga cgccgagaag aagaccaagg gccagtcgag cctggagctt    29640
cccatcgtcc aggcccagga cctgggccgc aacaagggcg acgaggtgcg tttccacttc    29700
gtgcagccgg cgaacgcctt cccgatcatg ggtagcgagt acgccgaggg caagggcact    29760
ggcctgaaga tcggcagcga ccaactgcgc gtcaaccaag cccgcttccc ggtggacctg    29820
ggcgatgtga tgtcgcagat tcgcaacccc tacgacctgc gccgcctcgg ccgtccgaag    29880
gcgaagtggt tcatggacgc ctacctggac cagtccatgc tggttcacct ggccggcgcc    29940
cgtggtaacc actacaacaa ggagtggtgc ctcccgctgg agacgcaccc gaagctggct    30000
gacatgctgg tcaaccgcgt caaggcgccg accaagaacc gtcacttcgt ggccagcgcc    30060
gatgccatca ctggcgttgc gccgaatgcg ggggagtaca acatcaccac cgccgacgtg    30120
ctggatgtgg atgtggtcga ctccatcgcc acctacatgg accagatcga gctgccgccg    30180
ccgcccgtga agttcgaggg cgacgaggcc gctgaggatt cgccgatccg cgtcctgctg    30240
tgctcgccgg cccagtacaa cagcttcgcc aagcaggaga gttccgtag ttggcaggct    30300 gccgcactgg cacgcgcgtc gaacgccaag cagcacccga tcttccgcgt cgatgcgggc    30360
ctgtggtcca acaccctcat catcaagatg ccgaagccga tccgcttcta cgcgggcgac    30420
accatcaagt attgcgccga ctacaactcg gaagccgagt cgagcgccgt ggtgccggat    30480
agcttcggca atcagtacgc ggtggaccgc gccctgctgc tgggcggtca ggccctggcg    30540
caagcctggg cggcttccga gcactccggc atgccgttct tctggtccga aaggacatg    30600 gaccacggcg acaagctgga actgctgatc ggcgcgatcc tcggctgctc caagattcgt    30660
ttcgccgtcg aggcgaccaa cggcctggag tacaccgacc acggcgtgat ggcgatcgac    30720
accgcggtca agatcatcgg cccccgcaag taagcgacaa gggtcggtga tcccggccct    30780
ttccttcgtc cagattgaaa ggaggcccgt tatggcccag tacaagacca tcccgctcgg    30840
cggccagttc ggcggtgtca cgccgtatgg caacctgacc accctgcgtt accagctcgc    30900
gaccaacgcg gccggcgttc tgctcaacag caatgccgcc gcctcgctgg cggttggaga    30960
tgtcgtggcg ttcgagttcc cgttgcccgc cggcttcgtc gccgaagacc tgcaactggt    31020
```

-continued

```
gatttccgac cacttcggtg ccggcgtgac cgctgacgtg ggctttgcct acgccgacgg   31080
cgtggacgac gcgacctatc cgcaggacgc cgcgtatttc ggcgctggcc tgctgctgtc   31140
ggccgctgcg cgcctgcgca ccagttccag caaggcgctg ttcgcgctgc ccaaggacgc   31200
caacctggtt atcaccatca aaggcgctgc cgtcgcggag cgggcaagc tccaggtgat    31260 cgtccacggc gagcgcctcg gcgcagtcta agcgccgccg ccccccgaag ggccggcccg   31320
cgctggccct tctgtcacgc aggagtagga cattcatgaa acccatcctc atcgccacca   31380
tcgcccacgc gatcaattcc gcctactgcc tcgccatcgg cgacaaggtg gcaccaccgt   31440
tcgccgagtg cccggaagac atgcagcgcg gcatcctggc cggcgtgcaa ctccacctgg   31500
acaacccaga caccaccccc gagcagtccc atgagtcctg gctggcggac aagctggcca   31560
acggctgggt ccatggcgag gtcaaggact cgaggcgaa gacgcacccg tgctgcgttc    31620
cctacgccga gttgcccgag tcgcagaagg tcaaggacta tctgttccgc gccgtggttc   31680
atgcactcaa ggacatcccg gacgccggga gccaggacgc cgacgcgcgc gtggctgagt   31740
tgcaagacca actcaacgag gtgctgggca agaatgcggc cctggtggcg cagatggcga   31800
gcgacggcgt gcccatgctg gataacggcg tgcccatcaa gtacatcgga ccgcgggaaa   31860
gcttcaccga ccgcctgtat ggctccgggc tgatgttcac ccaagggcag gtgcgtagcg   31920
tgcccggcga tctggcgcgt cgattcctca accatcgcga cctgttcgag cgctccaccg   31980
gccccgcgcc ggccggcgac gacatcaagc aggtgatcgc gcaggctcag caggcccagc   32040
aggagcgcgc tcgcaaggag gaagacctat cggccctgca ccgggaggtg gacaacttcg   32100
ccgacttcac cagcctggcg gcattcgcca aggaccgcta cggcctgaac ctggtcaagc   32160
agcacggctt ggcgcgttcc cgtgatgccg tccacgcgcg catcgaccag ttcggtggcg   32220
cggtatgacg ctggccgacc tgatccgccg agttcgcacg gacgcgaacg acatggtgga   32280
gccgtatttc tggtcggacc aggacgtggc cgactggctc aacgacgcag tgcgcgaagc   32340
cgccgtgcgc ggcaggctga tccacgagag ccaggccgac gccgtgtgcc gcatcgaggt   32400
ggtcgccgga actgccgtct accagttgca tgcgtcgcta tacgaactgt cgcacctggg   32460
cttctacccg gccgatatgt cgcgcccgac catgccggtg ctgaagtcgg ccgaggtgct   32520
ggacgtggag ctgccggaat ggcgcgcatg caccggcaag ccgctgtacg ccatccaggg   32580
cgacacttcg ctgcgcctgg tgccaacccc cgaccgggct ggcattctgc gcgtggaggg   32640
ctaccgcacg cccctggctg acatggcgct ggccgacaag gacaccgcgc agccggagat   32700
tcacgccgag caccaccggc atctggtcca gtgggcgctg catcgcggct tcagcatccc   32760
cgacatggag tcgttcgatc cgaaccgcgc cgcgctggcc gaagccgctt tcacggccta   32820
cttcggcgag cgcccgact ccgacctgcg gcgcatcacc cgtgaggatg ttccccacca    32880
tgtagaggca ttctggccat gagcaagaag atgagcgtgg acctgaaggt cggagaggta   32940
ctgctgatcg atggtactgc catccgcctg gaaaagaagt ccgggcaggt ggcgcgcctg   33000
cagatctcgg ccgacgaagg caccgttatt caaaaccccg cagcagcgcg caggagtgcg   33060
ctccaagacc tggagcacac ccctgatggc aaatacccc tatgactatg cccgccagcg    33120
cttcctggag ggtcagttca actgcatgac cgacacgatc aaggtgatcc tggtcgatac   33180
cggcgcctac acgccgcaga ctgcgatcca ccagtacctg tcggatatcc cgtcgtcgtc   33240
ccggatcgct ggcccggtca ctctcaccgc gaagaccacc actggcggcg ccgccgacgg   33300
tgcggatgtg acgttcacca gtgtgtccgg cgcgagcatc gaggcaatca tcatctacaa   33360
ggacaccggt accgagtcca ccagcccgct gattgcattc atcgacacgg ctaccggcct   33420
```

```
gccgatcacc cctaacggcg gtgacatcat cgtcacctgg gacaacggca cgaacaagat    33480
tttcaaagtc tgatcaacca cgcgcaggag tgcagaagat gctcaaacgc aagaataccg    33540
acgccaccac gcttgagatt gaacagatcc gcatcgaact tgctcgttcc aaggcccgtg    33600
agcagggcct gctgatcgaa cgggaaatgt gggtggagca ggggcgccag ctccagaacc    33660
aagtccagac ctggcagcgc atgtatgcca gcctgttcga ccagctcggc cgcggtgtgg    33720
tgacggacaa ggatattcag gacaacctgg cgctcgccac cgaggccatg cgccagccca    33780
tcaccgccgt ggaagccgtt cgcgccgcct cgccatgtg ccaggaggcg acacaaggcc    33840
agtacacaag cgtcgggcgc cgcaataagc gcgccgggt agcgaaggag ggcagcgatg    33900
agtggcacaa ctgagcaggc cgtgaaaccg ccgacgcaag gcatcggcgc gcaaggtatc    33960
gagcccaagc cgatcgaact aacgccgact caggacctac atgtcaactg caggccgtc    34020 ggcgcgctcc cgcccttcca gatgttcgtt cacgagcagg ctccatgtcc ggccggccgc    34080
tgccagcagc agtgggctat cgactacggt gtgcgctacg gcgcccaggt cggagacaag    34140
gtgctgctgg agcgctatgc ccagtggcac caggcgaaag gctactggcc caacgaaacg    34200
ttcctcggtc aaccggttga gggagcgaat taatggccga caccatcgac ctggacggcg    34260
aaaaattcgt ctctccatca ttcgtcacca gtgcggcatc gctcgacgac atctacaccg    34320
cctgggtggc cgacttccaa ggctcaacga ctgcctataa cccaagctgg ccgagtaccg    34380
atgatagtgc gacgctgcta ccaatcccgg cgctgtggac cggcggggcc gataggttgg    34440
tggtttctac cgagtgtggt gtggagattg tcccctacca gttcacctcg gcagtacgc    34500 actactcaca ggcgatcgca ggagttagcc ggtactactc gatcaactgc gggctacgcc    34560
tggcgattat cttccacccg actggtgtcg actcaggtat taccagcttt tcgggcaact    34620
acaacgccga cctggcgcta tttcgcggca cgcataaccg atccagtgaa aacgtccaat    34680
tcgtggcgcg tgtcgttccg ggcaggcaaa tcgatgtggc catcaagaac accgcccaaa    34740
ctgctggact ccccatcaag ctggtggtcc tcaacggcac cactgtggtg tcttccaccg    34800
acctgactac gatcgttcag ggtggtgtca cactggtgac atgctccatc tacggtggaa    34860
ccgtctcggg caccgtcgtg gaccaggctg gccagcctgc tacccgcatc gtccatgttc    34920
acgagcgcga aacagggtcg gtgatcggta gaggacgcag cgactcatca ggtctgttcg    34980
aaattccggt catcgcgaag gtgggtacca ccatgtacgt agtcggcctg gacgatgaga    35040
actcgccgct gatcaatgct gtgatcgccg atcgcatcgt gctggagtag ctatgaccac    35100
gggcgtagag ctgcgttttg acgcagtacc cagcggctac gtcccctcta gcagtcgcaa    35160
cgtcacgctg ggtggcggcc cgccggcgaa ccttcccgaa ggaaccatcg gagcttgggg    35220
cattcagcca ccgctgctct cgcgcgatgc ccgggtagtg cggacaatcc ttccggaccc    35280
gcacgcatcg gcggatctcg acttctctac cgttgacccc ggctacgtgc cgccagcgtc    35340
caatgctgtg ctgcttcagt ggggtgagtt ccgccggta gagggccaaa cggttttccc    35400
gggcggattc agcgattcca tggtaccgcc accggcgatc cgtactcagt atcgctttgt    35460
gttgcctgta ggatcgtcgc accaagtgtt cggcgccgcc aaggcttgga agtacagcac    35520
gttcgtttcg gcctacggct tcaattcgaa cgtcatcgga tcccacaacg cacagaacaa    35580
gcaccgaacg gttcagccga ccggatttgt cgcctaccaa agcgggcagg cgaacatcat    35640
caaccgaaac cgctatgtgg cggccggcaa cattgcgccg ccgccgtggg gcgcgaatcc    35700
cacggtttgg ctgtacaccc gctatctgaa gcctggcggc ctactggcga ccgcgatccc    35760
```

```
ggatgtccac cgcatcagcc acgaacgcca gttcgtgcag ctcaatgctg gtgttccagc    35820
gccaggcatg gggacggcat gggtcagtca gggaacgcgc gttctggagc ccattggcac    35880
gtttctggat gccgtggcca gacctatggt cggcggcacg cgcttcttgg agccgccagg    35940
ctgggattcc tcggcattcg gcacgcggat cattcccgag tcgcagacgg tcgcgcctca    36000
aggcttcgcc gagttgtggg ggcagcaggc gatcaacaac tggctcacct tgccgagcc     36060 ggccggattc cagagcaccg tccaggaaga ataccgctgg ggccgcgcag acgtgtggaa    36120
cctgcgccag tacgtggtcc aggagtacga cccggacagc gagttgaacc cgccacccctg  36180 gtcgcagtgg acgctggtgg agaaccgaaa ccgtcaagtg gcaccatcg gcatgccttc     36240 gccgccggcc ggcttcccgc agatcgacaa caatgccagg ccgatcttgc caggcggcgt    36300
ggcgccgccg cagatcacca ctgcagccat gattgcctac ggccgccgtt acctgccgct    36360
ggaaggcatc gaaccgccgc cgatcctgaa ttggcatgcc gtctacaacg gcgcgagggt    36420
gttggtgccg accggaatg ctcaaagcgc tttcggtgtg gcgagactgg agaacacgcg     36480
gcgttacttc gaccgcatcg gcggcttcga ctcggtggat atcggcatcg cgttcatcga    36540
tttcgccatt cgcggtatca gcatcgagcc gcgctacagc atcgagccgc cggatatcaa    36600
gttgcccgag gtcaagctgt acacgcgcta tgtcgatccg gtaagcaacg acatgctgaa    36660
catgggcctg gcggctctgt cgatccactt caacgcgatc gggccgaggt gggcgcacaa    36720
agacctgttc ggcgatccgc gcatccacaa cgtgacgccg gaggtcgcga ccttcggggc    36780
gaacgccgag gaattcggtt cggccttcgt gcgcctgcaa tggcgtccgg tggcgccgga    36840
cggcagtaac atgcagttgt tcggccaggc aaagatcgcc gaccgcaagc agaccatcac    36900
ggttccaggc accaacctgc tcaggatggg cgacaagctg gtggtgacca agaccggcgc    36960
gccgccgtac tcgccgcaga acatcatggt tgatcaggcg gttaacaccg gagcggtgct    37020
cggaaagccc ggtctgaatc agtacgtcct gtacgcgaca ggcatccggg cgccggacat    37080
cgaggagccg acggtgcgca tcatgggcgt gaacatcgac gccggcatca aggtggacgg    37140
ctacggcctg ccagccgtga gcttgaagct gcgcaagctg acggtggacg aatggcccga    37200
cgctgaagtg ttccagccat ccaagccgcg tctcacgccg cacaccatct gggcggtgaa    37260
ggaggcaccc gagcaggcca agcagaacca tccagccggt aacctgcact atgtagggga    37320
aacgctggtt tatccgccgg gtgagcgatt cggctcggcg cgcatcagca cctacctggg    37380
catcctcaag ccttttcccgc tgggcgacgt gtcgaagatg ggtgagcatg cgatctacct    37440
gaagcgtcgc tacctggagc cgcggggtct gcaggcgtat cgcatgggtt gggcgatcgt    37500
gggtgatggc actcagttcg tgacacagtt cgccggtgct gattcgatgt tactcggggt    37560
gcctgccgta gaccgtggcc cctattacgg cccgcaaaca gttcggcctg ctggtctgcc    37620
ggctcctggc ccgggtgggg ctacatgggt atcgctgctg gatcgtcgac tccagatgac    37680
cggattcccg tcgcaggcta tgggatattc gcgtggagaa ggtccgtacc agtggcagtc    37740
gctgcatgtt ggaccgccga tgccgaccat tccaagcggt accgacacat cagcattcgg    37800
tacagtctgg gtttcgctgc gggtgcgagg ggttgagccg gacggttggg agtcgttcat    37860
ctgcgaatac gacccgtcgc atttcgcgga tcgcatgcga gtccgcaacg tcttcacccc    37920
accgggtcca aatgcccagt ccgtggcacc tgtagggttg gattcagtgg atgtgggcgt    37980
gcccaatgtg cggccaggtg tccactacat ccgccctgac ggcaacgccg atcagtaccg    38040
caaaggagct ttctgatggc cacgacttcc ctggtgccgc tggccggcat caacaacgtc    38100
gccgaagatg ccgcgctgca acgcggcggc gagagcccga ggctctatgt gcgtgatgcg    38160
```

```
gtgaacatag acctgtcgcc ggccggcaag gcgcaactgc gggcctctgt gcgccaggtc   38220
acggaccagc cgttccgcca actctggcaa agcccactgc acggcgacgc cttcggcgcg   38280
ctgggcgacc agtggggaaa ggtcgatccg cattcatgga cgttcgagcc gctcgcacag   38340
atcggcgaag gggacctgtc ccacgaggtg ctgaacaatc gggtgtgcgt cgccggaacg   38400
gcgggcatct tcacctacga tggcgcgcag gccgagcgcc tgacgctgga caccccggcg   38460
ccgccgctgc tggtggcagg cgccggatcg ttgagtcaag gcacctacgg cgcggctgtg   38520
gcgtggctgc gcggccccca ggagtcggcg ccgtcgctga tcgccttcgc ggacgtgacc   38580
gatgccggcg cgctggaagt caccttccg ctgtgcttgg atgccagtgt gaccggcgcg   38640
```

```
cgcctctacc tgacgcgagc gaatggtggc gagctgctgt tggccggcga ctacccgctg   38700
ggcgcggcca cggtcatcct gccgacgcta ccggagctgg gccgaccggc gcagtttcgc   38760
cacctgtcgc ccatgccgac cggcaagcac ctggcctact ggcgcgggcg tctgctgatc   38820
gcgcgcgcca acgtgctgcg cttctccgag gccctggcct accacctgca cgatgagcgc   38880
tacggcttcg tgcagatgcc ccagcgcata accttcgtgc agccggtgga tggcggcatt   38940 tgggtggggcc aggtcgatca tgtcgccttt ctggatggcg ctgatccggc aagcctgagc   39000
gtgtcgcgtc gtgcatcgcg ggctccggtg cctggtagtg cagtcctggt ccctgccgag   39060
gtggtaggca ccaacgcatc accggatggc tcgccggtcg ccgtgtggct agcggagaac   39120
ggctacgtca tgggcaccag cagtggcgcc atcgccgagg ttcatgcagg cgtgctcgcc   39180
ggcatcaccg gccgtgccgg tacctctgta gtgttcgacc gccgtctact gacggcagta   39240
agctgaatca ccccgaatat cgggccttca atcgctgcgc aggagtgcgg catgggactt   39300
cggagagaac cctatgcaac gcattagcag cgctctgcgc aaagaaatgg ccgccgacct   39360
ggccactggt agcttcgaca tcaccgaaaa cggcattgcc ttcccgcggc tcagtgtact   39420
ggccggtggc gaatacttcg gccgcatcaa cagcggcgag tgggagaagg agggcgacaa   39480
cctgatcccc accgagggcc tggcgcacat cctcaacatc gcgctgggca gtaagcccaa   39540
ggtgtcgtat ttcctggccc tgttcgctgg gacggcagca cctgctgcta actggaccgc   39600
tgctaacttt gccgcggtgg cctcggagat caccagcatg accgagggtt acaccagcgc   39660
tacccgccca gcctggacgc cgaccgacac cgctaccggg tccatcgaca acatgaacac   39720 cgtgcgacc gtaaccatcg ccacagcgtc gcagctcaac gtcaacggcg ccgcgctgct   39780
gaccaacagc accaagggtg gcaccacggg tgcgctggta tcggcgtcga agtacgcggc   39840
gactcgtgtg ttccagaacg gcgataccta cgatatcggc taccggctga accttaccgt   39900
ctaagccgat gtattcgccg cgccctacg gacgtttcgc ggaagacgcg gaactctccg   39960
ccgacgatgc cgccgctgtc gagcggctgg ccaggaacct gacgaacttc aagcaggcgt   40020
ctgagctggc cagcctgaag cgcgttgctg atctgcccag cggtcggcag gcggtggcca   40080
tcgacatggg cggggtgttt cgcatcctgg tgctcgagca gcatgagctt ccgcaattcc   40140
gtttcgacgg tgtggcacag accaacatcc ccatgctgtt ctccggcgtc atcacccgcg   40200
cccaggtgct gaccgatggg cagggcgttg gcataaggtt gaccgagcag gcccggcgcc   40260
ggctggtggc ctacgacccg aaagcggcgc ttccgccgaa ggacgtggcg ttgcaacgct   40320
ttgtcatcaa gtacgaaccg cgtttccaat acttcgagcc gcgcgagcag ggcatctaca   40380
ccttcactca gtacgtcaag caacgcccga cttggtacag cggtgccatg gctgaagtca   40440
tgcaggtggt cggcggctat gggcgtcagc gcctggagga tcttccggag aacgatctgg   40500
```

```
agcgtgcccg catgctggta ccagagcgct acatggcgct ggtgcgcgag cagcttggaa   40560
acgtgcgtct gcccggctac agcggcttcc cggacgaagc gggtcaattc aaatgcgagt   40620
atgcggcctt tcgttgccat ggtgtggcct tcgactcaag taacagccca tggctgctac   40680
agatcgatgg ccggggcgtc tacgctatgc cgctgccggt agtgccggcg accacaaccg   40740
atgcgttccg ccgatatatg gaggaggtcg gcgacgatga aatcctgcga ctgttggatc   40800
gcttcggcgg gatgccgtcg ggggaaggtt tcccacccac tggcagcgag ttcgaggcat   40860
ggcgtcgcgc gggcgtcatc atcaaagtct gcgatcccgc tgacttctac agcgctaacc   40920
cgatgtatac ggcctgcggc tgggcgatga acagtcgagg tactgaaggt ttcaatacct   40980
gttggggtta tgacgacacc ggcctgatgc gggtccatgc gtacaaaatg cgcttgtcgc   41040
tggcgccagc aaagaatcag gggcgcatcg agaacgaatg gcagttcgat gacgaggagc   41100
agcgcgccaa gctcaatgcc tacctttcga aggtttacag cgcgttgtcc gccggcggcg   41160
cgcgtgagtt ggccatcatg tacaaagtca ggcgcgttcc ggttgcgcag atattggcgc   41220
gggccgcgat tgaagctggc aatgaccctcg aatattggga gaatctagaa cttcccccga   41280
tcgcgcagca tcaggggcac attagccgcg tggccagtgg accgttctac tggccgtcca   41340
aggtcgaaaa atcgtgcact cggctgaagt ttcccgagct gaccgctcag ggctgtgagt   41400
cgttcgtgca cgtgtcgcca gactacttcg gggctccggt ccagtgcgac acggttatat   41460
tcggctgcta cgtccaggac cagcttcggg ttatcaagta tttctacgac gagcggaagt   41520
tcaagaagga agctacgagt tcattcgaag acatcatgat cgttggtcag tgggagcaaa   41580
ttgagacttt cggtcttagc gggctgatgg gcttcttcta cacaaccgac ttcgacgacc   41640
ggcaggagca accggcggta acggtccata ccaccatcgt cggcaccgac atgggctatg   41700
gcaacccggc ttactccacg ccacccacac tctggtgcgt cggcggcgtg agccgatcca   41760
ggtactacat gcaccgcacc acggtagaca ctaccgagac gttcaccctg gacgtggcgg   41820
cgcttgtgcc ggtgttcgag cgcgattgca tgctctacgc ctaccaggac cataccgggg   41880
gacgcagttc ccacgaggaa acgacgcaag gctctgtgcc tgatcccacg tcctacgaac   41940
tctggtgcta cgacgacatc tggcactgga tggggcagac gcggaacggg aaccggggcg   42000
acccgccatc caaggatggg gtgccggtct atgtcgacac gctggtctac agcccaaccg   42060
aagtcagcga cttcgccgaa agcggcaact ggctgaacct gccacctggc ggtttttttgg   42120 atgtcacggg catctgtggg ccgtacacct accgcaactc cgtccacaac gccaacggcg   42180
tcattatcgg cggcgaagcg ccaggcttcg atccgtaccg gaaggacacc cagtaccca   42240 acgagaggag cgggcgcctg agtgtgtgcc tgtccgtggc cggcgctgtt caggtcaaca   42300
aggatatgcc gcactcgtgg tactgggact tctcgcccga gaacgacttt tacttctacc   42360
gcgacgccgt gcatgtcgcc atcggcgacg cccggtacgc cagcatctac gagacgagcc   42420
aggatggact gcgccgccgc tgggggcata ccgcgctcgc cgatcacaag gcggcccacc   42480
acttcatagg ggttatcaat gagtgactac cgcgacgact ccaacgacac ggcggtaatc   42540
agcgacacga cctggctggg gttgtcggcc gtcagcgaag gcaccgcgcg catcagcgag   42600
acggtgctgt acgggctgct ggtgttgcac accgatacgg cggcggtgtc ggatgaggct   42660
atcgaccgac cggcgcacct gctggtggat caggcaacca tcagcgatgc ggcgagcgac   42720
cggctccgcg ccagggtgct ggtggtcgat acgccacgg cggcggatcg cgttaccggc   42780
acccttcgtg tcctgcacgt cgatgacgcc ctggtgtcgg atggggtgct ggatcgcgtg   42840
cgcggcctga cggtggacgg tgccacggtg gccgacgaag cattcggcac ccgtcatgcg   42900
```

```
ttcaccctgg tgctggatgc cgcgcgcatc agcgacagca ctggccaggc cgccagtgtc    42960
ctggtcgagg acgccgccac cgtcagcgat caggcgactg gggcgctgca cggtcgcgta    43020
ctgctggtgg atggggcgtc cctcgccgac gaggtggtgg acgcgcatca ggccgtgcag    43080
gcgctgctgt tggacggggc atccattgcc gcgctggtgc tggaccatct ggcggcgcgc    43140
gacctggtat cggatgccgt ggtgatcgag acatcaccg tgggggcga ccaggacggc      43200 ggccaggctt ggaccgcaaa cgtcgatagt tgggcgatga ccgctacgc gccgtatacc     43260 ttccggtcgc ttgctgtgat cgacggtcgg ctgtacggca tcgccgaaga cggcgtttat    43320
gcgctggacg gtgacagcca gccggtggcc ggcagaatcg cgaccgggaa actggacatc    43380
ggccagggcg cgctggtgca tccgcatagc gcctatctgg agtatgcact ggatgctgat    43440
ggcacggtgg ccatggacgt gaccaccacg caaagcggca gcgcagcgac ctacagctac    43500
ccgctggaga gcgagcctgc agacgagttg accaatgggc gcttcaagtt cggccggggc    43560
ctgcgcggca ggcacttcac gttcacgctt cgcctgaccg gccggcacgg ctatatcaat    43620
gacctgagcg tcgaatcggc gccgaccaac aggagagtgt gatgggtatc gcaccggaca    43680
gcatccttgg cgtggcggtg gaaaccgtca ccgacaaaat caacgacctg gacacgctgg    43740
cgcgcaacta cagcgcgcaa ctcagcgaag ctctggcggc catcggcaac attacggtag    43800
cggatgtgcc ggcaccgacg cggccggatg cgcctatcgc gtcgccgccg cccgtcaacc    43860
tgggcgagca gccgacctat aacccgtcgc cgctggtcaa gccggaagcc cctggggcc     43920 tgaatatcga cgacctgctg gccgacctgg atgtgggcga catggacgac ctacccgacg    43980
cgccgacaat gattccgatc aacatcccgg acgcgccgag catgacggcc atcccggtgc    44040
cggaacgccc ggacatcgac acaacggtgg agattcccga tgcgccgcag atcgccatgc    44100
cggacatgga agcgctggaa cagatccgac tgccggaatt cgagttcccc gagttgccta    44160
cgttcgacgc cacgccgccg gacgcgagcg ggatacggt gcccaacgtc ttcatcaact      44220
ggctggagcc ggagtaccag tccgaggtgc tggacgagtt gcaagcgaag atcaaggaac    44280
tgatggcggg cggcaccgga ctgccggcgc ccatcgaaca ggcactgttc gcccgtgccc    44340
gcgaacgcga cagtggcgaa accacccgcg ccgtgcagga ggcggtcgat acttgggccg    44400
cccgcaattt ctccatgccg ccggggatgc tcgccaggca ggtagatgtg gtgcgcgagc    44460
aaggccggct gaaggcggcc gaactgaacc gcgacatcct ggtgcaagcg gccacctggg    44520
aaatcgagaa cctgcgcttc gccgtgcagc agggcctggc cctcgagcag ttgaccgaga    44580
acatgcacca gaacatggcg cagcgcctgt tcgaggtcgc ccgcttccac gcggaaagcc    44640
agatcaacgt gttcaacgcg cagatcagcc tgttcaacgc gcagaacgcg gccttcgaga    44700
cgctggcgca ggtctaccgc accaagctgg atgcggctat ctccaagctg actgcctaca    44760
agaccgccgt ggagggccag gtggcgctgg ggcaaatcaa ccagcagcgc gtcgaggtgt    44820
tcaaggccaa gctggacgcc gtacagtcga cgtcgaggt ctacaaggcg ctgatgcagg      44880
gggcatccgt gcgcgccgag acgatcaaga accagttcga cgcctaccgc gcagacgtgc    44940
aggcgtatgc cgagcagatc ggcgccgaga aggtcaagtt cgacgcctac gaggcccgcg    45000
tcaagggcga gtcggccaag gcggacgtgc tcgatgcgca ggcccgcgcc tacgcttcga    45060
ccattcaggg gttggcgaac aaggccgatg tcaaggtcaa gggcgcgcag atcaagatgg    45120
aggcggcgcg caccaaggtg tcgaagttct tggcggacgt ggacgcctac aaggccaccc    45180
tgcaggccaa cctgagcgag gtgcagtaca acacgtcggt gttccaggcc caggtagaag    45240
```

```
cctggcgcgc agcggccagc gccaacgtgg ccgacgccga aatgcaatct cgctttgccg    45300
acatgaacag ccggaccaac atcgcttacg ccgaaatgca gatcagcgag tacaccgcga    45360
agatgcagaa cgccgtacag caggcgcaga tcgctctgga ggcggcgaag gccctggggc    45420
agtacaccgc tcagctagcg gccggcgctc tgtcagcggc gcacgtgtcg gctagtatca    45480
gtggctccgg cagcgcgagc agttcggaaa gcaagagcga aagcacttcc accagctaca    45540
actacaacta ctgacgcccc ccgtagggtt cgtcccgatg cggcctggca ctggatcatg    45600
ctccggtatc aggccgtttc tattagggge tacccatgtt cggattcaag aaaggcgcga    45660
aatccaaagt tcagcagttg gctgaaggtg ggcgcgtgac tggcccgggg accggaacct    45720
ccgacgacat caaagcagaa gttccggcgg gctcctacat catgccggct gattccacgg    45780
aagcgatcgg cgaggaagca cttgggggc tcggggcgcc ggtagcggtt aacttgagcg    45840
acggcgagtt tcaactgcct ccggaacaag ttcatgccgt tggcgtgaag gctctggatg    45900
caatgaagga tgccacgcac accccagcgg atcggagttc cgatggcttc aaaccggaaa    45960
agagcgcccc cggcaagccg gagatgtttt ttgccgacgg tggcgtagtg gaagagcgac    46020
ggaagcggcc gcagcaggtc atcagcggct acagctcaaa ccctaccatg gcgaaggccc    46080
aggccaacat cgatgccgag cagcaggctc tcgctgtgca ccgtcagcgc actgctgatg    46140
ctgcaaagct ccagccaggt gttgcgccgg gatacagcga caatctctat accgccaacg    46200
cccaggcacg ttcggacgcg gcacggcagc aacaggccat tgcacaggcc ggaccactgc    46260
ccgatattcc gtcgacacaa ggcttcgcgc catcgcgaca aggtaatgac ccagccagag    46320
cggcaaggat gcaggctcag tttgatcaac cggtaacggg ccctgctcga tccaaagcgg    46380
ctggtttcac tccgcagtac cgtactgacg ggcctggctg gcgaaccgac tcggttctcc    46440
gcgggacggg cgacgacgta gcgcagcagt gggcatcggg tgagtatgcc cgtggctttg    46500
ggaccggcgt gcgtggggcg cttgcggcgg ttcccgcagc attcgctgat gctggagagg    46560
atgtcggtcg attggcggaa ccggtgatca acttcggtaa agggctattc ggatgggatg    46620
acactccgcc ggcgcttcgt ggtcagcaag cagcccaggg tgcagcggcg ccaagttcca    46680
gtgctgcgcc cgggcgaggc caggtgttgc cggctgctgg tgcgccaacc ggagcgctgg    46740
agtcggtggc gaatactgga actgctatgc caagcgccgg tggctcggac ctgcccaaca    46800
acgtgacacg ggtgggcaac agcttctccg gcacaacaat ccgcccgggc tacaccgtta    46860
acggggaagc tcaagctacg gggttcgccc caggtggtca gcggagtgcc caaaaccagc    46920
gcgcagtgga gaacctgctg gcccgaacgc ctgatctggg tttggggttc aggccgagtt    46980
ctgtctccca ggtaccgccg atggccccgg acgcgttggc tcagtacaac gccggtaact    47040
ccggcgcgcc tcgggtaacc gtggttcccg atagctctcg ggccgatagc gttcgccagg    47100
ccgccttgaa tgcagcctca acaccttatc gcggttcgcc gaacgggcag ttaactgccc    47160
gccagatcga caacctgttc gggctccagc agagcgatga ccgcaatgct acgtccctgg    47220
cgagcactcg ggcgaataac gacacggcct tggtgcggga gcaggtgcaa cagcagggcg    47280
caaatcagcg cgcggctcta caggaaatgg ggcagggcgc gcgcttcctc gccgccaacg    47340
aactcgatcg ccagcgcctg gctggtgagc aagaggccag gggtttccaa acccgcgccg    47400
cccagcgcat cgagaagctg tacgagcagt acgacaaggc tgctcccgaa gaccgcgccg    47460
cgatcgccga acagattcgt gtgcttgctg gtaaggacgc tccgaatcgc ttcaccgtgg    47520
tacctggcgg ccaggagtac gacccgcagt ccatgcaact tctgacgcgc cctgcacgag    47580
tactcaacaa ccagaccggc caatttatcg accagcaaac gcagtcggcg caacccgtcg    47640
```

```
ctccgcgaac tggtgaggtg cgaagtggat accggttcaa gggagggaac cctgccgacc   47700
agaataattg ggagaaggtg taatggccga taccagcaag ccatgggaag agttcgcgtc   47760
tcaacagcca gtaactggtg gcgagaagcc gtgggaggag ttcggtggcg agacgaagga   47820
ggagggaaga ggcctgatcg ggcatgcgcg cgaccttggc ctatccgtgg ccaagggggt   47880
gattggggtt ccggaagcgg ctgttggcct cgctgatatc ccaacagagg gccgcgtagg   47940
taagttcctc gagaatcagg acggcatgct cggcttccgg ccccgggagg cgaaggattt   48000
cctgagtgat ctacacaccg atcagtacaa acagcaacag caggactttc aggatgctga   48060
tggcgtcgta gacaagacgc tgcatgctgt acagaacccg tcgatggtcg tgaacaccgt   48120
agcggagtct ttgccttcca tgttggcggg gggcgcggtc ggtcgtggcg ttcgggcgct   48180
ggctccagcg ttggcacctg tggcagccgg cgcggctggc gaaggggcgg tgatggctgg   48240
tcagcaagca gagcagatcc gccaagaaac tgatgacggc ttgctcactc cggcgcagtc   48300
gggagccgcg gtgccactg gtgtgttggg aagcctgttt tcccttgccg gcggtagctt   48360
ggccaagaaa ctgggtatcg gtgatgcgga taccctcctc gctggtggtg ccaacccagg   48420
acaactggtc agcgaactgg cgtccatgcc ggcgaagagt attccgcgaa aggtgataga   48480
gggcgcaatc tccgagggct tccttgagga actgccacag tccgcatctg agcaggttct   48540
gcaaaacctg cgctggggc gggactgggc gagcggcctg gatgaagcga tggtaatggg   48600
aacgctggcc gggatggcta tgggcgggcc ggcggcggtt ctgcatggcg gtcagccggc   48660
cgcatcccgt ggcttgacgg atgcggacgc caccttcgag agtaccccag tccttgaggg   48720
gcagaccgag gcaactgcgc cactggcact cccagctcca gtgtatgagg ctggttctga   48780
cggccaggtc cggaccacgg tcgaccagaa ctccgctacc caggtacagc gtcagcaaga   48840
ggctgaacgt ctggaccgaa tccgtcgagg ggaagtcacc gatgtgactc cggtcccggc   48900
ggccccaaag cgctccgagc agatggggct ggatccggct actgggccac tttctggtgc   48960
tgctgcgcag gccgtggaca gtggcgcaac tgaccagttt gtgcagcagg ccgcgctcca   49020
gcaggctgcc gaggaggcac agaagagcgg caggaaaggc gaacaggtca acccggaaac   49080
cggtgagatt actgcggagc agggtgatct gttggcatca gatcctgtca ccgatctgca   49140
gggccgcctg gaatttgttc gccggcaagc ccgtgccact ggatgggacg cgaagaaaat   49200
cgccgagcgc gatcgcttgc aggaagaact ggacaagctc gcgccaccgc cggatgccgg   49260
ctacatgcag cgcgtcggtg agcgcgtgaa gcgtatcgag gccgcgcaga gccccgatga   49320
aattgccgcg atcctcgccg aggatcagca ggatgagcag cgccaccaga acgccgctgg   49380
ccgggtggag ctagccgccc gtgctcgcgg cttcgccctg gaccaggcgg cgcagcagca   49440
agccccgacg ccaatcggtg tgcaggacga catccagcag gcccaaggca aggctgacac   49500
gcagcaggcg caagccgcac aaccggttgc atcgccggcg ccggcagcgg aatccgtacc   49560
ggccgcgtct gcgcctgcga tagaggccgc gaagccgtcc aacctgaaag acgccatcgc   49620
caaggtgcgc caggacaagg cgcaagcgcc gaaggccgag ccggtccagc agaccgccgc   49680
acccgccgcc gatcaagcac gctacgccga cctggcgcag cagttcaatg ccatggttcc   49740
gcagttgaag gcgcgcgcg agggcggcaa cacttccgaa gtggagcgct tgaccaatgc   49800
catcgcccg ctggacaccg aaatgcgcca gctccaggcg cgcgaaacca agcgcacctt   49860
ggatcttggc cagcaggcat ccaaggcgaa gctcgagcag gaactgtccg gtgaggccat   49920
cggcacccgc cgccgcccga gtgagcacgc gccggagaag ggcctgtact gggaaaagac   49980
```

```
cggcaccaat gaatggatcg ggcgcggtgc gtggttccag aagagcaaga cccgcaccga    50040
cgcggacatg gcgcagttcg gcggcacgct ggtgatgccg tccgagcagg ccgcgcagaa    50100
ggccccgagc atcgaaggca aggacatcgg cgaaggctgg gcggagttca gcaaggaatc    50160
gggcaccgcg ggtatccctc gcgccgacat gccgcagatc aaggccgagc accgcggcgc    50220
gatggtgaac ttcctgagcg ctcgtggcgt gcagcatcag gaagagacag ttcccgcaga    50280
taccctcaaa ccgacgcagg cggagttcag ccgggataag gtggcgaagg ccaagggctt    50340
cgaaggtggc aaccgctcca ttctggtgtc gcgtgacggc catgtgctgg acggccatca    50400
ccagtggatg gcggcccgcg acaacggcga agaggtgaag gtgatccgcc tggatgcccc    50460
catccgcgac ctggtgaaac tggcccacga atttcccagt tccaccaccg atgccagcag    50520
cgggcagggc gccacggttg aagcgaagca ggtgaggccc aagcctgagc cagcagctcc    50580
tgatgtgcct aagaagaagc cgcgcggcgt gctggcaaag aggttacagg ccgaggccca    50640
ggcccgcgcc gaatacttca cccccggcaa cgtggtgcga ggttacggcg ccaactacga    50700
cagggttatc agctacaacc cgaccgaatc gggaagctgg accgtcacgg tgcgcagtgt    50760
acgcaaggaa ggcgacacct gggtggatgt cccgggcgag agcgagcgca ctcacatgac    50820
ggcgccggat gcgcgcgaca tgaagcgcgg cccggccggc cgtatcgcaa cagggggc    50880 gccaaccgcc gatgagttcc ccttgaagga agccgcagcc agctactccg gtatctcgaa    50940
cagcagcagc cagcgagcga agtccgatgc ggatgagttc cagacctaca tcgacgtggc    51000
ccgcgatgcg ggcgctgtcg tggcacgcac cgatgctcag caggcggccg tggagcaagc    51060
cacacgagaa ttgcgggccg attacctggc ccagtaccgg cgcctgatga acgtgcgcgc    51120
cggcacctac agcggctatg ttgtcgggcg ttctggactg aacagcaagc aggcggacag    51180
gcgcaacagc gcctacgacc gcgccatcga cacattcgtg gcctggcaga aggccaatca    51240
ggatcgcgtg cgccaggcgg ccctggacgc ccgtaccgac gaggaaaagg cggcagatcg    51300
ccaggccgcc gagcaggccc gcgccgacaa ggcgcagcgc aaggaagacg gggaccgcag    51360
cctgatgcgc aggattctgt cctggaagaa gggcagcgag ccggtggcga tcaccaagac    51420
cgcgcacctt gccggggtga acttcggcaa ggatggctac ccgaccagca ttaagttgac    51480
gccgaccgat ggcagcgtgc tgaccagcga caagttcgac ctggcgacgc tgttccgtga    51540
gcgcggcatg agcgtgccgg agtcgaaacg ccgcgtgcgt gaactggtcg atttcgtgcg    51600
cgccgaggat gcagcccggc cccagtccga accggcagag gcacccaagc ccgagcccga    51660
gcccgcgcag cccagcgatt cgaaaacccc gtcgctcgat gcgcatgtag ccctcatgca    51720
gcgcgtgcgc agcggggagg cgaccgccga cgagttccgc caggcattcg agcgtacgca    51780
gaacgcccgc gacgccctgg tggccgagct gggcaatatg aagaaggatg acctgctgaa    51840
gtcaggcggc tacagcttct tccaccgcta ccgcaacgag aagaaggcag cgattgtcga    51900
tgccctggcc ggtcgcgtgt ggaggaatt tgcgctgggc cgcagctacg gcccgagcag    51960
ctacgtgatg tcgctgctg gcctcgaagc gcaccgccag gccaaggcca gcgcgctggc    52020
cgagctggtg gcgaacacca ccgacgacga catcaaggcg cacgccgccg aggtcgccga    52080
ggcgcagcag gaaatccagg cccgccggc agcgcagcag aaggctgtcg ccaacccgca    52140
gaccctcgcc gagttccgcc aggcagtgag ctacaacatg gagacgcacg gggagtccct    52200
gcgggaggcg ttcatgcgcc tgacgccgga acagcgtatt cgctacgacg aactggaggc    52260
tgagagcacc aaggccctgc gtgggcaggc caaggcacag gccaagaccc gcgtagccag    52320
cgccgggcag actacggccg gcgacatcat cgagacgaag cacaccaagc acgggcatga    52380
```

```
tctgttcgtg gtccaactgg ccgagcgcgt cagccgcgag gactacgaca ccctgaacaa   52440
ttcggcgaag cggctgggcg gcagctacag cagttatcgt gggaatggcg ccgtccccgg   52500
cttccagttc cgcacccgcg aggcggccga agcattccgt aagctggtga caggcgacac   52560
cgccgacgcg caggccgttg cagaagcgcg ccgcgacgcc ttcgaggatg accgcagtca   52620
gggcgccgcc gagcgactgc gcaccatggc tcaggccctc aacgagcggg ccgatgaagc   52680
gctgaatcgc gagcgcaagc agaacaccga gcgccgtgcg cggatggccg cccgcgctga   52740
ggcctctgcg cggtccgaca aggcactggc cgccaccatg aacaacctgg ccgatgccat   52800
cgagggcggc aaggccaagt tcctggacac cgtgcggcag aaagtgcaag tggagttcct   52860
ggcgcgggaa ctgcgcaatg cgaaggacgc gcagattcgt gcgaagtacc cgacttacgg   52920
cgagcaggag aaaacaccgcg gcgagccggt ggacgccgag acggtggact actccacctt   52980
ccccagctac accgccatgc gctccgacct agcgagcctg gcgcgccaga tggcggatgt   53040
ggacggcctg aagaaattgg ccgcgcgcct ggagaaggtc gccgacgatg tgaccgaggc   53100
ctacacggac tgggccaagc agaatcttct gtccgtcagc cgcttcaccc gcggtgacca   53160
gttcgccgac ttcaagagtc gcgaggatgc cgagcgtgcc attcgccgct ccggcctcac   53220
cggcaaggcc atcgtgcttc cggtgaaacg cgggcagaac cgcatcgtca tggcccccag   53280
cgaagccatg aagctgggcc tctggcaggg cgacggcgac aagcgcataa cgctgtccgg   53340
cgagttcggc ggcgaactgg tgcaggccct cggccggcgc agtggcagca agatcaccgt   53400
tccgtgggcg ctggagagcg cgcacgaaaa gcgcaagcgc ctggagagca tgggcatcct   53460
caccggcagc gagtaccgct ctgcactgcg cgagttcgta gcgctgcgcg aggcgcccgc   53520
cgagcccgac aagatcaggg aaatggaacg gtccatgatc ggccgtcgaa atgacggact   53580
ggacttcttc ccgacttcgg ccgccgtcac cgaggaagcc gtcgacgccg ccgacatcca   53640
ggaaggcatg gacgtgctgg agccttccgc cggcatgggc catatggccg acgcgatccg   53700
cgagcagacc ggcgtagagc ccgatgtggt ggagctttcc agcgaacgcc gcgagttgct   53760
ggaggccaag ggctacaacc tggtcggctc cgacttcatg gaggtgtccg gcaagcagta   53820
cgaccgtatc gtgatgaacc cgccgttctc caaggggcgc gacatccagc acgtacagca   53880
cgcctacagc ctgctgaagc ccggcggccg cctggttgcc atcatgggcg aaggcgcctt   53940
cttccagagc aacaaggccg ccgagaactt ccgggcctgg ctggacgcc tgggtgccac   54000 cagtgaacgg ctgccggaag gttcgtttat ggacccggcg ctacccgtca ataccggcgt   54060
gaacgcacgc atggtggtga ttgacaagcc ggcagccgaa gagtcggcag cgccgcagcc   54120
cggcgaacaa ccgcccgtgc agtactcgtt cgccggccgc aatgccgtcg gcgccaacct   54180
gcatgccctg agcaccgcac agcagcgcat cgccattggc gaaaacgccg aggccgttcg   54240
ccgagatacc ggttggcacc gtagcgctga tggcaagtgg cgcttcgaaa tcagcgatca   54300
tcaggccagc atcgccgtgg ccggtgagac tgctggcgcc atcatcaata tggcccacct   54360
caatgccatc aacgacgagc gcagtcgacc gaccgtcggc gatgtgctca accatcctca   54420
actgttcgct gcatatcctg acctgcagcg tatcccggtg gcagtgatgc cagagggcat   54480
cactgcgctg gctcgcctac gtcggttcgc cacgggtaac caagttgagg ttcaggcgaa   54540
catgccgcgc accgaggttg cctcggcgat cctgcacgaa ctccagcatg cgatacagat   54600
ccgggaaggt ttcgccatgg gtggctcggc cagggcttc gtcagcaact tcgacaagac   54660
tggtgcggcg acctatcgtc gtttggctgg agaggtggag gcgcgcaaca cgcaggctcg   54720
```

```
gctgaaaatg acgccgcgcc tgcgccggga catcgcaccc gatgagtcgg cggacatccc    54780
tgcaagtcag gtgctggtgt cgttcaatgg ccgcgacatc gagaatggcc cgttgccgca    54840
gaacctgacg gggagtccgc cgatgacctc gcaaagcctg gttcgtgctt tcgacctgca    54900
gttcccagcc ctgggccagg ctgtgcgcaa gatgctgaag cgcggcaagg aaggacaacg    54960
gggcggcttg gtggtgatcg acagcgccga cccgttgcgc atcgcgcaca cctacgcgcg    55020
gaaatccggt accgcactga gcgatgccgt tcaactgttt gaggatggcg ggcgcatcaa    55080
tggcttctac gatgccagat caggtctaac ttttctggtc ggcccgaacc tgaatccggt    55140
aaccgcaccg gccgtggtgc ttcacgaaat ggttcacggc cagcagcggc agaatctcga    55200
ccaggctgcc cacgccatgc tgatgaatcg cggcaacgtg cggagcgccg aactgcgcac    55260
cttcctggac cgtgtggcca gccgcatgat cgaggccggc gagagccgca acatgaagga    55320
ggccgctccg tatatcgtgg agcaggctgt tattgaaggg cgagagcagg ggttcgccga    55380
ggctgatagc cggttcctgt cctgggtaga cagtgcgctg gcaagcagg tgggtgactt     55440
cctgcgtagg ttcctggcca acatccgtca gtggatgctg cgccacggtc tgccggttgg    55500
ccgtatcagc gtggacgatc tggtgcgata tgcgatggct ggcgtggaaa gcgccgccga    55560
aggccgggta cggggcgacg gcctagccat gagccaggac gacatgcgaa aggcgcgcgt    55620
gctgcaaggc ccgccggtgg ccatcctgga gggaaatgaa gcaccacagg gcttcgctgc    55680
ggttcgcgag tgggcggcga agctattcga gtctcaaggt ggcaaggcag tgaacccgga    55740
cctgggcgac gtggtgctgg atatgcgcgc tgtgcgcgac tcgatggcgc atggcaaggc    55800
caacccatac aagttctcgg cgttcgcggc cgtcaaggac gtgctggagc gaggtgtggt    55860
ggttcaccgc gcggactatg agaaggggga gagtttctac gtgtcggcgc cggtggtgat    55920
cgacgataag gatgacatcg tgactgtgtt ggtgcgccgc gatccgaaca tgcagcgcat    55980
gtatctgcat tcggtggcca caaaagaata tctcctgaac cgtcgagtat ccggtgctga    56040
tgccatgatg gcagcgcagc cttccggctc gtccagttca ggagacgtag ccagtgtact    56100
ccagcggctg ctgaccgcaa gcctgaatga accgaaggt ccgcagttca gtcgctccgg     56160
tctgcgcgaa ctcaccagca aggctaccgc cgaactgaac aagaccttca cgctccgggg    56220
aggcctgtcc tggtggcaca agaccatcgg caccatgtac aacctcgcag agcgttcccc    56280
ggcattcaag ccggtcttcg agtcggcgca aggatttatc gatgacgtga gctattacgc    56340
cagcgatgcg gctgatctgg cgccgaaact gctgccgaag ctggaaacct ggcgcgacat    56400
tgcaaagtcc ccggtgggcg ctgaggacaa caaggcggtg gccaagccgg tattcgaggg    56460
cacgctgatg tgggcgcgcg acgtggacgg caagccggtg cgcgtcgatt cgctggctga    56520
gcgcgccatg cgtctgacgg ccgacgagaa ggcggacatc ctgctgaagc agggcaagat    56580
tcccgaggga ctgctgcgcg cctggcgcgg cctgagcccc gagcagttcg ccaagatgat    56640
cgacagccgc tacgaggcgc agatgctcaa ggcaggcatc gtctggaccg acgctgagct    56700
gcgcgacata tggaagctca acgatgctca ggtcgcgctg taccgcgagt ccgcgccgc     56760
caccgaccgt agtctggaca ccatggcccg cgccgacatg ctgcgcttcg gcggcgagga    56820
tgtgaaggaa ctgcgcgacc aggtgatgga cgcggccgat gcgcaggagg gggccgcgat    56880
actgcgcgac cacctggcgc agatggctga tgcatggccg gaacgcgcca cgaacctgct    56940
gaacctggca cacggcatga cggatcgcgc cgagaaggtc gcccagttgc agggcgaggg    57000
ctatgcaccg ctgtcgcgct tcggcaagta cacagtggac gtggtgggtc aggatggtca    57060
gcgtgaatac ttcagcctgt tcgagacgaa gcgcgaggcc aaccaaatgg ctgagcagat    57120
```

-continued

```
gcgtggcgcg tttcctggcg ccaccgtgag ccagggcacc ctgtccgagg aagcgtacaa    57180
gctattcgcc ggcatcacac cggaaacgct ggaactgttc ggcaacgccc tcggtttcga    57240
ctcacagggc gatagcgcac gtgatcaggc tttccaagac tacctgcgcc tgacaaagac    57300
caaccgcagc gcaatgcgcc ggcttattca ccgaaagggc atcgctggtt atagcgagga    57360
cgtagggcgg gtactggcct cgttcgtata ctccaatgcg cggcaaaccg ccgctggcct    57420
gcacatgggc gacctttccg aggctgtgaa cggcatcccg caggcgcagg gcgaactgaa    57480
ggacgccgcg gtacggctgg ccgactacat caagaacccg caagaggagg gcaggcggt    57540 gcgcggactg ctgtttgcgc agtacctcgg cgggtccgtc gcgtctgcct tcgtcaacat    57600
gacccagccg gtccaagtga cttttccctg gctgagtcag tatggcgggg tgaagcgcgc    57660
tgcggcggaa ctgggcgggg cagcacgaca gatggcgcag cgctcctatc agttcgaacc    57720
ggacctggcc cggcattaa agcgcgcaga ggatgatggg gtggtgtccc cgcaggaggt    57780
ccaccagttg atggcgcagg cacgcggcgc cggctcgctg cgcgcggggg acgggacgcg    57840
cttgggtgat gctcgagcac ttgcgtccaa cagcgtggcg cgcctgtcga tggcctgggg    57900
caagttgttc ggcgccgcag agcagatcaa ccgccgcatg acctacatcg cgtcgtatcg    57960
cgtcgccaaa gcgcagaaca tggccaatcc tgacgagttc gcacgccggg ccgtgcgcga    58020
gacgcagttc gtatactcca aggccagcaa gatgcgctgg gggcgtggtg ccgtcggcgg    58080
cacattgatg accttcaaga cgtacagcgt ggcctatctt gagctgatgc atcgcttgtg    58140
gaatcagggt gagcctggtt cgcaggagcg caaggacggt cggaaggctg ctgccctgat    58200
gatcggcatg ctgctgctcg tcggcggcgc cggtggcttg ccgttcgccg aagacgccga    58260
agacctgatc gacggtgcgg cgcaactcat gggctacaac ttctctaccg cgaaggccaa    58320
gcaggagttt cttgaaggtc tgttcggtcg cgtgcttgcc gacttcattg accgcggggt    58380
gtccgggctg cctggtgctc cgctcgatgt ctcgggtcgg ctgggtatgg gaacttgat    58440 acccggtacc ggtctgctaa ctgaaaagac cagccatacg cgagacgttc tggaaatagc    58500
tggcccgatg ggagactttg ccagccgatt agcgagtggc actcgcaagg tgctgggagg    58560
tgatatcggc agcggtatcc tggagatgtc gccgggcgcg gtgcgaaatg cggccaaagg    58620
cgtggatatg ctggccactg gtatgtatag ggacgccaag ggctacaagg tgctcgacac    58680
caacgtgctc gaggccgcta tgaagtccat cggcttccag ccggccagcg tagccactat    58740
ccaaggggcc aacatgctca accagaaagc aaaggccttc tacaacttga agcccagga    58800 aattcgcagt atgtgggcgg ccggcatctt cgagaaagac cagggcaagg ttgagcgcgc    58860
gcggcaagca atagccgact ggaatcggcg caaccctgac cagccaatgg ccatccgagt    58920
gccagacatc atgcgacgag tccgcgaaat gtcgctatcg aaggacgaac ggatagcgaa    58980
gaccgcaccg aaagcgatgc ggcagcagat gcgagaggat ctggagcgca cccgcgcaac    59040
gctggactga acccctgta aggatttgcc gttctctggc tgtaccgaaa actacctgcc    59100
caagaagccg gggcgtgatg ccccggcctt tggagggtgg agttatgtcg agagggccg    59160 gaatggcggt agaggtggtg ggcgtttcgg tggccaacaa gaccacgctg gctggcgccc    59220
ttgcgggcgc gttgggctgg ctggcgcaga tcaactgggt ggggctgatc ggcgtgctgg    59280
tcgccgtcat cggtctgctg gccaatatct atttccaggt tcgccgcgac cgccgcgaat    59340
cagccgagag cgctgcccgc atcgaggcca tccgggggcg tggcgatgtc gaacagccgt    59400
aaccgcgtgc tggttgctgc gctgaccgtc agcctggccg gcttcggcgc ctggatgaag    59460
```

-continued

```
tcggaggatt tcagcgcgaa accatacgtg ccaaccaagg gcgacgttcc gaccatcggt    59520
tacggctcca cccgctacga gaatggccaa tcggtgaagc tgaccgatcc gccgatcacc    59580
cgccagcgcg gcgaacaact cgcgcgcaac ctgatggcga aggacgaaca gcagttccgc    59640
gactcgttgc ccggcgtgaa gctgttccag gaggagtatg acctgtacct ggatttcacg    59700
ggccagttcg gcatcaccaa ctggcgcggt agctcgatgc gccgcgactt gctcgccggc    59760
aactaccagc aggcgtgcga cgacctgctg aagtggcgca accaggcagg ccgcgactgc    59820
tcgctgccga agaactgggg gccgcagggc tgcaagggcg tgtggacgcg ccaacaaaag    59880
cggcatgcgc agtgcatcgc cgcgcaggag tgacgcatgg gtgccatcaa ggaatggata    59940
gtcggcgcgc tgctggcctt gtttgccacg gcgctgctgg tcggcctggg ttatctcggc    60000
ggacgtgtgt cgatggtgcg cgagtacggt gaactggtcg acagatgaa gcggcagaac    60060 cgcgaggccg ccgacaagct ggccgagttg accgccagc gcgacatgaa acaggcggcc    60120
ctgaacaagc aggccgccga ccaggaaagg aaggatgccg atgctaaagc tgaaatcgct    60180
cgccttgctg gtgagctgcg cgaccgccct gtgcgcgtgc gcatcgtccc cgccgcaggt    60240
gggggctgta gtggtggcgc cgcaggtgac gcagccggca ccgccgaagc tggtacagga    60300
gacgccgcct cggcctacgg gctactaccg gaagaaaatt ctcgacgctt taacgactcc    60360
ctgagcgaag tcgaaaccct gagcgcggcc tacaactcgt gtcgcgcccg gttgattccc    60420
caagagccga ccccgtaggg aggaaaccat ggcctacacc gcatatcggg tgctcaaggc    60480
acctatcgac cagatcgagc gcttcatgac cgaggccatc gccgatggct ggcagccgct    60540
cggtgcgcct atcctgcttt accccgacga caaggccgtc taccaggctt tggtcaaggg    60600
cacgccggat ggtagtggca ccggacctgt caccatcgtg gtggaggaca tcaccgatgc    60660
ttctgtcatc ggcaaatctc tgctgacggc cgtcaacgag gaagacgggc gtgcagcaat    60720
cggggccggc acttctaatc tgcagttggg cattaccgca accaccgcca agcgggaaa    60780 ctatgcgcct gcctgggggg atgtgacagg gaaaccggct gttattgcgg ctggtactga    60840
tgccgcgaca gcaaggggg ctattggcgc gggaacatcc agccttgcga tcggtacaac    60900
cgctactacc gcggcggctg gcgaccacaa ccatgcaatc actgctgatg ctgccagtgg    60960
gttggctgca gcctccagcg ttcaagatgc gttcgtagcg gtttcggcgc gaatcaaggc    61020
tctggagtcg gctgcgccgt agatgaatgc aatatgccat ggatggcgca tttgaaggca    61080
```

<210> SEQ ID NO 8
<211> LENGTH: 19
<212> TYPE: DNA
<213> ORGANISM: Artificial Sequence
<220> FEATURE:
<223> OTHER INFORMATION: Synthetic construct
<400> SEQUENCE: 8
agcacgccga tggacagat                                                    19

<210> SEQ ID NO 9
<211> LENGTH: 20
<212> TYPE: DNA
<213> ORGANISM: Artificial Sequence
<220> FEATURE:
<223> OTHER INFORMATION: Synthetic construct
<400> SEQUENCE: 9
ggcggaggta tgttatcccg                                                   20

-continued

```
<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
acaggtattc gacggcggtt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
tctggtcatt ccacggctcg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
tggctggcct tcgctactac                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
tggtcgttcc attgctccga                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
ttcgcgtgat gaggggagag                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15 gtgaacccg gcctatttcg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 16
ctgctcggaa agcacgttcg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
agtgtgagcc agacgtgctt                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
ggagagcagc tacgtcccag                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
tcgcagtaag ccccttcgtg                                              20
```

US 11,066,691 B1

THERAPEUTIC PHAGES AND METHODS THEREOF

CROSS-REFERENCE TO RELATED APPLICATION

This application claims the benefit of U.S. Provisional Application No. 62/731,453, filed Sep. 14, 2018, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD14412_0_ST25.txt," created on Sep. 4, 2018 (size of 414 kilobytes), which is hereby incorporated by reference in its entirety.

FIELD OF THE INVENTION

The present invention relates, in part, to engineered viruses (e.g., engineered phages), phage cocktails, and methods of producing and/or identifying viruses for targeting pathogenic bacteria.

BACKGROUND OF THE INVENTION

Antibiotic resistance is on the rise in pathogenic bacteria, and controlling infections from such bacteria remain challenging. Broad-spectrum antibiotics provide a therapeutic avenue, which could contribute to rising resistance. Accordingly, there is a need for additional methodologies to target bacteria in a directed manner that combats antibiotic resistance.

SUMMARY OF THE INVENTION

The present invention relates, in part, to methods of identifying and/or producing a virus (e.g., a phage) that can target a bacterium (e.g., a pathogenic bacterium). Gene transfer between bacteria and phages can result in the mobile genomic elements (derived from phage) to reside within bacterial genomes. These mobile genomic elements (or prophage) generally provide temperate phages, i.e., phages that can reside silently integrated within bacterial chromosomes, as genomic islands of the prophage class. Temperate phages from an initial host organism can be isolated and then employed to infect a target organism.

Accordingly, the methods herein, in part, relate to processes to identify prophage sequence(s) within a genome (e.g., from a host organism, such as a first bacterium or archaeon) and to produce a phage including the prophage sequence (or an engineered prophage sequence). In some embodiments, a phage including a prophage sequence from the host organism is then employed to infect a target organism (e.g., a second bacterium or archaeon). In this manner, prophage genome sequence(s) to produce a temperate phage from a first bacterium or archaeon can be engineered to provide a lytic phage that can attack a second bacterium or archaeon (e.g., in which the first and second bacterium or archaeon have a low phylogenetic distance, such as a MASH distance of from about 0 to about 0.15). In particular embodiments, the engineered prophage sequence includes a modified prophage sequence that lacks an integrase gene, thereby converting a temperate phage into a lytic phage.

Accordingly, in a first aspect, the present invention relates to a method of producing an engineered virus, the method including: identifying a prophage sequence (e.g., a first prophage sequence) within a bacterial genome from a first bacterium (or within an archaeal genome of a first archaeon), wherein the prophage sequence includes a genomic island including an integrase gene; producing an engineered phage genome including the prophage sequence that lacks the integrase gene; and targeting a colony with the engineered phage genome. In some embodiments, the colony includes a strain of a second bacterium that is different than a strain of the first bacterium. In other embodiments, the colony includes a strain of a second archaeon that is different than a strain of the first archaeon.

In some embodiments, the prophage sequence (e.g., the first prophage sequence) encodes a temperate phage. In other embodiments, the engineered phage genome encodes a virulent phage.

In a second aspect, the present invention features a method of producing an engineered virus, the method including: identifying a plurality of prophage sequences within a bacterial genome from a first bacterium (e.g., wherein each of the plurality of prophage sequences includes a genomic island including an integrase gene); producing an engineered phage genome including at least one of the plurality of prophage sequences that lacks the integrase gene; and targeting a colony with the engineered phage genome, wherein the colony includes a strain of a second bacterium that is different than a strain of the first bacterium.

In some embodiments, the identifying step includes identifying a first prophage sequence and a second prophage sequence. In other embodiments, the producing step includes producing a first engineered phage genome including the first prophage sequence and a second engineered phage genome including the second prophage sequence, and wherein each of the first and second prophage sequences includes a genomic island including an integrase gene.

In some embodiments, the targeting step includes targeting the colony with the first engineered phage genome and with the second engineered phage genome.

In a third aspect, the present invention features a method of producing a virus, the method including: identifying a first prophage sequence within a bacterial genome from a first bacterium, wherein the first prophage sequence includes an integrase gene; designing one or more primers to bind to the first prophage sequence or a portion thereof; cultivating a colony including a strain of the first bacterium; inducing formation of a first phage genome within the colony, wherein the first phage genome includes the first phage sequence; and identifying a sequence of the first phage genome by using the one or more primers to bind to the first prophage sequence or a portion thereof, thereby producing a first virus including the first phage genome.

In some embodiments, the method further includes (e.g., after identifying a sequence of the first phage genome): incubating the first phage genome with a first bacterial lawn including the strain of the first bacterium, thereby producing a plaque disposed on the first bacterial lawn; and/or identifying a genomic sequence from the plaque by using the one or more primers to bind to the first prophage sequence or a portion thereof.

In other embodiments, the method further includes (e.g., after identifying a sequence of the first phage genome): incubating the first phage genome with a first bacterial lawn including a strain of a second bacterium, thereby producing a plaque disposed on the first bacterial lawn, wherein the first bacterium and the second bacterium are different; and/or identifying a genomic sequence from the plaque by using the one or more primers to bind to the first prophage sequence or a portion thereof.

In some embodiments, the method further includes (e.g., after identifying a sequence of the first phage genome): producing an engineered phage or an engineered phage genome including the first phage genome that lacks the integrase gene.

In some embodiments, the engineered phage genome includes the first phage genome that lacks a repressor gene, a repressor-binding site, a virulence gene, a resistance gene, a toxin gene, a lysis gene, a phage receptor recognition gene, and/or a structural phage protein gene.

In other embodiments, the method further includes (e.g., after producing an engineered phage): incubating the engineered phage with a first bacterial lawn including the strain of the first bacterium, thereby producing a plaque disposed on the first bacterial lawn; and/or identifying a genomic sequence from the plaque by using the one or more primers to bind to the first prophage sequence or a portion thereof.

In some embodiments, the method further includes (e.g., after producing an engineered phage): incubating the engineered phage with a first bacterial lawn including a strain of a second bacterium, thereby producing a plaque disposed on the first bacterial lawn, wherein the first bacterium and the second bacterium are different; and identifying a genomic sequence from the plaque by using the one or more primers to bind to the first prophage sequence or a portion thereof.

In some embodiment, the identifying a first prophage sequence within a bacterial genome includes: identifying one or more genomic islands within the bacterial genome, wherein at least one of the one or more genomic islands includes a sequence for the integrase gene.

In some embodiments, the inducing formation of a first phage genome includes: exposing the colony to an antibiotic, a temperature change, a pH change, or an ultraviolet light source.

In a fourth aspect, the present invention features a method of producing a virus, the method including: identifying a first prophage sequence within a bacterial genome from a first bacterium, wherein the first prophage sequence includes a genomic island including an integrase gene; designing one or more primers to bind to the first prophage sequence or a portion thereof; cultivating a colony including a strain of the first bacterium; inducing formation of a first phage genome within the colony, wherein the first phage genome includes the first phage sequence; identifying a sequence of the first phage genome by using the one or more primers to bind to the first prophage sequence, thereby producing a first virus including the first phage genome; and producing an engineered phage including the first phage genome that lacks the integrase gene; incubating the engineered phage with a bacterial lawn including a strain of a second bacterium, wherein the first bacterium and the second bacterium are different, thereby producing a plaque disposed on the bacterial lawn; and identifying a genomic sequence from the plaque by using the one or more primers to bind to the first prophage sequence or a portion thereof.

In a fifth aspect, the present invention features a method of producing a virus, the method including: identifying a first prophage sequence within a bacterial genome from a first bacterium, wherein the first prophage sequence includes a genomic island including an integrase gene; designing one or more primers to bind to the first prophage sequence or a portion thereof; producing an engineered phage including the first prophage sequence that lacks the integrase gene; incubating the engineered phage with a bacterial lawn including a strain of a second bacterium, wherein the first bacterium and the second bacterium are different, thereby producing a plaque disposed on the bacterial lawn; and identifying a genomic sequence from the plaque by using the one or more primers to bind to the first prophage sequence or a portion thereof.

In a sixth aspect, the present invention features a phage cocktail including: a first engineered prophage sequence of a bacterial genome from a first bacterium, wherein the engineered prophage sequence includes a first genomic island; and a second engineered prophage sequences of a bacterial genome from the first bacterium, wherein the second engineered prophage sequence includes a second genomic island.

In a seventh aspect, the present invention features a phage cocktail including: a first prophage sequence of a bacterial genome from a first bacterium, wherein the first prophage sequence comprises a first genomic island; and a second prophage sequence of a bacterial genome from a second bacterium, wherein the second prophage sequence comprises a second genomic island and wherein the first and second bacteria are different.

In any embodiment herein, at least one of the one or more primers includes a nucleic acid sequence having at least 80% sequence identity to any one of SEQ ID NOs:8-19, or a complement of any of these or a fragment thereof.

In any embodiment herein, a prophage sequence (e.g., a first prophage sequence) includes a nucleic acid sequence having at least 80% sequence identity to any one of SEQ ID NOs:1-7, or a complement of any of these or a fragment thereof.

In any embodiment herein, the engineered phage or the engineered phage genome includes a nucleic acid sequence having at least 80% sequence identity to any one of SEQ ID NOs:1-7, or a complement of any of these or a fragment thereof.

In any embodiment herein, a bacterium (e.g., a first bacterium) includes *Pseudomonas, Staphylococcus, Burkholderia,* or *Klebsiella.*

In any embodiment herein, the integrase gene encodes a tyrosine integrase, a tyrosine recombinase, or a serine recombinase.

In any embodiment herein, the first virus is a temperate phage or the first prophage sequence encodes a temperate phage.

In any embodiment herein, the engineered phage is a virulent phage or the engineered phage genome encodes a virulent phage.

In any embodiment herein, the engineered phage includes the first phage genome that lacks a repressor gene, a repressor-binding site, a virulence gene, a resistance gene, a toxin gene, a phage receptor recognition gene, or a structural phage protein gene.

Definitions

As used herein, the term "about" means +/−10% of any recited value. As used herein, this term modifies any recited value, range of values, or endpoints of one or more ranges.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl. Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkoxyalkyl" is meant an alkyl group, as defined herein, which is substituted with an alkoxy group, as defined herein. Exemplary unsubstituted alkoxyalkyl groups include between 2 to 12 carbons ($C_{2-12}$ alkoxyalkyl), as well as those having an alkyl group with 1 to 6 carbons and an alkoxy group with 1 to 6 carbons (i.e., $C_{1-6}$ alkoxy-$C_{1-6}$ alkyl).

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O)Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylamino" is meant an amino group, as defined herein, attached to the parent molecular group through an alkylene group, as defined herein. The alkylamino group can be substituted or unsubstituted. For example, the alkylamino group can be substituted with one or more substitution groups, as described herein for alkyl.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "amino" is meant —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group, as defined herein.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., —OAk, in which Ak is an alkyl group, as defined herein); (4) $C_{1-6}$ alkoxy-$C_{1-6}$ alkyl (e.g., an alkyl group, which is substituted with an alkoxy group —OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —SO$_2$Ak, in which Ak is an alkyl group, as defined herein); (8) $C_{1-6}$ alkylsulfonyl-$C_{1-6}$ alkyl (e.g., an alkyl group, which is substituted by an alkylsulfonyl group —SO$_2$Ak, in which Ak is an alkyl group, as defined herein); (9) aryl; (10) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -A$^L$Ar, in which A$^L$ is an alkylene group and Ar is an aryl group, as defined herein); (14) aryloyl (e.g., —C(O)Ar, in which Ar is an aryl group, as defined herein); (15) azido (e.g., an —N$_3$ group); (16) cyano (e.g., a —CN group); (17) $C_{1-6}$ azidoalkyl (e.g., a —N$_3$ azido group attached to the parent molecular group through an alkyl group, as defined herein); (18) carboxyaldehyde (e.g., a —C(O)H group); (19) carboxyaldehyde-$C_{1-6}$ alkyl (e.g., -A$^L$C(O)H, in which A$^L$ is an alkylene group, as defined herein); (20) $C_{3-8}$ cycloalkyl; (21) $C_{1-6}$ alk-$C_{3-8}$ cycloalkyl (e.g., -A$^L$Cy, in which A$^L$ is an alkylene group and Cy is a cycloalkyl group, as defined herein); (22) halo (e.g., F, Cl, Br, or I); (23) $C_{1-6}$ haloalkyl (e.g., an alkyl group, as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (16) hydroxyl (e.g., a —OH group); (27) hydroxyl (e.g., a —OH group); (28) $C_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —NO$_2$ group); (30) $C_{1-6}$ nitroalkyl (e.g., an alkyl group, as defined herein, substituted by one to three nitro groups); (31) N-protected amino; (32) N-protected amino-$C_{1-6}$ alkyl; (33) oxo (e.g., an =O group); (34) $C_{1-6}$ thioalkoxy (e.g., —SAk, in which Ak is an alkyl group, as defined herein); (35) thio-$C_{1-6}$ alkoxy-$C_{1-6}$ alkyl (e.g., an alkyl group, which is substituted by an thioalkoxy group —SAk, in which Ak is an alkyl group, as defined herein); (36) —(CH$_2$)$_r$CO$_2$R$^A$, where r is an integer of from zero to four, and R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —(CH$_2$)$_r$SO$_2$R$^D$, where r is an integer of from zero to four and where R$^D$ is selected from the group consisting of (a) $C_{1-6}$ alkyl, (b) $C_{4-18}$ aryl, and (c) $C_{1-6}$ alk-$C_{4-18}$ aryl; (39) —(CH$_2$)$_r$SO$_2$NR$^E$R$^F$, where r is an integer of from zero to four and where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —(CH$_2$)$_r$NR$^G$R$^H$, where r is an integer of from zero to four and where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., —OCy, in which Cy is a cycloalkyl group, as defined herein); (46) cycloalkylalkoxy (e.g., —OA$^L$Cy, in which A$^L$ is an alkylene group and Cy is a cycloalkyl group, as defined herein); and (47) arylalkoxy (e.g., —OA$^L$AT, in which A$^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "azido" is meant an —N$_3$ group.

By "azidoalkyl" is meant an azido group attached to the parent molecular group through an alkyl group, as defined herein.

By "cyano" is meant a —CN group.

By "cyanoalkyl" is meant an cyano group attached to the parent molecular group through an alkyl group, as defined herein.

By "halo" is meant F, Cl, Br, or I.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, $N^4$-acetylcytidine, 5-formylcytidine, $N^4$-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, $N^6$-methyladenosine, $N^6$-isopentenyladenosine, $N^6$-(cis-hydroxy-isopentenyl)adenosine, 2-methylthio-$N^6$-(cis-hydroxyisopentenyl) adenosine, $N^6$-glycinylcarbamoyladenosine, $N^6$-threonylcarbamoyladenosine, 2-methylthio-$N^6$-threonyl carbamoyladenosine, $N^6,N^6$-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, $N^2$-methylguanosine, $N^2,N^2$-dimethylguanosine, 8-oxo-guanosine, 7-methyl-8-oxo-guanosine, 1-methyl-6-thio-guanosine, $N^2$-methyl-6-thio-guanosine, and $N^2,N^2$-dimethyl-6-thio-guanosine, and combinations thereof.

A sugar modification may include, but is not limited to, a locked nucleic acid (LNA, in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms (e.g., independently selected from the group consisting of nitrogen, oxygen, phosphorous, sulfur, or halo) bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. Exemplary modifications include modifications to the 2' position of a nucleic acid, such as 2'-O-methyl, 2'-halo (e.g., 2'-fluoro, 2'-chloro, etc.), 2'-alkyl (e.g., 2'-methyl, 2'-ethyl, 2'-propyl, 2'-allyl, etc.), 2'-aryl (e.g., 2'-phenyl), 2'-alkaryl (e.g., 2'-benzyl), 2'-amino (e.g., 2'-NH$_2$, 2'-NR$^{N1}$R$^{N2}$, which each of R$^{N1}$ and R' is, independently, H, alkyl, or alkaryl), 2'-alkoxy (e.g. 2'-O-methoxy, 2'-O-ethoxy, etc.), 2'-alkylamino (e.g., 2'-O-methylamino, 2'-O-ethylamino, etc.), 2'-O-alkylamino (e.g., 2'-O-methylamino, 2'-O-ethylamino, etc.), 2'-azido, 2'-O-cyanoalkyl (e.g., 2'-O-cyanomethyl), 2'-O-alkoxyalkyl (e.g., 2'-O-(2-methoxyethyl)), etc.

A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter, "Overview of principles of hybridization and the strategy of nucleic acid probe assay," Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. A "complement" can include a "reverse complement," in which a given sequence is reversed to provide a reverse sequence and then a complement, as defined herein, of that reverse sequence provides a reverse complement. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamic acid and aspartic acid; and a group of amino acids having sulfur containing side chains consists of cysteine and methionine. Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant nucleic acid molecule does not contain an appropriate start signal, such a start signal can be inserted in front of the gene.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, $\pi$ bond interactions, hydrophobic interactions, inclusion complexes, clathration, van der Waals interactions, and combinations thereof.

By "micro" is meant having at least one dimension that is less than 1 mm and, optionally, equal to or larger than about 1 μm. For instance, a microstructure (e.g., any structure described herein) can have a length, width, height, cross-sectional dimension, circumference, radius (e.g., external or internal radius), or diameter that is less than 1 mm.

By "nano" is meant having at least one dimension that is less than 1 μm but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than 1 μm but equal to or larger than 1 nm. In other instances, the nanostructure has a dimension that is of from about 1 nm to about 1 μm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

Antibiotic resistance is on the rise in pathogenic bacteria. The present approach, in part, combats antibiotic resistance by mining a uniquely large database of precisely mapped mobile genomic sequences in bacterial and/or archaeal genomes, thereby isolating diverse bacteriophage or viral genomes that lie dormant within bacterial or archaeal genomes. Such bacteriophages, in turn, can be combined into cocktails that can target and attack antibiotic-resistant pathogens. In some non-limiting embodiments, the use of multi-phage cocktails could reduce the possibility of escape by a target pathogen that develops resistance to any one phage. Without wishing to be limited by mechanism, this approach can include collecting numerous, diverse phages for attacking each target bacterial group.

Detection of such phages can be facilitated by using bioinformatic genomic tools (e.g., bioinformatic algorithms Islander and Comparator) to detect large phage genomes (prophages) integrated silently into bacterial genomes. These phage genomes (and resultant phages) can then be engineered to disable their ability to integrate into the target genome, so that they are only able to kill bacteria upon infection. Choosing phages from close relatives of the target bacteria makes it more likely that they will be highly active on the target. In particular embodiments, this approach can be implemented to generate numerous diverse phages to combine into a cocktail that will efficaciously kill virtually any pathogenic bacterium. Such cocktails, in turn, can provide countermeasures for various targets (e.g., emerging bacterial pathogens, bioremediation targets, etc.).

Figure 1A:
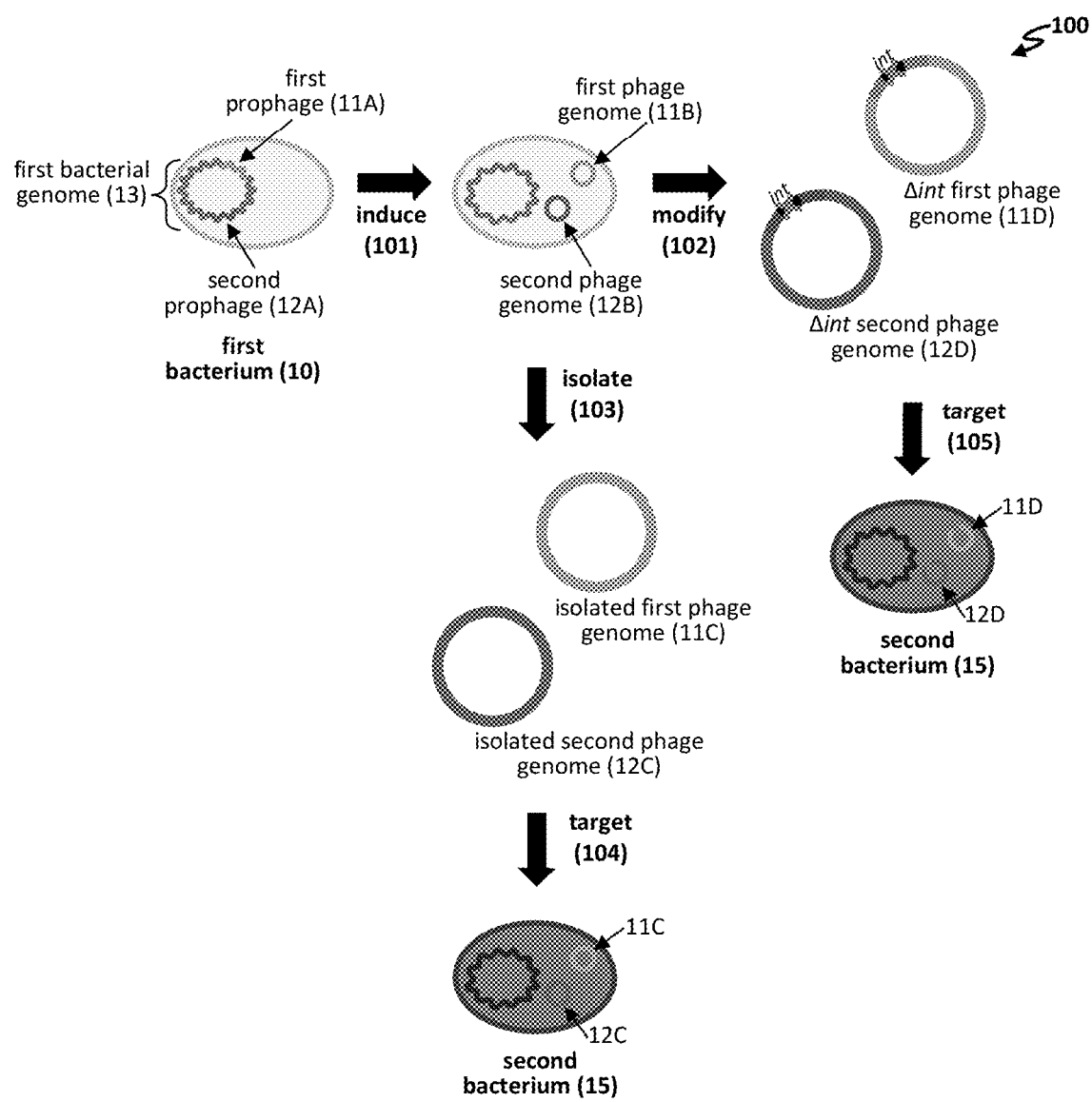
FIG. 1A-1B shows schematics of exemplary methods for producing and/or identifying a virus (e.g., an engineered virus). Provided is an exemplary method 100 of producing a virus based on prophage 11A,12A from a first bacterium 10 in order to target 104 a second bacterium 15 (FIG. 1A). Also provided is another exemplary method 110 of producing a virus (e.g., an isolated phage 126) from prophage 11A,12A of a first bacterium 10 (FIG. 1B).

FIG. 1A provides an exemplary method 100 for identifying and/or producing a virus (e.g., configured to target a colony having one or more bacteria). The method 100 includes identifying one or more prophage sequences (e.g., a first prophage sequence 11A and a second prophage sequence 12A) within a genome from a first host (e.g., within a first bacterial genome 13 from a first bacterium 10). A prophage generally includes a genomic sequence initially derived from a phage genome after the phage infects its bacterial or archaeal host, in which this genomic sequence then is inserted into the host genome. One or more prophages can be found latently residing within a host genome, such as in certain regions of the host genome indicative of horizontal gene transfer. Such regions include genomic islands. In particular embodiments, a genomic island including or in proximity to an integrase gene can indicate a prophage sequence. Other features can also indicate a prophage sequence (e.g., any one or more features described herein). A genomic island can be identified by comparing the host genome to a reference genome and identifying differences between those two genomes. Exemplary, non-limiting prophage sequences include a nucleic acid sequence having at least 80% sequence identity to any one of SEQ ID NOs:1-7, or a complement (e.g., a reverse complement) of any of these or a fragment thereof.

Temperate phages can persist within two different life cycles: a lytic phase in which a phage kills the host and a lysogenic phase in which a phage is maintained stably within the host (e.g., as a prophage). Thus, in some embodiments herein, the prophage sequence is that which encodes for a temperate phage. Under certain stress conditions, the phage will exit out of the lysogenic phase and into the lytic phase. Experimentally, a temperate phage residing within a host can be induced to enter into the lysogenic phase by being exposed to a stress condition (e.g., exposed to an antibiotic, a temperature change, a pH change, and/or an ultraviolet source), in which this exposure results in excision of the phage genome from the host genome. In this lysogenic phase, the host's cellular machinery then results in transcription, translation, and replication of the phage genome, thereby producing phage proteins that can be assembled into new phage.

In one embodiment, as seen in FIG. 1A, a method 100 herein includes a step of inducing 101 the formation of one or more phage genomes 11B,12B within the host organism. The resultant phage genome and phage can be employed in any useful manner. In one instance, the phage genome can be modified, thereby producing an engineered phage genome. This engineered phage genome, in turn, can be employed to provide an engineered phage. In one non-limiting embodiment, the method includes modifying the phage genome, thereby producing an engineered phage genome. In one instance, the modifying 102 includes deleting one or more integrase genes from one or more phage genomes 11B,12B, thereby producing one or more engineered phage genomes having an integrase deletion, Δint first phage genome 11D and Δint second phage genome 12D, respectively. In another instance, the modifying can include changing the phage genome for a temperate phage to provide a phage genome for a virulent phage.

In another non-limiting embodiment, the method 100 includes isolating 103 the one or more phage genomes, thereby producing one or more isolated phage genomes, an isolated first phage genome 11C and an isolated second phage genome 12C, respectively. Isolating and/or modifying the phage genome can include determining the sequence of the phage genome and then producing a phage genome based on the determined sequence or based on that determined sequence having desired modifications (e.g., deletion of an integrase gene or any other modifications described herein). Production (or synthesis) can include de novo assembly of the desired sequence, modification of phage genome to include desired modification(s), etc. Such production of synthesis can include any useful assembly method, such as the Gibson assembly method to join a plurality of double-stranded fragments to form a double-stranded sealed nucleic acid; the Bacteriophage Recombineering of Electroporated DNA (BRED) assembly method to modify phage DNA using a targeting substrate within a recombineering cell system; homologous recombination to modify phage DNA with plasmid DNA or electroporated to provide recombinant phage particles; CRISPR-Cas-mediated phage engineering; in vivo recombineering etc. Additional details are provided in Gibson D G et al., "Enzymatic assembly of DNA molecules up to several hundred kilobases," *Nat. Methods* 2009; 6:343-5; Gibson D G et al., "Chemical synthesis of the mouse mitochondrial genome," *Nat. Methods* 2010; 7:901-3; Barnes W M, "PCR amplification of up to 35-kb DNA with high fidelity and high yield from lambda bacteriophage templates," *Proc. Nat'l Acad. Sci. USA* 1994; 91:2216-20; van Kessel J C et al., "Recombineering in *Mycobacterium tuberculosis*," *Nat. Methods* 2007; 4:147-52; Marinelli L J et al., "BRED: a simple and powerful tool for constructing mutant and recombinant bacteriophage genomes," *PLoS One* 2008; 3(12): e3957; Sagona A P et al., "Genetically modified bacteriophages," *Integr. Biol.* 2016; 8:465-74; and Pires D P et al., "Genetically engineered phages: a review of advances over the last decade," *Microbiol. Mol. Biol. Rev.* 2016; 80:523-43, each of which is incorporated herein by reference in its entirety.

The resulting phage genome and/or phage can be used to target a target organism. In one non-limiting embodiment, the method 100 includes targeting 104 a second bacterium 15, thereby providing one or more phage genomes 11C,12C within the second bacterium. In another non-limiting embodiment, the method 100 includes targeting 105 a second bacterium 15, thereby providing one or more engineered phage genomes 11D,12D within the second bacterium.

Targeting the target organism can occur in any useful manner. In one instance, targeting can include delivering the phage genome itself (e.g., an isolated phage genome or an engineered phage genome) to the target organism. In another instance, targeting can include delivering a phage (e.g., a phage particle, including an isolated phage or an engineered phage) to the target organism. This phage, in turn, can be isolated directly from the host organism. Alternatively, the phage can be regenerated by transcription, translation, and replication of the isolated phage genome or the engineered phage genome.

Once isolated or produced, a phage genome (e.g., an isolated phage genome or an engineered phage genome) can optionally be rebooted within a cell-free system or in *E. coli* cells, thereby resulting in formation of phage including that phage genome. In brief, the phage genome or an engineered phage genome can be delivered to cell-free or cell-based system, thereby resulting in transcription of the genome and assembly of transcribed components into phages. Additional methods are described in Bundy B C et al., "*Escherichia coli*-based cell-free synthesis of virus-like particles," *Biotechnol. Bioeng.* 2008; 100:28-37; Shin J et al., "Genome replication, synthesis, and assembly of the bacteriophage T7 in a single cell-free reaction," *ACS Synth. Biol.* 2012; 1:408-13; Ando H et al., "Engineering modular viral scaffolds for targeted bacterial population editing," *Cell Syst.* 2015; 1:187-96; Jaschke P R et al., "A fully decompressed synthetic bacteriophage øX174 genome assembled and archived in yeast," *Virology* 2012; 434:278-84; and Kilcher S et al., "Cross-genus rebooting of custom-made, synthetic bacteriophage genomes in L-form bacteria," *Proc. Nat'l Acad. Sci. USA* 2018; 115:567-72, each of which is incorporated herein by reference in its entirety.

Targeting can include delivering the phage genome and/or phage to a target. Targets can include a bacterium, a plurality of bacteria (e.g., as in a colony), or a colony including two or more different types of bacteria. In one embodiment, the host organism and the target organism are different (e.g., different strains, different species, different serovars, different morphovars, different biovars, etc.).

Figure 1B:
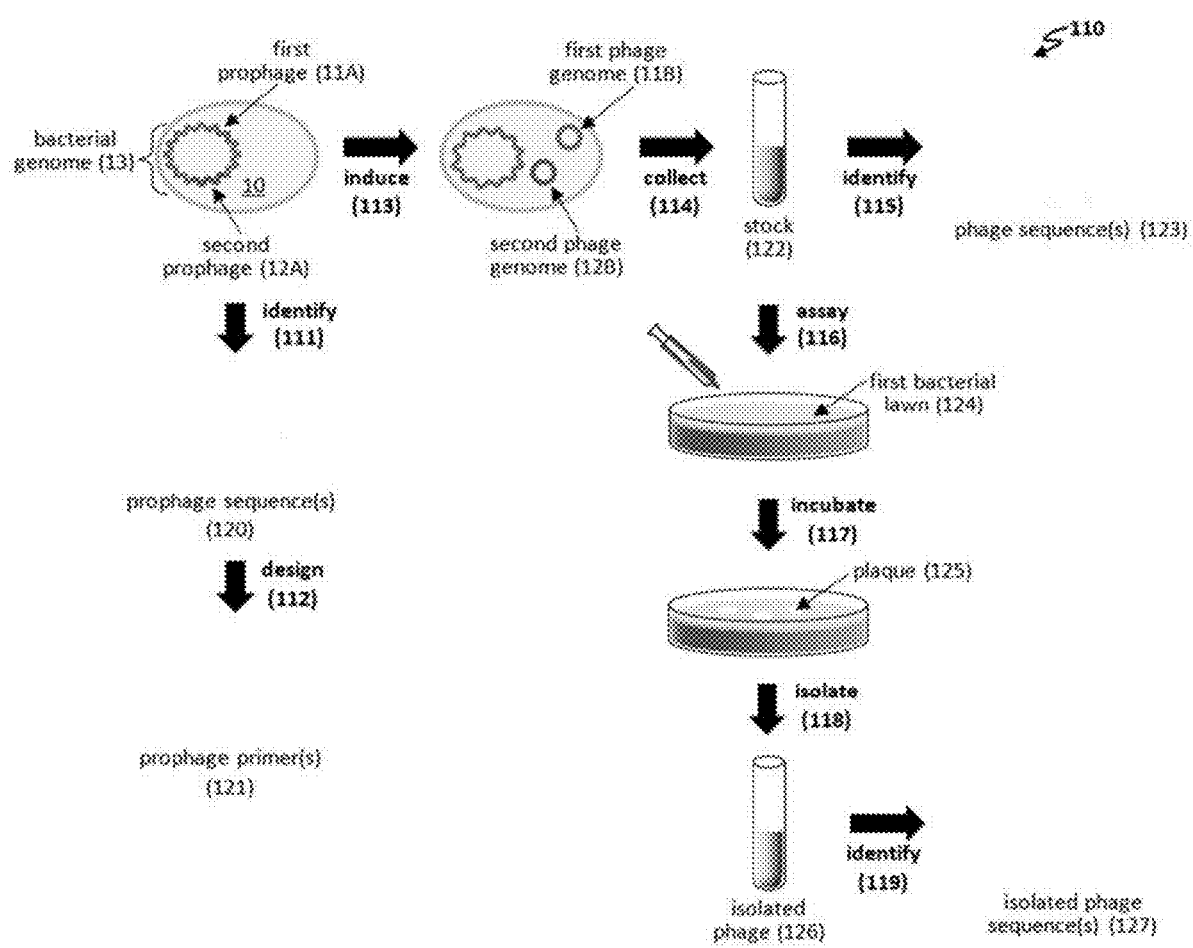

The present invention also relates, in part, to producing a virus by employing one or more prophage sequences from a host organism and producing an isolated phage or an isolated phage genome. FIG. 1B provides an exemplary method of producing a virus by identifying one or more prophage sequences within a host genome. In one embodiment, the method 110 includes identifying 111 one or more prophages (e.g., a first prophage 11A and a second prophage 12A or a sequence thereof) within a genome from a first host (e.g., within a first bacterial genome 13 from a first bacterium 10). Such identifying can include, e.g., employing the sequence of a host genome to provide one or more prophage sequences 120, such as by identifying one or more genomic islands within the host genome (e.g., one or more genomic islands including or in proximity to an integrase gene) and filtering out genomic islands that are false positives. Additional methodologies for identifying prophage sequences are described herein, such as the Islander process, the Comparator process, and the Juxtaposer process.

To determine the presence of a prophage sequence within a nucleic acid sample, one or more primers can be employed to bind to the prophage sequence, or a portion thereof. In one non-limiting embodiment, the method 110 can include designing 112 one or more prophage primers 121 configured to bind to the prophage sequence(s) or a portion thereof. Exemplary methodologies for designing primers and detecting sequences include polymerase chain reaction (PCR), Primer-BLAST, transcription-mediated amplification processes, single primer isothermal amplification (SPIA), loop mediated amplification (LMA), etc. Additional details are provided in Ye J et al., "Primer-BLAST: a tool to design target-specific primers for polymerase chain reaction," *BMC Bioinformatics* 2012; 13:134 (11 pp.); Diffenbach C W et al., "General concepts for PCR primer design," *Genome Res.* 1993; 3:S30-S37; and U.S. Pat. Nos. 5,422,252; and 5,470,723, each of which is incorporated herein by reference in its entirety. Exemplary primers include, e.g., a nucleic acid sequence having at least 80% sequence identity to any one of SEQ ID NOs:8-19, or a complement of any of these or a fragment there.

The method can include producing sufficient amounts of bacteria to provide a colony. In one embodiment, the exemplary method 110 can include cultivating a colony comprising a strain of a first bacterium and then inducing 113 the formation of one or more phage genomes (e.g., a first phage genome 11B and a second phage genome 12B) within the colony. In some embodiments, the first phage genome provides a first phage sequence; and the second phage genome provides a second phage sequence. The resulting phage genomes can then be collected 114 to provide a stock 122. The stock can include genomic components (e.g., one or more phage genome or host genome), cellular components (e.g., proteins, lipids, etc.), and/or chemical components (e.g., buffers, salts, etc.).

Portions of the stock can be analyzed (e.g., sequenced) in order to identify 115 the one or more phage sequence(s) 123. Identification can include any useful methodology, such as amplification (e.g., PCR or bridge PCR), next-generation sequencing, high throughput sequencing, massively parallel signature sequencing, the Sanger method, de novo sequencing, shotgun sequencing, Illumina sequencing, etc. Such identifying of the one or more phage sequences (e.g., one or more phage genomes) can employ one or more primers designed to bind to one or more prophage sequences or a portion thereof. Such primers and prophage sequences can be determined by using any useful bioinformatic processes, such as any described herein. Such phage sequences can then be employed to produce a virus including one or more of the phage genomes.

The present methods herein can optionally include one or more steps to determine whether the phage genome derived from the host organism (e.g., an isolated phage genome, an engineered phage genome, or a phage including any of these genome(s)), etc.) can provide a lytic phage. Accordingly, the present method can include steps of assaying 116 by introducing the phage genome or the phage to a culture including a colony of bacterium (e.g., a colony including a plurality of first bacteria or a colony including a plurality of second bacteria that is different than the host bacteria, such as a different strain or a different species). The colony can include a first bacterial lawn 124 disposed on a layer of media. Incubating 117 the phage or phage genome with the colony can produce one or more plaques 125, if the phage or phage genome is capable of infecting the bacteria within the first bacterial lawn. Then, the method can include isolating 118 the lytic phage or phage genome within a sample collected from the plaque, thereby providing an isolated phage 126 or isolated phage genome. Finally, the method can include identifying 119 one or more genomic sequences (e.g., isolated phage genome or genome from an isolated phage) from the plaque, thereby providing one or more isolated phage sequence(s) 127. Identifying can include using one or more prophage primers to bind to the one or more prophage sequences, or a portion thereof.

The methods herein can include one or more steps to produce and/or test an engineered phage or engineered phage genome. For instance, the method can include identifying a phage genome of a first bacterium and then modifying that phage genome in order to provide an engineered phage or engineered phage genome. In another instance, the method can include identifying a phage derived from the host genome of a first bacterium and then modifying the phage or genome from that phage in order to provide an engineered phage or an engineered phage genome. The engineered phage or engineered phage genome can include any useful modification, such as a genome that lacks a gene that contributes to lysogeny and/or virulence (e.g., an integrase gene, a repressor gene, a repressor-binding site, a virulence gene, a resistance gene, a toxin gene, a lysis gene, a phage receptor recognition gene, and/or a structural phage protein gene). For instance, if the modification alters the phage genome to minimize entry into the lysogeny phage, then the phage will more likely enter the lytic phage, thereby infecting the target organism and minimizing the chance of gene transfer between the phage and another organism. Exemplary modifications include deleting or inactivating a gene that promotes lysogeny, such as an integrase gene, a repressor gene, a repressor-binding site, and/or a virulence gene. In another instance, if the modification alters the phage genome to remove elements related to phage virulence or toxicity, then the phage will be less likely to provide a virulent strain. Exemplary modifications include deleting or inactivating a gene that promotes virulence or toxicity, such as a virulence gene, a resistance gene, a toxin gene, a phage receptor recognition gene, and/or a structural phage protein gene. Exemplary, non-limiting engineered phage sequences or engineered phage genomes include a nucleic acid sequence having at least 80% sequence identity to any one of SEQ ID NOs:1-7, or a complement (e.g., a reverse complement) of any of these or a fragment thereof.

Methods can include testing or employing one or more engineered phages or engineered phage genomes. Such methods can include incubating the engineered phage or phage genome with a bacterial lawn including a bacterium (e.g., the host bacterium, the target bacterium, or any bacterium different than the host bacterium), thereby producing a plaque disposed on the bacterial lawn; and identifying a genomic sequence from the plaque by using the one or more primers to bind to a prophage sequence or a portion thereof.

Figure 2:
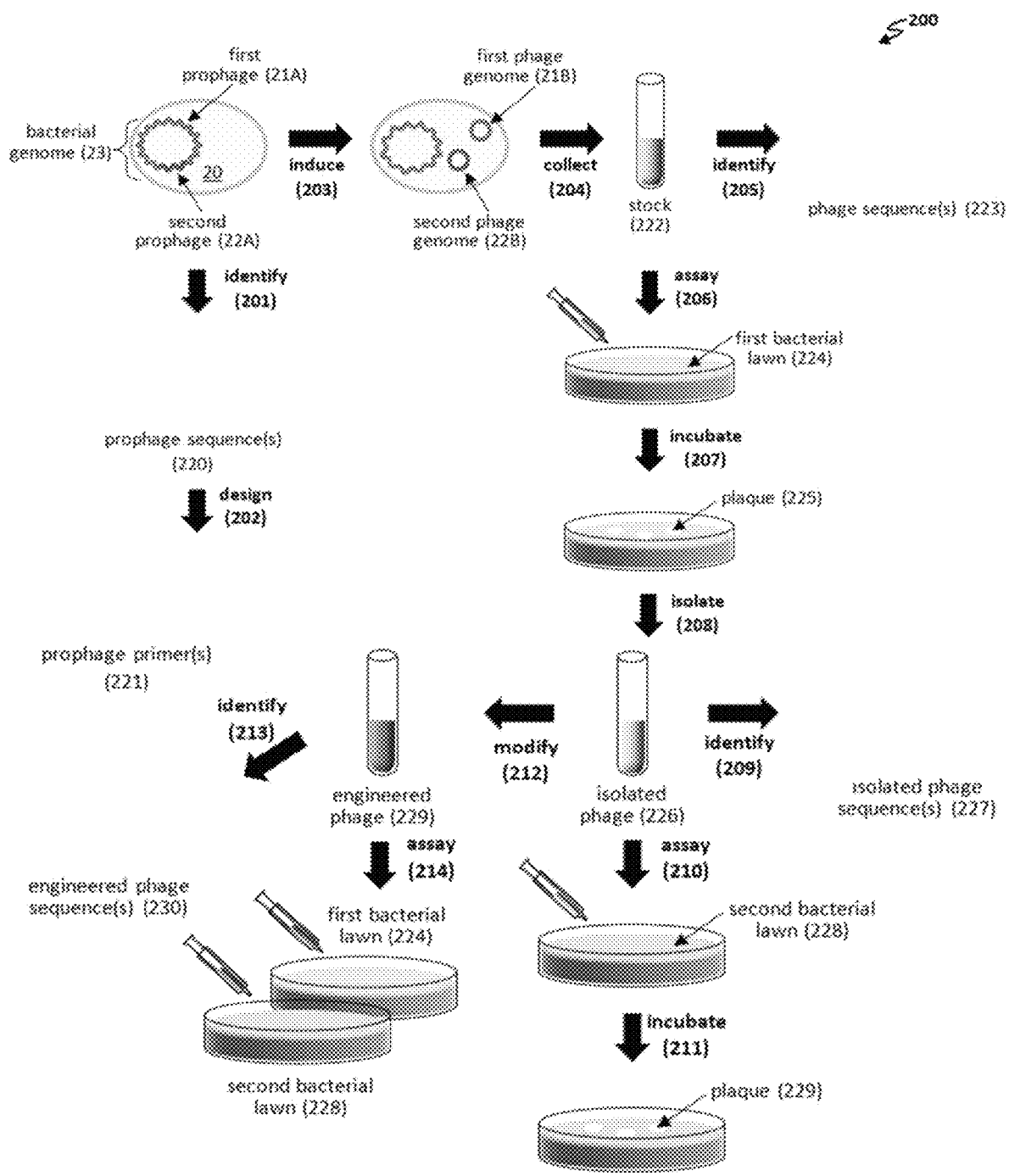
FIG. 2 shows a schematic of yet another exemplary method 200 for producing and/or identifying a virus (e.g., an isolated phage 226 or an engineered phage 229) from prophage 21A,22A of a first bacterium 20.

FIG. 2 provides an exemplary method 200 that includes identifying a prophage sequence from a host organism in order to produce a lytic phage that can infect a target organism. As can be seen, the method 200 include identifying 201 one or more prophages (e.g., a first prophage 21A and a second prophage 22A or a sequence thereof) within a genome from a first host (e.g., within a first bacterial genome 23 from a first bacterium 20), thereby providing one or more prophage sequences 220; and designing 202 one or more prophage primers 221 configured to bind to the prophage sequence(s) or a portion thereof.

The method can include one or more experimental steps to excise the phage genome from the host genome and to test the efficacy of the phage genome or a modified form thereof. Accordingly, an exemplary method 200 can include inducing 203 the formation of one or more phage genomes (e.g., a first phage genome 21B and a second phage genome 22B) and then collecting 204 a stock 222, in which the stock can include the phage or phage genome. Using the collected stock 222, the method 200 can include the step of identifying 205 the one or more phage sequences 223 (e.g., with any useful methodology described herein, such as next-generation sequencing).

Further experimental steps can include exposing a colony to the phage or phage genome in order to determine whether or not a plaque is formed. Plaques are indicative of lysing and killing of portions of the bacterial lawn, thus showing that the phage is lytic. Accordingly, an exemplary method 200 can include assaying 206 by introducing the phage genome or the phage to a culture including a first bacterial lawn 224 disposed on a layer of media; and incubating 207 the phage or phage genome with the colony, thereby producing one or more plaques 225 if the phage or phage genome is capable of infecting the bacteria within the first bacterial lawn. Then, the method can include isolating 208 the lytic phage or phage genome within a sample collected from the plaque, thereby providing an isolated phage 226 or isolated phage genome.

The exemplary method 200 can include identifying 209 one or more genomic sequences (e.g., isolated phage genome or genome from an isolated phage) from the plaque, thereby providing one or more isolated phage sequence(s) 227. Identifying can include using one or more prophage primers to bind to the one or more prophage sequences, or a portion thereof.

Furthermore, the method can include use of the phage with an organism that is different than the host organism (e.g., different strain, species, serovar, etc.). In one embodiment, the method 200 includes assaying 210 by introducing the phage genome or the phage to a culture including a second bacterial lawn 228 disposed on a layer of media; and incubating 211 the phage or phage genome with the colony, thereby producing one or more plaques 229 if the phage or phage genome is capable of infecting the bacteria within the second bacterial lawn. Then, the method can include optionally isolating the lytic phage or phage genome within a sample collected from the plaque upon the second bacterial lawn, thereby providing a further isolated phage or further isolated phage genome.

An isolated phage or phage genome can be further modified, and then the modified form can then be tested and used to target the host organism or another target organism. Thus, in one embodiment, the exemplary method 200 can include modifying 212 the phage or phage genome in order to provide an engineered phage 229 or engineered phage genome and assaying 214 by introducing the engineered phage or engineered phage genome to a culture including a first bacterial lawn 224 disposed on a layer of media and/or to a culture including a second bacterial lawn 228 disposed on a layer of media. The method can optionally include incubating the phage or phage genome with the colony, thereby producing one or more plaques if the phage or phage genome is capable of infecting the bacteria within the first and/or second bacterial lawn. In addition, the method can include optionally isolating the lytic phage or phage genome within a sample collected from the plaque upon the first and/or second bacterial lawn, thereby providing a further isolated engineered phage or further isolated engineered phage genome. Yet additional steps can include identifying 213 the one or more engineered phage sequences 230 (e.g., with any useful methodology described herein, such as next-generation sequencing).

Microorganisms, Including Bacteria and Archaea

The methods and compositions herein can employ genomes obtained from any useful organism (e.g., microorganism). In particular embodiments, genomes can be obtained from a bacterium or an archaeon. Exemplary microorganisms include a bacterium, such as such as *Bacillus* (e.g., *B. anthracis, B. cereus,* or *B. thuringiensis*), *Clostridium* (e.g., *C. difficile, C. botulinum, C. butyricum, C. perfringens, C. tetani,* or *C. sordellii*), Enterobacteriaceae (e.g., *Salmonella, Escherichia coli, Yersinia pestis, Klebsiella,* and *Shigella*), *Enterobacter* (e.g., *E. aerogenes* or *E. cloacae*), *Yersinia* (e.g., *Y. pestis* or *Y. enterocolitica*), *Klebsiella* (e.g., *K. pneumoniae* or *K. oxytoca*), *Staphylococcus* (e.g., *S. aureus*), *Streptococcus, Acinetobacter* (e.g., *A. baumannii*), Gonorrheae, *Enterococcus* (e.g., *E. faecalis* or *E. faecium*), *Listeria* (e.g., *L. monocytogenes*), *Brucella* (e.g., *B. abortus, B. melitensis, B. suis, B. neotomae, B. ovis,* or *B. canis*), *Vibrio* (e.g., *V. cholerae*), *Corynebacterium diphtheria, Pseudomonas* (e.g., *P. aeruginosa, P. pseudomallei, P. putida, P. syringae, P. protegens, P. fluorescens, P. entomophila, P. oryzihabitans,* or *P. plecoglossicida*), *Burkholderia* (e.g., *B. mallei, B. pseudomallei,* or *B. cepacia*), *Shigella* (e.g., *S. dysenteriae*), *Rickettsia* (e.g., *R. rickettsii, R. prowazekii, R. typhi,* or *R. felis*), *Francisella* (e.g., *F. tularensis, F. philomiragia,* or *F. novicida*), *Chlamydia* (e.g., *Ch. psittaci, Ch. abortus, Ch. pneumoniae,* or *Ch. trachomatis*), *Coxiella* (e.g., *C. burnetii*), *Mycoplasma* (e.g., M *mycoides* or *M. pneumoniae*), etc., as well as drug-resistant forms thereof (e.g., antibiotic-resistant forms thereof, antimicrobial-resistant forms thereof, multi-drug resistant forms thereof, such as methicillin-resistant *S. aureus*) and subspecies thereof.

Exemplary organisms can include an archaeon, such as *Methanococcus* (e.g., *M. maripaludis* or *M. jannaschii*), *Methanothermococcus* (e.g., *M. hermolithotrophicus*), *Aeropyrum* (e.g., *A. pernix*), *Archaeoglobus* (e.g., *A. fulgidus*), *Halobacterium* (e.g., *H. salinarum*), *Methanobacterium* (e.g., *M. thermoautotrophicum*), *Pyrococcus* (e.g., *P. abyssi, P. horikoshii,* or *P. furiosus*), *Sulfolobus* (e.g., *S. solfataricus*), *Thermoplasma* (e.g., T *acidophilum* or *T. volcanium*), etc.

Genomic Islands and Methods of Identifying Such Islands

The present methods can employ any useful process to identify one or more genomic islands within a genome from a host organism (e.g., a first bacterium or a first archaeon). Such genomes can include a bacterial genome or an archaeal genome. Genomic islands are mobile elements in many bacterial and archaeal genomes. They often contain genes related to pathogenicity (e.g., toxins and antibiotic resistance factors) and are of general interest in understanding evolution of microbes.

Various bioinformatic processes and tools can be employed to identify such genomic islands within the host organism. In particular embodiments, the bioinformatic process includes comparing a first genomic sequence to a reference genomic sequence for a particular organism, thereby identifying genomic differences between the first and reference genomic sequences (e.g., in which such differences provide one or more candidate island sequences). These candidate island sequences can arise from various endogenous or exogenous types of genomic recombination or shuffling events, but some features can be correlated with genomic insertion events that are effectuated by phage. In one non-limiting instance, an exemplary feature that indicates a genomic island is a candidate island sequence that is in close proximity to an integrase gene (e.g., a tyrosine integrase, a tyrosine recombinase, a serine recombinase, or a candidate integrase, such as a sequence having at least 80% identity to a known integrase gene or a gene encoding a known integrase).

An exemplary, non-limiting process includes Islander, which is a genomic tool to identify genomic islands integrated into tRNA and tmRNA genes. In particular embodiments, Islander requires a genomic island to possess an insert site specifically in their host organism via an integrase gene int. Thus, in some non-limiting embodiments, the genomic island includes a nucleic acid sequence in proximity to a sequence encoding an integrase gene. In other embodiments, the genomic island includes a nucleic acid sequence that is integrated into a known tRNA or tmRNA gene (a tDNA gene) and that possesses (or is in proximity to) both an attP site (or a portion thereof) and an attB site (or a portion thereof).

Figure 3A:
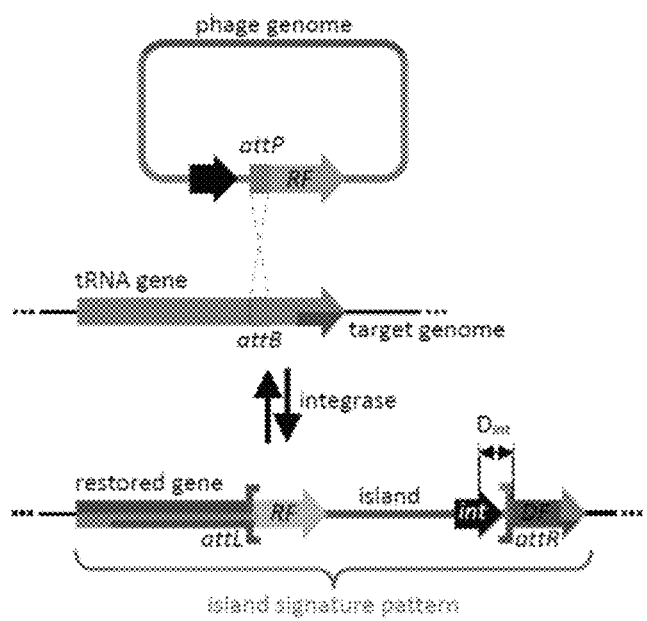
FIG. 3A-3C shows schematics of exemplary methods for identifying one or more genomic islands within a bacterial genome. Provided are schematics for various bioinformatics approaches, including an exemplary Islander process (FIG. 3A), an exemplary Comparator process (FIG. 3B), and an exemplary Juxtaposer process (FIG. 3C). Islander identifies tRNA and tmRNA genes, integrases, and then nearby candidate islands by using a series of filters to remove incorrectly sized and oriented islands. Comparator uses a BLAST search method to identify island regions when compared to a reference genome with no island. Juxtaposer is used to find recombination junctions from next generation sequence (NGS) data, and then identifies mobility events in the form of circularized junctions (CJs).

FIG. 3A provides an exemplary Islander process, which maps genomic islands that integrate into a tRNA gene by finding its displaced fragment DF. The Islander process assumes that a phage genome includes an attP site in proximity to an integrase gene int and a replacement fragment RF; and that a target genome includes a tRNA gene having an attB site. Integrase then catalyzes recombination between the attP and attB sites, thereby providing an island signature pattern including the restored gene, the candidate island sequence, the integrase gene int, and the displaced fragment DF. The restored gene includes a portion of the initial tRNA gene and the replacement fragment RF provided by the phage genome, in which RF and DF is generally identical. The distance between the integrase gene and the island end (att site) is indicated as Dint. The attL site includes a portion of the attP site and a portion of the attB site, and the attR site includes the remaining portion of the attP site and the remaining portion of the attB site.

The Islander process can include one or more other steps. In particular embodiments, the process includes comparing (e.g., by BLAST) tRNA/tmRNA genes against a reference genome (e.g., DNA of host organism); identifying integrase sequence(s); filtering out false positives (e.g., filtering out sequences that are not from an extreme end of tRNA/tmRNA gene, sequences or hits that are in known tRNA/tmRNA gene(s), sequences that are in the wrong orientation, etc.); resolving overlaps and tandem arrays; and/or testing for other features to filter out false positives. Exemplary other features can include, e.g., testing for a distance D between island end (att site) and integrase gene int, Dint, in which a low Dint indicates cohesion of the integration module; determining a length of the candidate island sequence (e.g., rejecting a candidate island sequences that is shorter than about 2 kilobases (kb) or longer than about 200 kb); housekeeping; hypothetical; foreignness; dinucleotide bias; and/or mononucleotide bias (e.g., G+C content). Further details regarding an exemplary Islander process is described in, e.g., Mantri Y et al., "Islander: a database of integrative islands in prokaryotic genomes, the associated integrases and their DNA site specificities," *Nucleic Acids Res.* 2004; 32:D55-D58; Hudson C M et al., "Resistance determinants and mobile genetic elements of an NDM-1 encoding *Klebsiella pneumoniae* strain," *PLoS One* 2014; 9:e99209 (14 pp.); and Hudson C M et al., "Islander: a database of precisely mapped genomic islands in tRNA and tmRNA genes," *Nucleic Acids Res.* 2015; 43:D48-53, each of which is incorporated herein by reference in its entirety.

Figure 3B:
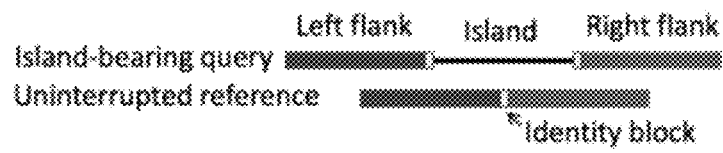
Figure 3B:
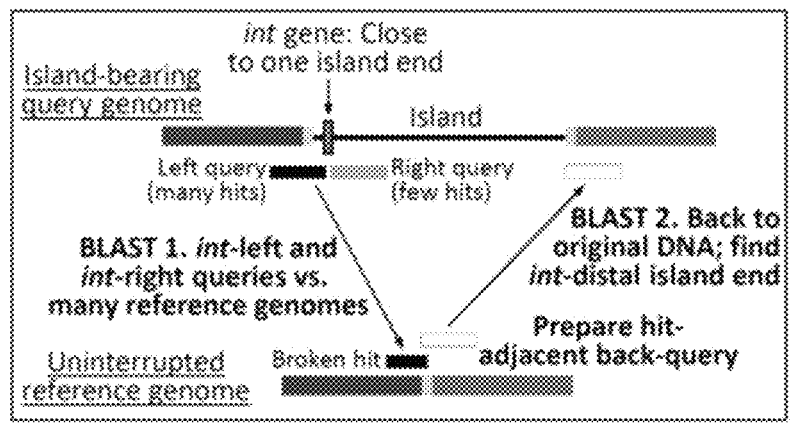

An exemplary, non-limiting process includes Comparator, which employs comparative genomics to find island insertions by comparing a host genome with an island to a related organism without it (see, e.g., FIG. 3B). If an island has inserted in one organism via an integrase, then a closely related uninterrupted reference will have similar sequence on either side of the insertion with a sudden plummet in similarity for the islands sequence (see, e.g., FIG. 3B, top and center panels). Using BLAST, Comparator finds the exact location of the lapse in coverage between the island bearing and uninterrupted reference genome (see, e.g., FIG. 3B, bottom panel). Comparator uses comparative genomics to identify genomic islands at any locus, based on cohesion of the integration module. Comparator can be employed to assess sporadic occurrence among closely related genomes. Comparator also looks for an uninterrupted reference genome; closely related species are more likely to bear evidence of an island, since they share common sequence on either side of the island.

Figure 3C:
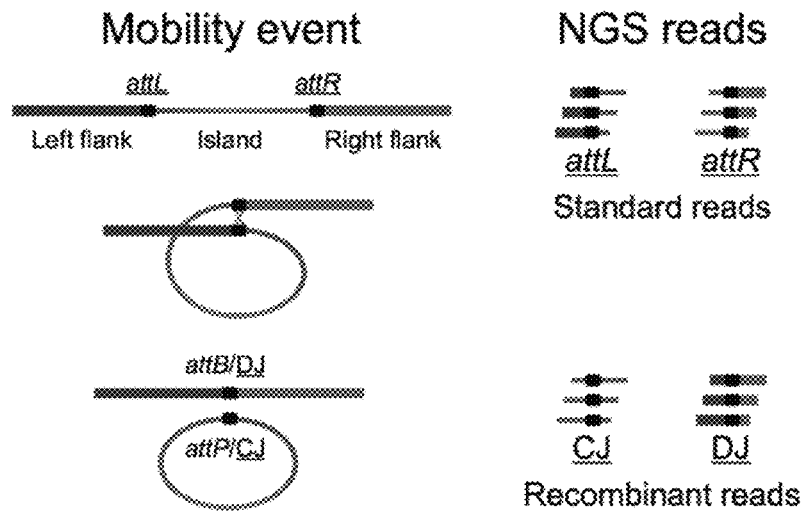

An exemplary, non-limiting process includes Juxtaposer, which is another process used to reveal genomic islands in data obtained through next-generation sequencing (NGS) (see, e.g., FIG. 3C). Mobile elements are integrated into the bacterial chromosome through binding between the phage attP site and the chromosomal attB site and catalytic action by a phage-encoded integrase, thereby providing a prophage flanked by recombinant attL and attR sites (see, e.g., FIG. 3C, left panel). Upon inducing the lysogeny, the mobile elements (or genomic islands) are excised, thereby providing (i) a phage genome having a circular junction (CJ) with a regenerated attP site and (ii) a bacterial genome having a deletion junction (DJ) with a regenerated attB site (see, e.g., FIG. 3C, left panel). Thus, island excision produced stoichiometric amounts of CJ and DJ, such that lysogeny can be induced (e.g., by use of antibiotics) and NGS can be employed to detect the presence of CJ and DJ reads (see, e.g., FIG. 3C, right panel). Juxtaposer software (e.g., with source code available at github.com/sandialabs/Juxtaposer) can be used to find NGS reads that correspond to recombination events of DNA mobility (e.g., circles/scars from mobile elements, transpositions of transposons, or a palindrome artifact). Additional details are provided in, e.g., Schoeniger J S et al., "Experimental single-strain mobilomics reveals events that shape pathogen emergence," *Nucleic Acids Res.* 2016; 44:6830-9, which is incorporated herein by reference in its entirety.

Inducing Excision of Mobile Genetic Elements

Host organisms can be induced to enter a lytic phase upon exposure to stress conditions. Under stress, the prophage sequences can be excised from the host genome, and such prophage sequences can be further transcribed, translated, and replicated by using the host's cellular machinery. Exemplary methods to induce excision of prophages include exposure to an antibiotic (e.g., mitomycin C, fluoroquinolone, ciprofloxacin, trimethoprim, etc.); a temperature change (e.g., exposure to elevated temperatures, such as greater than about 34° C. or of from about 34° C. to 38° C.); a pH change (e.g., exposure to acidic pH, such as a pH of from about 5.5 to about 6.5); and/or an ultraviolet (UV) light source (e.g., UVA light having a wavelength of from about 320 nm to about 400 nm; UVB light having a wavelength of from about 290 nm to about 320 nm; and UVC light having a wavelength of from about 200 nm to about 290 nm).

Phage Genome and Uses Thereof

The phage genome (e.g., including an engineered form thereof) can be delivered to a host organism (e.g., a cell, such as a bacterial cell or an archaeal cell) in any useful manner.

In one non-limiting instance, the phage genome can be provided as a package, a phage, a genetic construct, a plasmid, a complex (e.g., a complex between a nucleic acid and a lipoplex such as in a lipoplex complex, a complex between a nucleic acid and a particle such as in a particle complex, a complex between a nucleic acid and cationic proteins such as in a cationic protein complex, etc.), an expression vector (e.g., as a plasmid, phage, virus, or cosmid, to which another nucleic acid segment, i.e., an "insert", may be attached so as to bring about the replication of the attached segment in a host cell), or an expression cassette (e.g., including a nucleic acid coding sequence operably linked to a promoter sequence or an expression control sequence). In another instance, the phage genome is delivered directly to a cell (e.g., an electroporated cell or a recombineered cell).

Engineered Phages, Prophage Sequences, and Genomes

A phage or a genome derived from a phage (e.g., a prophage sequence, a phage genome, etc.) can be further modified, thereby providing an engineered form thereof. For instance, a sequence of a prophage or phage can be identified, and then that sequence can be synthesized de novo to provide a nucleic acid for that prophage or phage. Prior to synthesis, the sequence can be analyzed to determine a portion that encodes a gene, and then that gene can be deleted from the sequence to be synthesized. Alternatively, a prophage or a phage (a nucleic acid) can be isolated and then modified. Exemplary methods for synthesizing, modifying, and/or assembling phages and phage genomes are described herein.

Modifications can occur in any useful portion of the prophage or phage genome, including modifications to an integrase gene, a repressor gene, an anti-repressor gene, an operator, a repressor-binding site, a virulence gene, a resistance gene, a toxin gene, a lysis gene, a phage receptor recognition gene, a structural phage protein gene, or a packaging gene. Such modifications can include deletions (e.g., deletion of a gene or a portion thereof), mutations (e.g., one or more mutations that provide changes in expression of the gene, that provides structural mutants having changed activity, and/or that provide changes in binding, transcription, translation, etc.), etc.

Exemplary integrase genes to be modified can include genes encoding for, e.g., a tyrosine integrase (e.g., λ integrase, HP1 integrase, or Cre phage recombinase), a tyrosine recombinase (e.g., FLP yeast invertase or XerC bacterial recombinase), a serine integrase (e.g., R4 phage integrase, a TP901 integrase, or φC31 phage integrase), a serine recombinase (including integrases and transposases, e.g., Gin invertase or γδ resolvase), an XerD recombinase, a transposase, etc. Exemplary repressor genes to be modified can include genes encoding for a cI protein, a cro protein, etc. Exemplary operators to be modified including a site on a nucleic acid configured to bind a repressor protein (e.g., any repressor protein described herein).

Exemplary structural phage protein genes include genes encoding for a portal protein, a scaffold protein, a tail protein (e.g., a tail fiber protein, a major tail protein, a minor tail protein, a tail tape measure protein, a siphon tail protein, a phage endopeptidase, a lipase, or a hydrolase, including amidase protein K), a capsid protein, a head protein (e.g., a minor head protein, a major head protein, a scaffold protein, a connector protein, etc.), a head morphogenesis protein, a baseplate protein, a coat protein, a virion structural protein, etc. Exemplary lysis genes include genes encoding for a chitinase, a holin, a hemolysin, an endolysin, or an amidase. Exemplary virulence genes include genes encoding for the LuxR family transcription factor, lectin (e.g., galactophilic lectin), elastase (e.g., elastase precursor protein), leucocidin, exfoliative toxin (e.g., exfoliative toxin A), staphylokinase, chemotaxis inhibitory protein, staphylococcal complement inhibitor, or enterotoxin (e.g., enterotoxin S).

Other exemplary genes to be modified can include packaging genes (e.g., gene(s) encoding for a terminase), transcriptional regulator genes (e.g., gene(s) encoding for the XRE family transcriptional regulator), transcription factor genes (e.g., gene(s) encoding for the LuxR family transcription factor), a nuclease gene (e.g., gene(s) encoding for an endonuclease), a helicase gene (e.g., gene(s) encoding for a DNA helicase), an excisionase gene (e.g., gene(s) encoding for excisionase), a transferase gene (e.g., gene(s) encoding for an acetyl transferase), etc. Further additional genes and methodologies can include those from, e.g., Cao H et al., "Comparative genome and transcriptome analysis reveals distinctive surface characteristics and unique physiological potentials of *Pseudomonas aeruginosa* ATCC 27853," *BMC Genomics* 2017; 18:459 (17 pp.); Shen K et al., "Extensive genomic plasticity in *Pseudomonas aeruginosa* revealed by identification and distribution studies of novel genes among clinical isolates," *Infect. Immun.* 2006; 74:5272-83; Morales-Espinoza R et al., "Genotypic and phenotypic characterization of *Pseudomonas aeruginosa* population with high frequency of genomic islands," *PLoS One* 2012; 7:e37459 (11 pp.); Battle S E et al., "Genomic islands of *Pseudomonas aeruginosa*," *FEMS Microbiol. Lett.* 2009; 290:70-8; Jani M et al., "Identification of novel genomic islands in Liverpool epidemic strain of *Pseudomonas aeruginosa* using segmentation and clustering," *Front. Microbiol.* 2016; 7:1210 (18 pp.); Brussow H et al., "Phages and the evolution of bacterial pathogens: from genomic rearrangements to lysogenic conversion," *Microbiol. Mol. Biol. Rev.* 2004; 68:560-602; Xia G et al., "Phages of *Staphylococcus aureus* and their impact on host evolution," *Infect. Genet. Evol.* 2014; 21:593-601; Salmond G P C et al., "A century of the phage: past, present and future," *Nat. Rev. Microbiol.* 2015; 13:777-86; Oppenheim A B et al., "Switches in bacteriophage lambda development," *Annu. Rev. Genet.* 2005; 39:409-29; and Ofir G et al., "Contemporary phage biology," *Cell* 2018; 172:1260-70, each of which is incorporated herein by reference in its entirety.

Phage Cocktails

The method herein can be employed to generate numerous diverse phages, which in turn can be combined into a cocktail that will efficaciously kill virtually any pathogenic target. A phage cocktail generally includes two or more nucleic acids (e.g., prophage sequences, phage genomes, or engineered forms thereof, such as any described herein) or phages thereof (e.g., a phage including one of the two or more nucleic acids, such as a prophage sequence, phage genome, or engineered forms thereof). In one non-limiting embodiment, at least two nucleic acids include different genomic islands. In another non-limiting embodiment, a first nucleic acid has a sequence obtained from a prophage sequence of a first host (e.g., a first bacterium), and a second nucleic acid has a sequence obtained from a prophage sequence of a different host (e.g., a second host, such as a second bacterium that is different than the first bacterium).

Prophage sequences can be determined in a plurality of hosts, and a phage cocktail can include a plurality of phage genomes (or portions thereof) from a plurality of hosts. For instance, one or more prophage sequences can be identified in a first host, thereby providing a plurality of phage genomes. Then, one or more prophage sequences can be identified in a second host, thereby providing a plurality of additional phage genomes. An exemplary cocktail can include one or more phage genomes from the first host and one or more additional phage genomes from the second host. Each phage genome can be different (e.g., possess a different genomic island).

EXAMPLES

Example 1: Discovering and Converting Temperate Phages for Therapy

Temperate phages grow lytically in most of the bacterial cells they infect, yet produce a small fraction of lysogen cells by repressing lytic growth and establishing stable inheritance, usually through integration into the chromosome. Temperate phages have generally been shunned for therapy because the lysogens i) are not killed, ii) are resistant to reinfection by the original phage, iii) may have gained virulence/resistance/toxin genes enhancing the pathogenicity phenotype (lysogenic conversion), and iv) can occasionally transduce chromosomal markers flanking the integration site (see, e.g., Abedon S T et al., "Phage treatment of human infections," *Bacteriophage* 2011; 1:66-85). However, this guideline had set in before the development of a general PCR-based approach for multilocus engineering of bacteriophage genomes (see, e.g., Ando H et al., "Engineering modular viral scaffolds for targeted bacterial population editing," *Cell Syst.* 2015 1(3):187-96). Engineering knock-out mutations in integrase or repressor genes essential for lysogeny (e.g., and/or in virulence/resistance/toxin genes, if any) could convert temperance to virulence and remove the above objections.

This lysogeny-knockout approach would allow exploitation of the vast number of temperate phages that are integrated, in prophage form, within sequenced bacterial genomes. Prophages are the main class (integrative and conjugative elements, ICEs) being the other major class) within the larger category of genomic islands, which can be defined as mobile DNAs that integrate site-specifically into bacterial (or archaeal) genomes due to an integrase (e.g., integrases of the tyrosine recombinase family, or less frequently, of the serine recombinase family).

We have developed tools that identify and precisely map such genomic islands. Our experimental method Juxtaposer (see, e.g., Schoeniger J S et al., "Experimental single-strain mobilomics reveals events that shape pathogen emergence," *Nucleic Acids Res.* 2016; 44:6830-9) can detect mobility events due to genomic islands (and insertion sequences) in subpopulations of a culture, through the circularization and deletion junctions they produce among next-generation sequencing reads.

For higher throughput, we have developed two bioinformatic methods and applied them to a large set of sequenced genomes. Islander is based on the preference of genomic islands for inserting into tRNA genes (e.g., as described herein; see also, e.g., Hudson C M et al., "Islander: a database of precisely mapped genomic islands in tRNA and tmRNA genes," *Nucleic Acids Res.* 2015; 43:D48-D53). Comparator (e.g., as described herein) is based on two principles: the cohesion of the integration module, which practically means that the island's integrase gene will be found near one end of the integrated island; and a negative comparative genomic approach, meaning a search for a reference genome in which the integration site of the candidate island is uninterrupted. These complementary bioinformatic tools find large numbers of genomic islands, and Comparator can also be configured to find insertion sequences.

In a test set of 2168 genomes, we found 7949 islands. This process can be scaled up to assess the >80000 prokaryotic genomes at GenBank. This database could allow for selection and/or production of custom phage cocktails from very close relatives of nearly any target bacterium, which are more likely to be efficacious at killing the target than phages "fished" from environmental or clinical samples. Additional details are described herein.

Example 2: Diversified Therapeutic Phage Cocktails from Close Relatives of the Target Bacterium Bacteria resistant to multiple antibiotics have become an increasing problem in human health, both in combat medicine and in homeland clinics. Yet there have been no new antibiotic classes discovered since 1987, aside from the yet-unapproved teixobactin (see, e.g., Ling L L et al., "A new antibiotic kills pathogens without detectable resistance," *Nature* 2015; 517:455-9).

The methods herein can enable a leap forward in providing tailored viruses (or bacteriophages or phages) that can infect target pathogens. Phages have been applied therapeutically almost since their discovery in 1915, but their use in Western medicine was eclipsed by the rise of antibiotics (see, e.g., Abedon S T et al., *Bacteriophage* 2011; 1:66-85). With resistance to antibiotics now building, it is increasingly imperative to redeploy phages. In particular embodiments, phage cocktails can be tailored to effectively leave no survivors to propagate resistance (see, e.g., Gu J et al., "A method for generation phage cocktail with great therapeutic potential," *PLoS One* 2012; 7:e31698 (8 pp.)).

Whereas antibiotics are broad-spectrum, phages offer the advantage of targeting pathogens with precision, leaving the beneficial component of the microbiome virtually intact. Use of multi-phage cocktails can reduce the chance of target pathogens escaping through development of resistance to any one phage (see, e.g., Gu J et al., *PLoS One* 2012; 7:e31698 (8 pp.)). Thus, it is urgent to develop methods for collecting numerous, diverse phages for attacking each problematic pathogen group (e.g., pathogenic bacterial group).

Sequenced bacterial genomes represent a vast resource of temperate phages (e.g., phages that can reside silently integrated within bacterial chromosomes, as genomic islands of the prophage class), which have adapted over hundreds of millions of years for efficient infection of their hosts. In particular, we have developed tools that identify and precisely map prophages in bacterial genome sequences. Recent application of these tools suggests that, per bacterial genome, we can find three to four prophages on average (substantially higher when excluding non-pathogens with small genomes), with counts as high as twenty-nine for some genomes. Using this strategy, we can identify and produce numerous phages that will target (and optionally kill) virtually any pathogenic bacterium, with high efficacy due to sourcing them from bacteria very closely related to the target.

This approach challenges the existing paradigm for finding phages, which is to painstakingly fish among environmental or clinical samples, typically with low yields of phages that may be imperfectly adapted to the target. Our second challenge to current opinion in the phage therapy community is our plan to use temperate phages as raw material for manufacturing therapeutic anti-bacterials. Temperate phages have been shunned because, in their chromosome-integrated form, they protect bacteria from killing by reinfection with that same phage (see, e.g., Abedon S T et al., *Bacteriophage* 2011; 1:66-85). However, this orthodoxy had set in before the recent development of phage genome engineering tools (see, e.g., Ando H et al., *Cell Syst.* 2015 1(3):187-96) and current genome editing technology. With these methods, we can systematically knock out the ability of any temperate phage to integrate, rendering it fully lytic (bacteriocidal) and removing the objections previously raised against their use.

In one non-limiting approach, we will apply two bioinformatic algorithms (FIG. 3A-3B), Islander (see, e.g., Hudson C M et al., *Nucleic Acids Res.* 2015; 43:D48-D53) and Comparator to accurately find genomic islands, i.e., chromosome-integrated mobile DNAs that are primarily prophages. Islands also include a lesser class of nonviral DNAs transferred by conjugation, termed ICEs. Using the carefully developed Islander and Comparator algorithms to search these genomes, under existing funding, we safely anticipate generating a large database of genomic islands. We propose to employ this database to identify phage genomes, group them into families, and map the ranges of bacterial hosts they can infect. Phage cocktails can then be designed to kill virtually any bacterial target.

Genomic islands are mobile DNAs that are mobilized from one bacterial cell to another, either through phage particles (prophages) or through conjugation tubes (ICEs). We have developed an experimental method (Juxtaposer) for defining genomic islands based on detecting their circular or deletion junctions in next-generation sequencing data (see, e.g., Schoeniger J S et al., *Nucleic Acids Res.* 2016; 44:6830-9; and Hudson C M et al., *PLoS One* 2014; 9:e99209 (14 pp.)). For greater throughput we have additionally developed two complementary methods that are purely bioinformatic (FIG. 3A-3B). The Islander method is quite mature and is based on islands' preference to integrate into tRNA genes (see, e.g., Hudson C M et al., *Nucleic Acids Res.* 2015; 43:D48-D53; Mantri Y et al., *Nucleic Acids Res.* 2004; 32:D55-D58; Williams K P, "Traffic at the tmRNA gene," *J. Bacteriol.* 2003; 185:1059-70; and Williams K P, "Integration sites for genetic elements in prokaryotic tRNA and tmRNA genes: sublocation preference of integrase subfamilies," *Nucleic Acids Res.* 2002; 30:866-75). The new Comparator method is based on both cohesion of the island integration module, and a negative comparative genomics approach (i.e., a search for a reference genome from refseq_genomic with the uninterrupted integration site).

Although our approach is applicable to any target bacterium, as a proof of principle for extracting therapeutic phages through our phage database, we focused on two pathogens (*Pseudomonas aeruginosa* and *Staphylococcus aureus*) notorious for aggressive wound infection and multiple antibiotic resistance (see, e.g., Mayhall C G, "The epidemiology of burn wound infections: then and now," *Clin. Infect. Dis.* 2003; 37:543-50). Both the Islander and Comparator methods were employed to map genomic islands with single-nucleotide precision. Using these methods to 2,168 genomes, we found 7,949 islands, for an average of 3.7 islands/genome; this value rises for most pathogens, to 8.2 for *P. aeruginosa* and to 4.9 for *S. aureus* genomes. Scaling up to analyze 81,443 genomes, we extrapolate a yield of 298,612 islands, of which we expect more than 100,000 to be phages.

After using Islander, Comparator, and/or Juxtapower to identify genomic islands, one or more tools can be employed to identify which islands are phages and to sort phages into families. To identify which of the genomic islands are phages, one tool is the Phaster system (see, e.g., Arndt D et al., "PHASTER: a better, faster version of the PHAST phage search tool," *Nucleic Acids Res.* 2016; 44:W16-W21). Another approach includes building and collecting a set of hidden Markov models (HMMs) that identify known families of phage structural and regulatory proteins. Yet another approach will be to rule out members of the other main class of islands (ICEs), which are distinguished by bearing genes for a conjugation tube.

A second step can include grouping the phages into families. Our recent testing with the new Mash algorithm (see, e.g., Ondov B D et al., "Mash: fast genome and metagenome distance estimation using MinHash," *Genome Biol.* 2016; 17:132 (14 pp.)), which measures genomic distances based on nucleotide composition, supports its suitability for sorting phages into closely related families, although more refined HMM-based analyses examining gene function and content may be required to fully reveal family relationships. Grouping can be a challenging task for phages, as compared to that for bacteria, because there are less information content in their smaller genomes and no universal markers such as ribosomal RNA genes. Including reference phage and plasmid genomes already available at GenBank will improve this analysis and double-check identification of certain genomic islands as purported phage or ICE sequences. In addition, this sorting step can allow us to choose no more than one member of a phage family for inclusion in a cocktail, thereby preventing redundancy and interference among phages.

Family delineation can aid another task: to map phage host ranges. Since the bacterial host is known from the start for each prophage detected by Islander and Comparator, we can systematically map host ranges for each family of phages, which is both a fundamental problem in bacteriology and important knowledge for predicting the spectrum of bacterial species targeted by a given phage or cocktail.

We can develop further algorithms to identify the closest relatives of a target bacterium based on distance measurements by Mash (see, e.g., Ondov B D et al., *Genome Biol.* 2016; 17:132 (14 pp.)). From among the close relatives of the target, we can identify a small number of bacterial strains to which we have access (e.g., through ATCC, BEI Resources, colleagues, or our own collections) that together contain a large number of diverse prophages, and obtain those strains.

Upon obtaining prophage sequence, lysogeny can be disabled, thereby providing lytic phages. Virulent phages such as T4 are only capable of lytic (bacteria-killing) growth. In contrast, temperate phages, such as lambda and those that we find as genomic islands, have a genetic switch that directs most (e.g., 99%) infected cells to proceed with lytic phage growth, but also generates rare genomic integration events (e.g., 1%) that allow the cell to survive as a lysogen (see, e.g., Ptashne M, "A Genetic Switch, Third Edition, Phage Lamda Revisited," 2004, Cold Spring Harbor Laboratory Press, Cold Spring Harbor, N.Y. (154 pp.)). Two main temperate phage proteins promote lysogeny: the repressor protein prevents expression of genes required for lytic phage growth, while the integrase enzyme inserts the phage genome into the bacterial chromosome with stable inheritance. The lysogen cell is immune to killing upon reinfection with the same phage because its repressor molecules silence the incoming phage and continue to prevent lytic growth. One non-limiting approach to kill a lysogen cell resistant to a given phage is to attack with multiple other phages to which the lysogen is not immune.

Alternatively, phage mutants of three categories could be engineered to prevent any lysogeny: i) mutants in repressor expression, ii) integrase mutants, and iii) mutants of the repressor-binding DNA sites (operators). Operator mutants have the unique property that they cannot be repressed, even when entering a cell lysogenic for a closely related phage. However, a fully virulent phenotype may be more challenging to routinely engineer, since operators are small and may be difficult to identify in novel phages. Moreover variations on the repressor/operator paradigm are known (see, e.g., Villanueva V M et al., "An unusual phage repressor encoded by mycobacteriophage BPs," *PLoS One* 2015; 10:e0137187 (21 pp.)).

Integrase mutants abortively attempt lysogeny by expressing repressor as usual in 1% of infections, but these cells are not stable because the phage genome cannot replicate without integrating into the chromosome (see, e.g., Gottesman M E & Weisberg R A, "Prophage insertion and excision," in *The Bacteriophage Lambda* (ed. Hershey A D), 1971, Cold Spring Harbor Laboratory Press, Cold Spring Harbor, N.Y. (pp. 113-138)). Theoretically, the phage could also carry a plasmid origin that would allow its genome to replicate as a free circle. Our island-finding methods automatically identify the integrase gene int. Thus, one approach is to design mutations to knock out this gene entirely, and thereby routinely disable lysogeny in originally temperate phages.

Engineered phages can then be tested experimentally. We can quickly test the potential success of this approach by, e.g., inducing prophages in the laden bacteria (the host organism), isolating numerous released phages, preparing a cocktail, and testing it for effective killing of the target organism. Genomic engineering of our phages can disable lysogeny, thereby preventing development of resistance and improving the long-term utility of the cocktail. This could address the perceived risk that bacteria, surviving cocktail treatment and lysogenic with one or more cocktail phages, might escape and spread the protective prophage(s) through the target population. As described above, e.g., lysogeny can be fully eliminated, by disabling the integrase gene.

Any useful method can be employed for engineering phages, e.g., as described herein. In one instance, about 10 kbp segments of the phage genome can be designed with short (>30 bp) overlapping "homology arms" that specify fragment assembly order, and these segments can be amplified by long range PCR. When these segments are co-transformed into yeast, together with a yeast origin of replication segment, the cell assembles them through gap repair into a phage genome plasmid that can be purified and transformed into a bacterium to produce phage (see, e.g., Ando H et al., *Cell Syst.* 2015; 1(3):187-96). This is both a systematic way to produce numerous active phages from laden bacterial genomes, and an opportunity to engineer phages (e.g., deleting the integrase gene to eliminate lysogeny) at segment junctions. With this method, all that is needed is access to prophage-laden bacterial genomic DNA as a PCR template, thus possibly avoiding the steps of inducing and isolating phages by classical methods. Furthermore, such an assembly-in-yeast method is automatable and scalable for industrial scale production of lysogeny-inactivated phages ready to mix into cocktails.

Another type of modification can include altering host specificity of phages. For instance, such modification can include changing the recognition of bacterial cell-surface phage receptors, e.g., by altering structural proteins of the virion particle, particularly the baseplate and tail fiber proteins that typically recognize receptors. Such modifications can be optimized by creating DNA fragment pools that encode peptide segments from the portions of baseplate and tail fiber proteins involved in receptor recognition, further diversifying the pools with error-prone PCR, then using these pools to select for phage variants that shift host range to the target bacterium. For example, in a set of *Pseudomonas* phages, segments of their baseplate and tail fiber genes (virion structural proteins involved with receptor recognition) can be replaced using any useful genome synthesis system (see, e.g., Ando H et al., *Cell Syst.* 2015; 1(3):187-96) with a pool of such segments from *E. coli* (same phylum) or from *Staphylococcus* (different phylum) phages, to test the limits of host range engineering.

Example 3: Identification of Prophage Sequences from Close Relatives of an Exemplary Target, *P. aeruginosa* PAO1

Figure 4:
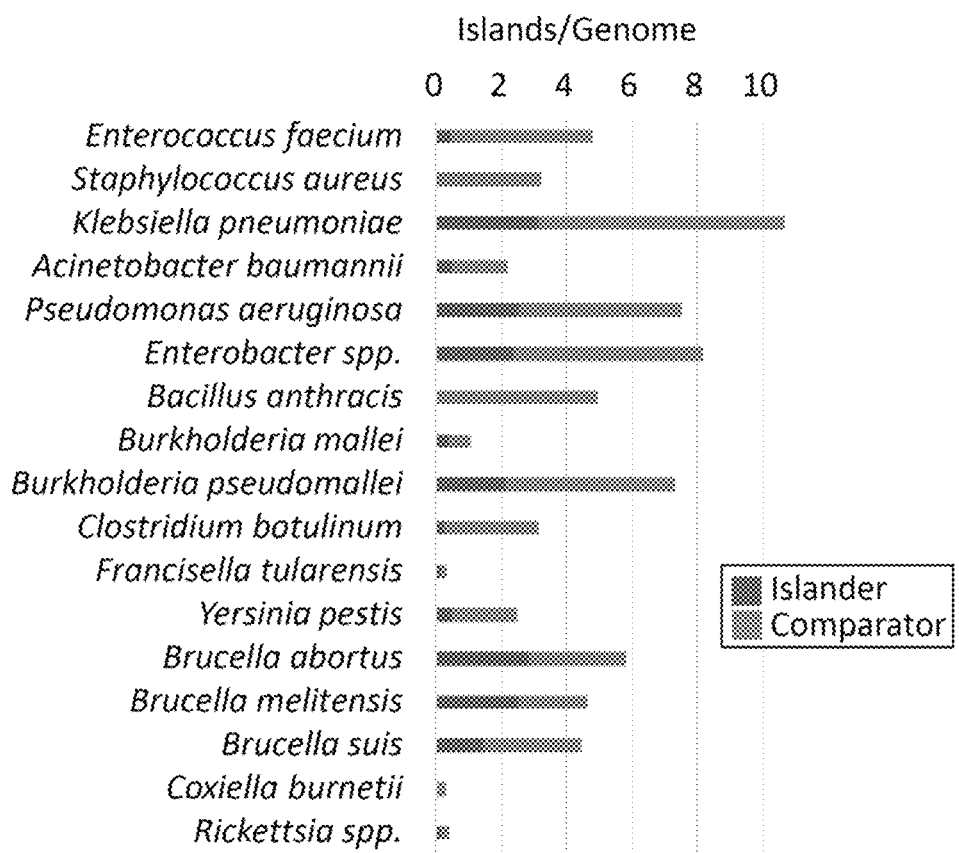
FIG. 4 is a graph showing the number of genomic islands per genome for various pathogens, as identified by Islander and Comparator.
Figure 5A:
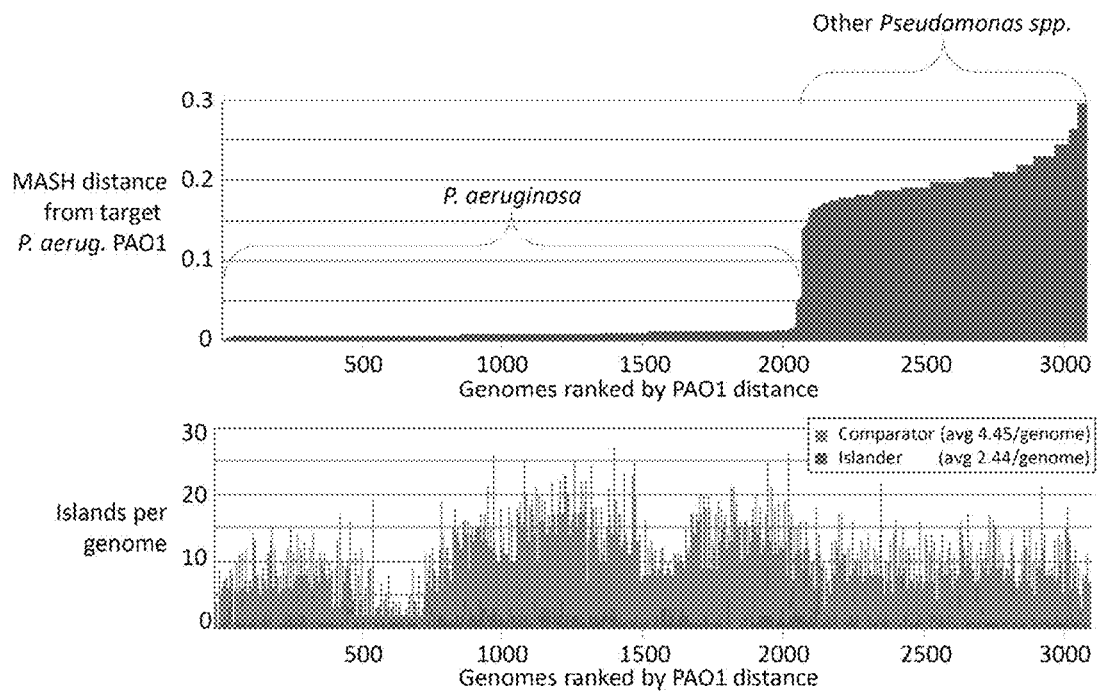
FIG. 5A-5B shows *Pseudomonas* genomes that were scored for phylogenetic distance from target strain *P. aeruginosa* PAO1 (top graphs in FIG. 5A-5B) and for genomic islands by Islander and Comparator methods (bottom graphs in FIG. 5A-5B). Provided are data for over 3,000 sequenced *Pseudomonas* genomes (FIG. 5A) and for 41 genomes for strains available at ATCC (FIG. 5B).
Figure 5B:
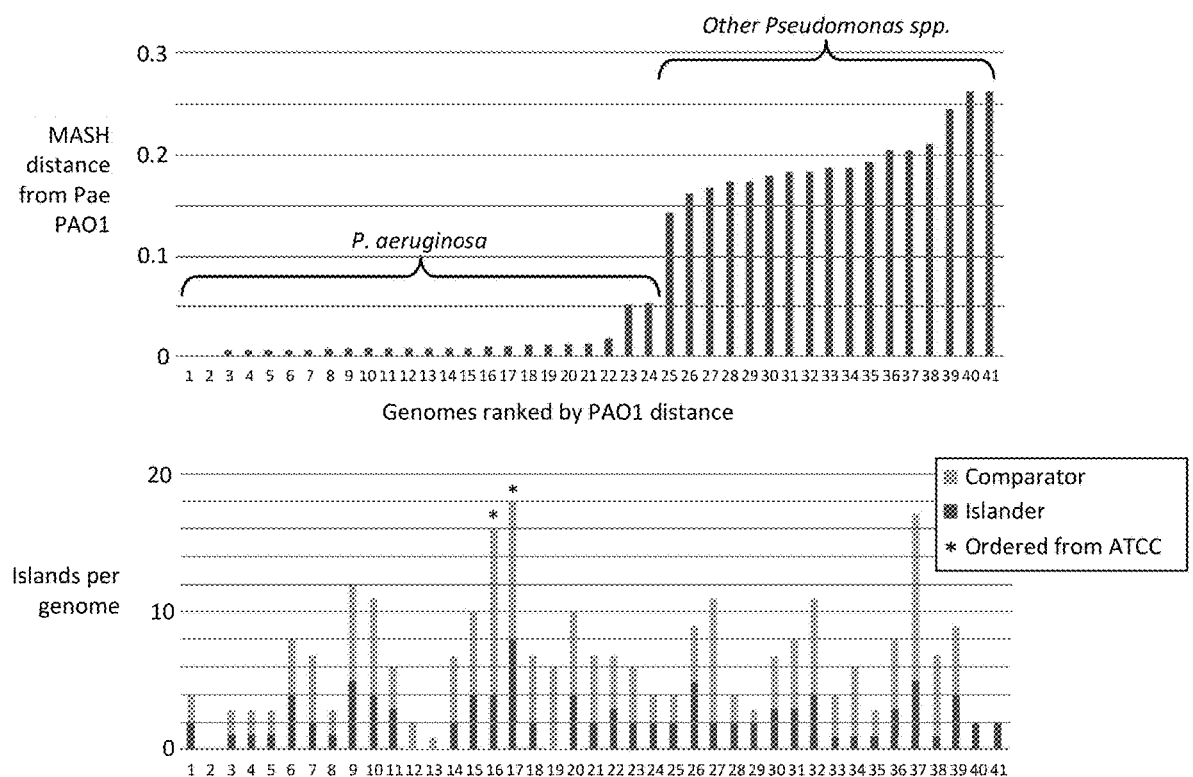

We have demonstrated the two main propositions, namely, identification of multiple active phages from prophage-laden close relatives of our target bacterium (*Pseudomonas aeruginosa* PAO1) and conversion of one of these temperate phages to a virulent phage. From our database of ~300,000 precisely mapped genomic islands for 80,000 prokaryotic genomes (see, e.g., FIG. 4), we analyzed 3,000 sequenced *Pseudomonas* genomes (FIG. 5A). Of these, we scored 41 *Pseudomonas* strains that are available from ATCC (FIG. 5B) and chose two prophage-laden strains (asterisks in FIG. 5B).

We designed a PCR primer pair to detect the circular junction of the excised prophage or virion for each of 11 prophages mapped for the two strains, Pae1505 (*P. aeruginosa* strain ATCC 27853, GenBank Accession No. CP015117.1) and Pae5 (*P. aeruginosa* 2192, ATCC 39324, GenBank accession no. CH482384.1).

For the Pae1505 strain, six genomic islands with putative prophage sequences were identified: 102K, 52S, 43spxA, 38G, 20ychF, and 12M. Sequences are provided for prophages including islands 52S or 43spxA but lacking the integrase gene: Pae1505.43spxAΔint (SEQ ID NO:1), Pae1505.43spxAΔint-rc (SEQ ID NO:2, a reverse complement of SEQ ID NO:1), and Pae1505.52SΔint (SEQ ID NO:3). Primers for these prophages are provided below in Table 1 (primers for Pae1505.52SΔint include SEQ ID NOs:8 and 9; and primers for Pae1505.43spxAA int include primers SEQ ID NOs:12 and 13).

For the Pae5 strain, five genomic islands with putative prophage sequences were identified: 64L, 52yheS, 42argF, 41L, and 11M. Sequences are provided for prophages including islands 41Z, 42argF, 52yheS, or 64L but lacking the integrase gene: Pae5.41ZΔint (SEQ ID NO:4), Pae5.42argFΔint (SEQ ID NO:5), Pae5.52yheSΔint (SEQ ID NO:6), and Pae5.64LΔint (SEQ ID NO:7). Primers for these prophages are provided below in Table 1 (primers for Pae5.41ZΔint include SEQ ID NOs:14 and 15; primers for Pae5.42argFΔint include primers SEQ ID NOs:16 and 17; and primers for Pae5.52yheSΔint include primers SEQ ID NOs:10, 11, 18, and 19).

TABLE 1

Engineering detection primers

| Name | Sequence | SEQ ID NO: |
|---|---|---|
| 52SL.dx | AGCACGCCGA TGGACAGAT | 8 |
| 52SR.dx | GGCGGAGGTA TGTTATCCCG | 9 |
| 52yheS.dxL | ACAGGTATTC GACGGCGGTT | 10 |
| 52yheS.dxR | TCTGGTCATT CCACGGCTCG | 11 |
| Pae1505.43spxA newdxL | TGGCTGGCCT TCGCTACTAC | 12 |
| Pae1505.43spxA newdxR | TGGTCGTTCC ATTGCTCCGA | 13 |
| Pae5.41Z.KL | TTCGCGTGAT GAGGGGAGAG | 14 |
| Pae5.41Z.KR | GTGAACCCCG GCCTATTTCG | 15 |
| Pae5.42argF.Lnewdx | CTGCTCGGAA AGCACGTTCG | 16 |
| Pae5.42argF.dxR | AGTGTGAGCC AGACGTGCTT | 17 |
| 52yheS forward | GGAGAGCAGC TACGTCCCAG | 18 |
| 52yheS reverse | TCGCAGTAAG CCCCTTCGTG | 19 |

Figure 6:
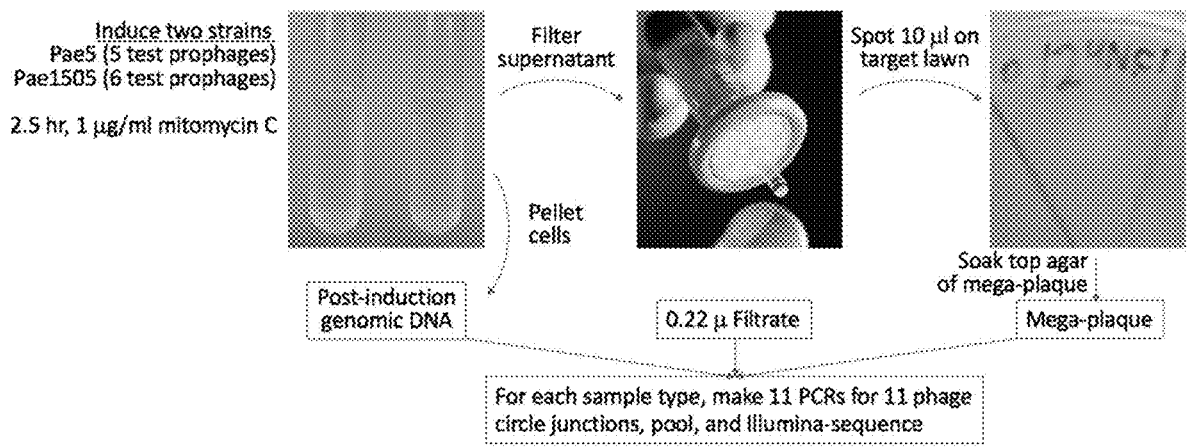
FIG. 6 shows an exemplary ensemble method for identifying target-active phages from prophage-laden strains.
Figure 7:
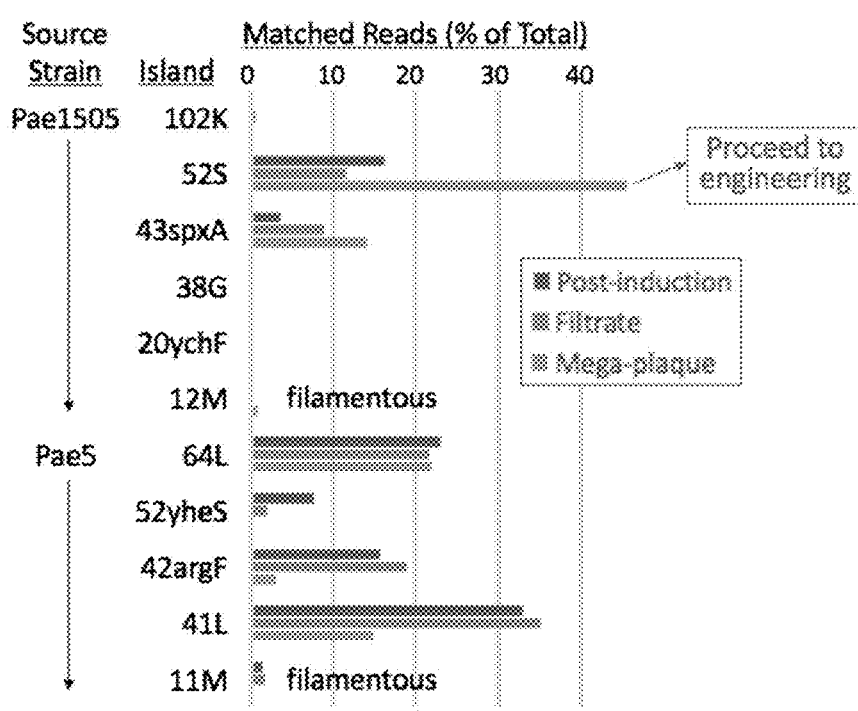
FIG. 7 is a graph showing yields among ILLUMINA reads for circle-junction PCRs for 11 prophages from two different bacterial source strains, Pae1505 (*P. aeruginosa* strain ATCC 15 27853, GenBank Accession No. CP015117.1) and Pae5 (*P. aeruginosa* 2192, ATCC 39324, GenBank accession no. CH482384.1)

We also developed an ensemble method for quickly identifying phages active on the target (FIG. 6). The two laden strains were induced at log phase with 1 μg/ml mitomycin C for 2 hr. Cells in the culture were pelleted, and their DNA was prepared. The virion-bearing supernatant was passed through a 0.22 μm filter. The filtrate was spotted in soft agar on a lawn of the target, and the "mega-plaque" was scraped off and soaked in buffer or medium. Each of these three samples (post-induction genomic, supernatant filtrate, and megaplaque soak) was subjected to PCR for each strain's subset of the 11 prophages. We ILLUMINA sequenced the ensemble of these PCR products. The results revealed that seven prophages had been induced to form circular DNAs and populate the supernatant presumably with phage particles (FIG. 7). Of these phages, only 5 were found among the target strain megaplaque, suggesting that the other two were unable to infect the target. A repeat of the experiment showed a sixth phage (52yheS) present in the megaplaque.

Figure 8:
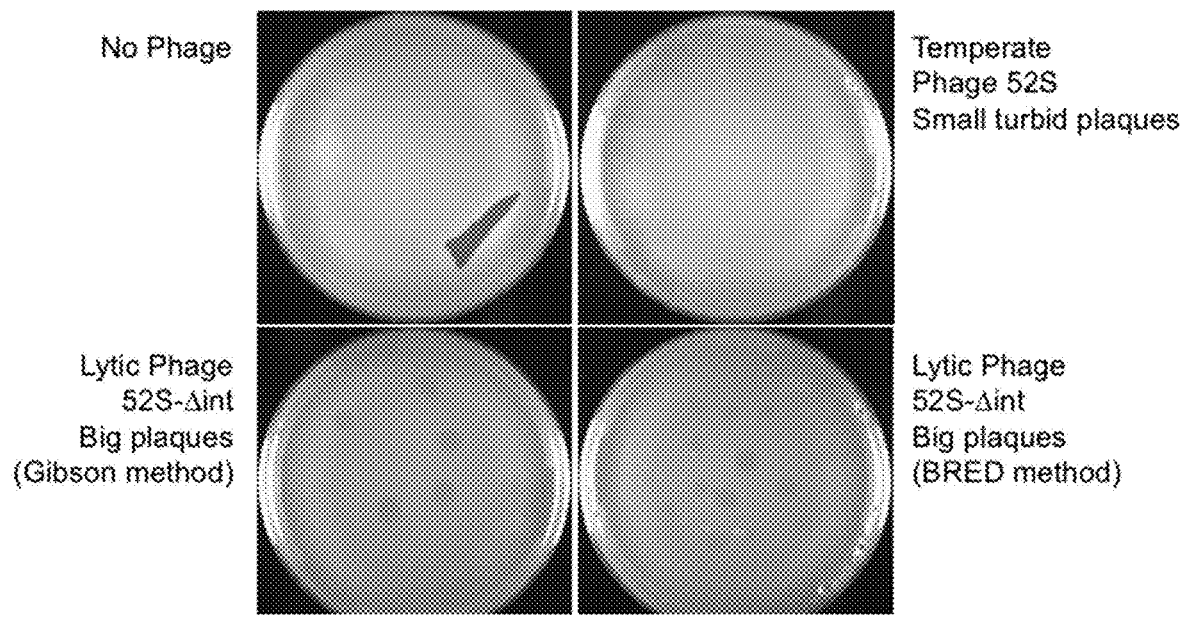
FIG. 8 shows conversion of wild-type temperate phage (Pae1505.52S, derived from the 52S island of Pae1505's genome) to an engineered phage (52S-Δint, a Δint mutant of Pae1505.52S). Provided are images of colonies having no phage, wild-type temperate 52S phage (showing small turbid plaques), engineered lytic 52S-Δint phage (showing big plaques, in which the phage was produced by the Gibson method), and another engineered lytic 52S-Δint phage (showing big plaques, in which the phage was produced by the BRED method).

One of these phages (Pae1505.52S) was chosen for initial processing and was isolated by plaque purification despite forming only tiny, turbid plaques. This phage was subjected to deletion of the integrase gene (int) by two methods: (i) Gibson assembly from four long PCR fragments and (ii) Bacteriophage Recombineering of Electroporated DNA (see, e.g., Marinelli L J et al., "BRED: a simple and powerful tool for constructing mutant and recombinant bacteriophage genomes," *PLoS One* 2008; 3:e3957 (8 pp.)), in which the target bacterium is infected by wildtype Pae1505.52S after transformation with a 1,000-bp PCR product containing the desired int deletion junction and its two 500-bp flanks. Both methods produced numerous plaques that were large and clear (FIG. 8) and were found positive for the Δint mutation by a PCR test. Overall, we have demonstrated identification of prophage-laden close relatives of the target bacterium through our bioinformatic front end and conversion of such a temperate phage to a virulent phage.

Example 4: Engineered Phages in Liquid Cultures

Figure 9:
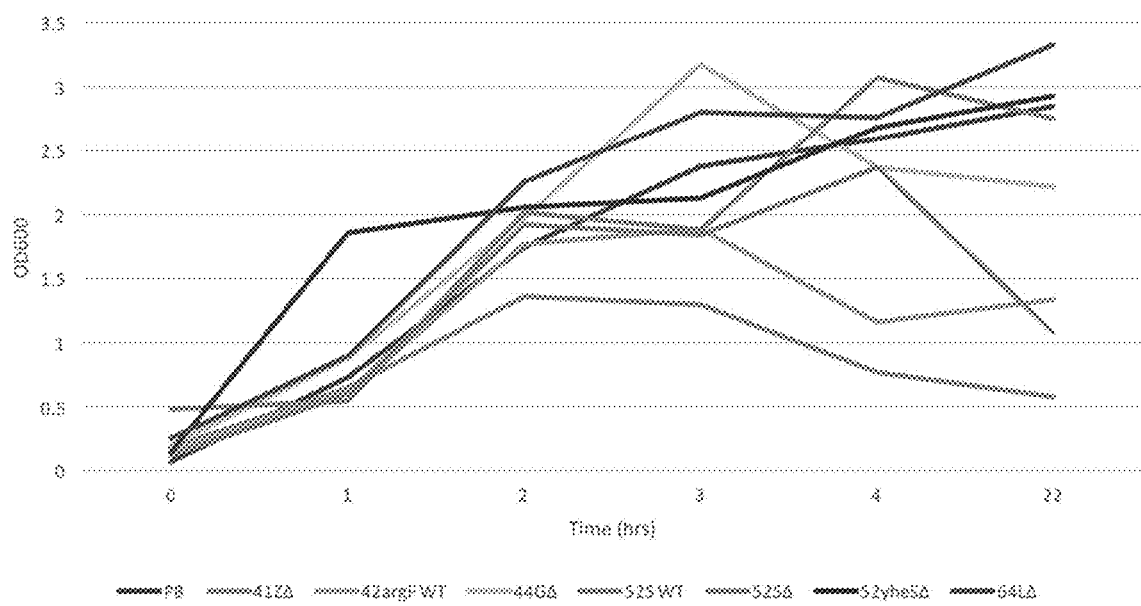
FIG. 9 shows phage efficacy in liquid cultures for killing *P. aeruginosa* PAO1 over time.

We have demonstrated that engineered phages kill *P. aeruginosa* PAO1 in liquid culture. *P. aeruginosa* strains used to isolate phages from are Pae5 (ATCC 2192; NCBI: CH482384.1) and Pae1505 (ATCC 27853; NCBI: CP015117.1). As seen in FIG. 9, the following phages killed PAO1 in liquid culture over time: Pae5.41ZΔint, Pae5.42argF WT, Pae5.44GΔint, and Pae1505.52S WT. Whereas WT (wild type) phages can generate resistance through lysogeny, Δint phages generally kill bacteria over time.

Example 5: Phage Therapy in *Galleria mellonella*

Figure 10A:
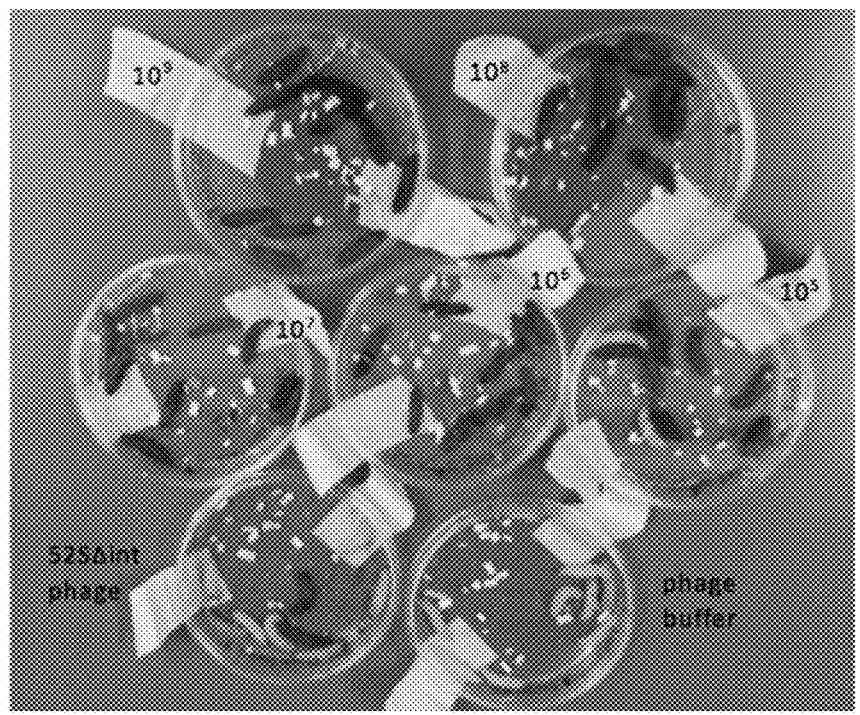
FIG. 10A-10B shows phage therapy in *Galleria mellonella*. Provided is (A) an image of larvae injected with *P. aeruginosa* from $10^9$ to $10^5$ CFU/mL or control (including phage buffer (PB) and phage) 24 hours post-infection, in which black worms are deceased. Also provided is (B) a survival curve of *G. mellonella* phage therapy and controls.
Figure 10B:
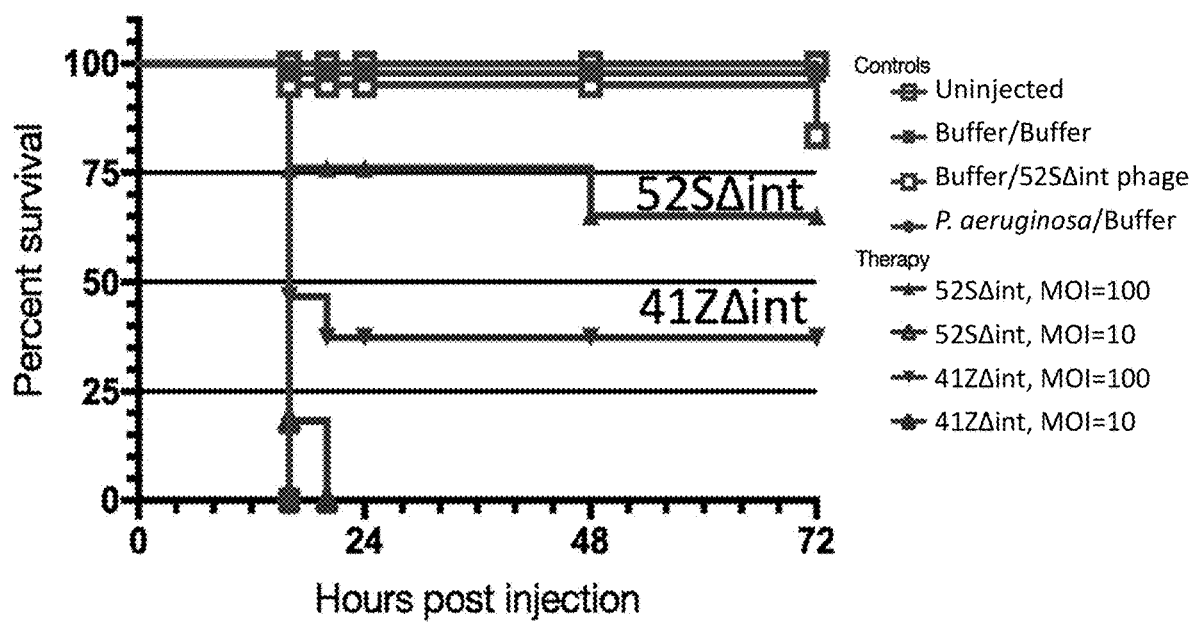
Figure 11A:
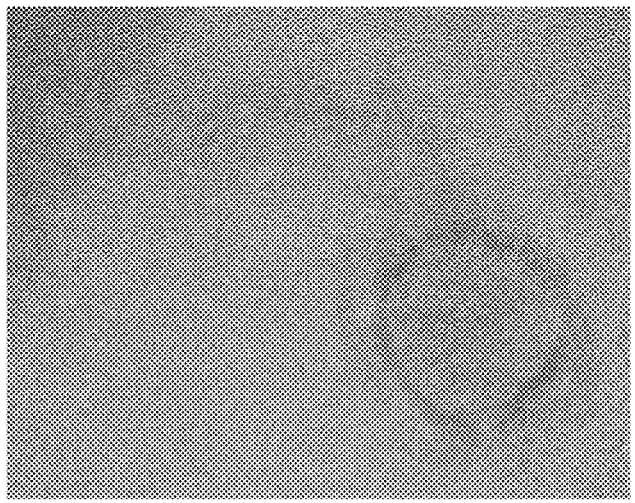
FIG. 11A-11B shows electron microscopy of (A) phage 52S wt and (B) phage 41Z Δint.
Figure 11B:
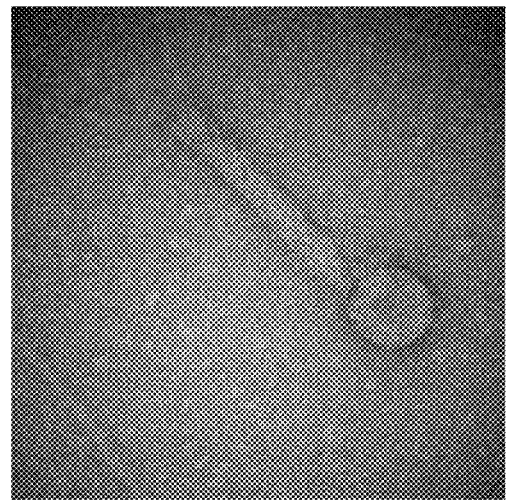

Waxworms (*Galleria mellonella*) were injected with *Pseudomonas* in the right lower pseudopod (FIG. 10A), then 20 minutes later with phage in the left lower pseudopod, and deaths were monitored over 3 days (FIG. 10B). In particular instances, a proportion of worms were saved with single phage injection of Pae5.41ZΔint, Pae5.42 WT, Pae1505.52S WT, Pae1505.52SΔint, or Pae5.64LΔint at MOI of 10. Structural characterization included electron microscopy of Pae1505.52S WT phage (FIG. 11A) and Pae5.41ZΔint phage (FIG. 11B).

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of producing an engineered phage for killing a bacterial colony, the method comprising:
   identifying islands within a bacterial genome of a first bacterium;
   identifying a genomic island comprising a first prophage sequence within the bacterial genome from the first bacterium,
   identifying close relatives of the first prophage sequence by sorting the first prophage sequence into a group with other prophage sequences based on genomic distances computed amongst the first and other prophages;
   wherein the first prophage sequence comprises a genomic island comprising an integrase gene;
   identifying relatives of a target bacterium based on genomic distance measurements;
   producing an engineered phage genome comprising the first prophage sequence that lacks the integrase gene, wherein the first prophage sequence is effective to kill the target bacterium and the first bacterium is a relative of the target bacterium, wherein the engineered phage genome encodes the engineered phage; and
   targeting a bacterial colony, which comprises the target bacterium, with the engineered phage genome, wherein the bacterial colony comprises a strain of a second bacterium that is different than a strain of the first bacterium.

2. The method of claim 1, wherein the first prophage sequence encodes a temperate phage and wherein the engineered phage genome encodes a virulent phage.

3. The method of claim 1, wherein the identifying step comprises identifying a plurality of prophage sequences within the bacterial genome from the first bacterium, wherein each of the plurality of prophage sequences comprises a genomic island comprising an integrase gene; and wherein the producing step comprises producing the engineered phage genome comprising at least one of the plurality of prophage sequences that lacks the integrase gene.

4. The method of claim 3, wherein the identifying step comprises identifying a first prophage sequence and a second prophage sequence, and wherein the producing step comprises producing a first engineered phage genome comprising the first prophage sequence and a second engineered phage genome comprising the second prophage sequence, and wherein each of the first and second prophage sequences comprises a genomic island.

5. The method of claim 4, wherein the targeting step comprises targeting the bacterial colony with the first engineered phage genome and with the second engineered phage genome.

6. The method of claim 1, wherein the engineered phage genome comprises the first phage genome that lacks a repressor gene, a repressor-binding site, a virulence gene, a resistance gene, a toxin gene, a lysis gene, a phage receptor recognition gene, or a structural phage protein gene.

7. The method of claim 1, further comprising, after producing an engineered phage genome:
   incubating the engineered phage genome with a first bacterial lawn comprising a strain of the first bacterium, thereby producing a plaque disposed on the first bacterial lawn; and identifying a genomic sequence from the plaque by using one or more primers to bind to the first prophage sequence or a portion thereof.

8. The method of claim 1, further comprising, after producing an engineered phage genome:
incubating the engineered phage genome with a first bacterial lawn comprising a strain of the second bacterium, thereby producing a plaque disposed on the first bacterial lawn, wherein the first bacterium and the second bacterium are different; and
identifying a genomic sequence from the plaque by using one or more primers to bind to the first prophage sequence or a portion thereof.

9. The method of claim 7, wherein at least one of the one or more primers comprises a nucleic acid sequence having at least 80% sequence identity to any one of SEQ ID NOs:8-19, or a complement of any of these or a fragment thereof.

10. The method of claim 1, wherein the first prophage sequence comprises a nucleic acid sequence having at least 80% sequence identity to any one of SEQ ID NOs: 1-7.

11. The method of claim 1, wherein the first bacterium comprises *Pseudomonas, Burkholderia*, or *Klebsiella*.

12. The method of claim 1, wherein the integrase gene encodes a tyrosine integrase, a tyrosine recombinase, or a serine recombinase.

13. The method of claim 1, wherein the engineered phage genome encodes a virulent phage.

14. The method of claim 1, further comprising, after producing an engineered phage genome:
incubating the engineered phage genome with a bacterial lawn comprising a strain of the second bacterium, wherein the first bacterium and the second bacterium are different,
thereby producing a plaque disposed on the bacterial lawn; and
identifying a genomic sequence from the plaque by using one or more primers to bind to the first prophage sequence or a portion thereof.

15. The method of claim 14, wherein the engineered phage genome comprises the first phage genome that lacks a repressor gene, a repressor-binding site, a virulence gene, a resistance gene, a toxin gene, a lysis gene, a phage receptor recognition gene, or a structural phage protein gene.

16. The method of claim 1, further comprising:
designing one or more primers to bind to the first prophage sequence or a portion thereof;
incubating the engineered phage with a bacterial lawn comprising a strain of the second bacterium, wherein the first bacterium and the second bacterium are different, thereby producing a plaque disposed on the bacterial lawn; and
identifying a genomic sequence from the plaque by using the one or more primers to bind to the first prophage sequence or a portion thereof.

17. The method of claim 16, wherein at least one of the one or more primers comprises a nucleic acid sequence having at least 80% sequence identity to any one of SEQ ID NOs: 8-19, or a complement of any of these or a fragment thereof.

18. The method of claim 1 further comprising: deleting an integrase gene from the genomic island of the first prophage sequence.

19. The method of claim 1, wherein the first bacterium and the target bacterium are different and have a MASH distance of from about 0 to about 0.15.

20. The method of claim 5, wherein the first engineered phage genome and the second engineered phage genome are from a different group based on genomic distances.

* * * * *